United States Patent
Debien et al.

(10) Patent No.: US 12,168,023 B2
(45) Date of Patent: Dec. 17, 2024

(54) INHIBITORS OF ADENOSINE 5'-NUCLEOTIDASE

(71) Applicant: Arcus Biosciences, Inc., Hayward, CA (US)

(72) Inventors: Laurent Pierre Paul Debien, San Francisco, CA (US); Jaroslaw Kalisiak, Newark, CA (US); Kenneth V. Lawson, San Francisco, CA (US); Manmohan Reddy Leleti, Dublin, CA (US); Erick Allen Lindsey, San Diego, CA (US); Dillon Harding Miles, Berkeley, CA (US); Eric Newcomb, Boulder, CO (US); Jay Patrick Powers, Sisters, OR (US); Brandon Reid Rosen, San Mateo, CA (US); Ehesan Ul Sharif, Castro Valley, CA (US)

(73) Assignee: Arcus Biosciences, Inc., Hayward, CA (US)

( * ) Notice: Subject to any disclaimer, the term of this patent is extended or adjusted under 35 U.S.C. 154(b) by 0 days.

(21) Appl. No.: 18/629,820

(22) Filed: Apr. 8, 2024

(65) Prior Publication Data

US 2024/0285665 A1    Aug. 29, 2024

Related U.S. Application Data

(63) Continuation of application No. 18/610,851, filed on Mar. 20, 2024, which is a continuation of application No. 18/364,141, filed on Aug. 2, 2023, now abandoned, which is a continuation of application No. 18/065,577, filed on Dec. 13, 2022, now abandoned, which is a continuation of application No. 17/741,296, filed on May 10, 2022, now abandoned, which is a continuation of application No. 17/514,131, filed on Oct. 29, 2021, now abandoned, which is a continuation of application No. 17/350,093, filed on Jun. 17, 2021, now abandoned, which is a continuation of application No. 16/338,975, filed as application No. PCT/US2017/054694 on Oct. 2, 2017, now Pat. No. 11,058,704.

(60) Provisional application No. 62/403,598, filed on Oct. 3, 2016.

(51) Int. Cl.
| | |
|---|---|
| A61K 31/7076 | (2006.01) |
| A61K 31/706 | (2006.01) |
| A61K 31/7064 | (2006.01) |
| A61K 39/395 | (2006.01) |
| C07H 19/20 | (2006.01) |
| C07H 19/207 | (2006.01) |
| C07H 19/23 | (2006.01) |

(52) U.S. Cl.
CPC ........ *A61K 31/7076* (2013.01); *A61K 31/706* (2013.01); *A61K 31/7064* (2013.01); *A61K 39/3955* (2013.01); *C07H 19/20* (2013.01); *C07H 19/207* (2013.01); *C07H 19/23* (2013.01)

(58) Field of Classification Search
None
See application file for complete search history.

(56) References Cited

U.S. PATENT DOCUMENTS

| | | |
|---|---|---|
| 9,090,697 B2 | 7/2015 | Sim |
| 11,058,704 B2 | 7/2021 | Debien et al. |
| 2004/0043955 A1 | 3/2004 | Beaudoin et al. |
| 2009/0156545 A1 | 6/2009 | Hostetler et al. |
| 2010/0048501 A1 | 2/2010 | Schrader et al. |
| 2017/0044203 A1 | 2/2017 | Cacatian et al. |

FOREIGN PATENT DOCUMENTS

| | | |
|---|---|---|
| EP | 0468866 | 1/1992 |
| WO | WO-2004096233 | 11/2004 |
| WO | WO-2006063281 | 6/2006 |
| WO | WO-2013142125 | 9/2013 |
| WO | WO-2015164573 | 10/2015 |
| WO | WO-2018067424 | 4/2018 |
| WO | WO-2018183635 | 10/2018 |

OTHER PUBLICATIONS

Cottarn, Howard B., Ganapathi R. Revankar, and Roland K. Robins. "A convenient Synthesis of 6-amino-1-β-D-ribofuranosylpyrazolo [3, 4-d] Pyrimidin-4-one and related 4, 6-disubstituted pyrazodopyrimidine nucleosldes." Nucleic Acids Research 11.3 (1983): 871-882.*
Barbee et al. Annals of Pharmacotherapy (2015), vol. 49(8), pp. 907-937.
Bhattarai et al., a, ß-Methylene-ADP (AOPCP) Derivatives and Analogues: Development of Potent and Selective ecto-5'-Nucleotidase (CD73) Inhibitors, Journal of Medicinal Chemistry 2015, vol. 58, pp. 6248-6263.
Compound Summary for CID71403382, PubChem, NIH U.S. National Library of Medicine, create date May 22, 2013.
Extended European Search Report for EP Application No. 17858945.3 mailed May 27, 2020, 16 pages.
Holy, Current Pharmaceutical Design (2003), vol. 9, pp. 2567-2591.
Holy et al. Collection Czechoslovak Chem. Commun. (1982), vol. 47, pp. 3447-3463.

(Continued)

*Primary Examiner* — Patrick T Lewis
(74) *Attorney, Agent, or Firm* — Sheppard Mullin Richter & Hampton LLP

(57) ABSTRACT

Compounds that modulate the conversion of AMP to adenosine by 5'-nucleotidase, ecto, and compositions containing the compounds and methods for synthesizing the compounds, are described herein. The use of such compounds and compositions for the treatment and/or prevention of a diverse array of diseases, disorders and conditions, including cancer- and immune-related disorders, that are mediated by 5'-nucleotidase, ecto is also provided.

24 Claims, 29 Drawing Sheets

(56) References Cited

OTHER PUBLICATIONS

Holy et al., "Preparation of 5'-o-phosphonylmethyl analogues of nucleoside-5'-phosphates, 5'- diphosphates and 5'-triphosphates", Collection Symposium Series (XIIITH Symposium on Chemistry of Nucleic Acid Components Spindleruv Mlyn, Czech Republic; Sep. 3-9, 2005, vol. 47, No. 12, Jan. 1982, pp. 3447-3463.

International Search Report for PCT/US2017/054694, mailed Jan. 26, 2018.

Jasko et al., "A new approach to the synthesis of 5-O-phosphonomethyl derivatives of nucleosides and their analogs", Bioorganicheskaya Khimiya, Izdatel'stvo Nauka, RU, vol. 20, No. 1, Jan. 1, 1994, pp. 50-54.

Knapp et al., "Crystal Structure of the Human Ecto-5'-Nucleotidase (CD73): Insights into the Regulation of Purinergic Signaling", Structure 20, Dec. 5, 2012, pp. 2161-2173.

Kosiova et al., "Synthesis of Nucleoside 5'-S-methylphosphonates and Related Compounds", Nucleic Acids Symposium Series, Sep. 1, 2008, vol. 52, No. 1, pp. 569-570.

Kosiova et al., Methyl 4-toluenesulfonyloxymethylphosphonate, a new and versatile reagent for the convenient synthesis of phosphonate-containing compounds, Tetrahedron Letters 2009, vol. 50, No. 49, pp. 6745-6747.

Krecmerova et al., "Preparation of Purine 2'-Deoxy-5'-O-phosphonomethylnucleosides and 2'- Deoxy-3'-O-phosphonomethylnucleosides", Collection Symposium Series (XIIITH Symposium on Chemistry of Nucleic Acid Components Spindleruv Mlyn, Czech Republic; Sep. 3-9, 2005, vol. 58, No. 2, Jan. 1, 1993, pp. 421-434.

Mackman et al., "Synthesis and anti-HIV activity of 2'-flourine modified nucleoside phosphonates: Analogs of GS-9148", Bioorganic & Medicinal Chemistry Letters, Pergamon, Amsterdam, NL. Dec. 5, 2007, vol. 18, No. 3, pp. 1116-1119.

Masojidkova et al., "Conformational study on ribonucleoside O-phosphonylmethyl derivatives by 1H NMR spectroscopy", Collection Symposium Series (XIIITH Symposium on Chemistry of Nucleic Acid Components Spindleruv Mlyn, Czech Republic; Sep. 3-9, 2005, vol. 50, No. 8, Jan. 1, 1985, pp. 1899-1905.

Nandanan et al., "Structure-Activity Relationships of Bisphosphate Nuceloside Derivatives as P2Y 1 Receptor Antagonists and Partial Agonists", Journal of Medicinal Chemistry, May 1, 1999, vol. 42, No. 9, pp. 1625-1635.

Pav et al., "Activation of human RNase L by 2'- and 5'-O-methylphosphonate-modified oligoadenylates", Bioorganic & Medicinal Chemistry Letters 2012, Pergamon, Amsterdam, NL, Nov. 23, 2011, vol. 22, No. 1, pp. 181-185.

Pav et al., Synthesis of oligoribonucleotides with phosphonate-modified linkages, Organic & Biomolecular Chemistry (2011), vol. 9, pp. 6120-6126.

Rejman et al., Nucleosidyl-O-Methylphosphonates: a pool of monomers for modified oligonucleotides, Nucleosides, Nucleotides & Nucleic Acids 2004, vol. 23, No. 11, pp. 1683-1705.

Rosenberg et al., "Synthesis of phosphonymethyl analogues of diribonucleoside monophosphates containing modified internucleotide bond", Collection Symposium Series (XIIITH Symposium on Chemistry of Nucleic Acid Components Spindleruv Mlyn, Czech Republic; Sep. 3-9, 2005, vol. 52, No. 10, Jan. 1, 1987, pp. 2572-2588.

Stagg et al., "Anti-CD73 antibody therapy inhibits breast tumor growth and metastasis", PNAS, Jan. 26, 2010, vol. 107, No. 4, pp. 1547-1552.

Written Opinion or International Application No. PCT/US2017/054694, mailed Jan. 26, 2018.

Bhattarai, Sanjay, Synthesis and structure-activity relationships of a,β-methylene-ADP derivatives: potent and selective ecto-5-nucleotidase inhibitors, Dissertation 2015.

Stagg et al., 10.1073/pnas.0908801107, Supporting Information 2010.

* cited by examiner

FIG. 2A
| STRUCTURE | Examples | Potency |
|---|---|---|
| 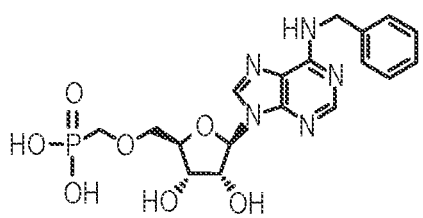 | A | ++ |
| 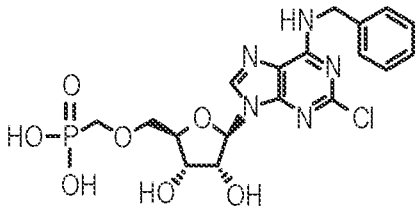 | B | +++ |
| 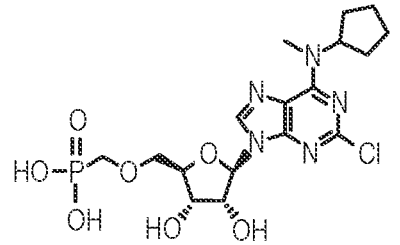 | C | +++ |
| 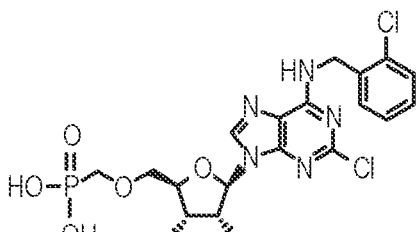 | D | +++ |
| 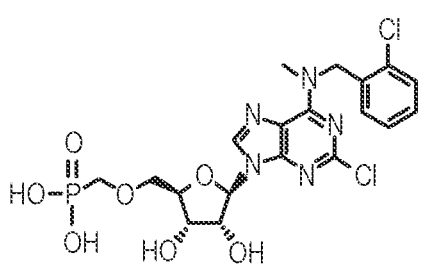 | E | +++ |

FIG. 2F
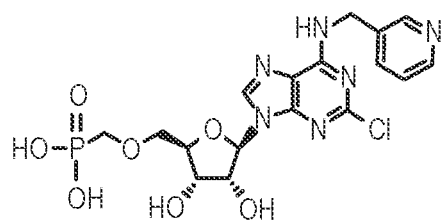   Z    ++
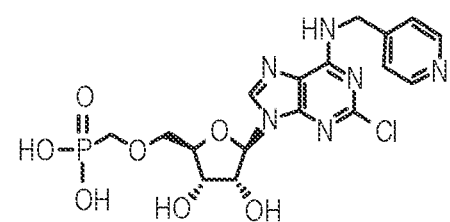   AA   ++
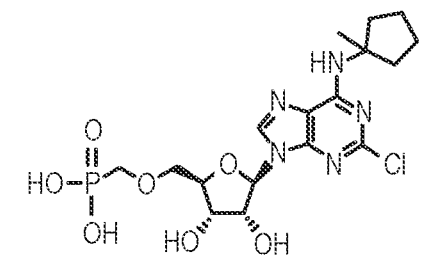   AB   ++
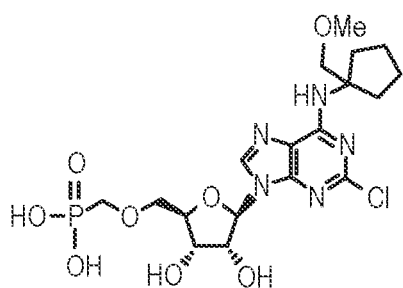   AC   ++
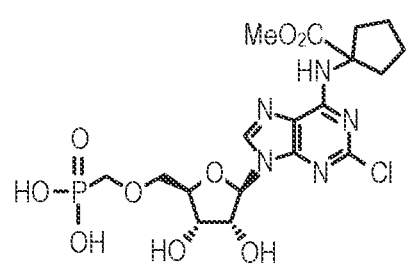   AD   +

FIG. 2M
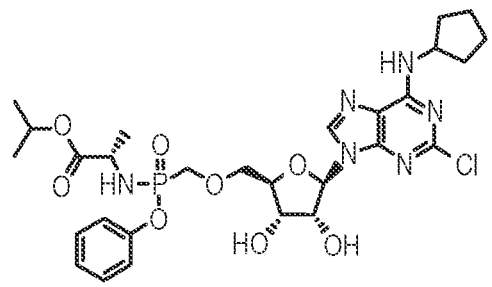
BG +
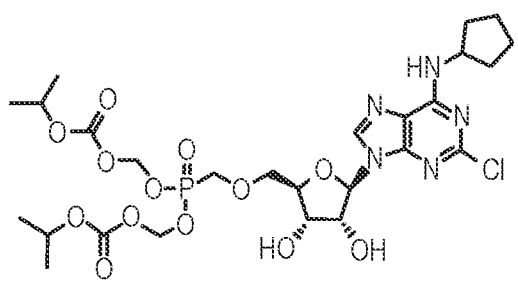
BH +
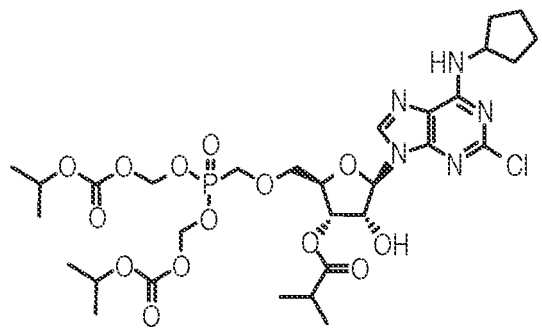
BI +
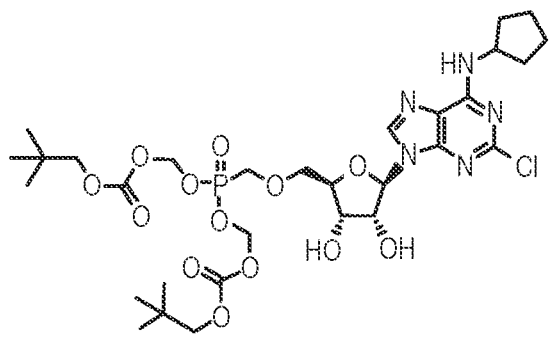
BJ +

FIG. 20
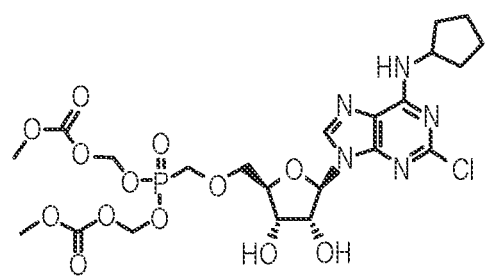
BN      +
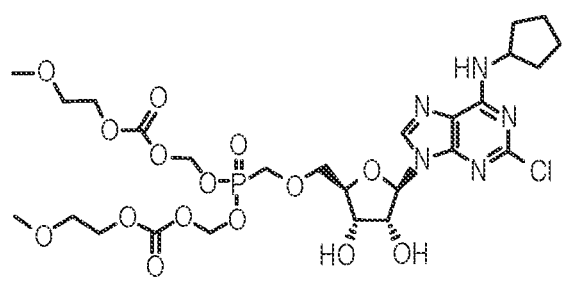
BO      +
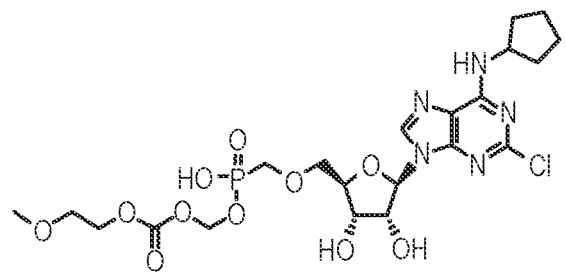
BP      +

FIG. 2W
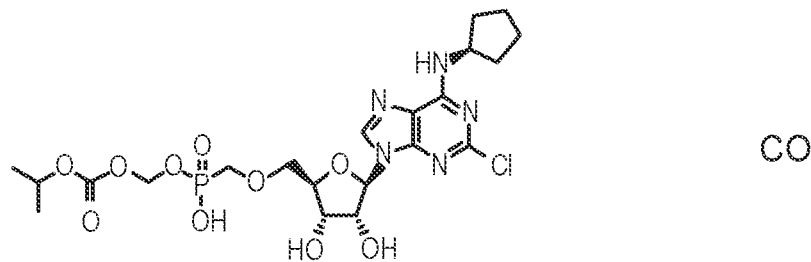 CO
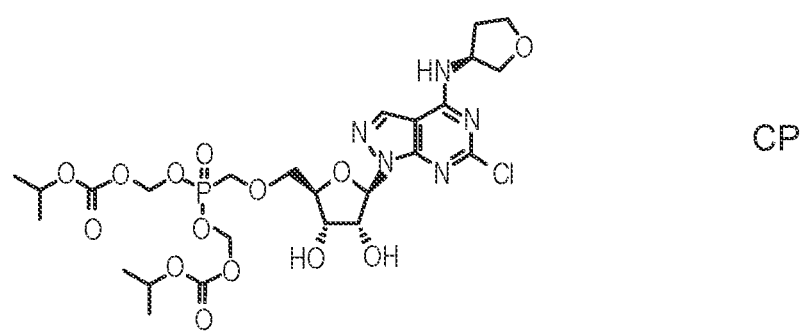 CP
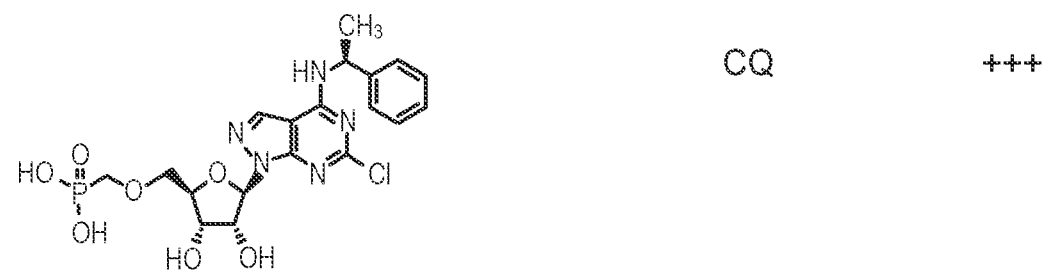 CQ +++
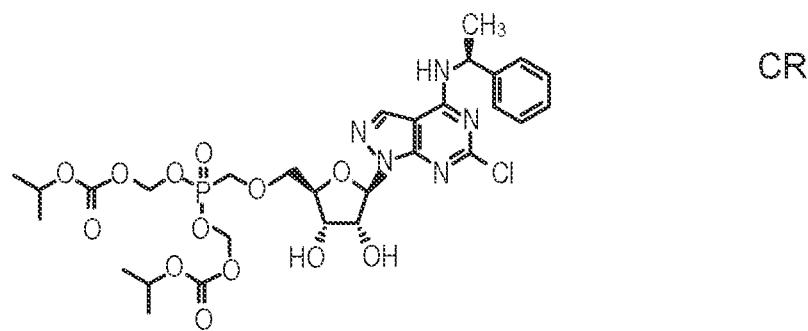 CR

FIG. 2X
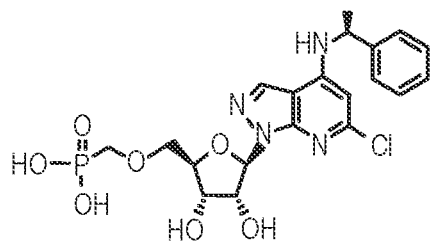  CS  +++
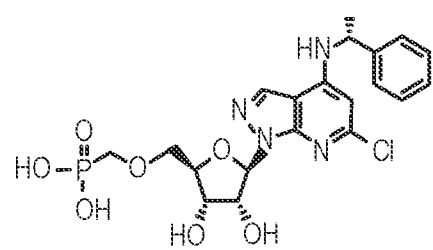  CT  +++
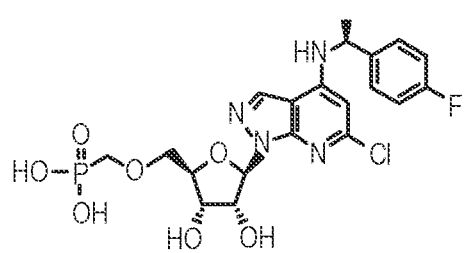  CU  +++
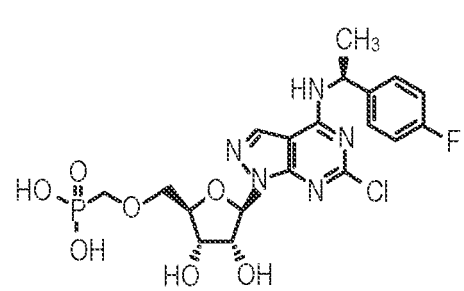  CV  +++

FIG. 2Z
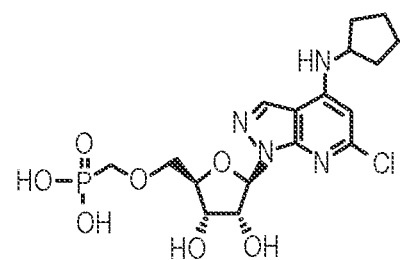  DA  +++
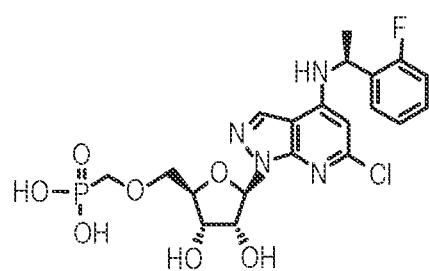  DB  +++
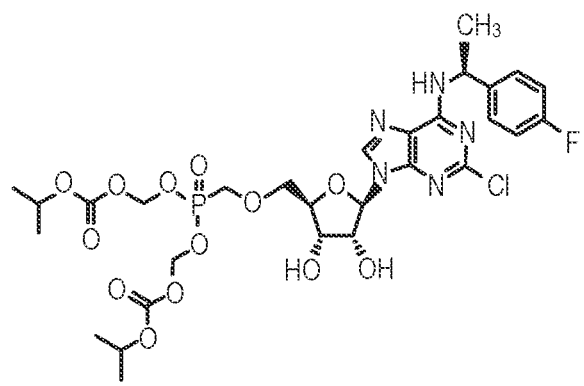  DC
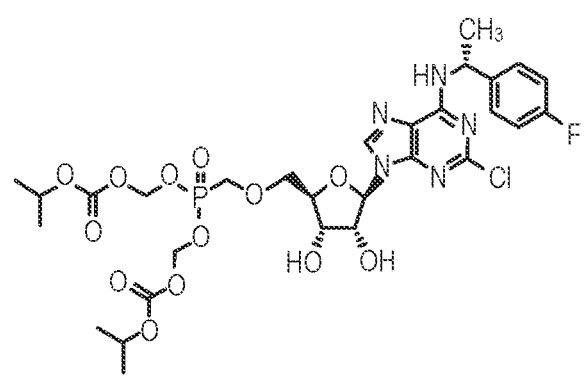  DD

FIG. 2AA
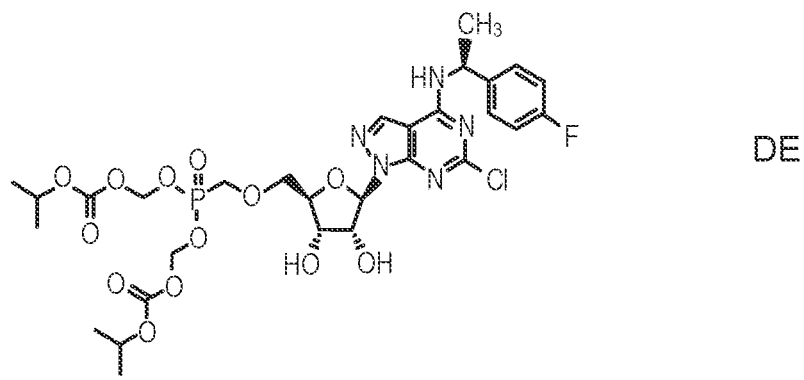 DE
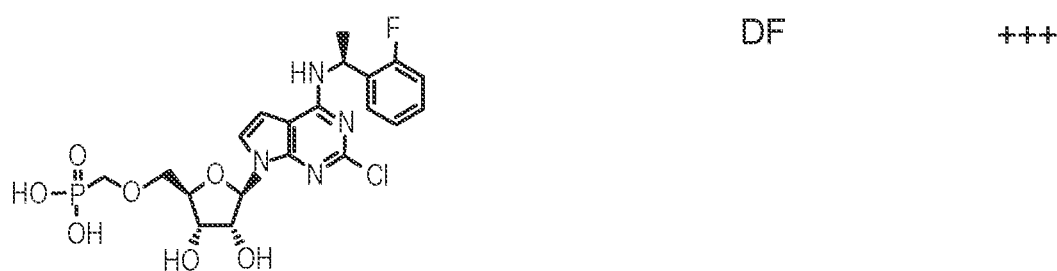 DF +++
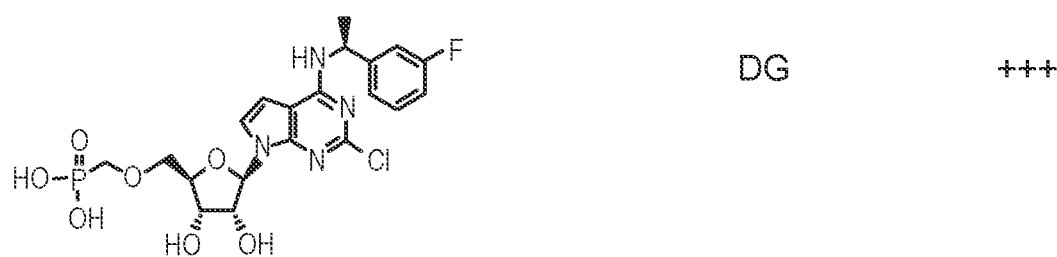 DG +++
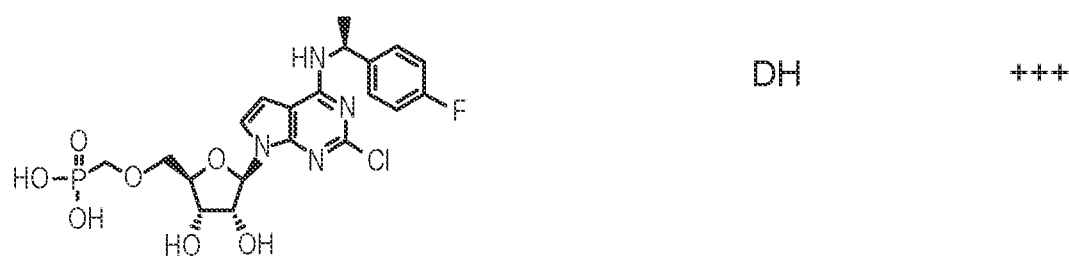 DH +++

FIG. 2AB
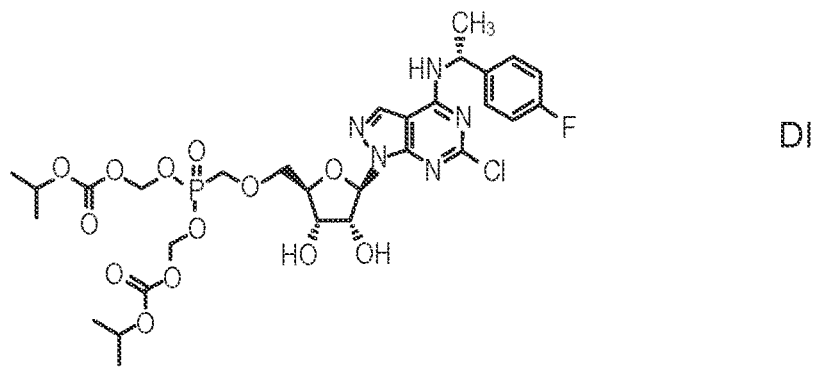
DI
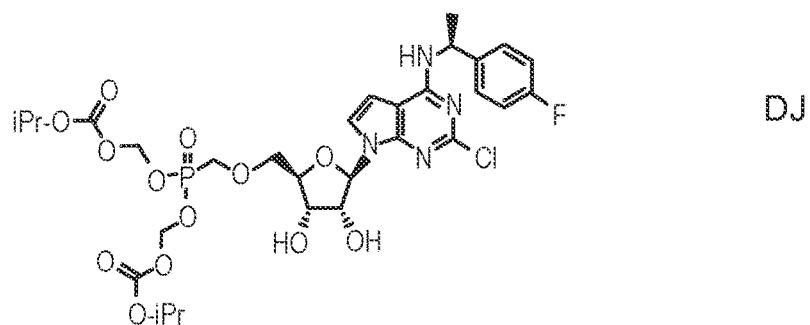
DJ
DK  +++
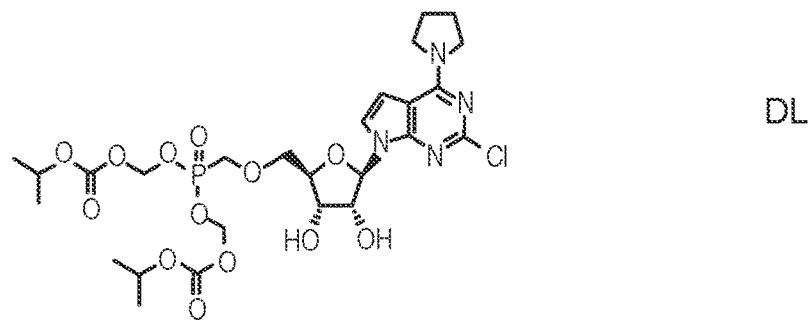
DL
Table 1: Specific Examples (Potency: CD73 IC$_{50}$: + means > 1 M, ++ means 100 nM to 1 M, +++ means < 100 nM).

INHIBITORS OF ADENOSINE 5'-NUCLEOTIDASE

CROSS-REFERENCES TO RELATED APPLICATIONS

This application is a continuation of U.S. patent application Ser. No. 18/610,851, filed Mar. 20, 2024, which is a continuation of U.S. patent application Ser. No. 18/364,141, filed Aug. 2, 2023, which is a continuation of U.S. patent application Ser. No. 18/065,577, filed Dec. 13, 2022, now abandoned, which is a continuation of U.S. patent application Ser. No. 17/741,296, filed May 10, 2022, now abandoned, which is a continuation of U.S. patent application Ser. No. 17/514,131, filed Oct. 29, 2021, now abandoned, which is a continuation of U.S. patent application Ser. No. 17/350,093, filed Jun. 17, 2021, now abandoned, which is a continuation of U.S. patent application Ser. No. 16/338,975, filed Apr. 2, 2019, now U.S. Pat. No. 11,058,704, which is a U.S. National Stage Entry under § 371 of International Application No. PCT/US2017/054694, filed Oct. 2, 2017, which claims the benefit of priority to U.S. Provisional Application No. 62/403,598, filed Oct. 3, 2016, all of which are incorporated herein in their entireties by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD

Provided herein are, for example, compounds and compositions for inhibition of adenosine by 5'-nucleotidase, ecto, also known as CD73, and pharmaceutical compositions comprising same. Also provided herein are, for example, methods of treating or preventing a disease, disorder or condition, or a symptom thereof, mediated by inhibition of adenosine by 5'-nucleotidase, ecto.

BACKGROUND OF THE INVENTION

Purinergic signaling, a type of extracellular signaling mediated by purine nucleotides and nucleosides such as ATP and adenosine, involves the activation of purinergic receptors in the cell and/or in nearby cells, resulting in the regulation of cellular functions. Most cells have the ability to release nucleotides, which generally occurs via regulated exocytosis (see Praetorius, H. A.; Leipziger, J (1 Mar. 2010) *Ann Rev Physiology* 72(1): 377-393). The released nucleotides can then be hydrolyzed extracellularly by a variety of cellular membrane-bound enzymes referred to as ectonucleotidases.

Ectonucleotides catalyze the conversion of ATP to adenosine, an endogenous modulator that impacts multiple systems, including the immune system, the cardiovascular system, the central nervous system, and the respiratory system. Adenosine also promotes fibrosis in a variety of tissues. In the first step of the production of adenosine, ectonucleoside triphosphate diphosphohydrolase 1 (ENTPD1), also known as CD39 (Cluster of Differentiation 39), hydrolyzes ATP to ADP, and then ADP to AMP. In the next step, AMP is converted to adenosine by 5'-nucleotidase, ecto (NT5E or 5NT), also known as CD73 (Cluster of Differentiation 73).

The enzymatic activities of CD39 and CD73 play strategic roles in calibrating the duration, magnitude, and chemical nature of purinergic signals delivered to various cells (e.g., immune cells). Alteration of these enzymatic activities can change the course or dictate the outcome of several pathophysiological events, including cancer, autoimmune diseases, infections, atherosclerosis, and ischemia-reperfusion injury, suggesting that these ecto-enzymes represent novel therapeutic targets for managing a variety of disorders.

CD73 inhibition with monoclonal antibodies, siRNA, or small molecules delays tumor growth and metastasis (Stagg, J. (2010) PNAS U.S.A. 107:1547-52). For example, anti-CD73 antibody therapy was shown to inhibit breast tumor growth and metastasis in animal models (Stagg, J. (26 Jan. 2010) PNAS U.S.A, 107(4):1547-52). In addition, the use of antibodies that specifically bind CD73 has been evaluated for the treatment of bleeding disorders (e.g., hemophilia) (U.S. Pat. No. 9,090,697). Recently, there have been several efforts to develop therapeutically useful CD73 small molecule inhibitors. For example, Bhattarai et al. ((2015) J Med Chem 58:6248-63) have studied derivatives and analogs of α,β-Methylene-ADP (AOPCP), one of the most metabolically stable, potent and selective CD73 inhibitors known, and purine CD73 derivatives have been reported in the patent literature (WO 2015/164573). However, the development of small molecules has been hampered due to, for example, less than ideal metabolic stability.

In view of the role played by CD73 in cancer, as well as a diverse array of other diseases, disorders and conditions, and the current lack of CD73 inhibitors available to medical practitioners, new CD73 inhibitors, and compositions and methods associated therewith, are needed.

BRIEF SUMMARY OF THE INVENTION

The present invention relates to compounds that modulate the conversion of AMP to adenosine by 5'-nucleotidase, ecto (NT5E or 5NT; also known as CD73), and compositions (e.g., pharmaceutical compositions) comprising the compounds. Such compounds, including methods of their synthesis, and compositions are described in detail below.

The present invention also relates to the use of such compounds and compositions for the treatment and/or prevention of a diverse array of diseases, disorders and conditions mediated, in whole or in part, by CD73. CD73 inhibitors have been linked to the treatment of a diverse array of disorders, including cancer, fibrosis, neurological and neurodegenerative disorders (e.g., depression and Parkinson's disease), cerebral and cardiac ischemic diseases, immune-related disorders, and disorders with an inflammatory component. [See, e.g., Sorrentino et al (2013) OncoImmunol, 2:e22448, doi: 10.4161/onci.22448; and Regateiro et al. (2012) Clin. Exp. Immunol, 171:1-7]. In particular embodiments, the compounds described herein act to inhibit the immunosuppressive activity and/or the anti-inflammatory activity of CD73, and are useful as therapeutic or prophylactic therapy when such inhibition is desired. Unless otherwise indicated, when uses of the compounds of the present invention are described herein, it is to be understood that such compounds may be in the form of a composition (e.g., a pharmaceutical composition).

As used herein, the terms "CD73 inhibitor", "CD73 blocker", "adenosine by 5'-nucleotidase, ecto inhibitor", "NT5E inhibitor", "5NT inhibitor" and all other related art-accepted terms refer to a compound capable of modulating, either directly or indirectly, the CD73 receptor in an in vitro assay, an in vivo model, and/or other means indicative of therapeutic efficacy. The terms also refer to compounds that exhibit at least some therapeutic benefit in a human subject.

Although the compounds of the present invention are believed to effect their activity by inhibition of CD73, a precise understanding of the compounds' underlying mechanism of action is not required to practice the invention. For example, the compounds can also effect their activity, at least in part, through modulation (e.g., inhibition) of other components of the purinergic signaling pathway (e.g., CD39). The purinergic signaling system consists of transporters, enzymes and receptors responsible for the synthesis, release, action, and extracellular inactivation of (primarily) ATP and its extracellular breakdown product adenosine (Sperlagh, B. et al. (December 2012) Neuropsychopharmacologia Hungarica 14(4):231-38). Because inhibition of CD73 results in decreased adenosine, CD73 inhibitors can be used for the treatment of diseases or disorders mediated by adenosine and its actions on adenosine receptors, including A1, A2A, A2B and A3. [see Yegutkin, GG (May 2008) *Biochimica Biophysica Acta* 1783(5):673-94].

For purposes of the present disclosure, the purinergic signaling process can be described as comprising the following components. The purinergic receptors (P1, P2X and P2Y), a first component, are membrane receptors that mediate various physiological functions (e.g., relaxation of gut smooth muscle) as a response to the release of ATP or adenosine; in general, all cells have the ability to release nucleotides into the extracellular environment, frequently through regulated exocytosis. The nucleoside transporters (NTs), a second component, are membrane transport proteins which transport nucleoside substrates (e.g., adenosine) across cell membranes; the extracellular concentration of adenosine can be regulated by NTs, possibly in the form of a feedback loop connecting receptor signaling with transporter function. As previously described, the ectonucleotidases (CD73 and CD39) hydrolyze nucleotides released into the extracellular environment and comprise a further component. Another component of the purinergic signaling process comprises the pannexins; in particular, the pannexin-1 channel (PANX1) is an integral component of the P2X/P2Y purinergic signaling pathway and the key contributor to pathophysiological ATP release.

In one particular aspect, the present invention provides compounds having Formula (I):

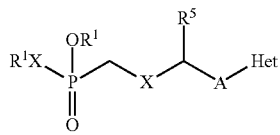

(I)

or a pharmaceutically acceptable salt, hydrate, or solvate thereof, wherein, each $R^1$ is independently selected from the group consisting of hydrogen, optionally substituted $C_1$-$C_6$ alkyl, optionally substituted aryl, —C($R^2R^2$)—O—C(O)—$OR^3$, —C($R^2R^2$)—O—C(O)$R^3$, and —C($R^2R^2$)C(O)$OR^3$; or two $R^1$ groups are optionally combined to form a 5- to 6-membered ring;

each $R^2$ is independently selected from the group consisting of H and optionally substituted $C_1$-$C_6$ alkyl;

each $R^3$ is independently selected from the group consisting of H, $C_1$-$C_6$ alkyl, $C_1$-$C_6$ alkoxy$C_1$-$C_6$ alkyl, and optionally substituted aryl;

$R^5$ is selected from the group consisting of H and optionally substituted $C_1$-$C_6$ alkyl;

X is selected from the group consisting of O, NH, and S;

A is selected from the group consisting of:

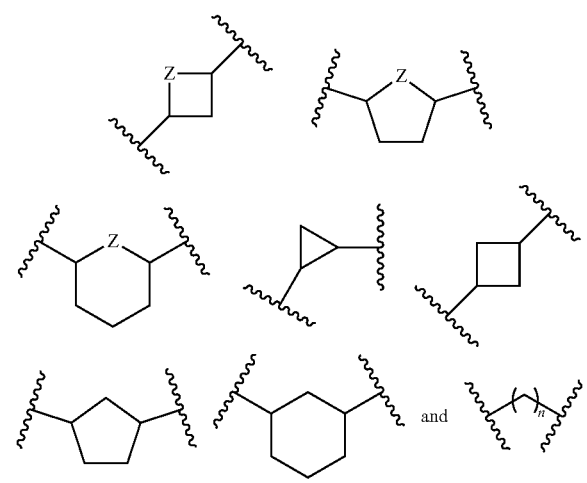

each of which is optionally substituted with from 1 to 5 $R^6$ substituents, and wherein the subscript n is an integer from 0 to 3;

Z is selected from the group consisting of $CH_2$, $CHR^6$, NH, $NR^6$, and O;

each $R^6$ is independently selected from the group consisting of $CH_3$, OH, CN, F, optionally substituted $C_1$-$C_6$ alkyl, and —OC(O)—$C_1$-$C_6$ alkyl; or two $R^6$ groups on adjacent ring vertices are optionally joined together to form a 5- to 6-membered ring having at least one heteroatom as a ring vertex; and Het is selected from the group consisting of:

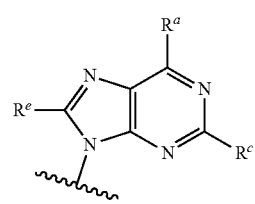

a1

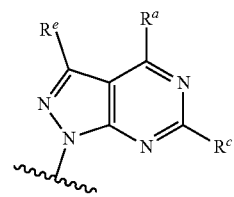

a2 a3 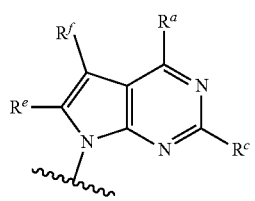

a4 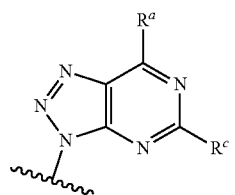

a5 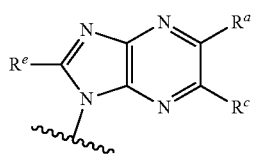

a6 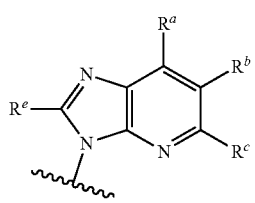

a7 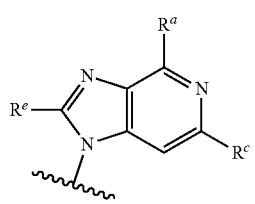

a8 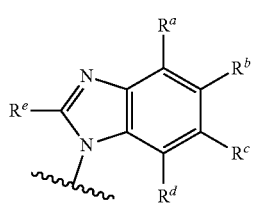

a9 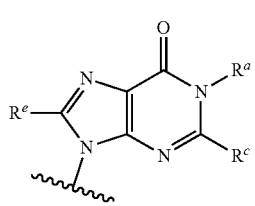

a10 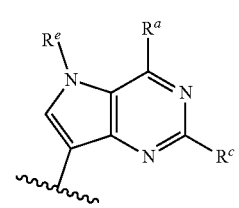

a11 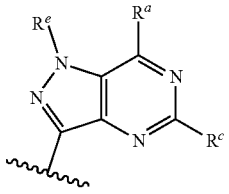

a12 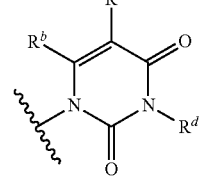

a13 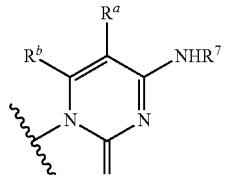

a14 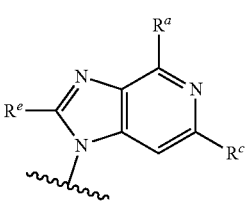

a15 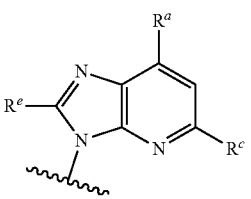

a16 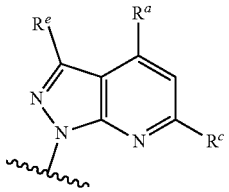

a17 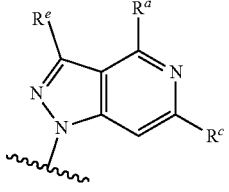

wherein the wavy line indicates the point of attachment to the remainder of the compound, and wherein:

$R^a$ is selected from the group consisting of H, $NH_2$, $NHR^7$, $NHC(O)R^7$, $NR^7R^7$, $R^7$, OH, $SR^7$ and $OR^7$;

$R^b$ is selected from the group consisting of H, halogen, $NH_2$, $NHR^7$, $NR^7R^7$, $R^7$, OH, and $OR^7$;

$R^c$ and $R^d$ are independently selected from the group consisting of H, halogen, haloalkyl, $NH_2$, $NHR^7$, $NR^7R^7$, $R^7$, OH, $OR^7$, $SR^7$, $SO_2R^7$, —$X^1$—$NH_2$, —$X^1$—$NHR^7$, —$X^1$—$NR^7R^7$, —$X^1$—OH, —$X^1$—$OR^7$, —$X^1$—$SR^7$ and —$X^1$—$SO_2R^7$;

$R^e$ and $R^f$ are independently selected from the group consisting of H, halogen, and optionally substituted $C_1$-$C_6$ alkyl;

each $X^1$ is $C_1$-$C_4$alkylene; and each $R^7$ is independently selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_7$ cycloalkyl, optionally substituted $C_3$-$C_7$ cycloalkyl$C_1$-$C_4$alkyl, optionally substituted 4-7 membered cycloheteroalkyl, optionally substituted 4-7 membered cycloheteroalkyl$C_1$-$C_4$alkyl, optionally substituted aryl, optionally substituted aryl$C_1$-$C_4$alkyl, optionally substituted aryl$C_2$-$C_4$alkenyl, optionally substituted aryl$C_2$-$C_4$alkynyl, optionally substituted heteroaryl, optionally substituted heteroaryl$C_1$-$C_4$alkyl, optionally substituted heteroaryl$C_2$-$C_4$alkenyl, and optionally substituted heteroaryl$C_2$-$C_4$alkynyl; or when two $R^7$ groups are attached to the same nitrogen atom, they are optionally joined together to form a 4- to 7-membered heterocyclic ring which is optionally fused to an aryl ring.

In some embodiments, the present invention contemplates methods for treating or preventing cancer in a subject (e.g., a human) comprising administering to the subject a therapeutically effective amount of at least one CD73 inhibitor described herein. The present invention includes methods of treating or preventing a cancer in a subject by administering to the subject a CD73 inhibitor in an amount effective to reverse or stop the progression of CD73-mediated immunosuppression. In some embodiments, the CD73-mediated immunosuppression is mediated by an antigen-presenting cell (APC).

Examples of the cancers that can be treated using the compounds and compositions described herein include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In some embodiments of the present invention, the cancer is melanoma, colon cancer, pancreatic cancer, breast cancer, prostate cancer, lung cancer, leukemia, a brain tumor, lymphoma, sarcoma, ovarian cancer, or Kaposi's sarcoma. Cancers that are candidates for treatment with the compounds and compositions of the present invention are discussed further hereafter.

The present invention contemplates methods of treating a subject receiving a bone marrow transplant or peripheral blood stem cell transplant by administering a therapeutically effective amount of an CD73 inhibitor sufficient to increase the delayed-type hypersensitivity reaction to tumor antigen, delay the time-to-relapse of post-transplant malignancy, increase relapse-free survival time post-transplant, and/or increase long-term post-transplant survival.

In certain embodiments, the present invention contemplates methods for treating or preventing an infective disorder (e.g., a viral infection) in a subject (e.g., a human) comprising administering to the subject a therapeutically effective amount of at least one CD73 inhibitor (e.g., a novel inhibitor of the instant invention). In some embodiments, the infective disorder is a viral infection (e.g., a chronic viral infection), a bacterial infection, a fungal infection, or a parasitic infection. In certain embodiments, the viral infection is human immunodeficiency virus or cytomegalovirus.

In still other embodiments, the present invention contemplates methods for treating and/or preventing immune-related diseases, disorders and conditions; diseases having an inflammatory component; as well as disorders associated with the foregoing; with at least one CD73 inhibitor of the instant invention. Examples of immune-related diseases, disorders and conditions are described hereafter.

Other diseases, disorders and conditions that can be treated or prevented, in whole or in part, by modulation of CD73 activity are candidate indications for the CD73 inhibitor compounds of the present invention.

The present invention further contemplates the use of the CD73 inhibitors described herein in combination with one or more additional agents. The one or more additional agents may have some CD73-modulating activity and/or they may function through distinct mechanisms of action. In some embodiments, such agents comprise radiation (e.g., localized radiation therapy or total body radiation therapy) and/or other treatment modalities of a non-pharmacological nature. When combination therapy is utilized, the CD73 inhibitor(s) and the one additional agent(s) may be in the form of a single composition or multiple compositions, and the treatment modalities can be administered concurrently, sequentially, or through some other regimen. By way of example, the present invention contemplates a treatment regimen wherein a radiation phase is followed by a chemotherapeutic phase. The combination therapy can have an additive or synergistic effect. Other benefits of combination therapy are described hereafter.

In some embodiments, the present invention further comprises the use of the CD73 inhibitors described herein in combination with bone marrow transplantation, peripheral blood stem cell transplantation, or other types of transplantation therapy.

In particular embodiments, the present invention contemplates the use of the inhibitors of CD73 function described herein in combination with immune checkpoint inhibitors. The blockade of immune checkpoints, which results in the amplification of antigen-specific T cell responses, has been shown to be a promising approach in human cancer therapeutics. Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); A2aR (adenosine A2a receptor A2aR); and Killer Inhibitory Receptors. Immune checkpoint inhibitors, and combination therapy therewith, are discussed in detail elsewhere herein.

In other embodiments, the present invention provides methods for treating cancer in a subject, comprising administering to the subject a therapeutically effective amount of at least one CD73 inhibitor and at least one chemotherapeutic agent, such agents including, but not limited to alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). The present invention also contemplates the use of the CD73 inhibitors in combination with other agents known in the art (e.g., arsenic trioxide) and other chemotherapeutic agents that may be developed in the future.

In some embodiments drawn to methods of treating cancer, the administration of a therapeutically effective amount of an CD73 inhibitor in combination with at least one chemotherapeutic agent results in a cancer survival rate greater than the cancer survival rate observed by administering either agent alone. In further embodiments drawn to methods of treating cancer, the administration of a therapeutically effective amount of an CD73 inhibitor in combination with at least one chemotherapeutic agent results in a reduction of tumor size or a slowing of tumor growth greater than reduction of the tumor size or tumor growth observed by administration of either agent alone.

In further embodiments, the present invention contemplates methods for treating or preventing cancer in a subject, comprising administering to the subject a therapeutically effective amount of at least one CD73 inhibitor and at least one signal transduction inhibitor (STI). In a particular embodiment, the at least one STI is selected from the group consisting of bcr/abl kinase inhibitors, epidermal growth factor (EGF) receptor inhibitors, her-2/neu receptor inhibitors, and farnesyl transferase inhibitors (FTIs). Other candidate STI agents are set forth elsewhere herein.

The present invention also contemplates methods of augmenting the rejection of tumor cells in a subject comprising administering an CD73 inhibitor in conjunction with at least one chemotherapeutic agent and/or radiation therapy, wherein the resulting rejection of tumor cells is greater than that obtained by administering either the CD73 inhibitor, the chemotherapeutic agent or the radiation therapy alone.

In further embodiments, the present invention provides methods for treating cancer in a subject, comprising administering to the subject a therapeutically effective amount of at least one CD73 inhibitor and at least one immunomodulator other than an CD73 inhibitor.

The present invention contemplates embodiments comprising methods for treating or preventing an infective disorder (e.g., a viral infection) in a subject (e.g., a human) comprising administering to the subject a therapeutically effective amount of at least one CD73 inhibitor and a therapeutically effective amount of an anti-infective agent(s), such as one or more antimicrobial agents.

In additional embodiments, treatment of an infective disorder is effected through the co-administration of a vaccine in combination with administration of a therapeutically effective amount of an CD73 inhibitor of the present invention. In some embodiments, the vaccine is an anti-viral vaccine, including, for example, an anti-HIV vaccine. In other embodiments, the vaccine is effective against tuberculosis or malaria. In still other embodiments, the vaccine is a tumor vaccine (e.g., a vaccine effective against melanoma); the tumor vaccine can comprise genetically modified tumor cells or a genetically modified cell line, including genetically modified tumor cells or a genetically modified cell line that has been transfected to express granulocyte-macrophage stimulating factor (GM-CSF). In particular embodiments, the vaccine includes one or more immunogenic peptides and/or dendritic cells.

In certain embodiments drawn to treatment of an infection by administering an CD73 inhibitor and at least one additional therapeutic agent, a symptom of infection observed after administering both the CD73 inhibitor and the additional therapeutic agent is improved over the same symptom of infection observed after administering either alone. In some embodiments, the symptom of infection observed can be reduction in viral load, increase in $CD4^+$ T cell count, decrease in opportunistic infections, increased survival time, eradication of chronic infection, or a combination thereof.

DETAILED DESCRIPTION OF THE INVENTION

Figure 1:
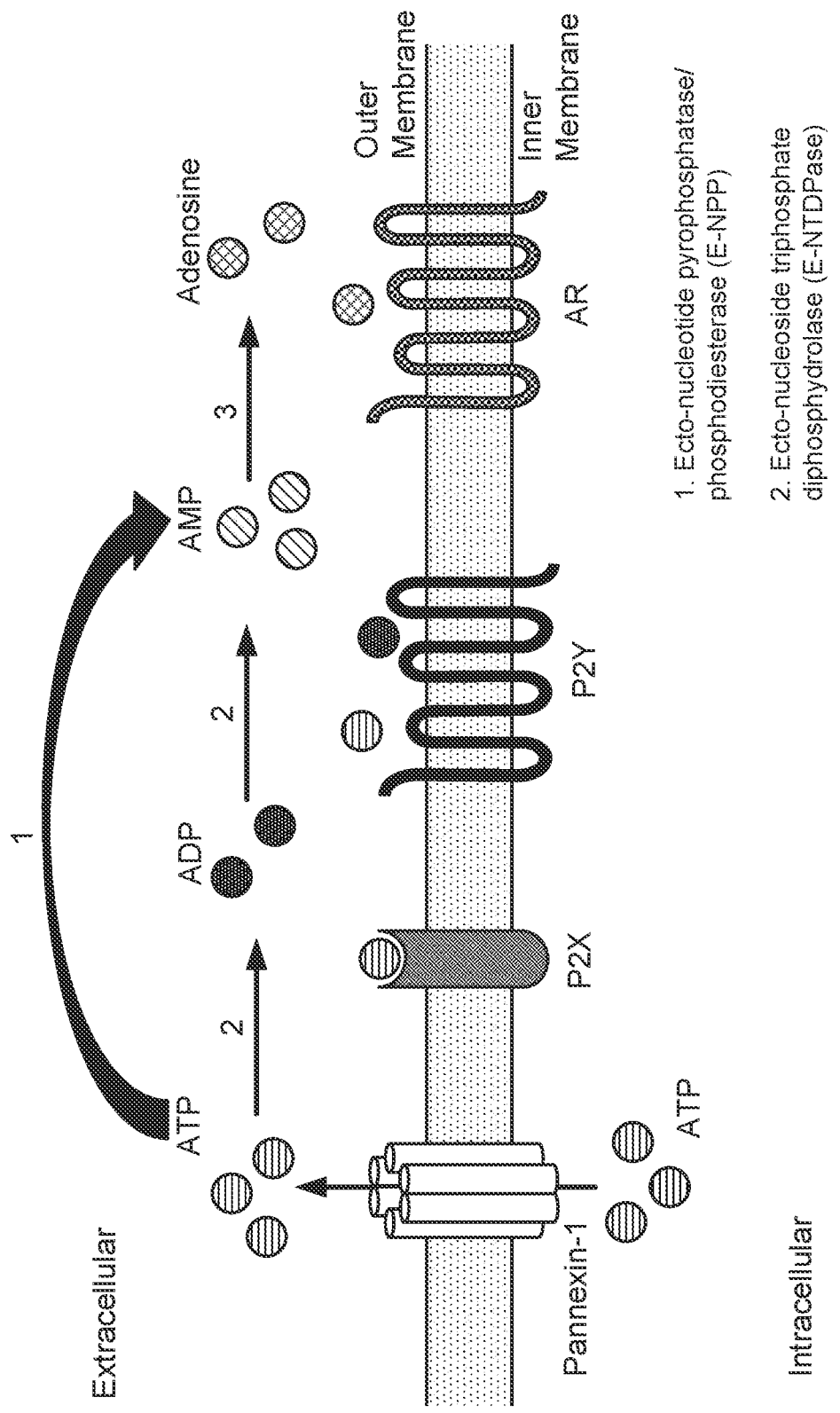
FIG. 1 depicts a simplified representation of extracellular purinergic signaling.
Figure 2B:
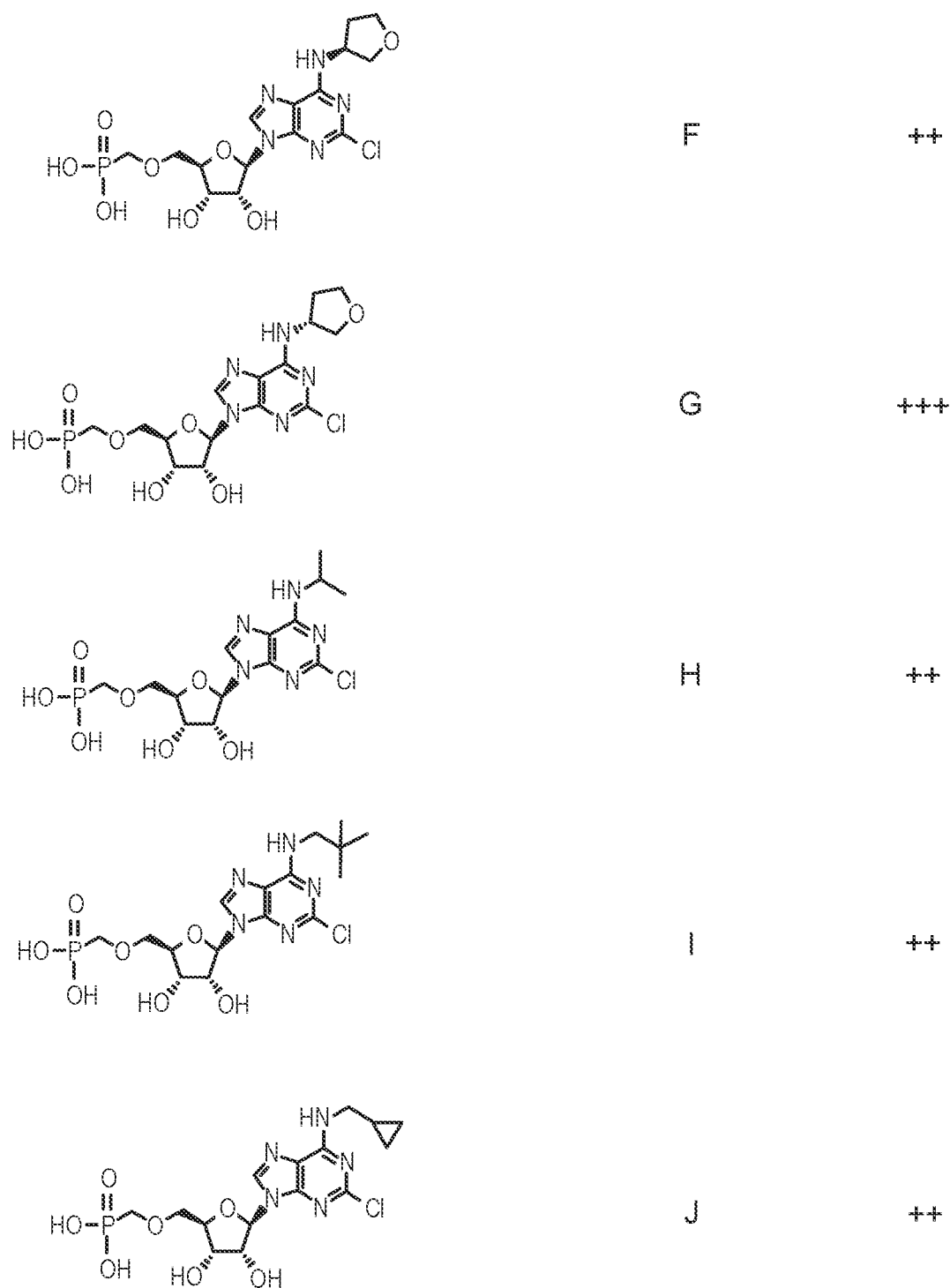
FIG. 2A-2AB depicts particular embodiments of Formula (I) and activity levels as described herein.
Figure 2C:
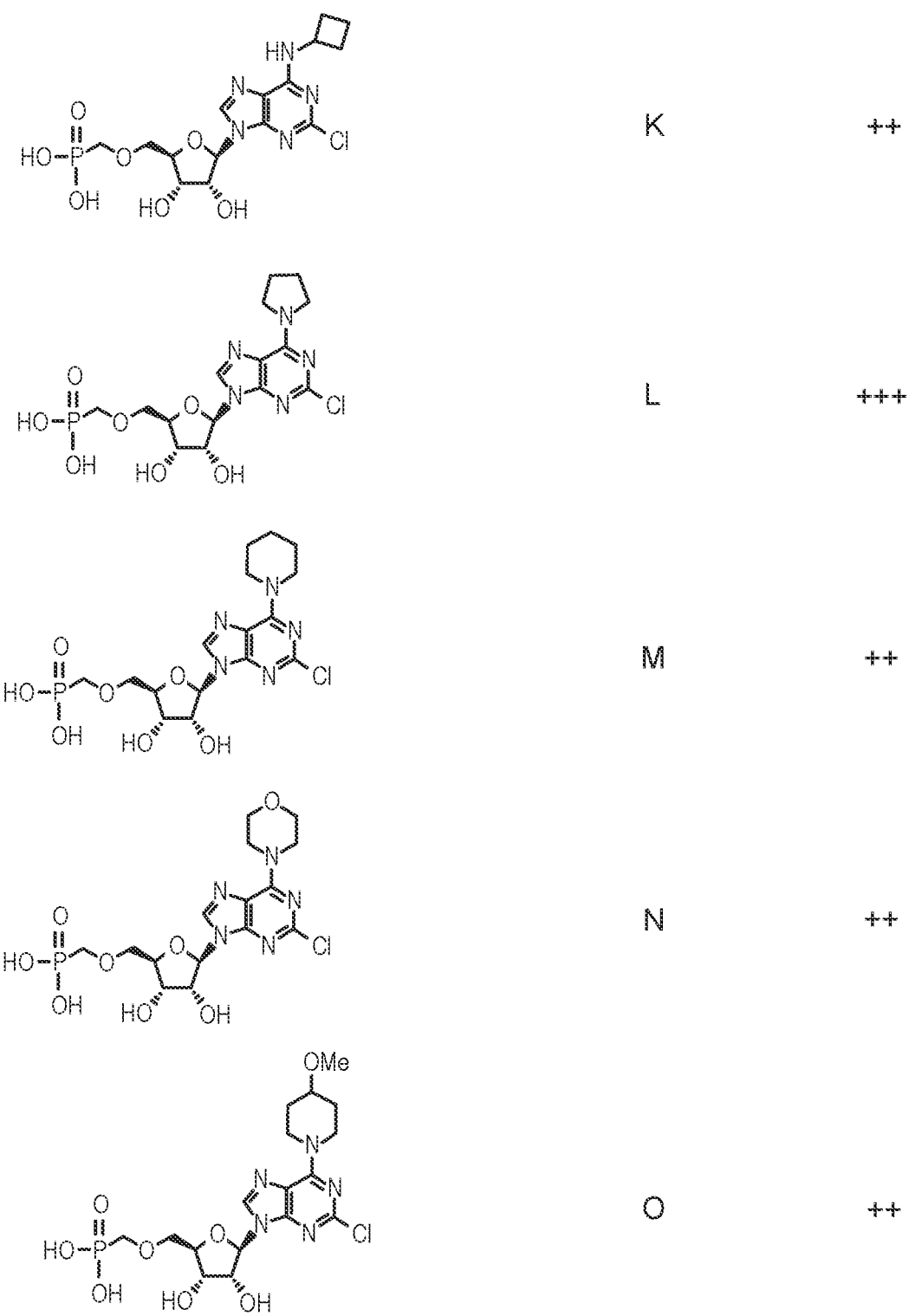
Figure 2D:
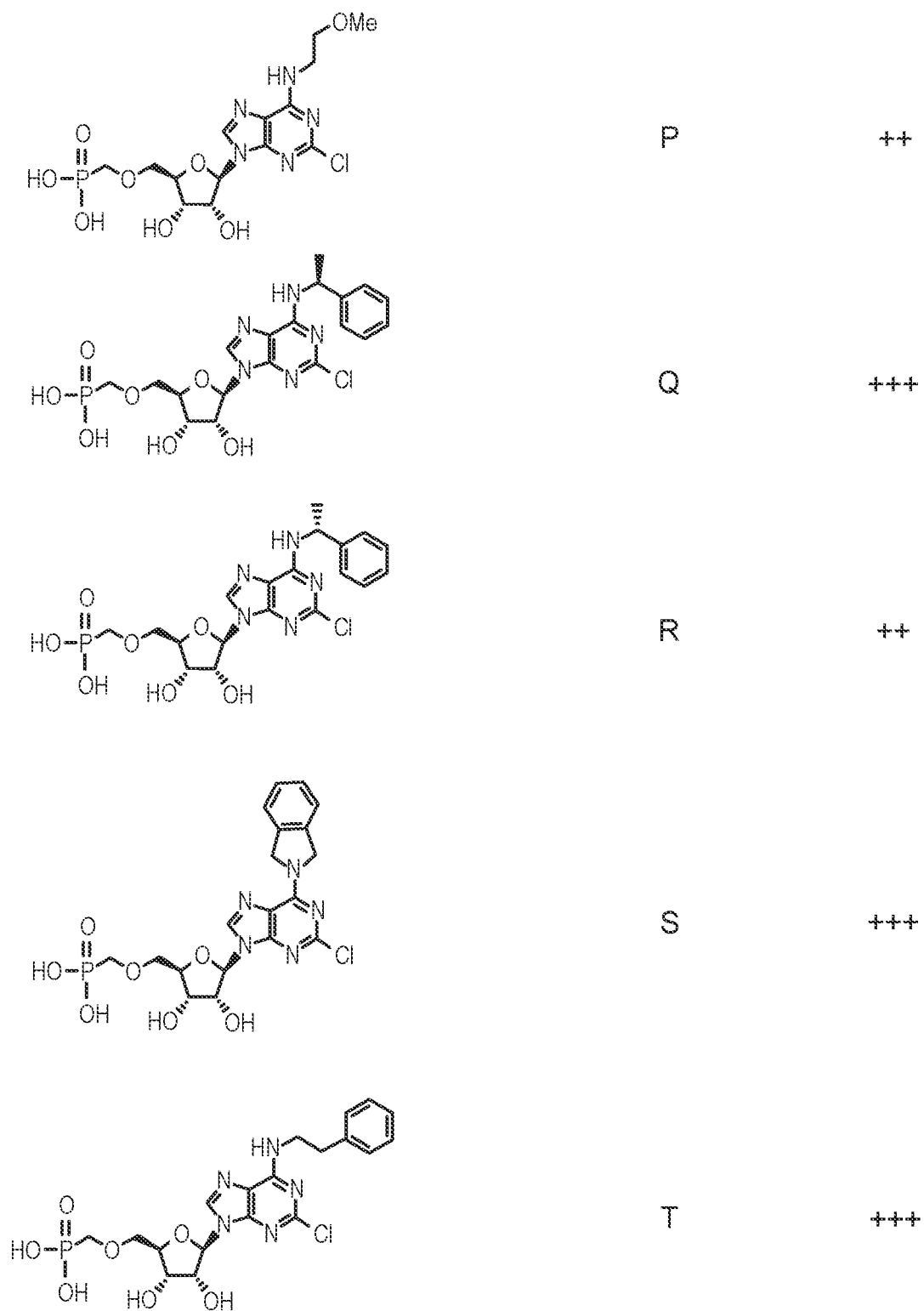
Figure 2E:
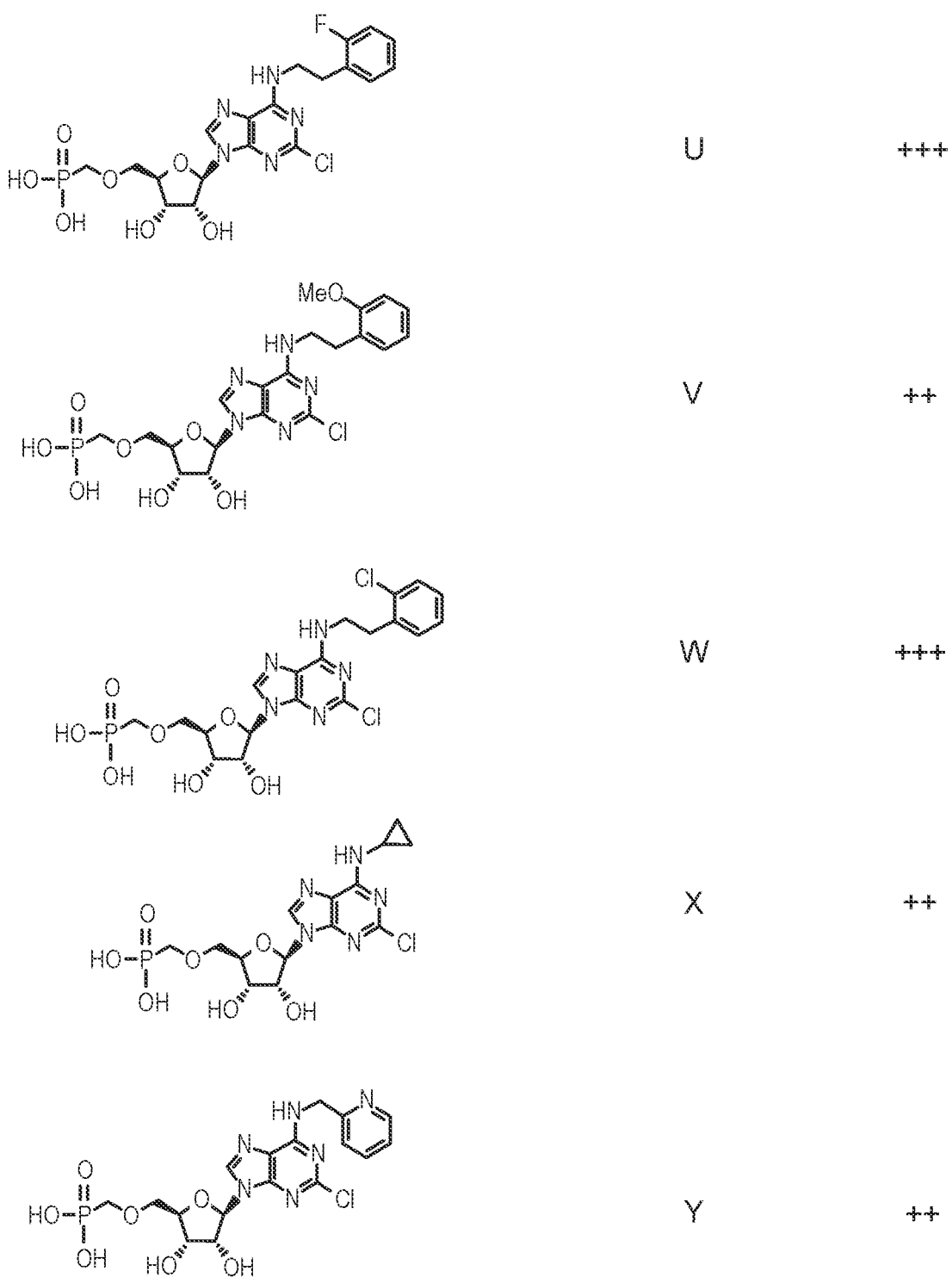
Figure 2G:
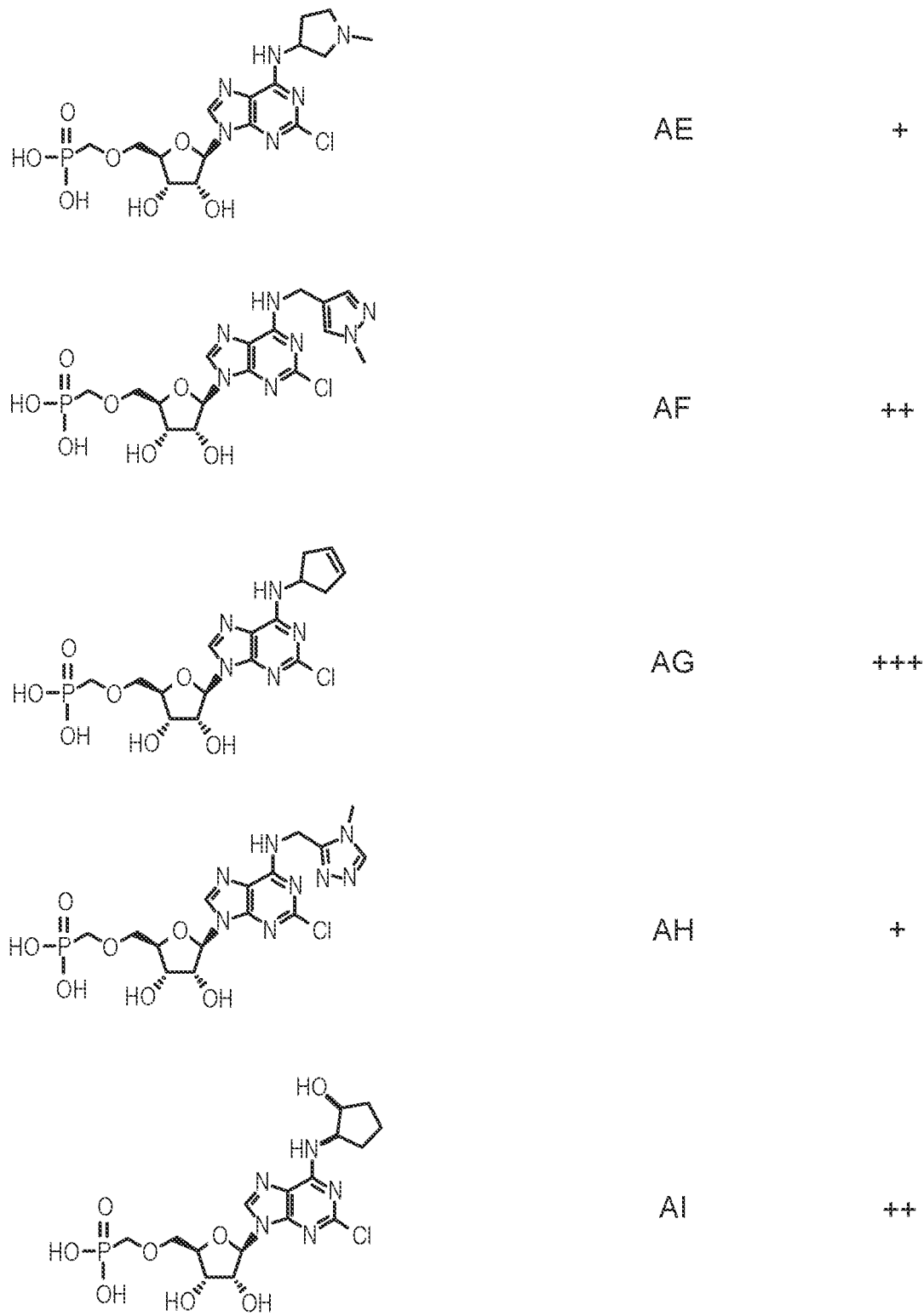
Figure 2H:
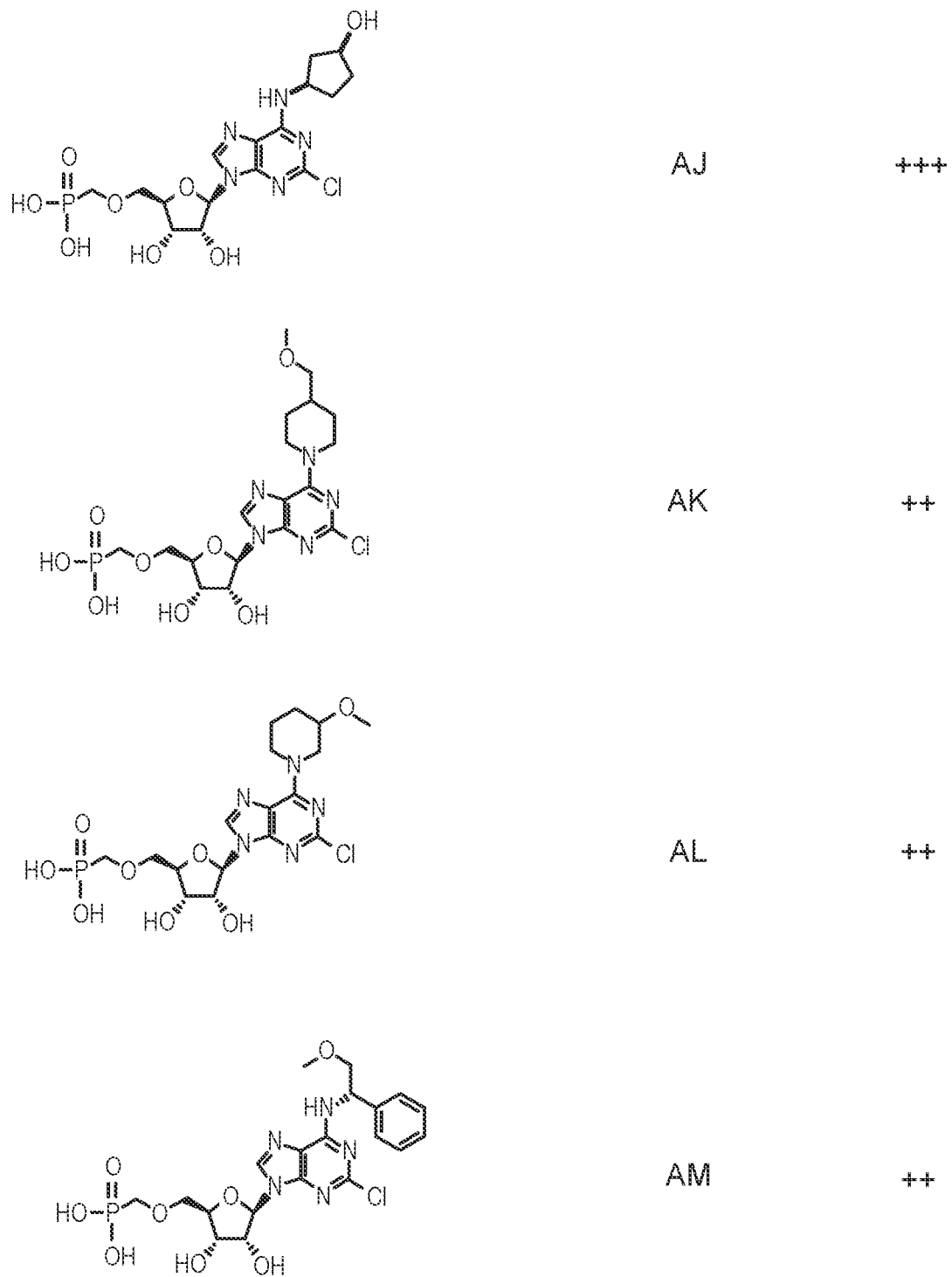
Figure 2I:
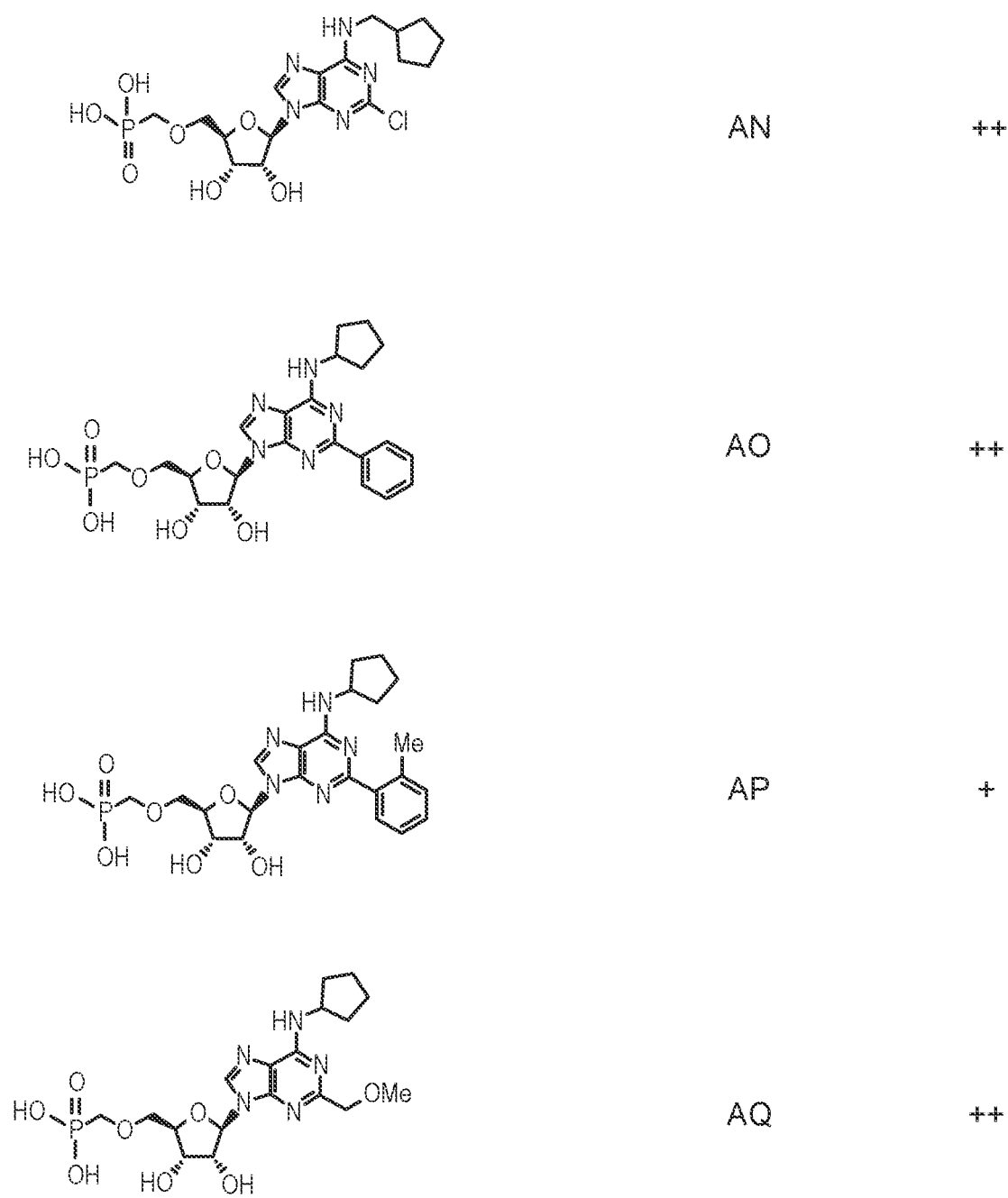
Figure 2J:
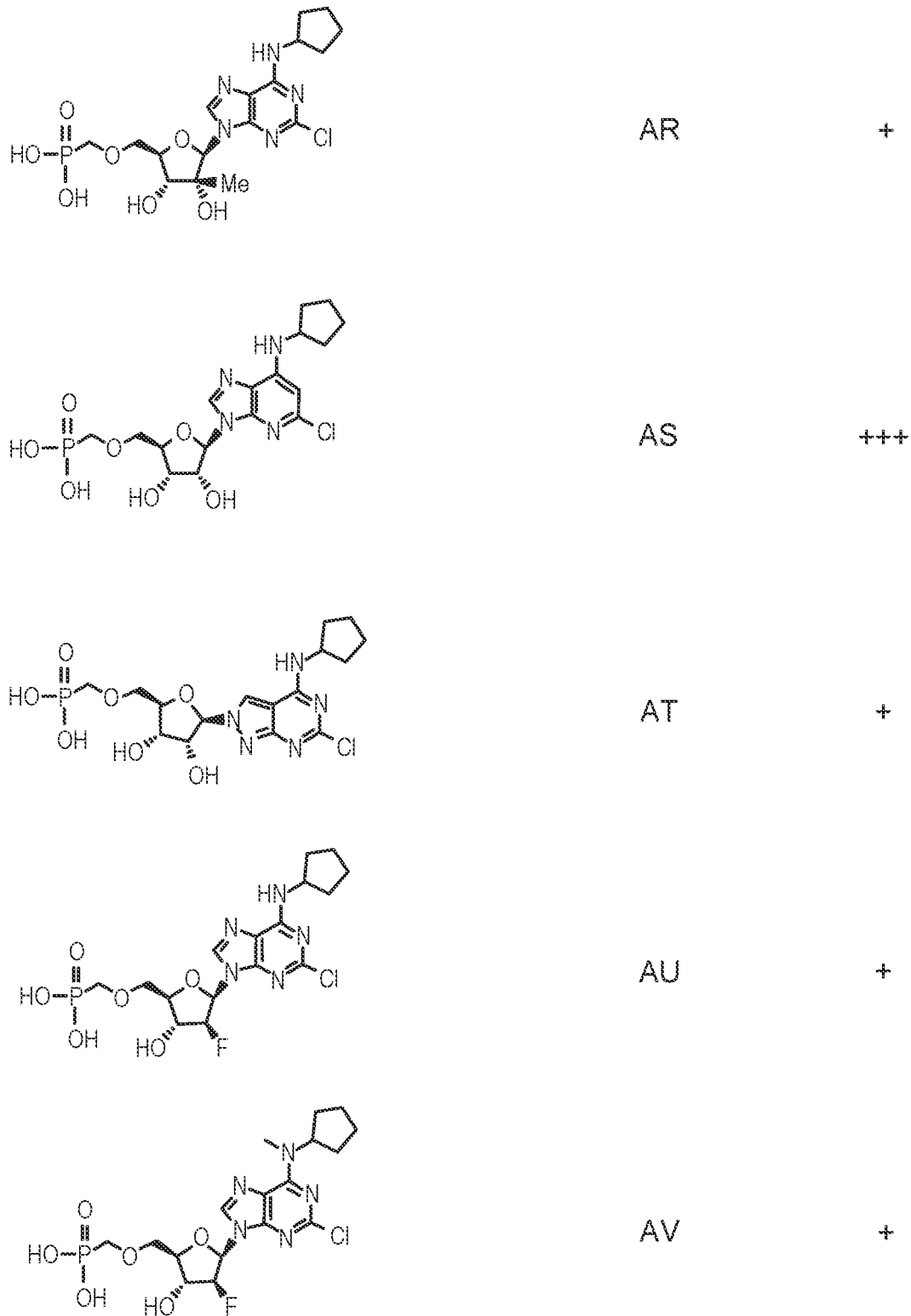
Figure 2K:
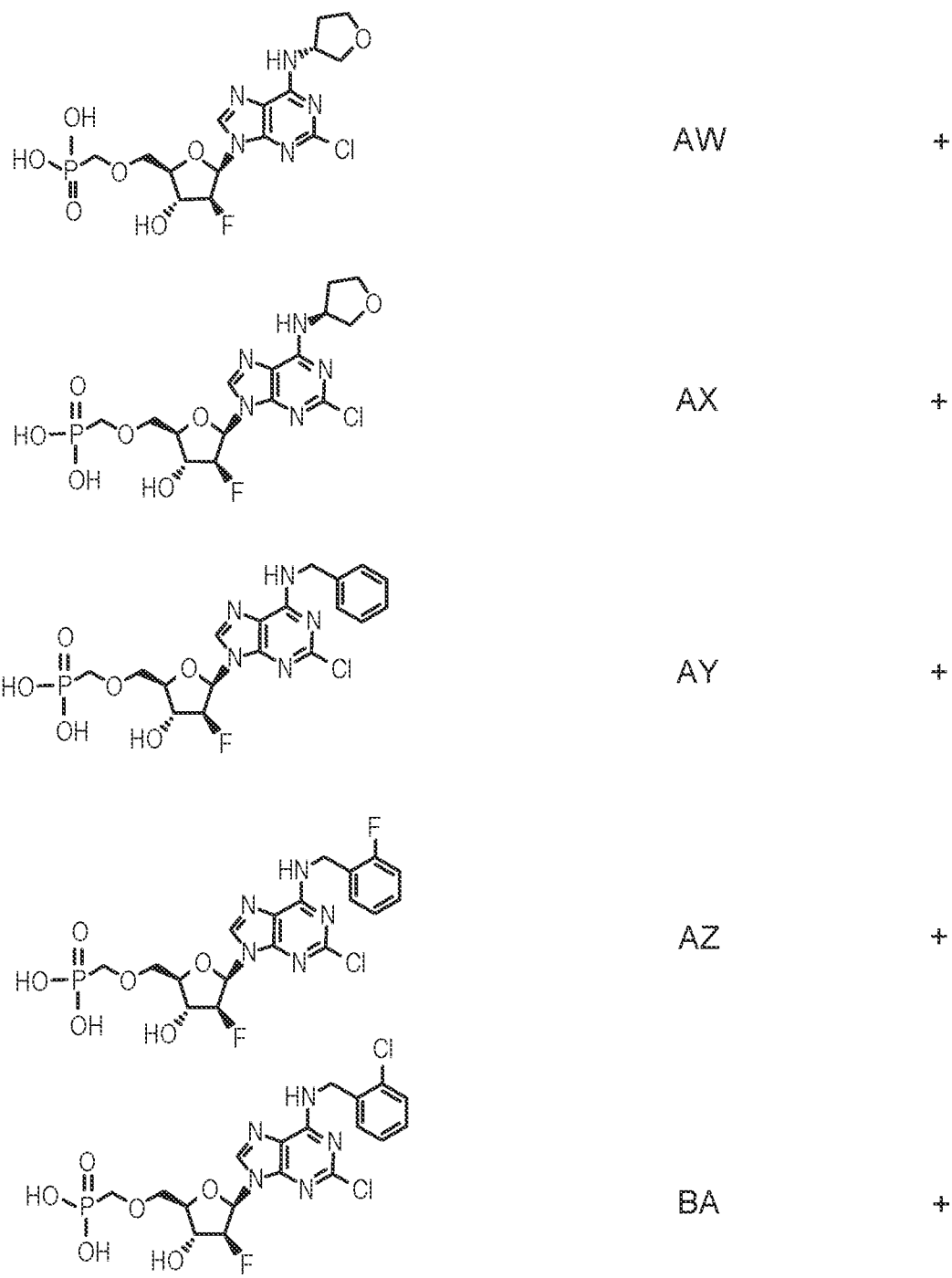
Figure 2L:
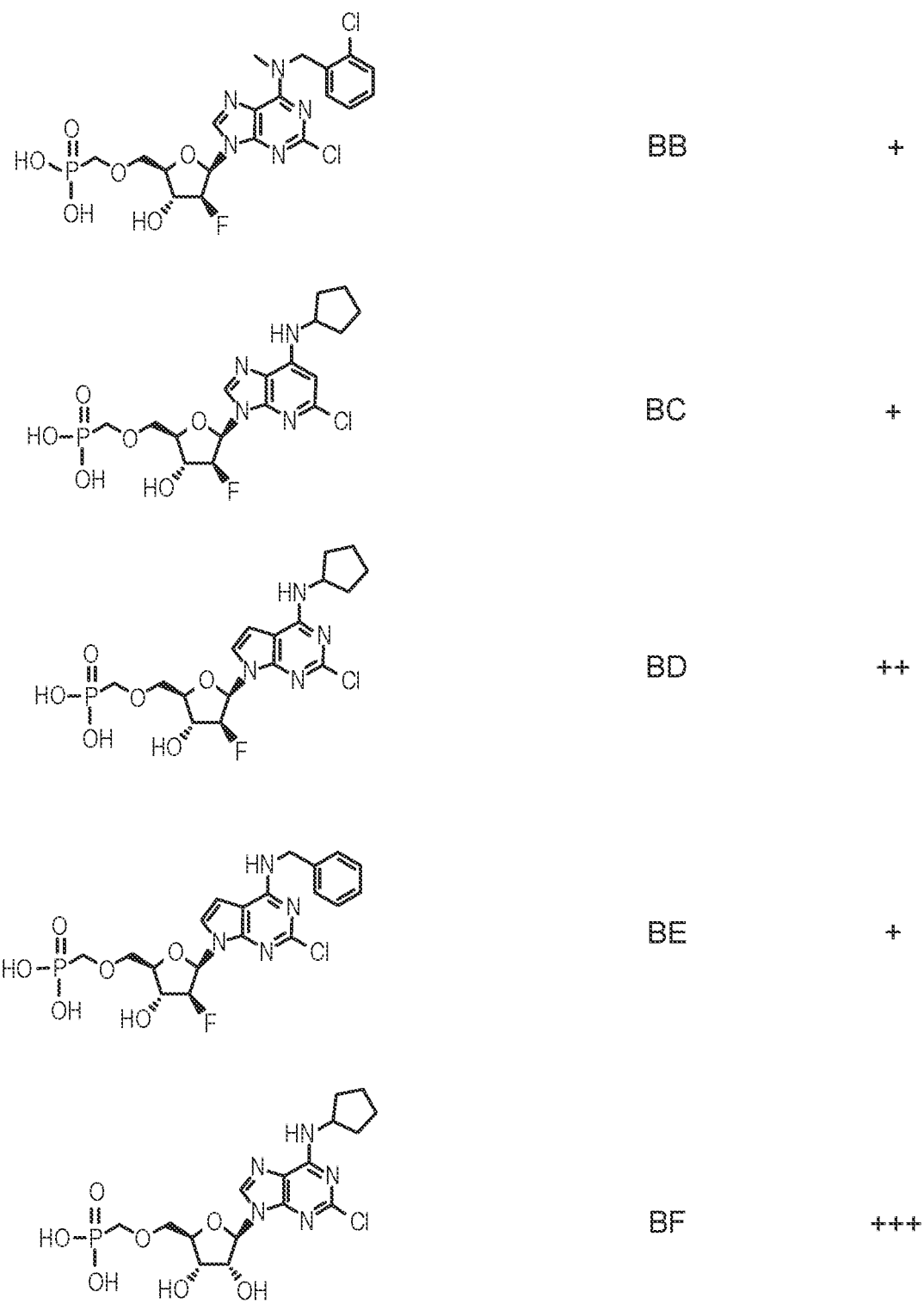
Figure 2N:
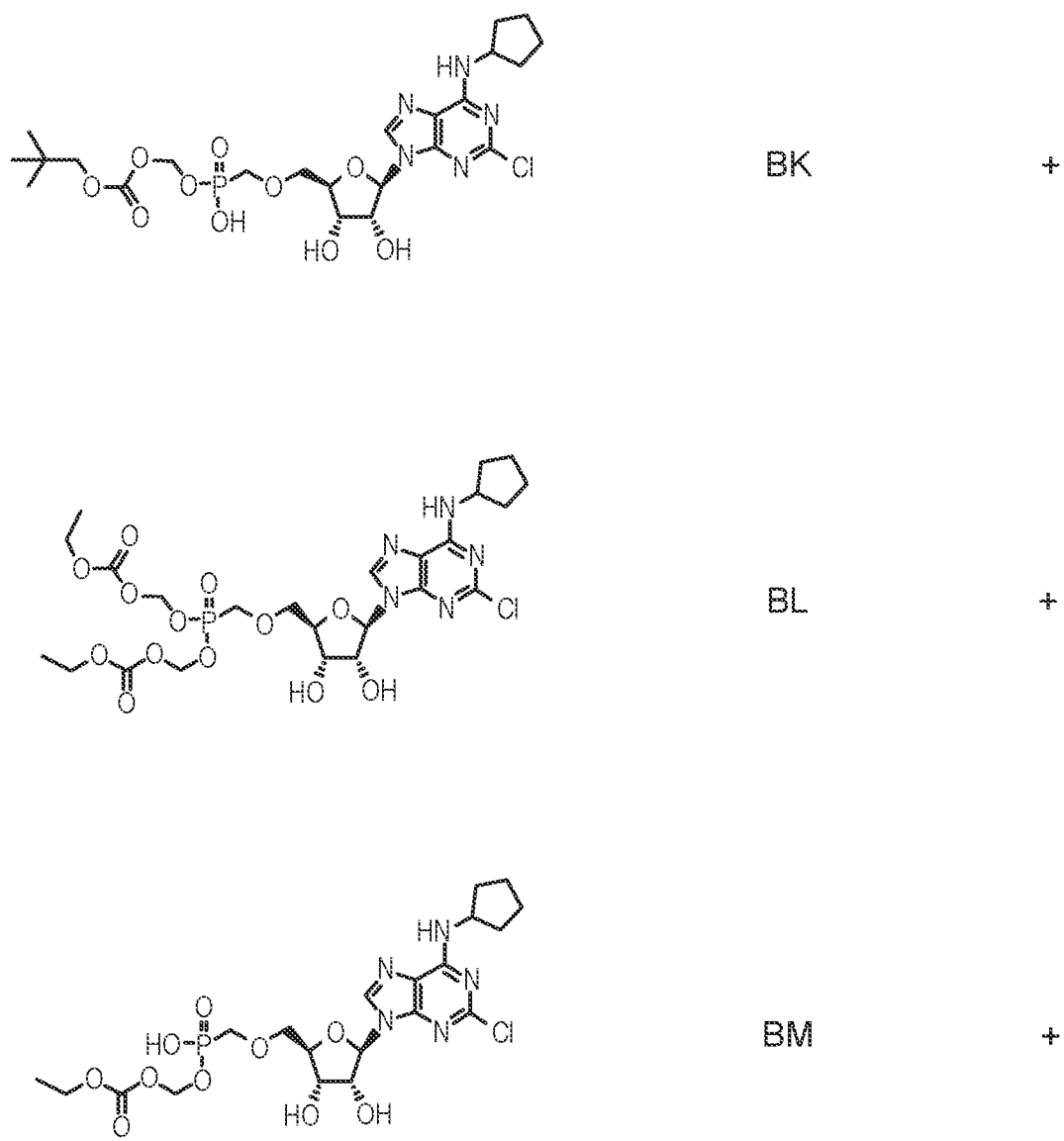
Figure 2P:
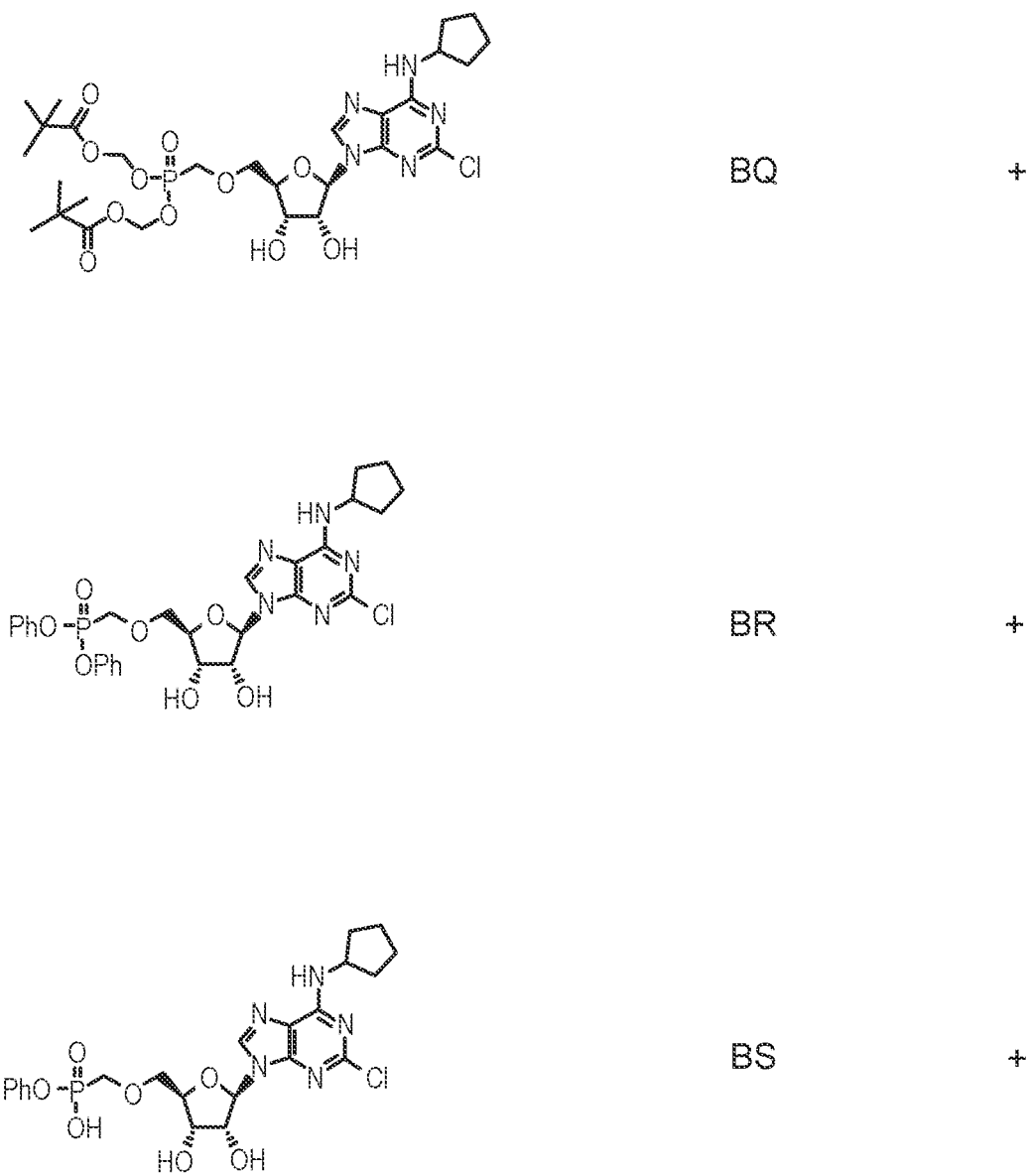
Figure 2Q:
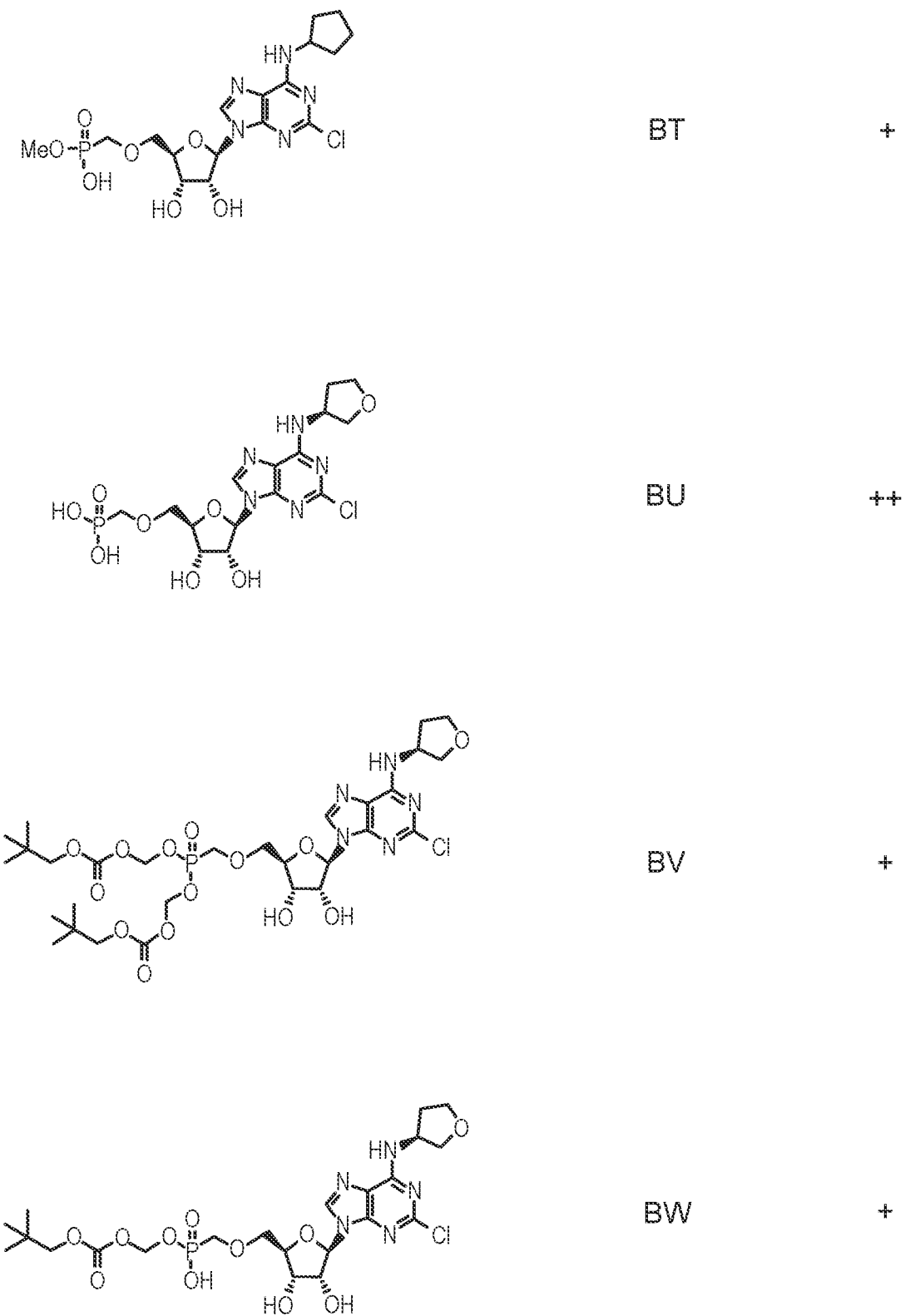
Figure 2R:
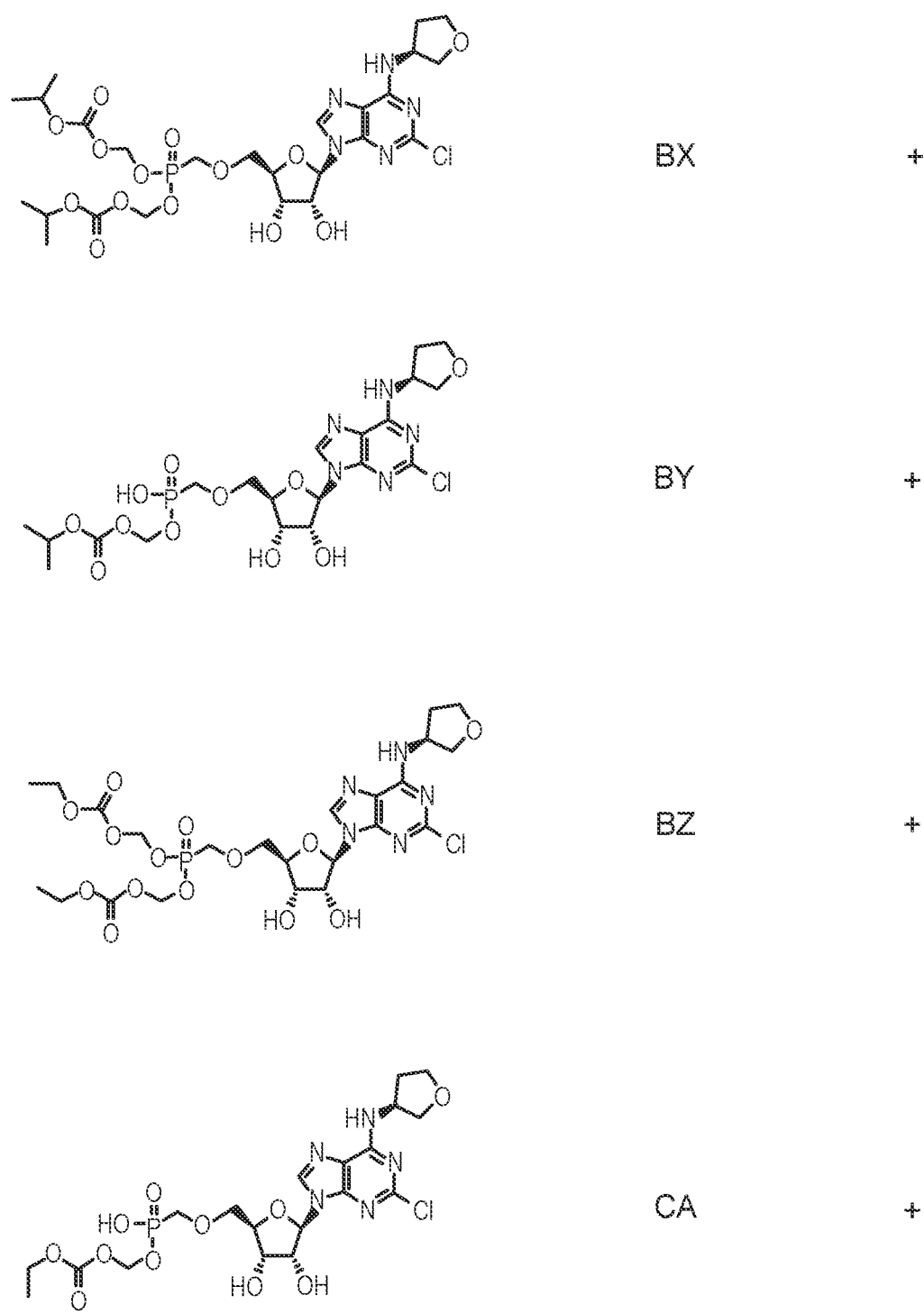
Figure 2S:
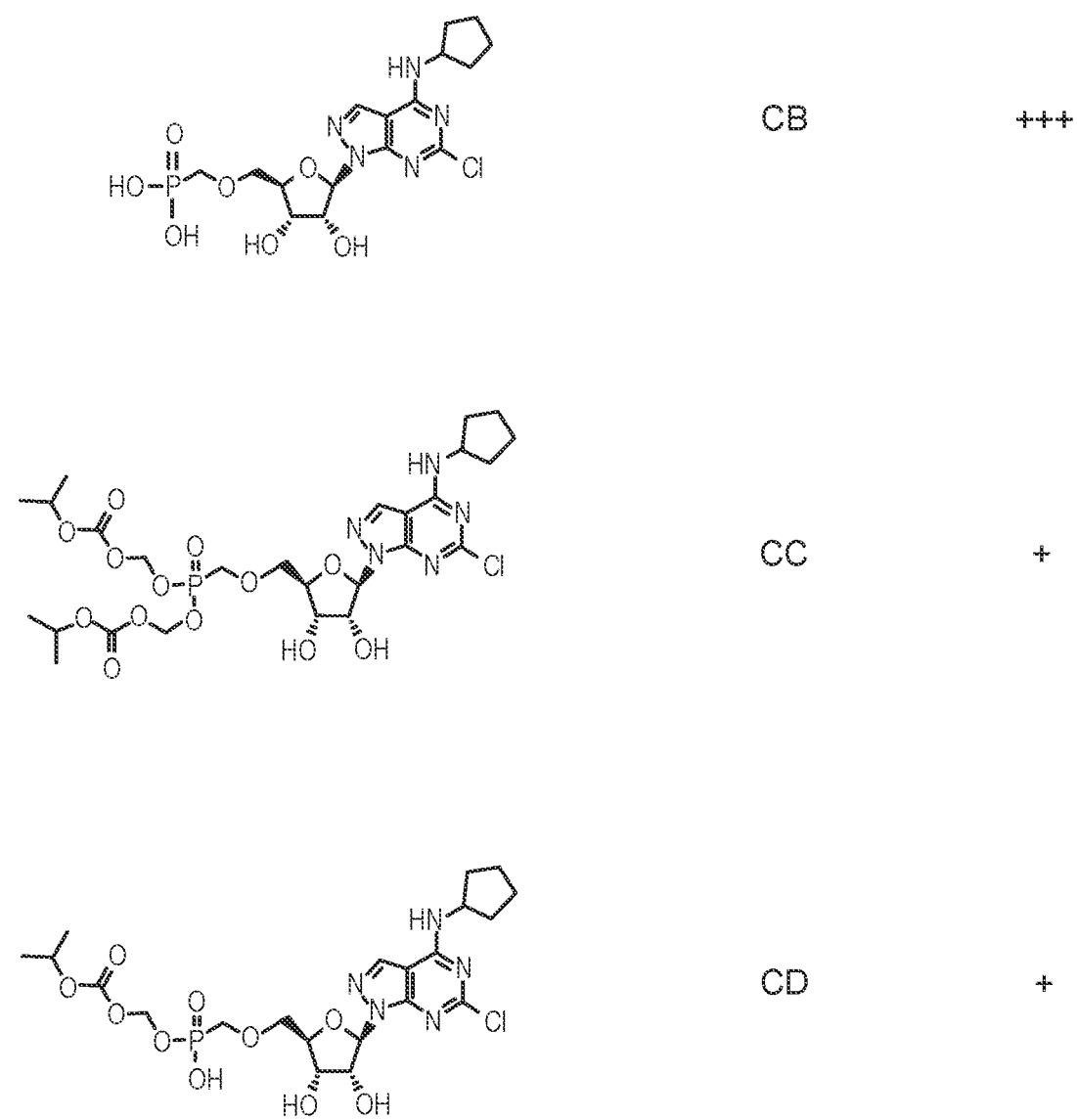
Figure 2T:
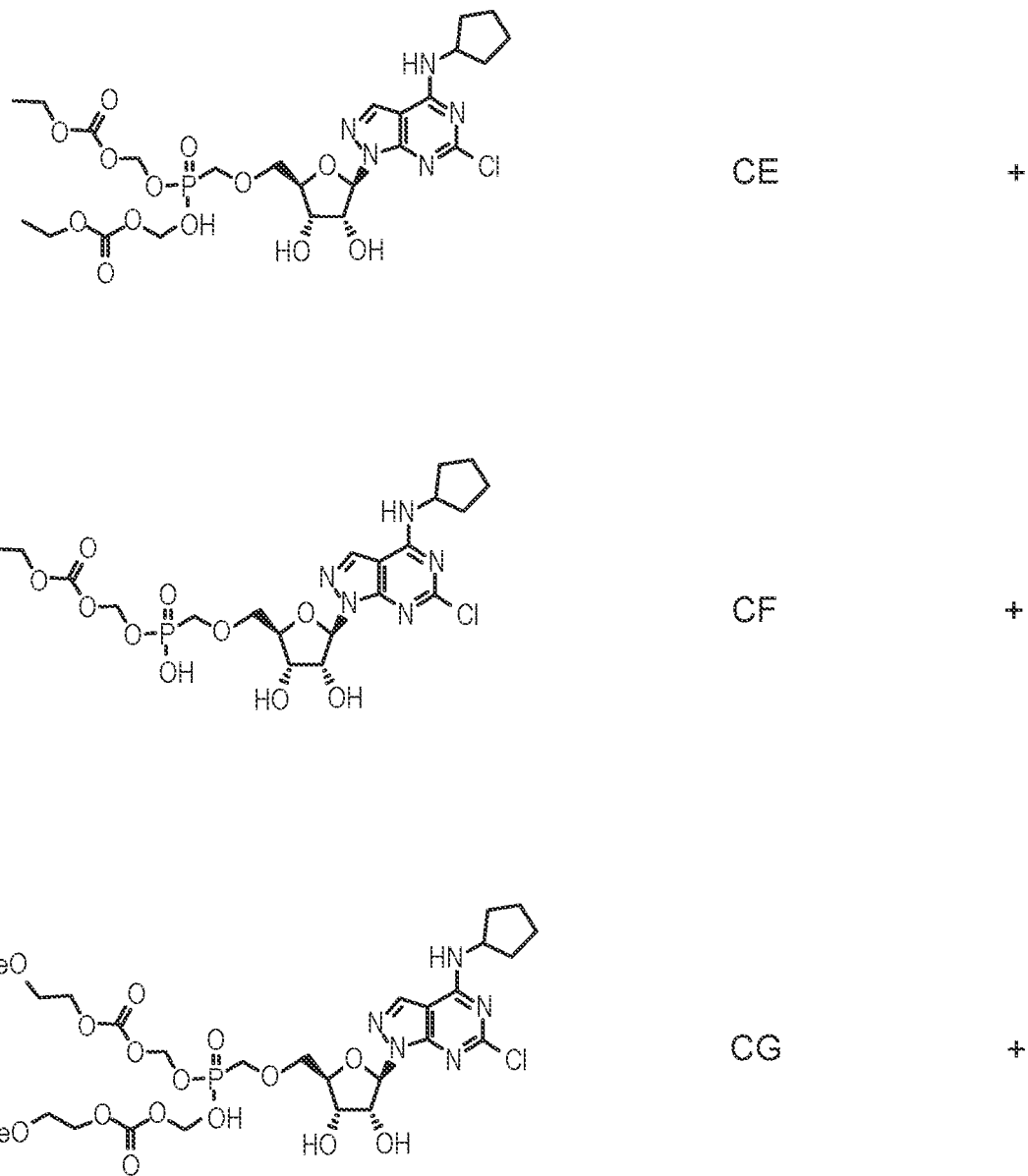
Figure 2U:
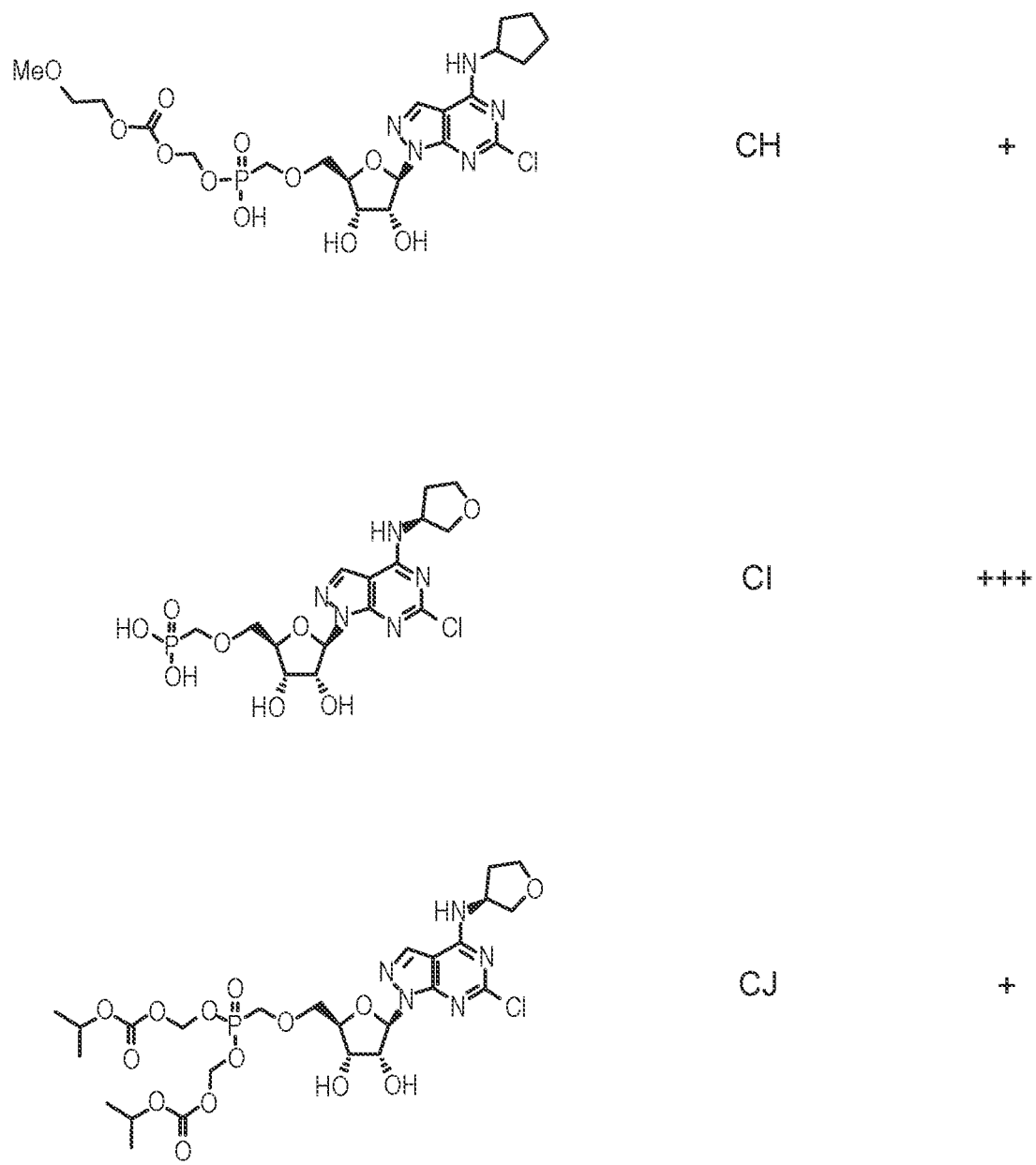
Figure 2V:
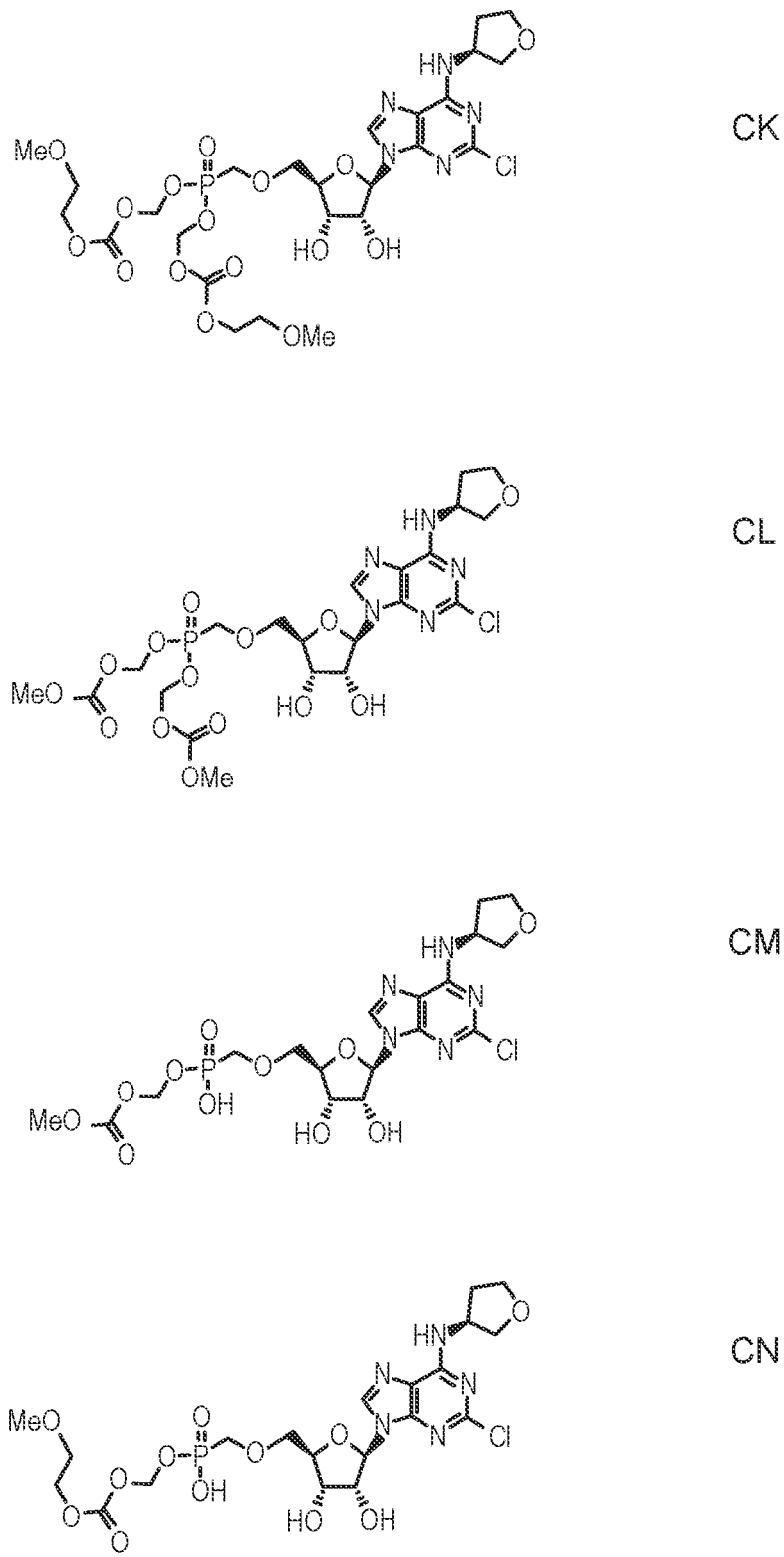
Figure 2Y:
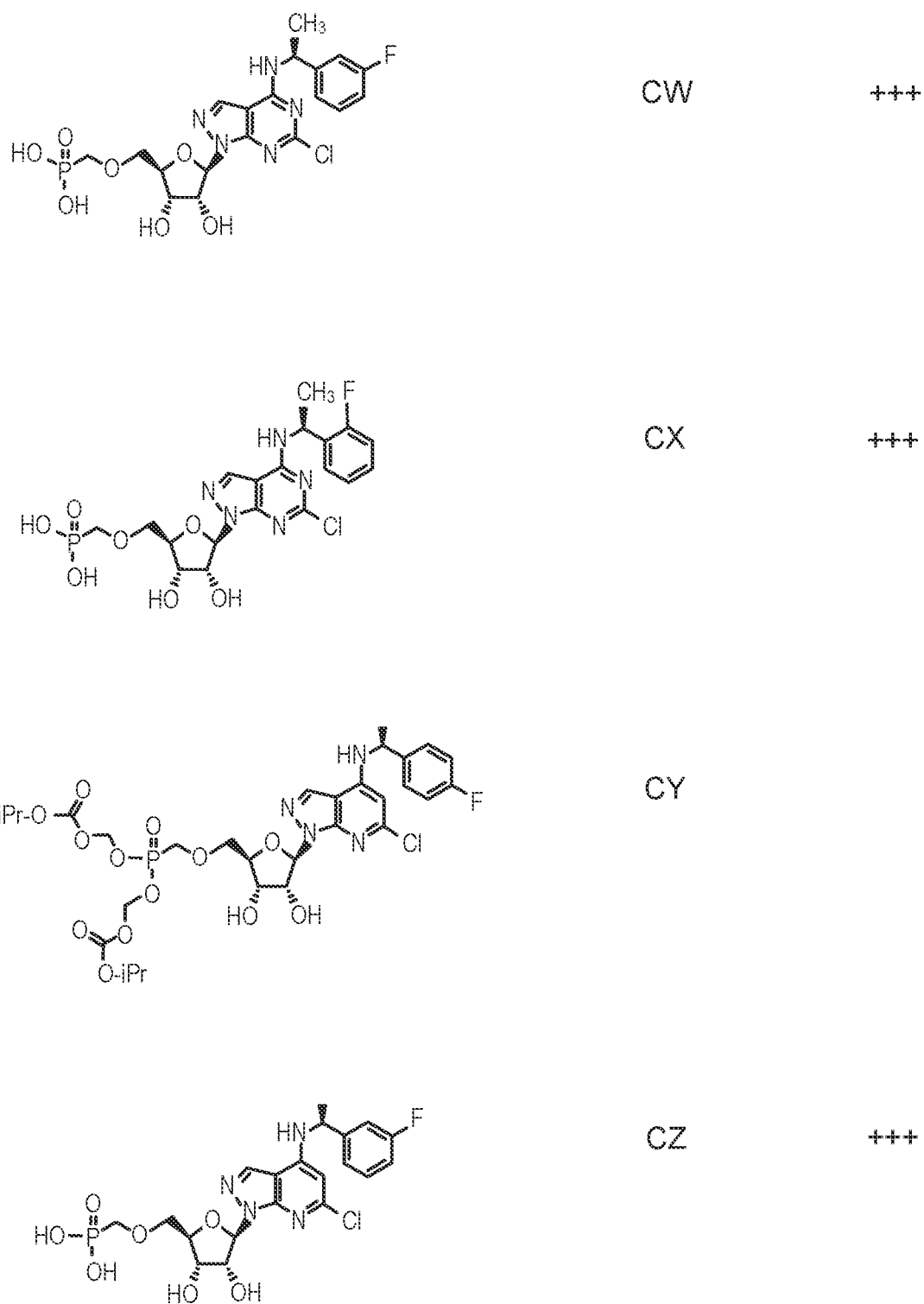

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

The number of subjects diagnosed with cancer and the number of deaths attributable to cancer continue to rise. Traditional treatment approaches comprising chemotherapy and radiotherapy are generally difficult for the patient to tolerate and become less effective as cancers (e.g., tumors) evolve to circumvent such treatments. Recent experimental evidence indicates that CD73 inhibitors may represent an important new treatment modality for cancer (e.g., breast cancer) treatment.

Promising data also support the role of inhibitors of CD73 function to inhibit the anti-inflammatory activity of CD73 and/or the immunosuppressive activity of CD73, and thus CD73 inhibitors may be useful to treat, for example, immunosuppressive diseases (e.g., HIV and AIDs). Inhibition of CD73 may also be an important treatment strategy for patients with neurological or neuropsychiatric diseases or disorders such as depression.

The present invention is drawn to, inter alia, small molecule compounds having CD73 inhibitory activity, as well as compositions thereof, and methods of using the compounds and compositions for the treatment and prevention of the diseases, disorders and conditions described herein.

Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "cycloheteroalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The cycloheteroalkyl may be a monocyclic, a bicyclic or a polycylic ring system. Non limiting examples of cycloheteroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A cycloheteroalkyl group can be attached to the remainder of the molecule through a ring carbon or a heteroatom.

As used herein, a wavy line, "$\sim$", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse). For example, the group "—C(O)NH—" is meant to include a linkage in either orientation: —C(O)NH— or —NHC(O)—, and similarly, "—O—$CH_2CH_2$—" is meant to include both —O—$CH_2CH_2$— and —$CH_2CH_2$—O—.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —$NR^aR^b$ is meant to include piperidinyl, pyrrolidinyl, morpholinyl, azetidinyl and the like.

The terms "arylalkyl" and "heteroarylalkyl" are used in their conventional sense, and refer to those groups wherein an aryl group or a heteroaryl group is attached remainder of the molecule via $C_1$-$C_4$ alkylene linker. An exemplary embodiment of "arylalkyl" is phenylmethyl (or benzyl). Similarly, an exemplary embodiment of "heteroarylalkyl" is, for example, 3-pyridylpropyl. When 'optionally substituted' is used to describe either of the terms "arylalkyl" or "heteroarylalkyl", it is meant to refer to those groups wherein the aryl or heteroaryl portion is optionally substituted as in the definitions below, and the alkyl portion is optionally substituted as in the definitions below The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for a heteroaryl ring can be selected from the group of acceptable substituents described below.

The above terms (e.g., "alkyl," "aryl" and "heteroaryl"), in some embodiments, will be optionally substituted. Selected substituents for each type of radical are provided below.

Optional substituents for the alkyl radicals (including those groups often referred to as alkylene, alkenyl, alkynyl and cycloalkyl) can be a variety of groups selected from: halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R'" each independently refer to hydrogen, unsubstituted $C_{1-8}$ alkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, optional substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention. In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are described in more detail elsewhere herein.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of CD73, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of CD73 or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an CD73 inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an CD73 inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The term "ligand" refers to, for example, a peptide, a polypeptide, a membrane-associated or membrane-bound molecule, or a complex thereof, that can act as an agonist or antagonist of a receptor. A ligand encompasses natural and synthetic ligands, e.g., cytokines, cytokine variants, analogs, muteins, and binding compositions derived from antibodies, as well as small molecules. The term also encompasses an agent that is neither an agonist nor antagonist, but that can bind to a receptor without significantly influencing its biological properties, e.g., signaling or adhesion. Moreover, the term includes a membrane-bound ligand that has been changed by, e.g., chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex."

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of CD73, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

As used herein, the terms "variants" and "homologs" are used interchangeably to refer to amino acid or DNA sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring DNA sequences and proteins encoded thereby and their isoforms, as well as splice variants of a protein or gene. The terms also encompass nucleic acid sequences that vary in one or more bases from a naturally-occurring DNA sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

5'-Nucleotidase, Ecto and Inhibition Thereof

Human CD73 (also referred to as 5'-nucleotidase, ecto; NT5E; or 5NT) is a 574 amino acid residue protein (Accession No. AAH6593). Eukaryotic CD73 functions as a non-covalent homodimer with two structural domains, wherein the N- and C-terminal domains are connected by a hinge region that enables the enzyme to undergo large domain movements and switch between open and closed conformations (Knapp, K. et al. (2012) Structure 20:2161-73).

As used herein, the terms "CD73 inhibitor", "CD73 blocker", "adenosine by 5'-nucleotidase, ecto inhibitor", "NT5E inhibitor", "5NT inhibitor" and all other related art-accepted terms refer to a compound capable of modulating, either directly or indirectly, the CD73 receptor in an in vitro assay, an in vivo model, and/or other means indicative of therapeutic efficacy. The terms also refer to compounds that exhibit at least some therapeutic benefit in a human subject. An CD73 inhibitor may be a competitive, noncompetitive, or irreversible CD73 inhibitor. "A competitive CD73 inhibitor" is a compound that reversibly inhibits CD73 enzyme activity at the catalytic site; "a noncompetitive CD73 inhibitor" is a compound that reversibly inhibits CD73 enzyme activity at a non-catalytic site; and "an irreversible CD73 inhibitor" is a compound that irreversibly eliminates CD73 enzyme activity by forming a covalent bond (or other stable means of inhibiting enzyme function) with the enzyme.

CD73 inhibitors can modulate purinergic signaling, a type of extracellular signaling mediated by purine nucleotides and nucleosides such as ATP and adenosine. Purinergic signaling involves the activation of purinergic receptors in the cell and/or in nearby cells, resulting in the regulation of cellular functions. The enzymatic activity of CD73 plays a strategic role in calibrating the duration, magnitude, and chemical nature of purinergic signals delivered to various cells (e.g., immune cells). Alteration of these enzymatic activities can change the course or dictate the outcome of several pathophysiological events, including cancer, autoimmune and inflammatory diseases, infections, atherosclerosis, and ischemia-reperfusion injury, suggesting that these ecto-enzymes represent novel therapeutic targets for managing a variety of disorders.

Studies using tissues that overexpress CD73 and using CD73 knock-out mice have provided evidence that CD73 inhibitors have potential utility for melanomas, lung cancer, prostate cancer, and breast cancer (see, e.g., Sadej R. (2006) Melanoma Res 16:213-22). Because higher expression levels of CD73 are associated with tumor neovascularization, invasiveness, resistance to chemotherapy, and metastasis, CD73 inhibitors can be used to control tumor progression and metastasis. Other potential utilities are discussed elsewhere herein.

As set forth above, although the compounds of the present invention are believed to effect their activity by inhibition of CD73, a precise understanding of the compounds' underlying mechanism of action is not required to practice the invention. For example, the compounds can also effect their activity, at least in part, through modulation (e.g., inhibition) of other components of the purinergic signaling pathway (e.g., CD39). The purinergic signaling system consists of transporters, enzymes and receptors responsible for the synthesis, release, action, and extracellular inactivation of (primarily) ATP and its extracellular breakdown product adenosine (Sperlagh, B. et al. (December 2012) Neuropsychopharmacologia Hungarica 14(4):231-38). FIG. 1 depicts a simplified representation of extracellular purinergic signaling (see, e.g., North RA (October 2002) *Physiological Reviews* 82(4):1013-67).

Identification of CD73 Inhibitors Possessing Desirable Characteristics

The present invention is drawn, in part, to the identification of inhibitors of CD73 with at least one property or characteristic that is of therapeutic relevance. Candidate inhibitors may be identified by using, for example, an art-accepted assay or model, examples of which are will be apparent to the skilled artisan. The assay used to determine the CD73 inhibitory activity of the compounds described herein is set forth in the Experimental section.

After identification, candidate inhibitors can be further evaluated by using techniques that provide data regarding characteristics of the inhibitors (e.g., pharmacokinetic parameters). Comparisons of the candidate inhibitors to a reference standard (which may the "best-of-class" of current inhibitors) are indicative of the potential viability of such candidates.

CD73 inhibitors that can serve as reference or benchmark compounds include α,β-Methylene-ADP (AOPCP) and its derivatives and analogs described by Bhattarai et al. ((2015)

J Med Chem 58:6248-63) and the purine CD73 derivatives reported in PCT Publn. 2015/164573. Other reference compounds subsequently identified by the skilled artisan can also be used to assess the viability of candidate CD73 inhibitors.

Compounds of the Invention

Provided herein are compounds having Formula (I):

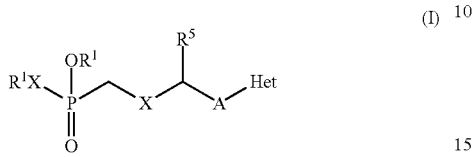

(I)

or a pharmaceutically acceptable salt, hydrate, or solvate thereof, wherein,

- each $R^1$ is independently selected from the group consisting of hydrogen, optionally substituted $C_1$-$C_6$ alkyl, optionally substituted aryl, —C($R^2R^2$)—O—C(O)—$OR^3$, —C($R^2R^2$)—O—C(O)$R^3$, and —C($R^2R^2$)C(O)$OR^3$; or two $R^1$ groups are optionally combined to form a 5- to 6-membered ring;
- each $R^2$ is independently selected from the group consisting of H and optionally substituted $C_1$-$C_6$ alkyl;
- each $R^3$ is independently selected from the group consisting of H, $C_1$-$C_6$ alkyl, $C_1$-$C_6$ alkoxy$C_1$-$C_6$ alkyl, and optionally substituted aryl;
- $R^5$ is selected from the group consisting of H and optionally substituted $C_1$-$C_6$ alkyl;
- X is selected from the group consisting of O, NH, and S;
- A is selected from the group consisting of:

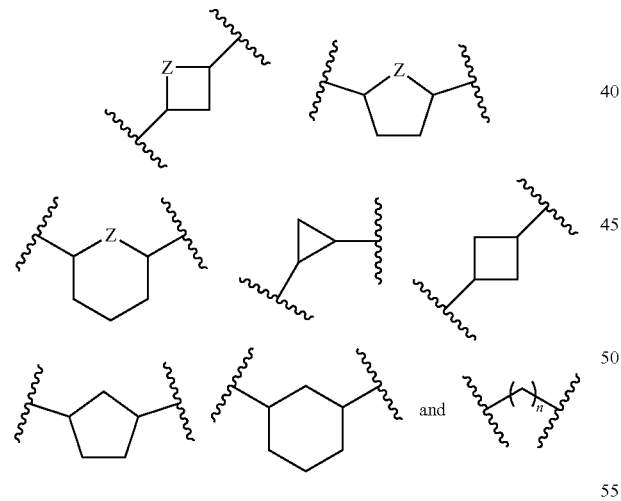

each of which is optionally substituted with from 1 to 5 $R^6$ substituents, and wherein the subscript n is an integer from 0 to 3;
- Z is selected from the group consisting of $CH_2$, $CHR^6$, NH, $NR^6$, and O;
- each $R^6$ is independently selected from the group consisting of $CH_3$, OH, CN, F, optionally substituted $C_1$-$C_6$ alkyl, and —OC(O)—$C_1$-$C_6$ alkyl; or two $R^6$ groups on adjacent ring vertices are optionally joined together to form a 5- to 6-membered ring having at least one heteroatom as a ring vertex; and Het is selected from the group consisting of:

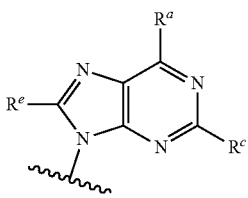
a1

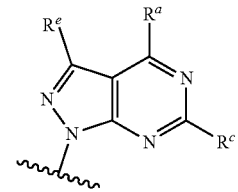
a2

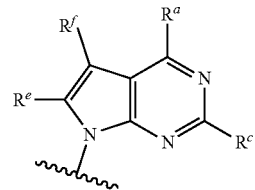
a3

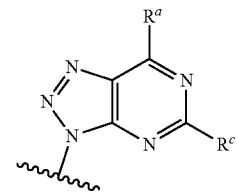
a4

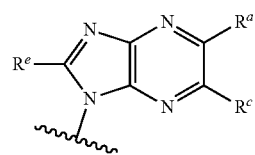
a5

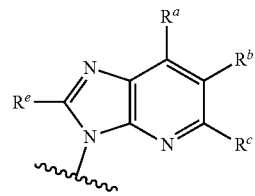
a6

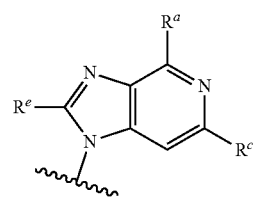
a7

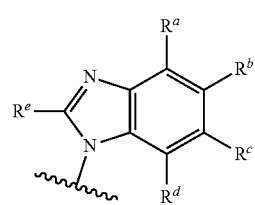
a8

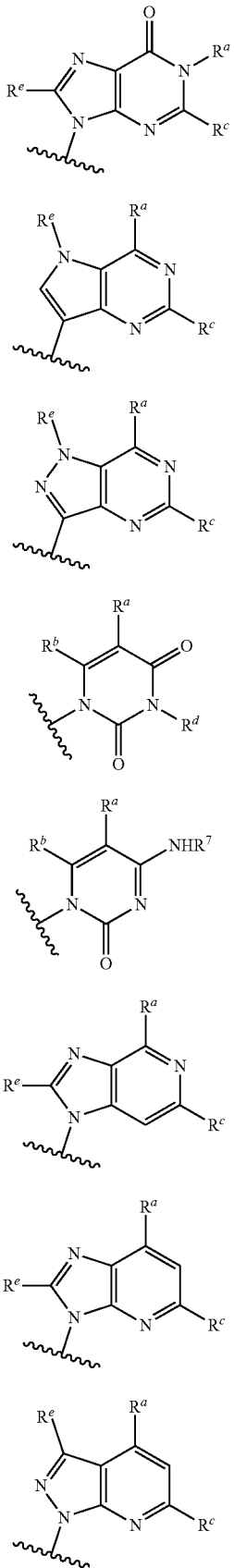

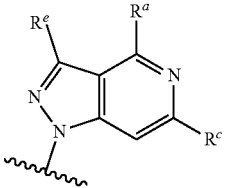

wherein the wavy line indicates the point of attachment to the remainder of the compound, and wherein:

$R^a$ is selected from the group consisting of H, $NH_2$, $NHR^7$, $NHC(O)R^7$, $NR^7R^7$, $R^7$, OH, $SR^7$ and $OR^7$;

$R^b$ is selected from the group consisting of H, halogen, $NH_2$, $NHR^7$, $NR^7R^7$, $R^7$, OH, and $OR^7$;

$R^c$ and $R^d$ are independently selected from the group consisting of H, halogen, haloalkyl, $NH_2$, $NHR^7$, $NR^7R^7$, $R^7$, OH, $OR^7$, $SR^7$, $SO_2R^7$, —$X^1$—$NH_2$, —$X^1$—$NHR^7$, —$X^1$—$NR^7R^7$, —$X^1$—OH, —$X^1$—$OR^7$, —$X^1$—$SR^7$ and —$X^1$—$SO_2R^7$;

$R^e$ and $R^f$ are independently selected from the group consisting of H, halogen, and optionally substituted $C_1$-$C_6$ alkyl;

each $X^1$ is $C_1$-$C_4$alkylene; and each $R^7$ is independently selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_7$ cycloalkyl, optionally substituted $C_3$-$C_7$ cycloalkyl$C_1$-$C_4$alkyl, optionally substituted 4-7 membered cycloheteroalkyl, optionally substituted 4-7 membered cycloheteroalkyl$C_1$-$C_4$alkyl, optionally substituted aryl, optionally substituted aryl$C_1$-$C_4$alkyl, optionally substituted aryl$C_2$-$C_4$alkenyl, optionally substituted aryl$C_2$-$C_4$alkynyl, optionally substituted heteroaryl, optionally substituted heteroaryl$C_1$-$C_4$alkyl, optionally substituted heteroaryl$C_2$-$C_4$alkenyl, and optionally substituted heteroaryl$C_2$-$C_4$alkynyl; and, optionally, two $R^7$ groups attached to a nitrogen atom are joined together to form a 4- to 7-membered heterocyclic ring which is optionally fused to an aryl ring.

For the above formula, the term 'optionally substituted' is used in connection with alkyl groups, cycloalkyl groups, cycloheteroalkyl groups, aryl groups and heteroaryl groups. Within each of these groups, some selected optional substituents are as follows:

Alkyl groups: halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —CN and —NO$_2$. R', R" and R'" each independently refer to hydrogen, unsubstituted $C_{1-4}$ alkyl, or $C_{1-4}$ haloalkyl. When R' and R" are attached to the same nitrogen atom, or when R" and R'" are attached to the same nitrogen, they can be combined with the nitrogen atom to form a 3-, 4-, 5-, 6-, or 7-membered ring. For example, —NR'R" is meant to include 1-pyrrolidinyl and 4-morpholinyl.

Cycloalkyl groups and cycloheteroalkyl groups: The selected substituents noted above for 'alkyl groups' are also useful with cycloalkyl and cycloheteroalkyl groups. Additionally, each of the cycloalkyl and cycloheteroalkyl groups can be optionally substituted with oxo (=O) or a hydroxyl.

Aryl groups and heteroaryl groups: -halogen, —OR', —OC(O)R', —NR'R", —R', —CN, —NO$_2$, —CO$_2$R', —CONR'R"', —C(O)R', —OC(O)NR'R", —NR"C(O)R', —NR"C(O)$_2$R', —NR'—C(O)NR"R"', —S(O)$_2$R', —S(O)$_2$NR'R", —NR'S(O)$_2$R", and perfluoro(C$_1$-C$_4$)alkyl, where R', R" and R"' are independently selected from hydrogen, C$_{1-4}$ alkyl, C$_{1-4}$haloalkyl and C$_{3-6}$ cycloalkyl. In some embodiments, aryl groups are optionally substituted with one or more halogens.

In one selected group of embodiments, compounds of Formula (I) are provided wherein each R$^3$ is independently selected from the group consisting of H, C$_1$-C$_6$ alkyl, and optionally substituted aryl.

In one selected group of embodiments, compounds of Formula (I) are provided wherein A has the formula:

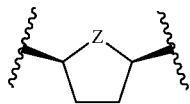

which is optionally substituted with from 1 to 5 R$^6$.

In another selected group of embodiments, compounds of Formula (I) are provided wherein A has a formula selected from the group consisting of:

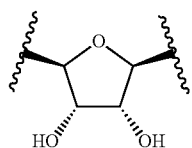
b1

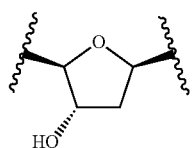
b2

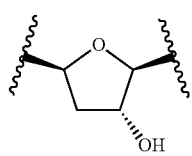
b3

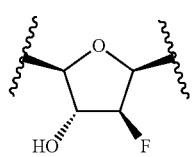
b4

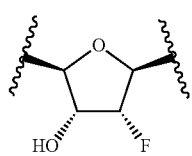
b5

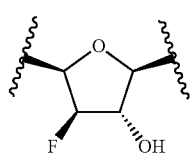
b6

-continued

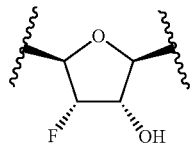
b7

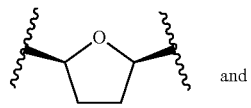
b8
and

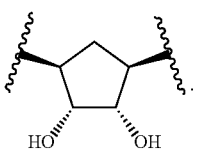
b9

In some selected embodiments, any one of a1 through a17 can be independently combined with any one of b1 through b9, to provide selected embodiments of Formula (I).

In some selected embodiments, compounds of Formula (I) are provided wherein Het has the formula:

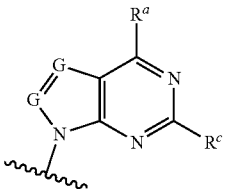

wherein each G is independently selected from the group consisting of N and CR$^e$.

In still other selected embodiments, compounds of Formula (I) are provided wherein Het has the formula:

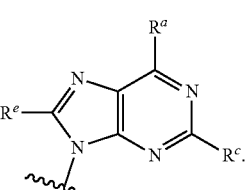
(a1)

In still other selected embodiments, compounds of Formula (I) are provided wherein Het has the formula:

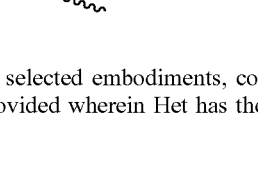
(a6)

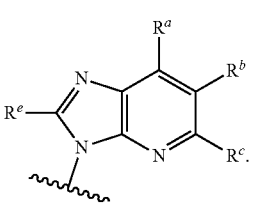

In still other selected embodiments, compounds of Formula (I) are provided wherein Het has the formula:

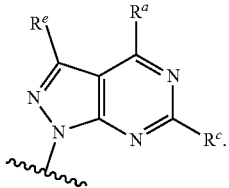
(a2)

In still other selected embodiments, compounds of Formula (I) are provided wherein Het has the formula:

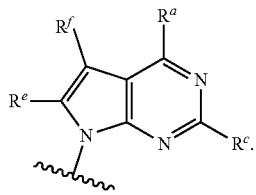
(a3)

In still other selected embodiments, compounds of Formula (I) are provided wherein Het has the formula:

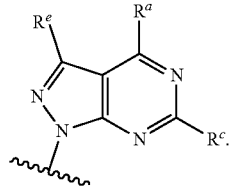
(a16)

In some selected embodiments, $R^c$ is other than H.

In yet other selected embodiments, compounds of Formula (I) are provided that are represented by one of the following subformulae:

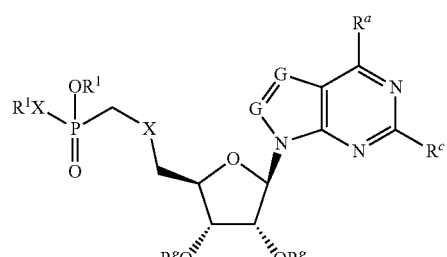

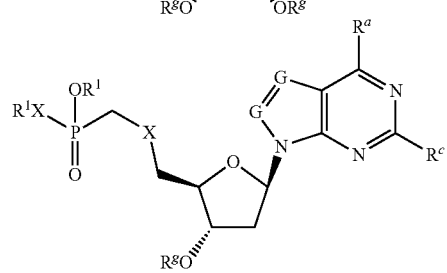

-continued

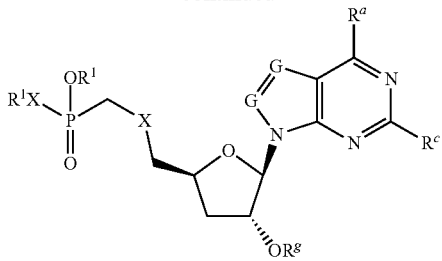

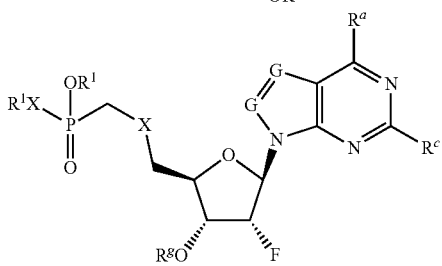

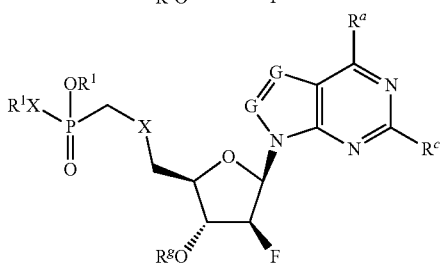

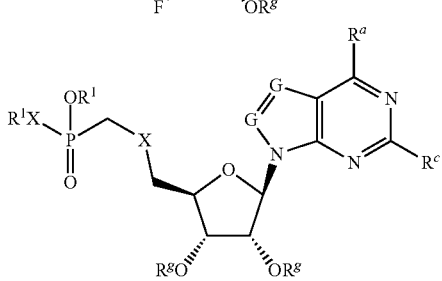

and wherein each $R^g$ is independently selected from the group consisting of H and $C(O)$—$C_1$-$C_6$ alkyl. Still further selected embodiments of the subformulae above, are those wherein X is oxygen. In other selected embodiments of the subformulae above, X is oxygen and $R^e$ is hydrogen. In still other selected embodiments of the subformulae above, X is oxygen, $R^e$ is hydrogen, and each $R^g$ is hydrogen.

In some embodiments, $R^5$ is H. In other embodiments, $R^5$ is H, and X is O. In still other embodiments, $R^5$ is H, X is O, and each $R^1$ is H.

In another group of selected embodiments, compounds of Formula (I) are provided wherein Het is selected from:

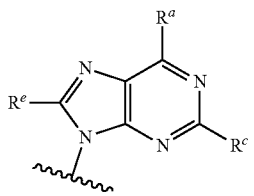
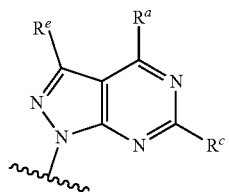
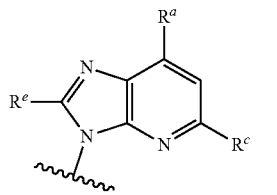 and 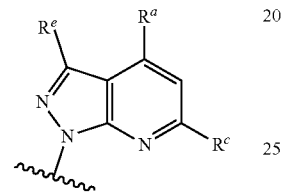

wherein $R^a$, $R^c$ and $R^e$ have the meanings provided with reference to Formula (I) above.

In some selected embodiments, $R^5$ is H, X is O, and each $R^1$ is H. In still other selected embodiments, $R^5$ is H, X is O, each $R^1$ is H, $R^e$ is H, and $R^a$ is selected from the group consisting of $NH_2$, $NHR^7$ and $N(R^7)_2$. In yet other selected embodiments, $R^5$ is H, X is O, each $R^1$ is H, $R^e$ is H, $R^c$ is other than H, and $R^a$ is $NHR^7$.

Still other selected embodiments of the Formula (I), are compounds having a subformulae selected from the following:

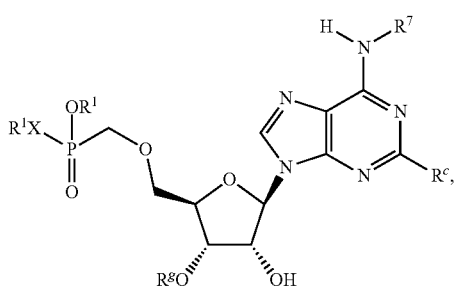
(IIa)

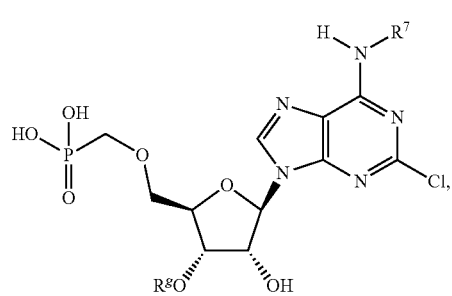
(IIb)

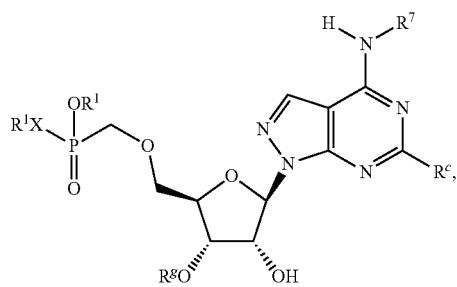
(IIIa)

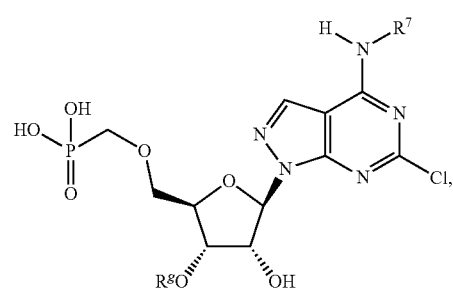
(IIIb)

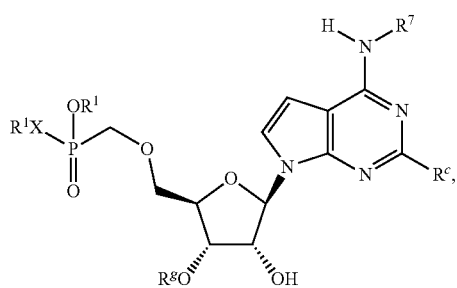
(IVa)

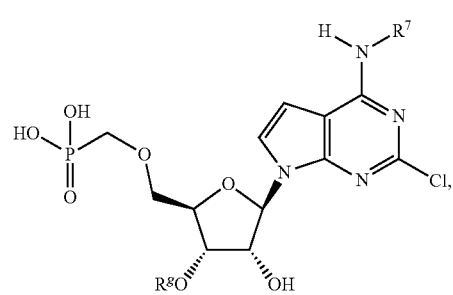
(IVb)

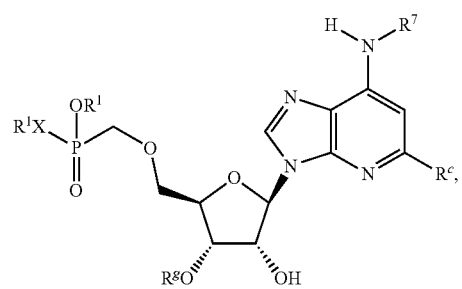
(Va)

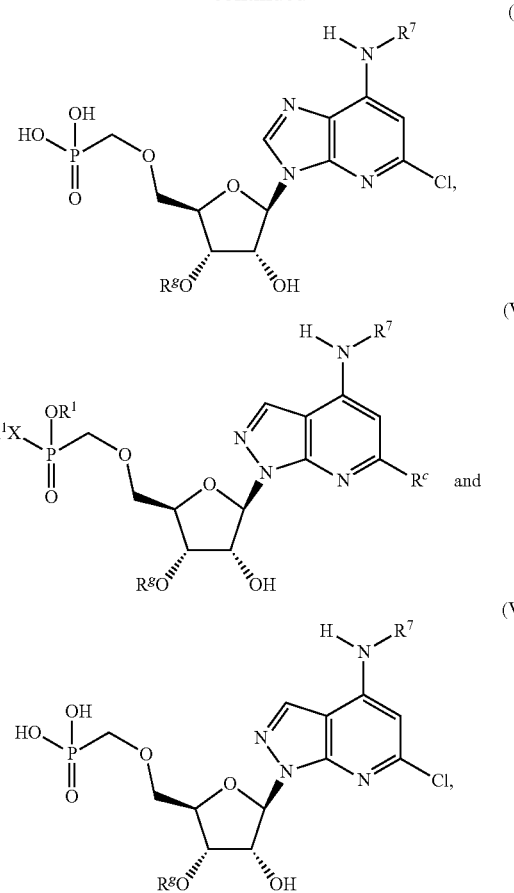

(Vb)

(VIa)

(VIb)

wherein R[7], R[c], R[g], R[1], and X have the meanings provided with respect to Formula (I), and certain selected embodiments as described herein.

In some embodiments, each R[7] is independently selected from the group consisting of optionally substituted $C_1$-$C_{10}$ alkyl, optionally substituted $C_3$-$C_7$ cycloalkyl, optionally substituted $C_3$-$C_7$ cycloalkyl$C_1$-$C_4$alkyl, optionally substituted 4-7 membered cycloheteroalkyl, optionally substituted 4-7 membered cycloheteroalkyl$C_1$-$C_4$alkyl, optionally substituted aryl, and optionally substituted aryl$C_1$-$C_4$alkyl; or when two R[7] groups are attached to the same nitrogen atom, they are optionally joined together to form a 4- to 7-membered heterocyclic ring which is optionally fused to an aryl ring; provided that when two R[7] groups are attached to the same nitrogen and are not joined together to form a heterocyclic ring, at least one R[7] is optionally substituted $C_{1-10}$alkyl.

In some embodiments, each R[7] is independently selected from the group consisting of optionally substituted $C_1$-$C_{10}$ alkyl, optionally substituted $C_3$-$C_7$ cycloalkyl, optionally substituted 4-7 membered cycloheteroalkyl, and optionally substituted aryl$C_1$-$C_4$alkyl; or when two R[7] groups are attached to the same nitrogen atom, they are optionally joined together to form a 4- to 7-membered heterocyclic ring which is optionally fused to an aryl ring.

In still other embodiments, each R[7] is independently selected from the group consisting of $C_{1-4}$alkyl, optionally substituted $C_5$ cycloalkyl, optionally substituted tetrahydrofuran, and optionally substituted phenyl$C_{1-2}$alkyl; or when two R[7] groups are attached to the same nitrogen atom are joined together to form a 5-membered heterocyclic ring which is optionally fused to an phenyl ring, wherein when two R[7] groups are attached to the same nitrogen and they are not joined together to form a heterocyclic ring, at least one R[7] $C_{1-4}$alkyl.

In yet other embodiments, each R[7] is independently selected from the group consisting of $C_{1-4}$alkyl, optionally substituted $C_5$ cycloalkyl, optionally substituted tetrahydrofuran, and optionally substituted phenyl$C_{1-2}$alkyl; or when two R[7] groups are attached to the same nitrogen atom, they are optionally joined together to form a 5-membered heterocyclic ring which is optionally fused to an phenyl ring, wherein the 5-membered heterocyclic ring contains no additional heteroatoms.

In some embodiments, each R[7] is independently selected from the group consisting of methyl,

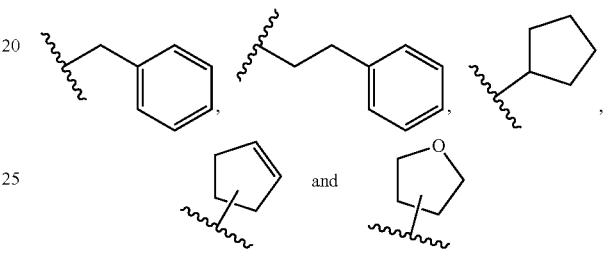

and or when two R[7] groups are attached to the same nitrogen atom, the moiety NR[7]R[7] is

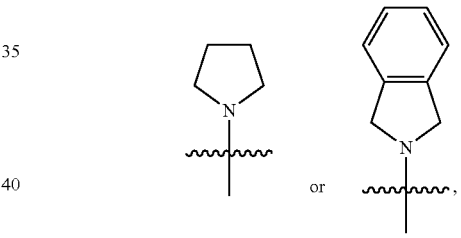

or wherein each aryl, cycloalkyl, and heterocycloalkyl group is optionally substituted with one or more halogens or hydroxyl groups.

Methods of Synthesis

In general, the compounds provided herein can be prepare by conventional methods as described in the Examples below.

Prodrugs and Other Means of Drug Delivery and/or Half-Life Extension

In some aspects of the present invention, compounds described herein are administered in prodrug form.

In order to effect extension of therapeutic activity, drug molecules may be engineered to utilize carriers for delivery. Such carriers are either used in a non-covalent fashion, with the drug moiety physicochemically formulated into a solvent-carrier mixture, or by permanent covalent attachment of a carrier reagent to one of the drug moiety's functional groups (see generally WO 20150202317).

Several non-covalent approaches are favored. By way of example, but not limitation, in certain embodiments depot formulations comprising non-covalent drug encapsulation into polymeric carriers are employed. In such formulations, the drug molecule is combined with carrier material and processed such that the drug molecule becomes distributed inside the bulk carrier. Examples include microparticle polymer-drug aggregates (e.g., Degradex® Microspheres (Phosphorex, Inc.)), which are administered as an injectable suspension; polymer-drug molecule aggregates formulated as gels (e.g., Lupron Depot® (AbbVie Inc.)), which are administered as a single bolus injection; and liposomal formulations (e.g., DepoCyt® (Pacira Pharmaceuticals)), where the carrier may be a polymeric or non-polymeric entity capable of solubilizing the drug. In these formulations, release of the drug molecule may occur when the carrier swells or physically deteriorates. In other instances, chemical degradation allows diffusion of the drug into the biological environment; such chemical degradation processes may be autohydrolytic or enzyme-catalyzed. Among other limitations, non-covalent drug encapsulation requires prevention of uncontrolled release of the drug, and dependence of the release mechanism of the drug upon biodegradation may cause interpatient variability.

In particular embodiments, drug molecules, including both small molecules and large molecules, are conjugated to a carrier through permanent covalent bonds. Certain small molecule therapeutics that exhibit low solubility in aqueous fluids may be solubilized by conjugation to hydrophilic polymers, examples of which are described elsewhere herein. Regarding large molecule proteins, half-life extension may be achieved by, for example, permanent covalent modification with a palmitoyl moiety, and by permanent covalent modification with another protein that itself has an extended half-life (e.g., Albuferon®). In general, drug molecules show decreased biological activity when a carrier is covalently conjugated to the drug.

In certain instances, limitations associated with either drug molecules comprising non-covalent polymer mixtures or permanent covalent attachment may be successfully addressed by employing a prodrug approach for chemical conjugation of the drug to the polymer carrier. In this context, therapeutic agents that are inactive or less active than the drug moiety itself are predictably transformed into active molecular entities. The reduced biological activity of the prodrug as compared to the released drug is advantageous if a slow or controlled release of the drug is desired. In such instances, release of the drug occurs over time, thereby reducing the necessity of repeated and frequent administration of the drug. A prodrug approach may also be advantageous when the drug moiety itself is not absorbed, or has less than optimal absorption, in the gastrointestinal tract; in these instances, the prodrug facilitates absorption of the drug moiety and is then cleaved off at some later time (e.g., via first-pass metabolism). The biologically active drug molecule is typically linked to the polymeric carrier moiety by a temporary bond formed between the carrier moiety and a hydroxy, amino or carboxy group of the drug molecule.

The approaches described above are associated with several limitations. Prodrug activation may occur by enzymatic or non-enzymatic cleavage of the temporary bond between the carrier and the drug molecule, or a sequential combination of both (e.g., an enzymatic step followed by a non-enzymatic modification). In an enzyme-free in vitro environment (e.g., an aqueous buffer solution), a temporary bond such as an ester or amide may undergo hydrolysis, but the corresponding rate of hydrolysis may be such that it is outside the therapeutically useful range. In contrast, in an in vivo environment, esterases or amidases are typically present, and the esterases and amidases may cause significant catalytic acceleration of the kinetics of hydrolysis from two-fold up to several orders of magnitude (see, e.g., Greenwald et al., (1999) J Med Chem 42(18):3857-67).

As described herein, prodrugs may be classified as i) bioprecursors and ii) carrier-linked prodrugs. Bioprecursors do not contain a carrier group and are activated by the metabolic creation of a functional group. In contrast, in carrier-linked prodrugs the active substance is conjugated to a carrier moiety via a temporary linkage at a functional group of the bioactive entity. Preferred functional groups are hydroxyl or amino groups. Both the attachment chemistry and hydrolysis conditions depend on the type of functional group employed. The carrier may be biologically inert (e.g., PEG) or may have targeting properties (e.g., an antibody). Cleavage of the carrier moiety of a carrier-linked prodrug results in the bioactive entity of interest, and the nature of the deprotected functional group of the bioactive entity often contributes to its bioactivity.

The patent and scientific literature describe many macromolecular prodrugs where the temporary linkage is a labile ester bond. In these cases, the functional group of the bioactive entity is either a hydroxyl group or a carboxylic acid (see, e.g. Cheng et al. (2003) Bioconjugate Chem 14:1007-17). In addition, it is often advantageous for biomacromolecules and certain small molecule drugs to link the carrier to an amino group(s) of the bioactive entity (e.g., the N-terminus or lysine amino groups of proteins). During preparation of the prodrug, the amino groups may be more chemoselectively addressed due to their greater nucleophilicity compared to hydroxylic or phenolic groups. This is especially relevant for proteins and peptides containing a great variety of different reactive functionalities, where non-selective conjugation reactions lead to undesired product mixtures requiring extensive characterization or purification, thus decreasing reaction yield and therapeutic efficiency of the active moiety.

In general, amide bonds are more stable against hydrolysis than ester bonds, and the rate of cleavage of the amide bond may be too slow for therapeutic utility in a carrier-linked prodrug. As a result, it may be advantageous to add structural chemical components in order to effect control over the cleavability of the prodrug amide bond. These additional cleavage-controlling chemical components that are provided neither by the carrier entity nor by the drug are generally referred to as "linkers". Prodrug linkers can have a major effect on the rate of hydrolysis of temporary bond, and variation of the chemical nature of the linkers often results in particular properties. Prodrug activation of amine-containing biologically active moieties by specific enzymes for targeted release requires that the structure of the linker display a structural motif recognized as a substrate by a corresponding endogenous enzyme. In these cases, the cleavage of the temporary bond occurs in a one-step process which is catalyzed by the enzyme. For example, the enzymatic release of cytarabin is effected by the protease plasmin, which concentration is relatively high in various kinds of tumor mass.

Interpatient variability is a major drawback of predominant enzymatic cleavage. Enzyme levels may differ significantly between subjects resulting in biological variation of prodrug activation by the enzymatic cleavage. Enzyme levels may also vary depending on the site of administration (e.g., for subcutaneous injection, certain areas of the body yield more predictable therapeutic effects than others). In addition, it is difficult to establish an in vivo—in vitro correlation of the pharmacokinetic properties for enzyme-dependent carrier-linked prodrugs.

Other carrier prodrugs employing temporary linkages to amino groups in the drug moiety are based on a cascade mechanism. Cascade cleavage is enabled by linker compounds that are composed of a structural combination of a masking group and an activating group. The masking group is attached to the activating group by means of a first temporary linkage such as an ester or a carbamate. The activating group is attached to an amino group of the drug molecule through a second temporary linkage (e.g., a carbamate). The stability or susceptibility to hydrolysis of the second temporary linkage is dependent on the presence or absence of the masking group. In the presence of the masking group, the second temporary linkage is highly stable and unlikely to release the drug molecule with therapeutically useful kinetics, whereas in the absence of the masking group this linkage becomes highly labile, resulting in rapid cleavage and release of the drug moiety.

The cleavage of the first temporary linkage is the rate-limiting step in the cascade mechanism. The first step may induce a molecular rearrangement of the activating group (e.g., a 1,6-elimination as described in Greenwald et al. (1999) J Med Chem 42:3657-67), and the rearrangement renders the second temporary linkage much more labile such that its cleavage is induced. Ideally, the cleavage rate of the first temporary linkage is identical to the desired release rate for the drug molecule in a given therapeutic scenario. In addition, it is desirable that the cleavage of the second temporary linkage be substantially instantaneous after its lability has been induced by cleavage of the first temporary bond.

Another embodiment comprises polymeric amino-containing prodrugs based on trimethyl lock lactonization (see, e.g., Greenwald et al. (2000) J Med Chem 43(3):457-87). In this prodrug system, substituted o-hydroxyphenyl-dimethylpropionic acid is linked to PEG by an ester, carbonate, or carbamate group as a first temporary linkage and to an amino group of a drug molecule by means of an amide bond as a second temporary linkage. The rate-determining step in drug release is the enzymatic cleavage of the first linkage, which is followed by fast amide cleavage by lactonization, releasing an aromatic lactone side product. The primary disadvantage of the prodrug systems described by Greenwald et al. is the release of highly reactive and potentially toxic aromatic small molecule side products like quinone methides or aromatic lactones after cleavage of the temporary linkage. The potentially toxic entities are released in a 1:1 stoichiometry with the drug and can assume high in vivo concentrations.

In certain embodiments of cascade prodrugs comprising aromatic activating groups based on 1,6-elimination, the masking group is structurally separate from the carrier. This may be effected by employing a stable bond between the polymer carrier and the activating group, wherein the stable bond does not participate in the cascade cleavage mechanism. If the carrier is not serving as a masking group and the activating group is coupled to the carrier by means of a stable bond, release of potentially toxic side products (such as the activating group) is avoided. The stable attachment of the activating group and the polymer also suppresses the release of drug-linker intermediates with undefined pharmacology.

A first example of the approach described in the preceding paragraph comprises a polymeric prodrug system based on a mandelic acid activating group (see, e.g., Shabat et al. (2004) Chem Eur J 10:2626-34). In this approach the masking group is linked to the activating group by a carbamate bond. The activating group is conjugated permanently to a polyacrylamide polymer via an amide bond. After enzymatic activation of the masking group by a catalytic antibody, the masking group is cleaved by cyclization and the drug is released; the activating group is still connected to the polyacrylamide polymer after drug release. A similar prodrug system is based on a mandelic acid activating group and an enzymatically cleavable ester-linked masking group (see, e.g., Lee et al. (2004) Angew Chem 116:1707-10).

When the aforementioned linkers are used, the 1,6-elimination step still generates a highly reactive aromatic intermediate. Even if the aromatic moiety remains permanently attached to the polymeric carrier, side reactions with potentially toxic by-products or immunogenic effects may result. Thus, it is advantageous to generate linker technologies for forming polymeric prodrugs of amine-containing active agents using aliphatic prodrug linkers that are not enzyme-dependent and do not generate reactive aromatic intermediates during cleavage. One such example uses PEG5000-maleic anhydride for the reversible modification of amino groups in tissue-type plasminogen activator and urokinase (see, e.g. (1987) Garman et al. FEBS Lett 223(2):361-65). Regeneration of functional enzyme from PEG-uPA conjugate upon incubation at pH 7.4 buffer by cleavage of the maleamic acid linkage follows first order kinetics with a half-life of roughly 6 hours. A disadvantage of the maleamic acid linkage is the lack of stability of the conjugate at lower pH values.

A further approach comprises a PEG cascade prodrug system based on N,N-bis-(2-hydroxyethyl)glycine amide (bicine) linker (see e.g. (2004) J Med Chem 47:726-34). In this system, two PEG carrier molecules are linked via temporary bonds to a bicine molecule coupled to an amino group of the drug molecule. The first steps in prodrug activation involves the enzymatic cleavage of the first temporary linkages connecting both PEG carrier molecules with the hydroxy groups of the bicine activating group. Different linkages between PEG and bicine result in different prodrug activation kinetics. The second step in prodrug activation involves the cleavage of the second temporary linkage connecting the bicine activating group to the amino group of the drug molecule. A disadvantage of this system is the slow hydrolysis rate of this second temporary bicine amide linkage, which results in the release of a bicine-modified prodrug intermediate that may show different pharmacokinetic, immunogenic, toxicity and pharmacodynamic properties as compared to the native parent drug molecule.

In particular embodiments, dipeptides are utilized for prodrug development for targeting or targeted transport as they are substrates for enzymes or biotransport systems. The non-enzymatic route for dipeptide prodrug formation, that is, the ability to undergo intramolecular cyclization to form the corresponding diketopiperazine (DKP) and release the active drug, is not well defined.

In some embodiments, dipeptides are attached to a drug moiety via ester bonds, as was described for dipeptide esters of the drug paracetamol (Gomes et al. (2005) Bio & Med Chem Lett). In this case, the cyclization reaction consists of a nucleophilic attack of the N-terminal amine of the peptide on the ester carbon atom to form a tetrahedral intermediate, which is followed by a proton transfer from the amine to the leaving group oxyanion with simultaneous formation of a peptide bond to give the cyclic DKP product and free drug. This method is applicable to hydroxyl-containing drugs in vitro but has been found to compete with enzymatic hydrolysis of the ester bond in vivo, as corresponding dipeptide esters released paracetamol at a much faster rate than in buffer (Gomes et al. (Molecules 12 (2007) 2484-2506). Susceptibility of dipeptide-based prodrugs to peptidases may be addressed by incorporating at least one non-natural amino acid in the dipeptide motif. However, endogenous enzymes capable of cleaving ester bonds are not limited to peptidases, and the enzyme-dependence of such prodrug cleavage still gives rise to unpredictable in vivo performance.

In some embodiments, enzyme-dependence is intentionally engineered into DKP prodrugs, such as where dipeptide ester prodrugs are formylated at the amino terminus of the dipeptide, and enzymatic deformylation is used to initiate diketopiperazine formation and subsequent cleavage of the ester-dipeptide bond, followed by release of the drug molecule (see, e.g., U.S. Pat. No. 7,163,923). By way of further example, an octapeptide is attached by an ester linkage to the 4-hydroxyl group of vinblastine and undergoes ester bond cleavage by DKP formation after specific enzymatic removal of the N-terminal hexapeptide (see Brady et al. (2002) J Med Chem 45:4706-15).

The scope of the DKP formation reaction has also been extended to amide prodrugs. By way of example, U.S. Pat. No. 5,952,294 describes prodrug activation using diketopiperazine formation for dipeptidyl amide prodrugs of cytarabine. In this case, the temporary linkage is formed between the carbonyl of a dipeptide and the aromatic amino group of cytarabine. However, it is unlikely that a slow-release effect can be achieved for such conjugates as there is no carrier or other half-life extending moiety or functionality present.

Dipeptide prodrugs comprising bioactive peptides such as GLP-1 capable of releasing the peptide through diketopiperazine formation of the dipeptidic extension have also been described (see, e.g., WO 2009/099763). The bioactive peptide moiety may include an additional PEG chain on one of its amino acid side chain residues to achieve extended circulation of the bioactive peptide. However, this approach is associated with several significant disadvantages. First, the PEG chain has to be linked to the peptide without compromising its bioactivity, which can be difficult to achieve for many peptide-based bioactive agents. Second, as the pegylated peptide itself is bioactive, the dipeptidic promoiety has an effect on the peptide's bioactivity and may negatively affect its receptor binding properties.

Modifications to Enhance Inhibitor Characteristics

It is frequently beneficial, and sometimes imperative, to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity.

Modifications known in the art include pegylation, Fc-fusion and albumin fusion. Although generally associated with large molecule agents (e.g., polypeptides), such modifications have recently been evaluated with particular small molecules. By way of example, Chiang, M. et al. (*J. Am. Chem. Soc.,* 2014, 136(9):3370-73) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., Progress in Polymer Science, 2013 38:421-44).

Therapeutic and Prophylactic Uses

The present invention contemplates the use of the CD73 inhibitors described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

Oncology-related Disorders. In accordance with the present invention, an CD73 inhibitor can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates reducing tolerance to a tumor cell or cancer cell antigen, e.g., by modulating activity of a regulatory T-cell and/or a CD8+ T-cell (see, e.g., Ramirez-Montagut, et al. (2003) *Oncogene* 22:3180-87; and Sawaya, et al. (2003) *New Engl. J. Med.* 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer be metastatic or at risk of becoming metastatic, or may occur in a diffuse tissue, including cancers of the blood or bone marrow (e.g., leukemia). In some further embodiments, the compounds of the invention can be used to overcome T-cell tolerance.

In some embodiments, the present invention provides methods for treating a proliferative condition, cancer, tumor, or precancerous condition with an CD73 inhibitor and at least one additional therapeutic or diagnostic agent, examples of which are set forth elsewhere herein.

Immune-related Disorders and Disorders with an Inflammatory Component. As used herein, terms such as "immune disease", "immune condition", "immune disorder", "inflammatory disease", "inflammatory condition", "inflammatory disorder" and the like are meant to broadly encompass any immune-related condition (e.g., an autoimmune disease) or a disorder with an inflammatory component that can be treated by the CD73 inhibitors described herein such that some therapeutic benefit is obtained. Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

The CD73 inhibitors of the present invention can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The CD73 inhibitors can also be used to stimulate the immune system of patients suffering from iatrogenically-induced immune suppression, including those who have undergone bone marrow transplants, chemotherapy, or radiotherapy.

In particular embodiments of the present disclosure, the CD73 inhibitors are used to increase or enhance an immune response to an antigen by providing adjuvant activity. In a particular embodiment, at least one antigen or vaccine is administered to a subject in combination with at least one CD73 inhibitor of the present invention to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with at least one CD73 inhibitor of the present invention.

Microbial-related Disorders. By inhibiting the immunosuppressive and anti-inflammatory activity of CD73, the present invention contemplates the use of the CD73 inhibitors described herein in the treatment and/or prevention of any viral, bacterial, fungal, parasitic or other infective disease, disorder or condition for which treatment with an CD73 inhibitor may be beneficial. Examples of such diseases and disorders include HIV and AIDS, staphylococcal and streptococcal infections (e.g., *Staphylococcus aureus* and *Streptococcus sanguinis*, respectively), *leishmania, toxoplasma, trichomonas, Giardia, Candida albicans, Bacillus anthracis*, and *Pseudomonas aeruginosa*. Compounds of the invention can be used to treat sepsis, decrease or inhibit bacterial growth, and reduce or inhibit inflammatory cytokines.

CNS-related and Neurological Disorders. Inhibition of CD73 may also be an important treatment strategy for patients with neurological, neuropsychiatric, neurodegenerative or other diseases, disorders and conditions having some association with the central nervous system, including disorders associated with impairment of cognitive function and motor function. Examples include Parkinson's disease, extra pyramidal syndrome (EPS), dystonia, akathisia, tardive dyskinesia, restless leg syndrome (RLS), epilepsy, periodic limb movement in sleep (PLMS), attention deficit disorders, depression, anxiety, dementia, Alzheimer's disease, Huntington's disease, multiple sclerosis, cerebral ischemia, hemorrhagic stroke, subarachnoid hemorrhage, and traumatic brain injury.

Other Disorders. Embodiments of the present invention contemplate the administration of the CD73 inhibitors described herein to a subject for the treatment or prevention of any other disorder that may benefit from at least some level of CD73 inhibition. Such diseases, disorders and conditions include, for example, cardiovascular (e.g., cardiac ischemia), gastrointestinal (e.g., Crohn's disease), metabolic (e.g., diabetes), hepatic (e.g., hepatic fibrosis, NASH, and NAFLD), pulmonary (e.g., COPD and asthma), ophthalmologic (e.g., diabetic retinopathy), and renal (e.g., renal failure) disorders.

In some embodiments, the CD73 inhibitors of the present invention may be used to inhibit statin-induced adenosine production, or reduce or decrease increases in blood glucose caused by a statin in a subject taking a statin (e.g., lovastatin and pravastatin)

Pharmaceutical Compositions

The CD73 inhibitors of the present invention may be in the form of compositions suitable for administration to a subject. In general, such compositions are "pharmaceutical compositions" comprising an CD73 inhibitor(s) and one or more pharmaceutically acceptable or physiologically acceptable diluents, carriers or excipients. In certain embodiments, the CD73 inhibitors are present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., an inhibitor of CD73 function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxy-ethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of an CD73 inhibitor contemplated by the present invention and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver an CD73 inhibitor, including implants (e.g., implantable pumps) and catheter systems, slow injection pumps and devices, all of which are well known to the skilled artisan.

Depot injections, which are generally administered subcutaneously or intramuscularly, may also be utilized to release the CD73 inhibitors disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, NJ) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the CD73 inhibitors in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The CD73 inhibitors contemplated by the present invention may be in the form of any other suitable pharmaceutical composition (e.g., sprays for nasal or inhalation use) currently known or developed in the future.

Routes of Administration

The present invention contemplates the administration of CD73 inhibitors, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the CD73 inhibitors disclosed herein over a defined period of time.

Particular embodiments of the present invention contemplate oral administration.

Combination Therapy

The present invention contemplates the use of CD73 inhibitors alone or in combination with one or more active therapeutic agents. The additional active therapeutic agents can be small chemical molecules; macromolecules such as proteins, antibodies, peptibodies, peptides, DNA, RNA or fragments of such macromolecules; or cellular or gene therapies. In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the CD73 inhibitors are administered or applied sequentially, e.g., where one agent is administered prior to one or more other agents. In other embodiments, the CD73 inhibitors are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The CD73 inhibitors of the present invention may be used in combination with at least one other (active) agent in any manner appropriate under the circumstances. In one embodiment, treatment with the at least one active agent and at least one CD73 inhibitor of the present invention is maintained over a period of time. In another embodiment, treatment with the at least one active agent is reduced or discontinued (e.g., when the subject is stable), while treatment with an CD73 inhibitor of the present invention is maintained at a constant dosing regimen. In a further embodiment, treatment with the at least one active agent is reduced or discontinued (e.g., when the subject is stable), while treatment with an CD73 inhibitor of the present invention is reduced (e.g., lower dose, less frequent dosing or shorter treatment regimen). In yet another embodiment, treatment with the at least one active agent is reduced or discontinued (e.g., when the subject is stable), and treatment with the CD73 inhibitor of the present invention is increased (e.g., higher dose, more frequent dosing or longer treatment regimen). In yet another embodiment, treatment with the at least one active agent is maintained and treatment with the CD73 inhibitor of the present invention is reduced or discontinued (e.g., lower dose, less frequent dosing or shorter treatment regimen). In yet another embodiment, treatment with the at least one active agent and treatment with the CD73 inhibitor of the present invention are reduced or discontinued (e.g., lower dose, less frequent dosing or shorter treatment regimen).

Oncology-related Disorders. The present invention provides methods for treating and/or preventing a proliferative condition, cancer, tumor, or precancerous disease, disorder or condition with an CD73 inhibitor and at least one additional therapeutic or diagnostic agent.

In certain embodiments, the present invention provides methods for tumor suppression of tumor growth comprising administration of an CD73 inhibitor described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in in immunomodulation can also be used in combination with the CD73 inhibitors described herein for the suppression of tumor growth in cancer patients.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Additional treatment modalities that may be used in combination with an CD73 inhibitor include radiotherapy, a monoclonal antibody against a tumor antigen, a complex of a monoclonal antibody and toxin, a T-cell adjuvant, bone marrow transplant, or antigen presenting cells (e.g., dendritic cell therapy), including TLR agonists which are used to stimulate such antigen presenting cells.

In certain embodiments, the present invention contemplates the use of the compounds described herein in combination with adoptive cell therapy, a new and promising form of personalized immunotherapy in which immune cells with anti-tumor activity are administered to cancer patients. Adoptive cell therapy is being explored using tumor-infiltrating lymphocytes (TIL) and T cells engineered to express, for example, chimeric antigen receptors (CAR) or T cell receptors (TCR). Adoptive cell therapy generally involves collecting T cells from an individual, genetically modifying them to target a specific antigen and/or to enhance their anti-tumor effects, amplifying them to a sufficient number, and infusion of the genetically modified T cells into a cancer patient. T cells can be collected from the patient to whom the expanded cells are later reinfused (e.g., autologous) or can be collected from donor patients (e.g., allogeneic).

In certain embodiments, the present invention contemplates the use of the compounds described herein in combination with RNA interference-based therapies to silence gene expression. RNAi begins with the cleavage of longer double-stranded RNAs into small interfering RNAs (siRNAs). One strand of the siRNA is incorporated into a ribonucleoprotein complex known as the RNA-induced silencing complex (RISC), which is then used to identify mRNA molecules that are at least partially complementary to the incorporated siRNA strand. RISC can bind to or cleave the mRNA, both of which inhibits translation.

Immune Checkpoint Inhibitors. The present invention contemplates the use of the inhibitors of CD73 function described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); TIGIT (T cell immunoreceptor with Ig and ITIM domains); A2aR (adenosine A2a receptor A2aR); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

The present invention contemplates the use of the inhibitors of CD73 function described herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus. PD1 antibodies are under development (e.g., nivolumab (Bristol-Myers Squibb) and lambrolizumab (Merck)), and anti-PDL1 antibodies are also being evaluated (e.g., MPDL3280A (Roche)). Nivolumab has shown promise in patients with melanoma, lung and kidney cancer.

The present invention encompasses pharmaceutically acceptable salts, acids or derivatives of any of the above.

Metabolic and Cardiovascular Diseases. The present invention provides methods for treating and/or preventing certain cardiovascular- and/or metabolic-related diseases, disorders and conditions, as well as disorders associated therewith, with an CD73 inhibitor and at least one additional therapeutic or diagnostic agent.

Examples of therapeutic agents useful in combination therapy for the treatment of hypercholesterolemia (and atherosclerosis as well) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the CD73 inhibitors described herein include various supplements and herbs (e.g., garlic, policosanol, and guggul).

The present invention encompasses pharmaceutically acceptable salts, acids or derivatives of any of the above.

Immune-related Disorders and Disorders Having an Inflammatory Component. The present invention provides methods for treating and/or preventing immune-related diseases, disorders and conditions; and diseases, disorders and conditions having an inflammatory component; with an CD73 inhibitor and at least one additional therapeutic or diagnostic agent.

Examples of therapeutic agents useful in combination therapy are specific to the underlying disease, disorder or condition, and are known to the skilled artisan.

Microbial Diseases. The present invention provides methods for treating and/or preventing viral, bacterial, fungal and parasitic diseases, disorders and conditions, as well as disorders associated therewith, with an CD73 inhibitor and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddl, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with an CD73 inhibitor include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, http://en.wikipedia.org/wiki/Fusion_inhibitor ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present invention contemplates the use of the inhibitors of CD73 function described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

Embodiments of the present invention contemplate the use of the CD73 inhibitors described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of anti-bacterial agents that are appropriate for use in specific bacterial infections.

Embodiments of the present invention contemplate the use of the CD73 inhibitors described herein in combination with agents useful in the treatment or prevention of fungal disorders. Antifungal agents include polyenes (e.g., amphotericin, nystatin, and pimaricin); azoles (e.g., fluconazole, itraconazole, and ketoconazole); allylamines (e.g., naftifine, and terbinafine) and morpholines (e.g., amorolfine); and antimetabolies (e.g., 5-fluorocytosine).

The present invention encompasses pharmaceutically acceptable salts, acids or derivatives of the agents (and members of the classes of agents) set forth above.

Dosing

The CD73 inhibitors of the present invention may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the CD73 inhibitors of the present invention may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the CD73 inhibitors contemplated by the present invention may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired CD73 inhibitor is contained in a "unit dosage form". The phrase "unit dosage form" refers to physically discrete units, each unit containing a predetermined amount of the CD73 inhibitor, either alone or in combination with one or more additional agents, sufficient to produce the desired effect. It will be appreciated that the parameters of a unit dosage form will depend on the particular agent and the effect to be achieved.

Kits

The present invention also contemplates kits comprising an CD73 inhibitor, and pharmaceutical compositions thereof. The kits are generally in the form of a physical structure housing various components, as described below, and may be utilized, for example, in practicing the methods described above.

A kit can include one or more of the CD73 inhibitors disclosed herein (provided in, e.g., a sterile container), which may be in the form of a pharmaceutical composition suitable for administration to a subject. The CD73 inhibitors can be provided in a form that is ready for use (e.g., a tablet or capsule) or in a form requiring, for example, reconstitution or dilution (e.g., a powder) prior to administration. When the CD73 inhibitors are in a form that needs to be reconstituted or diluted by a user, the kit may also include diluents (e.g., sterile water), buffers, pharmaceutically acceptable excipients, and the like, packaged with or separately from the CD73 inhibitors. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for. Selected intermediates used in the Examples below can be found in the published literature, including, for example WO 2017/120508, incorporated herein by reference.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; g=microgram; mg=milligram; g=gram; kg=kilogram; dl or dL=deciliter; μl or μL=microliter; ml or mL=milliliter; l or L=liter; M=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbeco's Modification of Eagle's Medium; EDTA=ethylenediaminetetraacetic acid.

LC: Agilent 1100 series; Mass spectrometer: Agilent G6120BA, single quad
LC-MS method: Agilent Zorbax Eclipse Plus C18, 4.6×100 mm, 3.5 μM, 35° C., 1.5 mL/min flow rate, a 2.5 min gradient of 0% to 100% B with 0.5 min wash at 100% B; A=0.1% of formic acid/5% acetonitrile/94.9% water; B=0.1% of formic acid/5% water/94.9% acetonitrile
Flash column: ISCO Rf+
Reverse phase HPLC: ISCO-EZ; Column: Kinetex 5 μm EVO C18 100 A; 250×21.2 mm (Phenomenex)

Example 1

Synthesis of ({[(2R,3S,4R,5R)-5-[2-chloro-6-(cyclopentylamino)-9H-purin-9-yl]-3,4-dihydroxyoxolan-2-yl]methoxy}methyl)phosphonic acid at rt for overnight. 7M NH$_3$ in MeOH (20 mL) was added and reaction was stirred at rt for 1 day. Reaction mixture was evaporated and the crude product was used in the next step without purification. ESI MS [M+H]$^+$ for C$_{15}$H$_{21}$ClN$_5$O$_4$, calcd 370.1, found 370.2.

Step b: The product from Step a was dissolved in acetone (100 mL) and 2,2-dimethoxypropane (40 mL) and p-TsOH x H$_2$O (7.1 g, 37.5 mmol, 1.25 equiv.) was added. The reaction mixture was stirred at rt for overnight, then diluted with brine (100 mL) and carefully quenched with saturated NaHCO$_3$ (200 mL). After extraction with EtOAc (2×200 mL), combined organics were dried over MgSO$_4$, filtered and evaporated to give crude product that was used in the next step without purification (12.2 g, 98%). ESI MS [M+H]$^+$ for C$_{18}$H$_{25}$ClN$_5$O$_4$, calcd 410.2, found 410.1.

Step c: The product from Step b (410 mg, 1 mmol) was dissolved in anhydrous DMF (5 mL) and cooled to 0° C., then 60% NaH (60 mg, 1.5 mmol, 1.5 equiv.) was added and reaction mixture was stirred at 0° C. for 1 h. Diethyl p-toluenesulfonyloxy methylphosphonate (386 mg, 1.2 mmol, 1.2 equiv.) was added and reaction was slowly warmed up to rt and stirred for overnight. Diluted with H$_2$O (20 mL) and extracted with MTBE (2×10 mL), combined organics were dried over MgSO$_4$, filtered and evaporated to give crude product that was used in the next step without purification. ESI MS [M+H]$^+$ for C$_{23}$H$_{36}$ClN$_5$O$_7$P, calcd 560.2, found 560.1.

Step d: The product from Step c was dissolved in anhydrous CH$_3$CN (5 mL), TMS-Br (0.5 mL) was added and reaction was stirred at rt for overnight. Quenched with H$_2$O (1 mL) and stirred at rt for 4 h, or until LCMS analysis shows complete cleavage of the acetonide protecting group. The reaction mixture was evaporated and purified by reverse phase HPLC (C18 column, 0 to 30% gradient of acetonitrile and water with 0.1% TFA) to give the product as a white

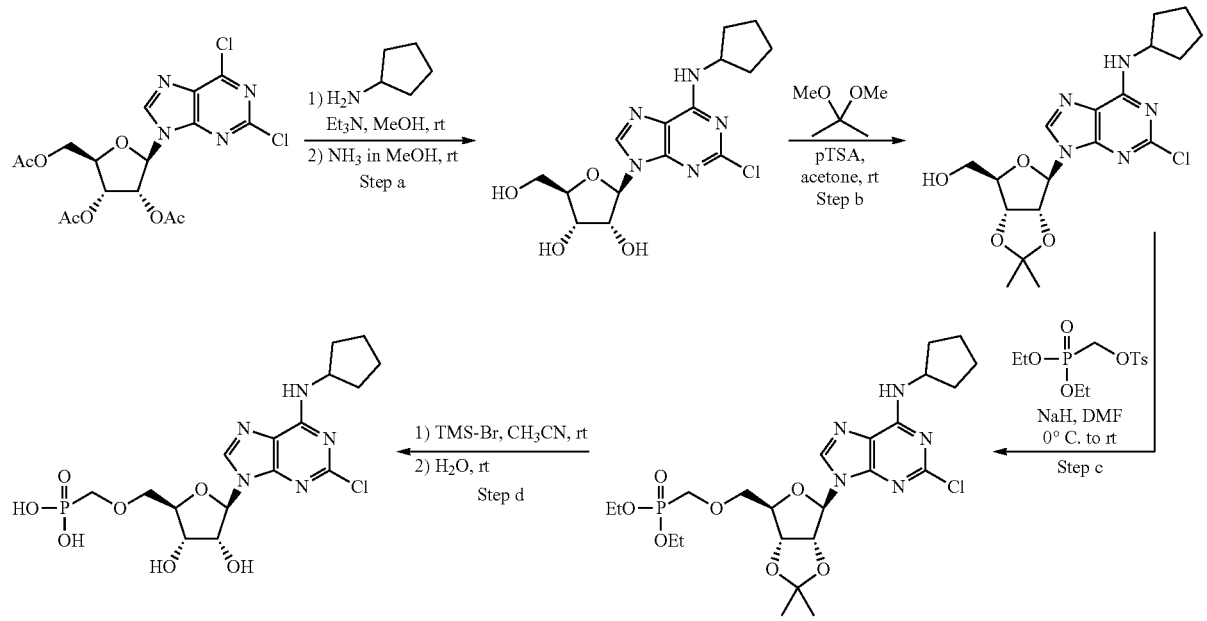

Step a: A mixture of 2,6-dichloro-9-(2,3,5-tri-O-acetyl-beta-D-ribofuranosyl)purine (13.5 g, 30 mmol), cyclopentylamine (3.2 mL, 33 mmol, 1.1 equiv.), and triethylamine (4.6 mL, 33 mmol, 1.1 equiv.) in MeOH (60 mL) was stirred solid in 18.5% yield (107 mg): $^1$H NMR (400 MHz, DMSO-d$_6$) δ 8.41 (s, 1H), 8.39-8.26 (m, 1H), 5.84 (d, J=5.9 Hz, 1H), 4.53 (t, J=5.5 Hz, 1H), 4.48-4.35 (m, 1H), 4.12 (dd, J=4.9, 3.3 Hz, 1H), 4.05 (q, J=3.8 Hz, 1H), 3.79-3.65 (m, 2H), 3.62

(d, J=8.9 Hz, 2H), 2.05-1.85 (m, 2H), 1.78-1.44 (m, 6H). ESI MS [M+H]$^+$ for C$_{16}$H$_{24}$ClN$_5$O$_7$P, calcd 464.1, found 464.2.

Example 2

Synthesis of ({[(2R,3S,4R,5R)-5-[6-(benzylamino)-9H-purin-9-yl]-3,4-dihydroxyoxolan-2-yl]methoxy}methyl)phosphonic acid

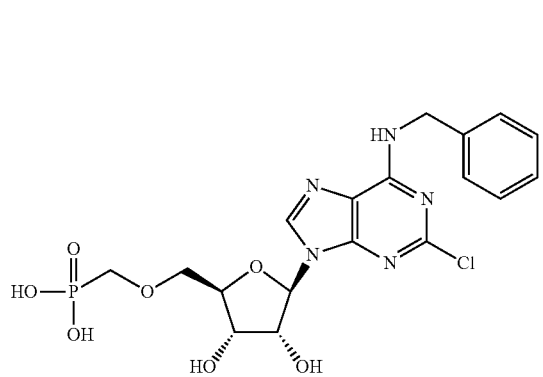 [SMILES: O=P(O)(O)COC[C@H]1O[C@@H](n2cnc3c(NCc4ccccc4)nc(Cl)nc32)[C@H](O)[C@@H]1O]

The title compound was synthesized in similar fashion to example 1: $^1$H NMR (400 MHz, DMSO-d$_6$) δ 8.65 (s, 1H), 8.47 (s, 1H), 8.26 (s, 1H), 7.40-7.18 (m, 5H), 5.94 (d, J=5.8 Hz, 1H), 4.72 (s, 2H), 4.60 (t, J=5.4 Hz, 1H), 4.15 (t, J=4.2 Hz, 1H), 4.05 (q, J=3.9 Hz, 1H), 3.78-3.64 (m, 2H), 3.61 (d, J=8.8 Hz, 2H). ESI MS [M+H]$^+$ for C$_{18}$H$_{23}$N$_5$O$_7$P, calcd 452.1, found 452.2.

Example 3

Synthesis of ({[(2R,3S,4R,5R)-5-[6-(benzylamino)-2-chloro-9H-purin-9-yl]-3,4-dihydroxyoxolan-2-yl]methoxy}methyl)phosphonic acid

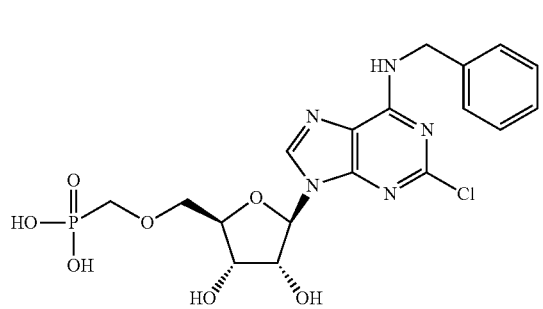 [SMILES: O=P(O)(O)COC[C@H]1O[C@@H](n2cnc3c(NCc4ccccc4)nc(Cl)nc32)[C@H](O)[C@@H]1O]

The title compound was synthesized in similar fashion to example 1: $^1$H NMR (400 MHz, DMSO-d$_6$) δ 8.93 (t, J=6.2 Hz, 1H), 8.44 (s, 1H), 7.37-7.22 (m, 5H), 5.85 (d, J=6.0 Hz, 1H), 4.68-4.61 (m, 2H), 4.54 (t, J=5.5 Hz, 1H), 4.15-4.09 (m, 1H), 4.05 (q, J=3.8 Hz, 1H), 3.77-3.65 (m, 2H), 3.61 (d, J=8.9 Hz, 2H). ESI MS [M+H]$^+$ for C$_{18}$H$_{22}$ClN$_5$O$_7$P, calcd 486.1, found 486.2.

Example 4

Synthesis of ({[(2R,3S,4R,5R)-5-{2-chloro-6-[cyclopentyl(methyl)amino]-9H-purin-9-yl}-3,4-dihydroxyoxolan-2-yl]methoxy}methyl)phosphonic acid

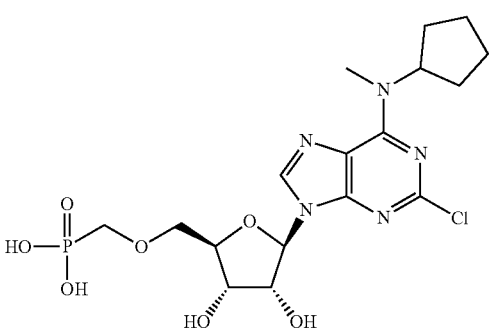 [SMILES: CN(c1nc(Cl)nc2c1ncn2[C@@H]1O[C@H](COCP(=O)(O)O)[C@@H](O)[C@H]1O)C1CCCC1]

The title compound was synthesized in similar fashion to example 1: $^1$H NMR (400 MHz, DMSO-d$_6$) δ 8.36 (s, 1H), 5.81 (d, J=6.1 Hz, 1H), 4.48-4.43 (m, 1H), 4.07-4.02 (m, 1H), 3.98 (q, J=3.6 Hz, 1H), 3.69-3.59 (m, 2H), 3.55 (d, J=8.8 Hz, 2H), 3.42-2.76 (m, 3H), 1.91-1.39 (m, 8H). ESI MS [M+H]$^+$ for C$_{17}$H$_{26}$ClN$_5$O$_7$P, calcd 478.1, found 478.2.

Example 5

Synthesis of ({[(2R,3S,4R,5R)-5-(2-chloro-6-{[(2-chlorophenyl)methyl]amino}-9H-purin-9-yl)-3,4-dihydroxyoxolan-2-yl]methoxy}methyl)phosphonic acid

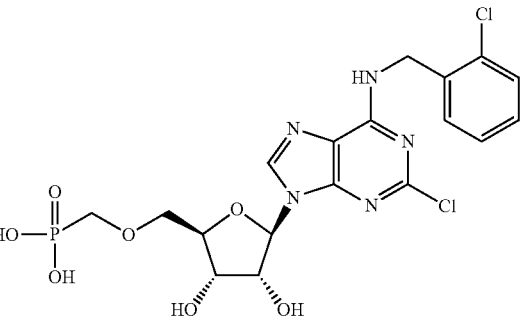

The title compound was synthesized in similar fashion to example 1: $^1$H NMR (400 MHz, DMSO-d$_6$) δ 8.97-8.90 (m, 1H), 8.49 (s, 1H), 7.50-7.43 (m, 1H), 7.33-7.25 (m, 3H), 5.87 (d, J=6.0 Hz, 1H), 4.75-4.67 (m, 2H), 4.56 (t, J=5.5 Hz, 1H), 4.16-4.02 (m, 2H), 3.78-3.65 (m, 2H), 3.62 (d, J=8.9 Hz, 2H). ESI MS [M+H]$^+$ for C$_{18}$H$_{21}$Cl$_2$N$_5$O$_7$P, calcd 520.1, found 520.1.

Example 6

Synthesis of ({[(2R,3S,4R,5R)-5-(2-chloro-6-{[(2-chlorophenyl)methyl](methyl)amino}-9H-purin-9-yl)-3,4-dihydroxyoxolan-2-yl]methoxy}methyl)phosphonic acid

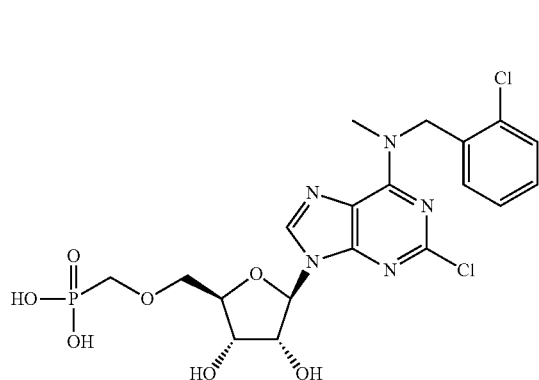 [SMILES: CN(Cc1ccccc1Cl)c1nc(Cl)nc2c1ncn2[C@@H]1O[C@H](COCP(=O)(O)O)[C@@H](O)[C@H]1O]

The title compound was synthesized in similar fashion to example 1: $^1$H NMR (400 MHz, DMSO-d$_6$) δ 8.56-8.33 (m, 1H), 7.54-7.48 (m, 1H), 7.36-7.27 (m, 2H), 7.23-7.08 (m, 1H), 5.88 (d, J=6.1 Hz, 1H), 5.63 (s, 1H), 5.00 (s, 1H), 4.54 (s, 1H), 4.15-4.01 (m, 2H), 3.78-3.55 (m, 5H), 3.17 (s, 2H). ESI MS [M+H]$^+$ for C$_{19}$H$_{23}$Cl$_2$N$_5$O$_7$P, calcd 534.1, found 534.1.

Example 7

Synthesis of ({[(2R,3S,4R,5R)-5-(2-chloro-6-{[(3S)-oxolan-3-yl]amino}-9H-purin-9-yl)-3,4-dihydroxyoxolan-2-yl]methoxy}methyl)phosphonic acid

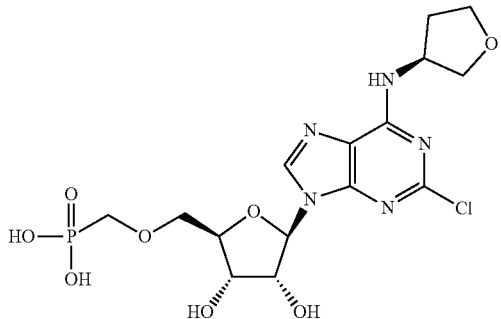 [SMILES: O=P(O)(O)COC[C@H]1O[C@@H](n2cnc3c(N[C@H]4CCOC4)nc(Cl)nc32)[C@H](O)[C@@H]1O]

The title compound was synthesized in similar fashion to example 1: $^1$H NMR (400 MHz, DMSO-d$_6$) δ 8.64-8.52 (m, 1H), 8.46 (s, 1H), 5.86 (d, J=6.0 Hz, 1H), 4.63 (s, 1H), 4.54 (t, J=5.5 Hz, 1H), 4.12 (dd, J=4.9, 3.3 Hz, 1H), 4.05 (q, J=3.8 Hz, 1H), 3.96-3.83 (m, 2H), 3.78-3.66 (m, 3H), 3.64-3.59 (m, 3H), 2.27-1.88 (m, 2H). ESI MS [M+H]$^+$ for C$_{15}$H$_{22}$ClN$_5$O$_8$P, calcd 466.1, found 466.1.

Example 8

Synthesis of ({[(2R,3S,4R,5R)-5-(2-chloro-6-{[(3R)-oxolan-3-yl]amino}-9H-purin-9-yl)-3,4-dihydroxyoxolan-2-yl]methoxy}methyl)phosphonic acid

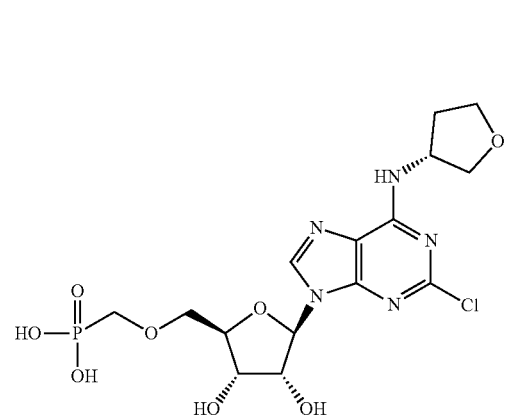 [SMILES: O=P(O)(O)COC[C@H]1O[C@@H](n2cnc3c(N[C@@H]4CCOC4)nc(Cl)nc32)[C@H](O)[C@@H]1O]

The title compound was synthesized in similar fashion to example 1: $^1$H NMR (400 MHz, DMSO-d$_6$) δ 8.63-8.51 (m, 1H), 8.45 (s, 1H), 5.86 (d, J=6.0 Hz, 1H), 4.63 (s, 1H), 4.57-4.51 (m, 1H), 4.12 (dd, J=4.9, 3.3 Hz, 1H), 4.05 (q, J=3.7 Hz, 1H), 3.96-3.83 (m, 2H), 3.79-3.66 (m, 3H), 3.62 (d, J=8.9 Hz, 3H), 2.29-1.83 (m, 2H). ESI MS [M+H]$^+$ for C$_{15}$H$_{22}$ClN$_5$O$_8$P, calcd 466.1, found 466.1.

Example 9

Synthesis of ({[(2R,3S,4R,5R)-5-{2-chloro-6-[(propan-2-yl)amino]-9H-purin-9-yl}-3,4-dihydroxyoxolan-2-yl]methoxy}methyl)phosphonic acid

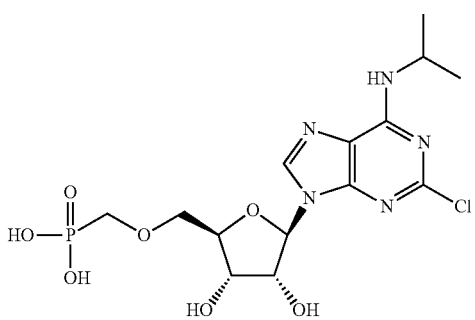 [SMILES: CC(C)Nc1nc(Cl)nc2c1ncn2[C@@H]1O[C@H](COCP(=O)(O)O)[C@@H](O)[C@H]1O]

The title compound was synthesized in similar fashion to example 1: $^1$H NMR (400 MHz, DMSO-d$_6$) δ 8.67 (s, 1H), 8.21-8.09 (m, 1H), 5.79 (d, J=7.1 Hz, 1H), 4.23 (dd, J=4.8, 1.9 Hz, 1H), 4.02 (s, 1H), 3.66-3.50 (m, 3H), 3.42-3.19 (m, 3H), 1.21 (dd, J=6.5, 2.1 Hz, 6H). ESI MS [M+H]$^+$ for C$_{14}$H$_{22}$ClN$_5$O$_7$P, calcd 438.1, found 438.1.

Example 10

Synthesis of ({[(2R,3S,4R,5R)-5-{2-chloro-6-[(2,2-dimethylpropyl)amino]-9H-purin-9-yl}-3,4-dihydroxyoxolan-2-yl]methoxy}methyl)phosphonic acid

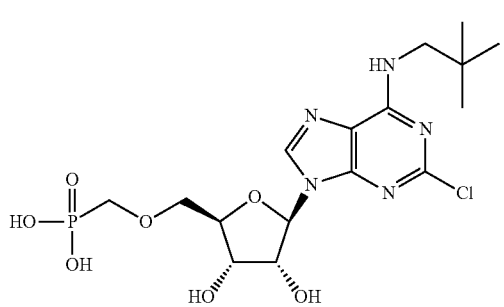 [SMILES: CC(C)(C)CNc1nc(Cl)nc2c1ncn2[C@@H]1O[C@H](COCP(=O)(O)O)[C@@H](O)[C@H]1O]

The title compound was synthesized in similar fashion to example 1: H NMR (400 MHz, DMSO-$d_6$) δ 8.44 (s, 1H), 8.30 (t, J=6.5 Hz, 1H), 5.84 (d, J=6.0 Hz, 1H), 4.54 (t, J=5.5 Hz, 1H), 4.15-4.08 (m, 1H), 4.07-4.03 (m, 1H), 3.82 (d, J=7.0 Hz, 1H), 3.77-3.66 (m, 2H), 3.61 (dd, J=8.9, 1.4 Hz, 2H), 3.38-3.21 (m, 1H), 0.91 (s, 9H). ESI MS [M+H]$^+$ for $C_{16}H_{26}ClN_5O_7P$, calcd 466.1, found 466.2.

Example 11

Synthesis of ({[(2R,3S,4R,5R)-5-{2-chloro-6-[(cyclopropylmethyl)amino]-9H-purin-9-yl}-3,4-dihydroxyoxolan-2-yl]methoxy}methyl)phosphonic acid

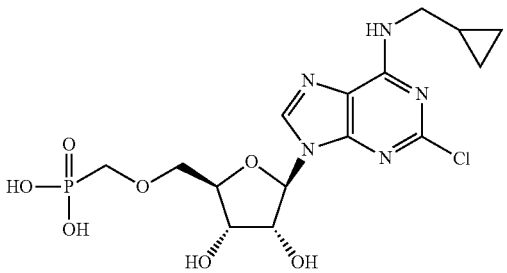 [SMILES: O=P(O)(O)COC[C@H]1O[C@@H](n2cnc3c(NCC4CC4)nc(Cl)nc32)[C@H](O)[C@@H]1O]

The title compound was synthesized in similar fashion to example 1: $^1$H NMR (400 MHz, DMSO-$d_6$) δ 8.49 (t, J=5.8 Hz, 1H), 8.43 (s, 1H), 5.84 (d, J=5.9 Hz, 1H), 4.54 (dd, J=6.1, 4.9 Hz, 1H), 4.15-4.09 (m, 1H), 4.05 (q, J=3.8 Hz, 1H), 3.78-3.66 (m, 2H), 3.62 (dd, J=8.9, 1.2 Hz, 2H), 3.33-3.27 (m, 2H), 1.17-1.06 (m, 1H), 0.46-0.39 (m, 2H), 0.31-0.24 (m, 2H). ESI MS [M+H]$^+$ for $C_{15}H_{22}ClN_5O_7P$, calcd 450.1, found 450.1.

Example 12

Synthesis of ({[(2R,3S,4R,5R)-5-[2-chloro-6-(cyclobutylamino)-9H-purin-9-yl]-3,4-dihydroxyoxolan-2-yl]methoxy}methyl)phosphonic acid

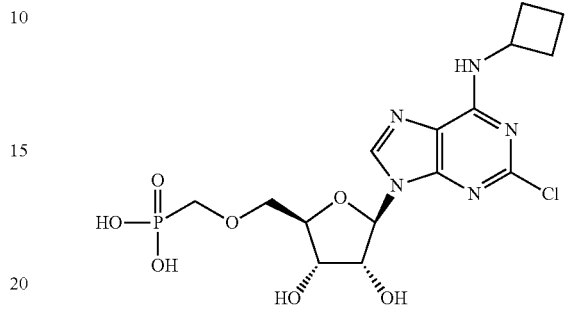

The title compound was synthesized in similar fashion to example 1: $^1$H NMR (400 MHz, DMSO-$d_6$) δ 8.67 (d, J=7.7 Hz, 1H), 8.43 (s, 1H), 5.84 (d, J=5.9 Hz, 1H), 4.61 (q, J=8.1 Hz, 1H), 4.56-4.50 (m, 1H), 4.15-4.09 (m, 1H), 4.05 (q, J=3.7 Hz, 1H), 3.78-3.65 (m, 2H), 3.61 (d, J=8.8 Hz, 2H), 2.35-2.00 (m, 4H), 1.74-1.61 (m, 2H). ESI MS [M+H]$^+$ for $C_{15}H_{22}ClN_5O_7P$, calcd 450.1, found 450.1.

Example 13

Synthesis of ({[(2R,3S,4R,5R)-5-[2-chloro-6-(pyrrolidin-1-yl)-9H-purin-9-yl]-3,4-dihydroxyoxolan-2-yl]methoxy}methyl)phosphonic acid

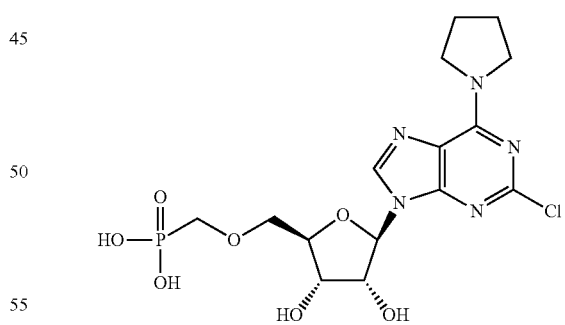

The title compound was synthesized in similar fashion to example 1: $^1$H NMR (400 MHz, DMSO-$d_6$) δ 8.41 (s, 1H), 5.86 (d, J=6.1 Hz, 1H), 4.53 (dd, J=6.2, 4.9 Hz, 1H), 4.11 (dd, J=4.9, 3.2 Hz, 1H), 4.09-4.00 (m, 3H), 3.76-3.65 (m, 2H), 3.65-3.56 (m, 4H), 2.05-1.86 (m, 4H). ESI MS [M+H]$^+$ for $C_{15}H_{22}ClN_5O_7P$, calcd 450.1, found 450.2.

Example 14

Synthesis of ({[(2R,3S,4R,5R)-5-[2-chloro-6-(piperidin-1-yl)-9H-purin-9-yl]-3,4-dihydroxyoxolan-2-yl]methoxy}methyl)phosphonic acid

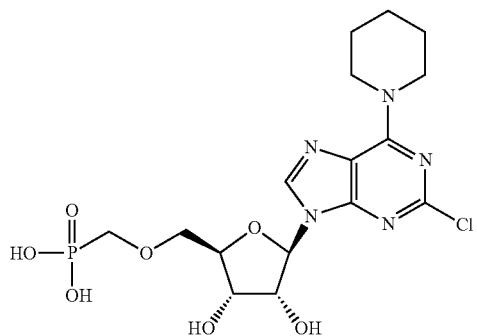 [SMILES: O=P(O)(O)COC[C@H]1O[C@@H](n2cnc3c(N4CCCCC4)nc(Cl)nc32)[C@H](O)[C@@H]1O]

The title compound was synthesized in similar fashion to example 1: $^1$H NMR (400 MHz, DMSO-d$_6$) δ 8.44 (s, 1H), 5.87 (d, J=6.1 Hz, 1H), 4.53 (dd, J=6.1, 4.9 Hz, 1H), 4.11 (dd, J=4.9, 3.2 Hz, 1H), 4.05 (q, J=3.6 Hz, 1H), 3.76-3.65 (m, 2H), 3.61 (dd, J=8.9, 1.0 Hz, 2H), 1.72-1.54 (m, 5H). ESI MS [M+H]$^+$ for C$_{16}$H$_{24}$ClN$_5$O$_7$P, calcd 464.1, found 464.2.

Example 15

Synthesis of ({[(2R,3S,4R,5R)-5-[2-chloro-6-(morpholin-4-yl)-9H-purin-9-yl]-3,4-dihydroxyoxolan-2-yl]methoxy}methyl)phosphonic acid

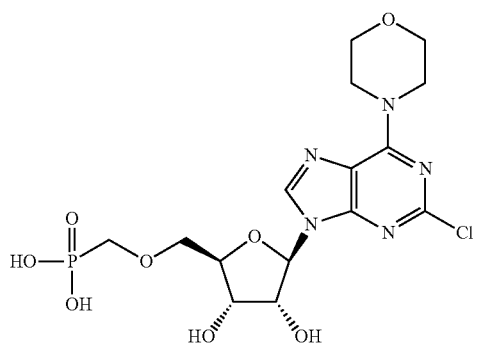 [SMILES: O=P(O)(O)COC[C@H]1O[C@@H](n2cnc3c(N4CCOCC4)nc(Cl)nc32)[C@H](O)[C@@H]1O]

The title compound was synthesized in similar fashion to example 1: $^1$H NMR (400 MHz, DMSO-d$_6$) δ 8.77 (s, 1H), 5.82 (d, J=7.5 Hz, 1H), 5.14 (dd, J=7.5, 4.7 Hz, 1H), 4.27-4.21 (m, 1H), 4.05-4.00 (m, 1H), 3.78-3.66 (m, 4H), 3.61-3.48 (m, 2H), 3.35 (dd, J=12.1, 7.6 Hz, 1H), 3.27-3.15 (m, 1H). ESI MS [M+H]$^+$ for C$_{15}$H$_{22}$ClN$_5$O$_8$P, calcd 466.1, found 466.1.

Example 16

Synthesis of ({[(2R,3S,4R,5R)-5-[2-chloro-6-(4-methoxypiperidin-1-yl)-9H-purin-9-yl]-3,4-dihydroxyoxolan-2-yl]methoxy}methyl)phosphonic acid

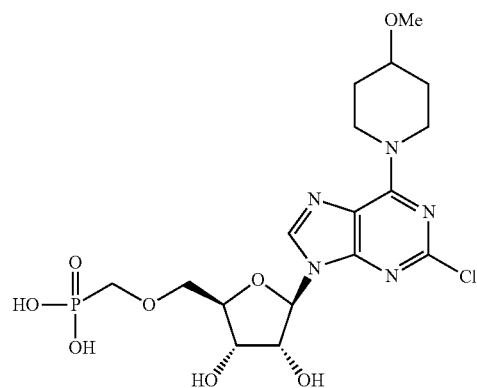 [SMILES: COC1CCN(c2nc(Cl)nc3c2ncn3[C@@H]2O[C@H](COCP(=O)(O)O)[C@@H](O)[C@H]2O)CC1]

The title compound was synthesized in similar fashion to example 1: $^1$H NMR (400 MHz, DMSO-d$_6$) δ 8.46 (s, 1H), 5.87 (d, J=6.1 Hz, 1H), 4.53 (dd, J=6.1, 4.9 Hz, 1H), 4.11 (dd, J=4.9, 3.2 Hz, 1H), 4.05 (q, J=3.6 Hz, 1H), 3.77-3.64 (m, 2H), 3.61 (dd, J=8.9, 1.2 Hz, 2H), 3.56-3.45 (m, 1H), 3.29 (s, 3H), 1.94 (dd, J=8.1, 4.8 Hz, 2H), 1.57-1.45 (m, 2H). ESI MS [M+H]$^+$ for C$_{17}$H$_{26}$ClN$_5$O$_8$P, calcd 494.1, found 494.2.

Example 17

Synthesis of ({[(2R,3S,4R,5R)-5-{2-chloro-6-[(2-methoxyethyl)amino]-9H-purin-9-yl}-3,4-dihydroxyoxolan-2-yl]methoxy}methyl)phosphonic acid

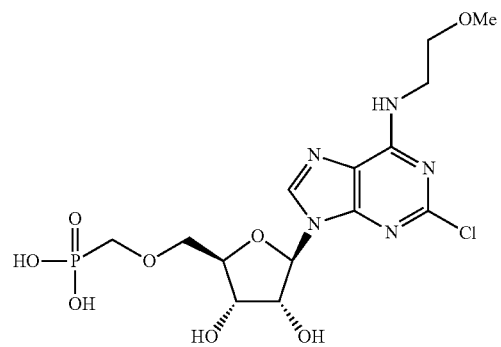 [SMILES: COCCNc1nc(Cl)nc2c1ncn2[C@@H]1O[C@H](COCP(=O)(O)O)[C@@H](O)[C@H]1O]

The title compound was synthesized in similar fashion to example 1: $^1$H NMR (400 MHz, DMSO-d$_6$) δ 8.70 (s, 1H), 8.49-8.12 (m, 1H), 5.79 (d, J=7.1 Hz, 1H), 5.03 (s, 1H), 4.24 (dd, J=4.7, 1.9 Hz, 1H), 4.03 (s, 1H), 3.69-3.46 (m, 4H), 3.42-3.18 (m, 4H). ESI MS [M+H]$^+$ for C$_{14}$H$_{22}$ClN$_5$O$_8$P, calcd 454.1, found 454.2.

Example 18

Synthesis of ({[(2R,3S,4R,5R)-5-(2-chloro-6-{[(1S)-1-phenylethyl]amino}-9H-purin-9-yl)-3,4-dihydroxyoxolan-2-yl]methoxy}methyl)phosphonic acid

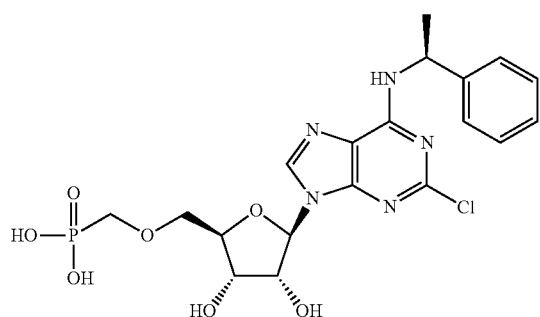 [SMILES: C[C@H](Nc1nc(Cl)nc2c1ncn2[C@@H]1O[C@H](COCP(=O)(O)O)[C@@H](O)[C@H]1O)c1ccccc1]

The title compound was synthesized in similar fashion to example 1: $^1$H NMR (400 MHz, DMSO-d$_6$) δ 8.89 (d, J=8.4 Hz, 1H), 8.45 (s, 1H), 7.43 (d, J=7.5 Hz, 2H), 7.31 (t, J=7.6 Hz, 2H), 7.21 (t, J=7.3 Hz, 1H), 5.84 (d, J=6.0 Hz, 1H), 5.41 (p, J=7.6 Hz, 1H), 4.51 (t, J=5.4 Hz, 1H), 4.15-4.08 (m, 1H), 4.07-4.01 (m, 1H), 3.78-3.65 (m, 2H), 3.61 (d, J=9.0 Hz, 2H), 1.54 (d, J=7.0 Hz, 3H). ESI MS [M+H]$^+$ for C$_{19}$H$_{24}$ClN$_5$O$_7$P, calcd 500.1, found 500.2.

Example 19

Synthesis of ({[(2R,3S,4R,5R)-5-(2-chloro-6-{[(1R)-1-phenylethyl]amino}-9H-purin-9-yl)-3,4-dihydroxyoxolan-2-yl]methoxy}methyl)phosphonic acid

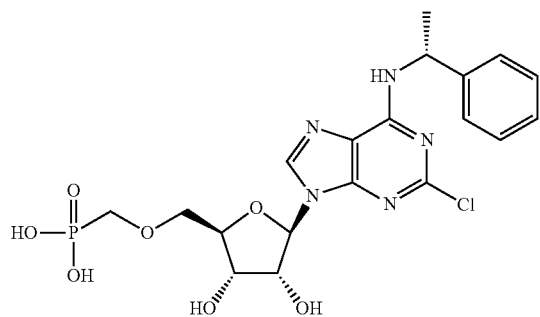 [SMILES: C[C@@H](Nc1nc(Cl)nc2c1ncn2[C@@H]1O[C@H](COCP(=O)(O)O)[C@@H](O)[C@H]1O)c1ccccc1]

The title compound was synthesized in similar fashion to example 1: $^1$H NMR (400 MHz, DMSO-d$_6$) δ 8.89 (d, J=8.4 Hz, 1H), 8.46 (s, 1H), 7.44 (d, J=7.4 Hz, 2H), 7.31 (t, J=7.6 Hz, 2H), 7.21 (t, J=7.2 Hz, 1H), 5.84 (d, J=6.1 Hz, 1H), 5.41 (p, J=7.6 Hz, 1H), 4.54 (t, J=5.5 Hz, 1H), 4.15-4.07 (m, 1H), 4.07-4.01 (m, 1H), 3.77-3.65 (m, 2H), 3.61 (dd, J=8.9, 1.8 Hz, 2H), 1.54 (d, J=6.9 Hz, 3H). ESI MS [M+H]$^+$ for C$_{19}$H$_{24}$ClN$_5$O$_7$P, calcd 500.1, found 500.2.

Example 20

Synthesis of ({[(2R,3S,4R,5R)-5-[2-chloro-6-(2,3-dihydro-1H-isoindol-2-yl)-9H-purin-9-yl]-3,4-dihydroxyoxolan-2-yl]methoxy}methyl)phosphonic acid

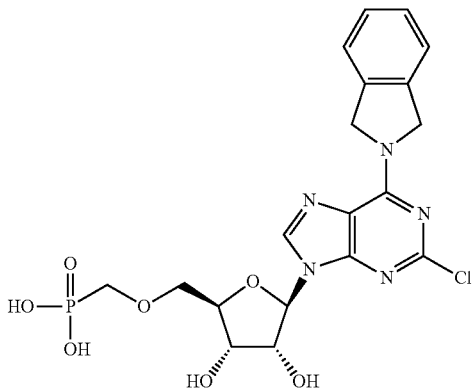 [SMILES: O=P(O)(O)COC[C@H]1O[C@@H](n2cnc3c(N4Cc5ccccc5C4)nc(Cl)nc32)[C@H](O)[C@@H]1O]

The title compound was synthesized in similar fashion to example 1: $^1$H NMR (400 MHz, DMSO-d$_6$) δ 8.52 (s, 1H), 7.54-7.43 (m, 2H), 7.41-7.32 (m, 2H), 5.91 (d, J=6.2 Hz, 1H), 5.41 (s, 2H), 4.98 (s, 2H), 4.61-4.55 (m, 1H), 4.14 (dd, J=4.9, 3.1 Hz, 1H), 4.07 (q, J=3.5 Hz, 1H), 3.80-3.67 (m, 2H), 3.63 (d, J=8.9 Hz, 2H). ESI MS [M+H]$^+$ for C$_{19}$H$_{22}$ClN$_5$O$_7$P, calcd 498.1, found 498.1.

Example 21

Synthesis of ({[(2R,3S,4R,5R)-5-{2-chloro-6-[(2-phenylethyl)amino]-9H-purin-9-yl}-3,4-dihydroxyoxolan-2-yl]methoxy}methyl)phosphonic acid

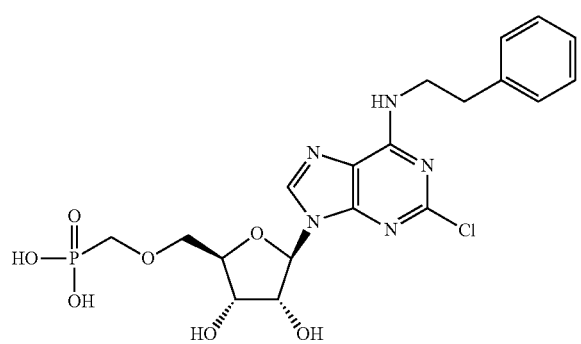 [SMILES: O=P(O)(O)COC[C@H]1O[C@@H](n2cnc3c(NCCc4ccccc4)nc(Cl)nc32)[C@H](O)[C@@H]1O]

The title compound was synthesized in similar fashion to example 1: $^1$H NMR (400 MHz, DMSO-d$_6$) δ 8.50-8.33 (m, 2H), 7.33-7.17 (m, 5H), 5.84 (d, J=6.1 Hz, 1H), 4.54 (t, J=5.5 Hz, 1H), 4.12 (dd, J=4.9, 3.2 Hz, 1H), 4.05 (q, J=3.7 Hz, 1H), 3.79-3.57 (m, 6H), 2.92 (t, J=7.4 Hz, 2H). ESI MS [M+H]$^+$ for C$_{19}$H$_{24}$ClN$_5$O$_7$P, calcd 500.1, found 500.2.

Example 22

Synthesis of ({[(2R,3S,4R,5R)-5-(2-chloro-6-{[2-(2-fluorophenyl)ethyl]amino}-9H-purin-9-yl)-3,4-dihydroxyoxolan-2-yl]methoxy}methyl)phosphonic acid

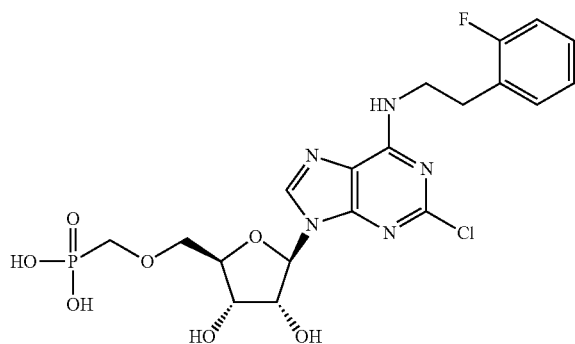

The title compound was synthesized in similar fashion to example 1: $^1$H NMR (400 MHz, DMSO-d$_6$) δ 8.54-8.39 (m, 2H), 7.33-7.07 (m, 5H), 5.84 (d, J=6.1 Hz, 1H), 4.57-4.52 (m, 1H), 4.12 (dd, J=4.9, 3.2 Hz, 1H), 4.05 (q, J=3.8 Hz, 1H), 3.77-3.57 (m, 6H), 2.96 (t, J=7.2 Hz, 2H). ESI MS [M+H]$^+$ for C$_{19}$H$_{23}$ClFN$_5$O$_7$P, calcd 518.1, found 518.2.

Example 23

Synthesis of ({[(2R,3S,4R,5R)-5-(2-chloro-6-{[2-(2-methoxyphenyl)ethyl]amino}-9H-purin-9-yl)-3,4-dihydroxyoxolan-2-yl]methoxy}methyl)phosphonic acid

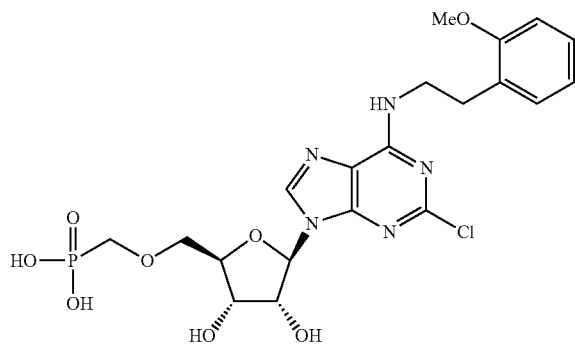 [SMILES: COc1ccccc1CCNc1nc(Cl)nc2c1ncn2[C@@H]1O[C@H](COCP(=O)(O)O)[C@@H](O)[C@H]1O]

The title compound was synthesized in similar fashion to example 1: H NMR (400 MHz, DMSO-d$_6$) δ 8.46-8.33 (m, 2H), 7.22-7.11 (m, 2H), 6.96 (d, J=8.2 Hz, 1H), 6.84 (t, J=7.4 Hz, 1H), 5.84 (d, J=6.1 Hz, 1H), 4.57-4.51 (m, 1H), 4.12 (dd, J=4.9, 3.2 Hz, 1H), 4.05 (q, J=3.7 Hz, 1H), 3.82-3.56 (m, 9H), 2.89 (t, J=7.3 Hz, 2H). ESI MS [M+H]$^+$ for C$_{20}$H$_{26}$ClN$_5$O$_8$P, calcd 530.1, found 530.2.

Example 24

Synthesis of ({[(2R,3S,4R,5R)-5-(2-chloro-6-{[2-(2-chlorophenyl)ethyl]amino}-9H-purin-9-yl)-3,4-dihydroxyoxolan-2-yl]methoxy}methyl)phosphonic acid

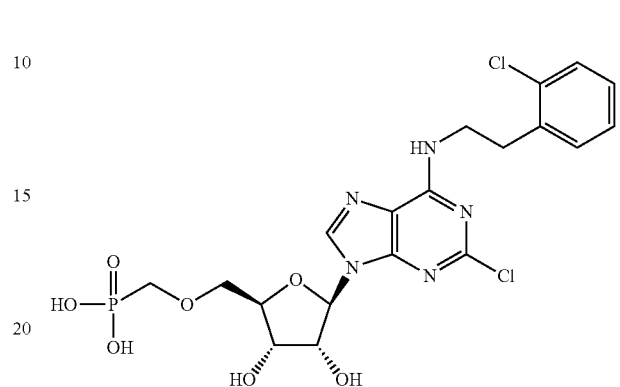

The title compound was synthesized in similar fashion to example 1: $^1$H NMR (400 MHz, DMSO-d$_6$) δ 8.54-8.39 (m, 2H), 7.45-7.40 (m, 1H), 7.36-7.32 (m, 1H), 7.29-7.22 (m, 2H), 5.84 (d, J=6.1 Hz, 1H), 4.54 (dd, J=6.1, 4.9 Hz, 1H), 4.12 (dd, J=4.9, 3.2 Hz, 1H), 4.05 (q, J=3.7 Hz, 1H), 3.77-3.57 (m, 6H), 3.08-3.03 (m, 2H). ESI MS [M+H]$^+$ for C$_{19}$H$_{23}$Cl$_2$N$_5$O$_7$P, calcd 534.1, found 534.2.

Example 25

Synthesis of ({[(2R,3S,4R,5R)-5-[2-chloro-6-(cyclopropylamino)-9H-purin-9-yl]-3,4-dihydroxyoxolan-2-yl]methoxy}methyl)phosphonic acid

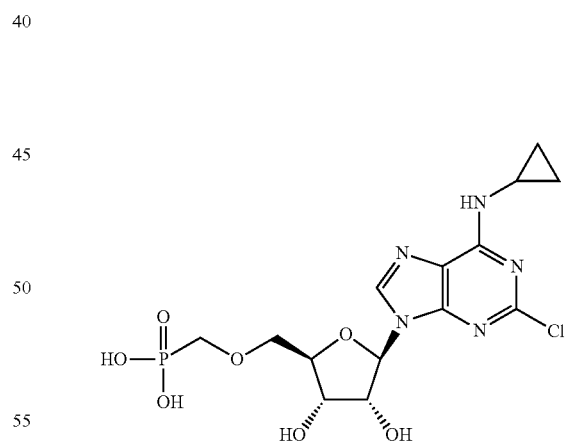

The title compound was synthesized in similar fashion to example 1: $^1$H NMR (400 MHz, DMSO-d$_6$) δ 8.53 (s, 1H), 8.42 (s, 1H), 5.85 (d, J=6.0 Hz, 1H), 4.54 (t, J=5.5 Hz, 1H), 4.12 (dd, J=4.9, 3.2 Hz, 1H), 4.05 (q, J=3.7 Hz, 1H), 3.77-3.65 (m, 2H), 3.61 (dd, J=8.9, 1.4 Hz, 2H), 2.97 (s, 1H), 0.84-0.56 (m, 4H). ESI MS [M+H]$^+$ for C$_{14}$H$_{20}$ClN$_5$O$_7$P, calcd 436.1, found 436.1.

Example 26

Synthesis of ({[(2R,3S,4R,5R)-5-{2-chloro-6-[(pyridin-2-ylmethyl)amino]-9H-purin-9-yl}-3,4-dihydroxyoxolan-2-yl]methoxy}methyl)phosphonic acid

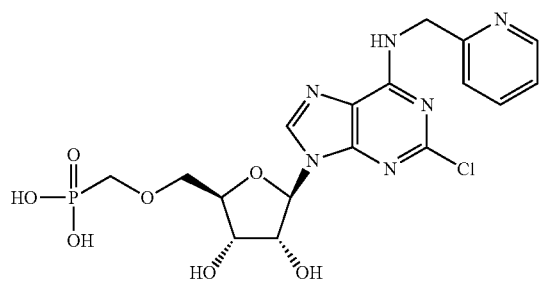 [SMILES: O=P(O)(O)COC[C@H]1O[C@@H](n2cnc3c(NCc4ccccn4)nc(Cl)nc32)[C@H](O)[C@@H]1O]

The title compound was synthesized in similar fashion to example 1: $^1$H NMR (400 MHz, DMSO-$d_6$) δ 9.05 (t, J=6.2 Hz, 1H), 8.82-8.78 (m, 1H), 8.72-8.68 (m, 1H), 8.49 (s, 1H), 8.26 (d, J=8.1 Hz, 1H), 7.83-7.76 (m, 1H), 5.86 (d, J=6.1 Hz, 1H), 4.78 (d, J=6.0 Hz, 2H), 4.54 (dd, J=6.1, 4.9 Hz, 1H), 4.12 (dd, J=4.9, 3.2 Hz, 1H), 4.05 (q, J=3.7 Hz, 1H), 3.77-3.66 (m, 2H), 3.61 (dd, J=8.9, 1.5 Hz, 2H). ESI MS [M+H]$^+$ for $C_{17}H_{21}ClN_6O_7P$, calcd 487.1, found 487.1.

Example 27

Synthesis of ({[(2R,3S,4R,5R)-5-{2-chloro-6-[(pyridin-3-ylmethyl)amino]-9H-purin-9-yl}-3,4-dihydroxyoxolan-2-yl]methoxy}methyl)phosphonic acid

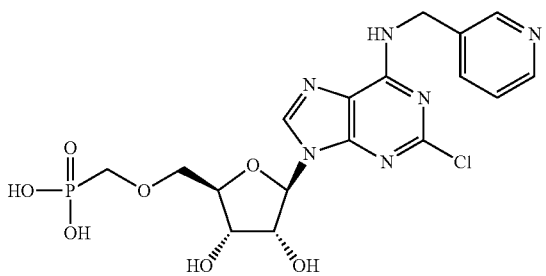 [SMILES: O=P(O)(O)COC[C@H]1O[C@@H](n2cnc3c(NCc4cccnc4)nc(Cl)nc32)[C@H](O)[C@@H]1O]

The title compound was synthesized in similar fashion to example 1: $^1$H NMR (400 MHz, DMSO-$d_6$) δ 9.06 (t, J=6.1 Hz, 1H), 8.84 (s, 1H), 8.74 (d, J=5.5 Hz, 1H), 8.50 (s, 1H), 8.33 (d, J=8.0 Hz, 1H), 7.89-7.83 (m, 1H), 5.86 (d, J=6.1 Hz, 1H), 4.80 (d, J=6.1 Hz, 2H), 4.55 (t, J=6.1 Hz, 1H), 4.15-4.10 (m, 1H), 4.06 (q, J=3.7 Hz, 1H), 3.77-3.65 (m, 2H), 3.62 (dd, J=9.0, 1.5 Hz, 2H). ESI MS [M+H]$^+$ for $C_{17}H_{21}ClN_6O_7P$, calcd 487.1, found 487.2.

Example 28

Synthesis of ({[(2R,3S,4R,5R)-5-{2-chloro-6-[(pyridin-4-ylmethyl)amino]-9H-purin-9-yl}-3,4-dihydroxyoxolan-2-yl]methoxy}methyl)phosphonic acid

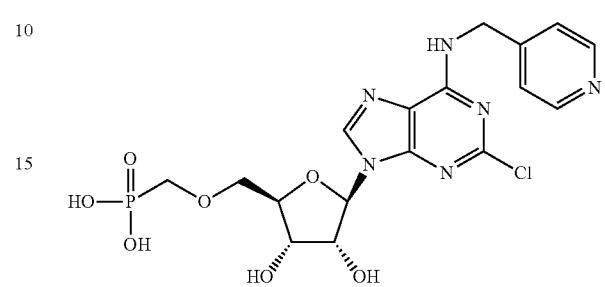

The title compound was synthesized in similar fashion to example 1: $^1$H NMR (400 MHz, DMSO-$d_6$) δ 9.15 (t, J=6.1 Hz, 1H), 8.78 (d, J=6.7 Hz, 2H), 8.54 (s, 1H), 7.85 (d, J=6.7 Hz, 2H), 5.87 (d, J=6.1 Hz, 1H), 4.88 (d, J=6.1 Hz, 2H), 4.57 (t, J=5.5 Hz, 1H), 4.16-4.02 (m, 2H), 3.78-3.66 (m, 2H), 3.65-3.59 (m, 2H). ESI MS [M+H]$^+$ for $C_{17}H_{21}ClN_6O_7P$, calcd 487.1, found 487.1.

Example 29

Synthesis of ({[(2R,3S,4R,5R)-5-{2-chloro-6-[(1-methylcyclopentyl)amino]-9H-purin-9-yl}-3,4-dihydroxyoxolan-2-yl]methoxy}methyl)phosphonic acid

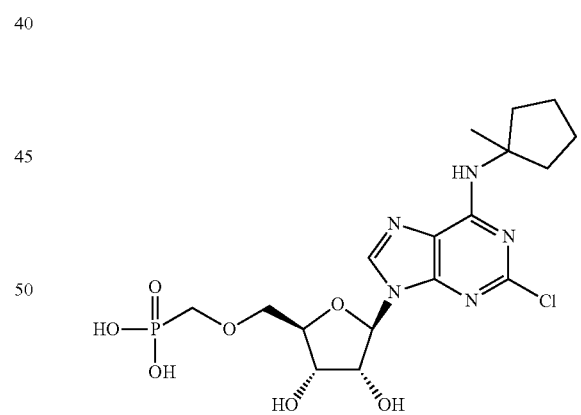

The title compound was synthesized in similar fashion to example 1: $^1$H NMR (400 MHz, DMSO-$d_6$) δ 8.44 (s, 1H), 7.82 (s, 1H), 5.84 (d, J=6.0 Hz, 1H), 4.54 (dd, J=6.0, 4.9 Hz, 1H), 4.12 (dd, J=4.9, 3.4 Hz, 1H), 4.05 (q, J=3.8 Hz, 1H), 3.79-3.64 (m, 2H), 3.62 (dd, J=8.9, 2.1 Hz, 2H), 2.30-2.19 (m, 2H), 1.77-1.57 (m, 6H), 1.50 (s, 3H). ESI MS [M+H]$^+$ for $C_{17}H_{26}ClN_5O_7P$, calcd 478.1, found 478.2.

Example 30

Synthesis of ({[(2R,3S,4R,5R)-5-(2-chloro-6-{[1-(methoxymethyl)cyclopentyl]amino}-9H-purin-9-yl)-3,4-dihydroxyoxolan-2-yl]methoxy}methyl)phosphonic acid

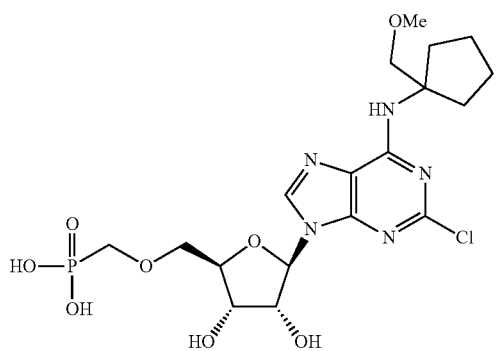 [SMILES: COCC1(Nc2nc(Cl)nc3c2ncn3[C@@H]2O[C@H](COCP(=O)(O)O)[C@@H](O)[C@H]2O)CCCC1]

The title compound was synthesized in similar fashion to example 1: $^1$H NMR (400 MHz, DMSO-d$_6$) δ 8.45 (s, 1H), 7.56 (s, 1H), 5.85 (d, J=6.0 Hz, 1H), 4.54 (dd, J=6.1, 4.9 Hz, 1H), 4.12 (dd, J=4.9, 3.3 Hz, 1H), 4.05 (q, J=3.8 Hz, 1H), 3.79-3.65 (m, 4H), 3.62 (dd, J=8.9, 2.1 Hz, 2H), 3.24 (s, 3H), 2.27-2.12 (m, 2H), 1.85-1.50 (m, 6H). ESI MS [M+H]$^+$ for C$_{18}$H$_{28}$ClN$_5$O$_8$P, calcd 508.1, found 508.2.

Example 31

Synthesis of ({[(2R,3S,4R,5R)-5-(2-chloro-6-{[1-(methoxycarbonyl)cyclopentyl]amino}-9H-purin-9-yl)-3,4-dihydroxyoxolan-2-yl]methoxy}methyl)phosphonic acid

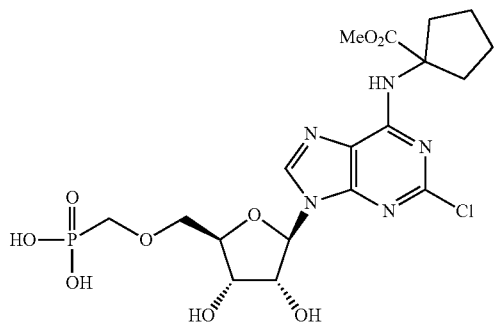 [SMILES: COC(=O)C1(Nc2nc(Cl)nc3c2ncn3[C@@H]2O[C@H](COCP(=O)(O)O)[C@@H](O)[C@H]2O)CCCC1]

The title compound was synthesized in similar fashion to example 1: $^1$H NMR (400 MHz, DMSO-d$_6$) δ 8.82 (s, 1H), 8.48 (s, 1H), 5.85 (d, J=6.0 Hz, 1H), 4.55 (dd, J=6.2, 4.9 Hz, 1H), 4.15-4.08 (m, 1H), 4.05 (q, J=3.7 Hz, 1H), 3.79-3.65 (m, 2H), 3.61 (dd, J=8.9, 2.1 Hz, 2H), 3.55 (s, 3H), 2.30-2.06 (m, 4H), 1.84-1.60 (m, 4H). ESI MS [M+H]$^+$ for C$_{18}$H$_{26}$ClN$_5$O$_9$P, calcd 522.1, found 522.2.

Example 32

Synthesis of ({[(2R,3S,4R,5R)-5-{2-chloro-6-[(1-methylpyrrolidin-3-yl)amino]-9H-purin-9-yl}-3,4-dihydroxyoxolan-2-yl]methoxy}methyl)phosphonic acid

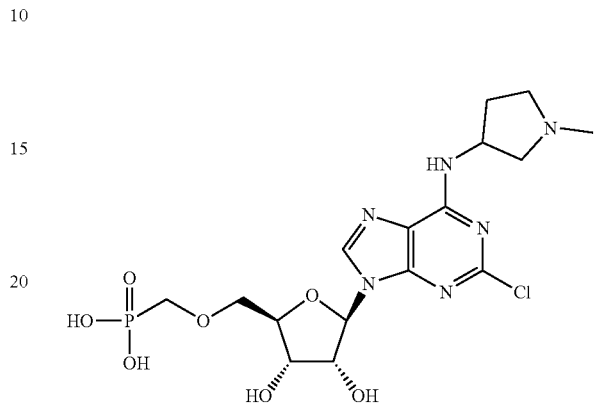

The title compound was synthesized in similar fashion to example 1: $^1$H NMR (400 MHz, DMSO-d$_6$) δ 8.94-8.63 (m, 1H), 8.51 (s, 1H), 5.87 (d, J=6.1 Hz, 1H), 4.90-4.73 (m, 1H), 4.55 (t, J=5.6 Hz, 1H), 4.12 (dd, J=4.9, 3.2 Hz, 1H), 4.06 (q, J=3.7 Hz, 1H), 3.80-3.52 (m, 5H), 3.49-3.02 (m, 2H), 2.89 (dd, J=16.0, 4.7 Hz, 4H), 2.36-2.06 (m, 2H). ESI MS [M+H]$^+$ for C$_{16}$H$_{25}$ClN$_6$O$_7$P, calcd 479.1, found 479.2.

Example 33

Synthesis of ({[(2R,3S,4R,5R)-5-(2-chloro-6-{[(1-methyl-1H-pyrazol-4-yl)methyl]amino}-9H-purin-9-yl)-3,4-dihydroxyoxolan-2-yl]methoxy}methyl)phospho c acid

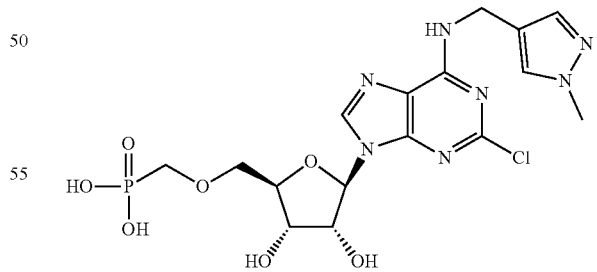

The title compound was synthesized in similar fashion to example 1: $^1$H NMR (400 MHz, DMSO-d$_6$) δ 8.72 (t, J=6.1 Hz, 1H), 8.43 (s, 1H), 7.58 (s, 1H), 7.38 (s, 1H), 5.84 (d, J=6.0 Hz, 1H), 4.54 (t, J=5.5 Hz, 1H), 4.48-4.43 (m, 2H), 4.12 (dd, J=4.9, 3.3 Hz, 1H), 4.05 (q, J=3.7 Hz, 1H), 3.76 (s, 3H), 3.75-3.65 (m, 2H), 3.62 (d, J=8.9 Hz, 2H). ESI MS [M+H]$^+$ for C$_{16}$H$_{22}$ClN$_7$O$_7$P, calcd 490.1, found 490.2.

Example 34

Synthesis of ({[(2R,3S,4R,5R)-5-{2-chloro-6-[(cyclopent-3-en-1-yl)amino]-9H-purin-9-yl}-3,4-dihydroxyoxolan-2-yl]methoxy}methyl)phosphonic acid

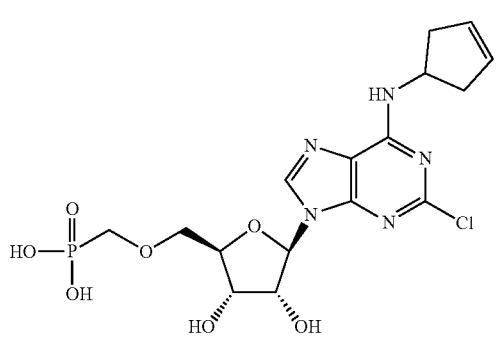 [SMILES: O=P(O)(O)COC[C@H]1O[C@@H](n2cnc3c(NC4CC=CC4)nc(Cl)nc32)[C@H](O)[C@@H]1O]

The title compound was synthesized in similar fashion to example 1: $^1$H NMR (400 MHz, DMSO-d$_6$) δ 8.53 (d, J=7.2 Hz, 1H), 8.43 (s, 1H), 5.85 (d, J=5.8 Hz, 1H), 5.73 (s, 2H), 4.78-4.66 (m, 1H), 4.54 (t, J=5.5 Hz, 1H), 4.14-4.09 (m, 1H), 4.05 (q, J=3.7 Hz, 1H), 3.80-3.65 (m, 2H), 3.61 (d, J=8.9 Hz, 2H), 2.85-2.61 (m, 2H), 2.46-2.27 (m, 2H). ESI MS [M+H]$^+$ for C$_{16}$H$_{22}$ClN$_5$O$_7$P, calcd 462.1, found 462.1.

Example 35

Synthesis of ({[(2R,3S,4R,5R)-5-(2-chloro-6-{[(4-methyl-4H-1,2,4-triazol-3-yl)methyl]amino}-9H-purin-9-yl)-3,4-dihydroxyoxolan-2-yl]methoxy}methyl)phosphonic acid

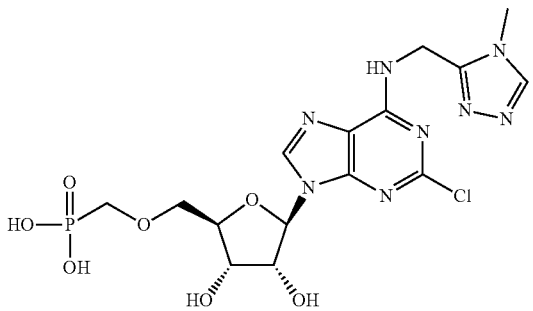 [SMILES: Cn1cnnc1CNc1nc(Cl)nc2c1ncn2[C@@H]1O[C@H](COCP(=O)(O)O)[C@@H](O)[C@H]1O]

The title compound was synthesized in similar fashion to example 1: $^1$H NMR (400 MHz, DMSO-d$_6$) δ 9.12-8.99 (m, 2H), 8.51 (s, 1H), 5.86 (d, J=6.1 Hz, 1H), 4.87 (s, 2H), 4.54 (t, J=5.5 Hz, 1H), 4.12 (dd, J=4.9, 3.2 Hz, 1H), 4.06 (q, J=3.7 Hz, 1H), 3.86 (s, 3H), 3.77-3.65 (m, 2H), 3.61 (dd, J=8.9, 1.6 Hz, 2H). ESI MS [M+H]$^+$ for C$_{15}$H$_{21}$ClN$_8$O$_7$P, calcd 491.1, found 491.2.

Example 36

Synthesis of ({[(2R,3S,4R,5R)-5-{2-chloro-6-[cis-(2-hydroxycyclopentyl)amino]-9H-purin-9-yl}-3,4-dihydroxyoxolan-2-yl]methoxy}methyl)phosphonic acid

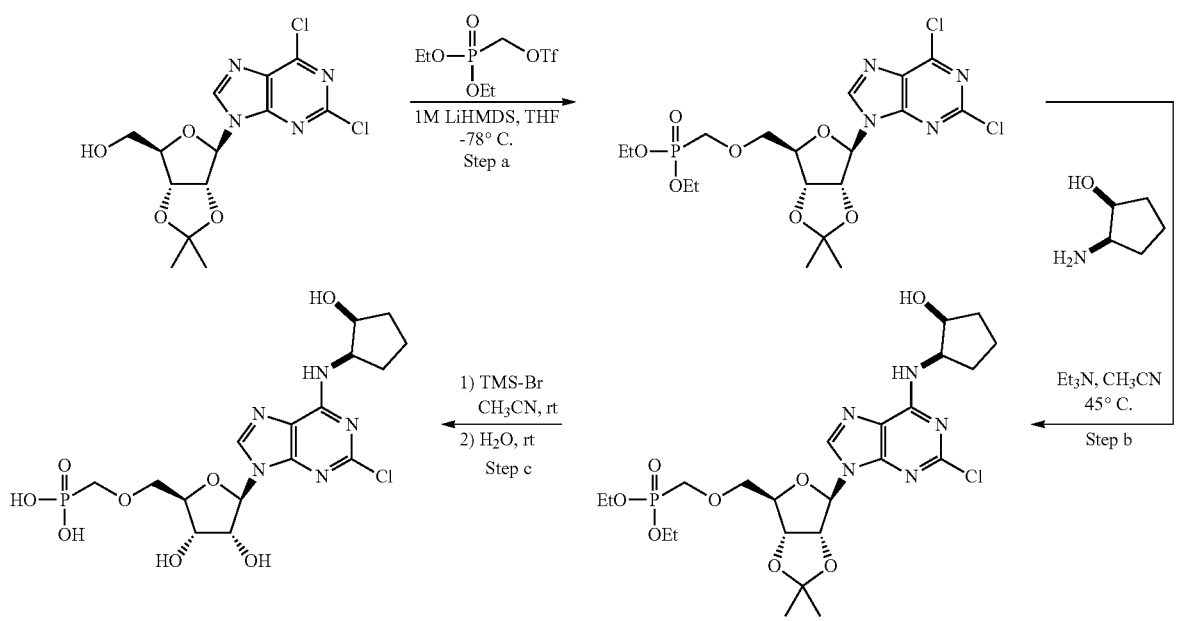

Step a: The mixture of acetonide protected 2,6-dichloropurine riboside (361 mg, 1 mmol) and the triflate (326 mg, 1.2 mmol, 1.2 equiv.) in anhydrous THF (10 mL) was cooled to −78° C., then 1M LiHMDS in THF (1.2 mL, 1.2 mmol, 1.2 equiv.) was added dropwise. Reaction mixture was stirred at −78° C. for 1.5 h then quenched with saturated solution of NH$_4$C$_1$ (2 mL)+H$_2$O (2 mL), diluted with EtOAc (5 mL). Organic layer was separated, dried over MgSO$_4$, filtered and evaporated. Crude product was purified by column chromatography (SiO$_2$, DCM→DCM:MeOH, 9:1) to give yellow oil (270 mg, 53%). Reaction mixture was evaporated and the crude product was used in the next step without purification. ESI MS [M+H]$^+$ for C$_{18}$H$_{26}$C$_{12}$N$_4$O$_7$P, calcd 511.1, found 511.2.

Steps b and c were similar to example 1: The product was purified by reverse phase HPLC (C18 column, 0 to 30% gradient of acetonitrile and water with 0.1% TFA) to give the product as a white solid: $^1$H NMR (400 MHz, DMSO-d$_6$) δ 8.46 (s, 1H), 7.37 (d, J=7.5 Hz, 1H), 5.85 (d, J=6.0 Hz, 1H), 4.54 (dd, J=6.0, 4.9 Hz, 1H), 4.24-4.15 (m, 1H), 4.15-4.09 (m, 2H), 4.05 (q, J=3.8 Hz, 1H), 3.79-3.65 (m, 2H), 3.64-3.58 (m, 2H), 2.03-1.46 (m, 6H). ESI MS [M+H]$^+$ for C$_{16}$H$_{24}$ClN$_5$O$_8$P, calcd 480.1, found 480.2.

Example 37

Synthesis of ({[(2R,3S,4R,5R)-5-{2-chloro-6-[cis-(3-hydroxycyclopentyl)amino]-9H-purin-9-yl}-3,4-dihydroxyoxolan-2-yl]methoxy}methyl)phosphonic acid

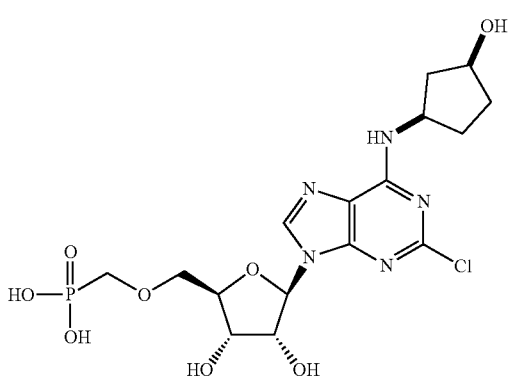

The title compound was synthesized in similar fashion to example 36: $^1$H NMR (400 MHz, DMSO-d$_6$) δ 8.42 (s, 1H), 8.13 (d, J=7.9 Hz, 1H), 5.84 (d, J=6.0 Hz, 1H), 4.53 (t, J=5.4 Hz, 1H), 4.50-4.39 (m, 1H), 4.19-4.09 (m, 2H), 4.05 (q, J=3.7 Hz, 1H), 3.78-3.65 (m, 2H), 3.61 (d, J=8.9 Hz, 2H), 2.19-2.08 (m, 1H), 2.02-1.88 (m, 1H), 1.82-1.69 (m, 2H), 1.67-1.51 (m, 2H). ESI MS [M+H]$^+$ for C$_{16}$H$_{24}$ClN$_5$O$_8$P, calcd 480.1, found 480.2.

Example 38

Synthesis of ({[(2R,3S,4R,5R)-5-{2-chloro-6-[4-(methoxymethyl)piperidin-1-yl]-9H-purin-9-yl}-3,4-dihydroxyoxolan-2-yl]methoxy}methyl)phosphonic acid

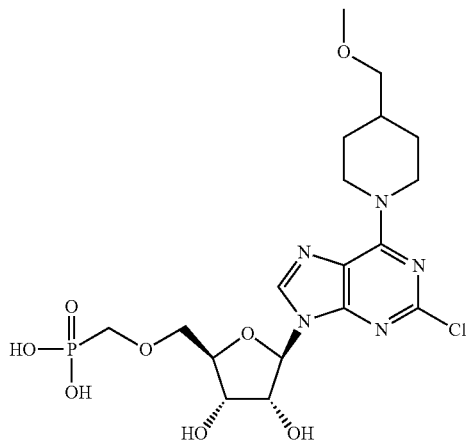 [SMILES: COCC1CCN(c2nc(Cl)nc3c2ncn3[C@@H]2O[C@H](COCP(=O)(O)O)[C@@H](O)[C@H]2O)CC1]

The title compound was synthesized in similar fashion to example 1 using 4-(methoxymethyl)-piperidine in place of cyclopentylamine: $^1$H NMR (400 MHz, DMSO-d$_6$) δ 8.45 (s, 1H), 5.87 (d, J=6.2 Hz, 1H), 4.53 (dd, J=6.2, 4.9 Hz, 1H), 4.11 (dd, J=4.9, 3.2 Hz, 1H), 4.05 (q, J=3.6 Hz, 1H), 3.81-3.64 (m, 2H), 3.61 (dd, J=8.9, 1.1 Hz, 2H), 3.23 (s, 3H), 3.19 (d, J=6.4 Hz, 2H), 2.03-1.84 (m, 1H), 1.79 (d, J=12.9 Hz, 2H), 1.18 (q, J=11.2, 10.6 Hz, 2H). ESI MS [M+H]$^+$ for C$_{18}$H$_{28}$ClN$_5$O$_8$P, calcd 508.1, found 508.2.

Example 39

Synthesis of ({[(2R,3S,4R,5R)-5-[2-chloro-6-(3-methoxypiperidin-1-yl)-9H-purin-9-yl]-3,4-dihydroxyoxolan-2-yl]methoxy}methyl)phosphonic acid

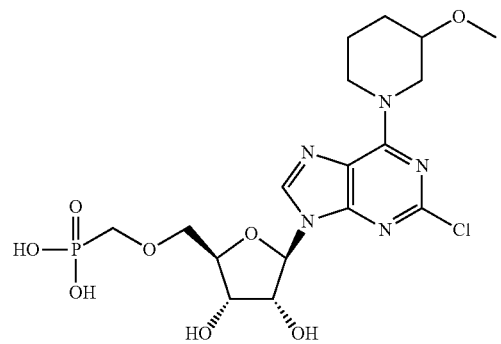 [SMILES: COC1CCCN(c2nc(Cl)nc3c2ncn3[C@@H]2O[C@H](COCP(=O)(O)O)[C@@H](O)[C@H]2O)C1]

The title compound was synthesized in similar fashion to example 1 using 3-methoxypiperidine in place of cyclopentylamine: $^1$H NMR (400 MHz, DMSO-d$_6$) δ 8.46 (d, J=1.2 Hz, 1H), 5.87 (d, J=6.2 Hz, 1H), 4.53 (dt, J=6.1, 4.7 Hz, 1H), 4.12 (dd, J=4.9, 3.2 Hz, 1H), 4.05 (q, J=3.6 Hz, 1H), 3.76-3.65 (m, 2H), 3.64-3.58 (m, 2H), 3.38 (s, 1H), 3.27 (s, 3H), 1.99-1.86 (m, 1H), 1.76 (s, 1H), 1.68 (dd, J=12.0, 7.1 Hz, 1H), 1.51 (s, 1H). ESI MS [M+H]+ for C17H26ClN5O8P, calcd 494.1, found 494.4.

Example 40

Synthesis of ({[(2R,3S,4R,5R)-5-{2-chloro-6-[(2-methoxy-1-phenylethyl)amino]-9H-purin-9-yl}-3,4-dihydroxyoxolan-2-yl]methoxy}methyl)phosphonic acid

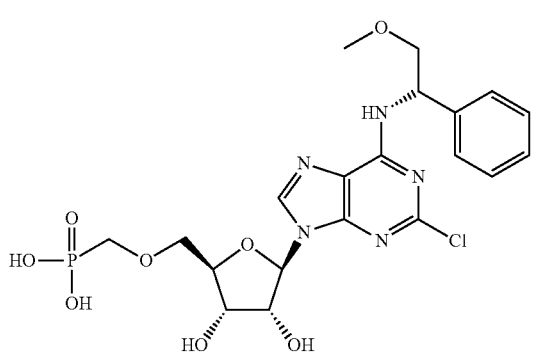

The title compound was synthesized in similar fashion to example 1 using (1S)-2-methoxy-1-phenylethanamine in place of cyclopentylamine: 1H NMR (400 MHz, DMSO-d6) δ 8.89 (d, J=8.7 Hz, 1H), 8.45 (d, J=17.9 Hz, 1H), 7.47 (d, J=7.5 Hz, 2H), 7.33 (dd, J=8.3, 6.8 Hz, 3H), 7.25 (t, J=7.3 Hz, 1H), 5.84 (d, J=6.0 Hz, 1H), 5.52 (q, J=3.9 Hz, 1H), 4.54 (t, J=5.5 Hz, 1H), 4.12 (t, J=4.2 Hz, 1H), 4.04 (d, J=3.8 Hz, 1H), 3.81 (t, J=9.6 Hz, 1H), 3.69 (td, J=11.2, 4.0 Hz, 2H), 3.60 (ddd, J=12.3, 8.2, 3.5 Hz, 3H), 3.28 (d, J=3.9 Hz, 3H). ESI MS [M+H]+ C20H26ClN5O8P, calcd 530.1, found 530.2.

Example 41

Synthesis of ({[(2R,3S,4R,5R)-5-{2-chloro-6-[(cyclopentylmethyl)amino]-9H-purin-9-yl}-3,4-dihydroxyoxolan-2-yl]methoxy}methyl)phosphonic acid

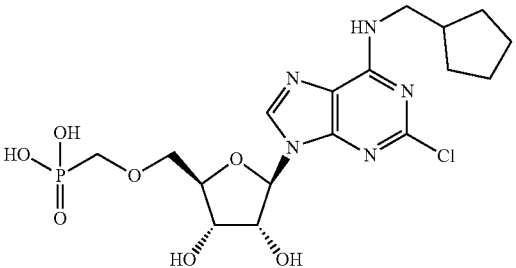 [SMILES: O=P(O)(O)COC[C@H]1O[C@@H](n2cnc3c(NCC4CCCC4)nc(Cl)nc32)[C@H](O)[C@@H]1O]

The title compound was synthesized in similar fashion to example 1: 1H NMR (400 MHz, DMSO-d6) δ 8.45 (t, J=2.4 Hz, 1H), 8.41 (s, 1H), 5.84 (d, J=6.0 Hz, 1H), 4.61-4.47 (m, 1H), 4.12 (t, J=4.1 Hz, 1H), 4.04 (d, J=3.7 Hz, 1H), 3.85-3.51 (m, 5H), 3.36 (m, 1H), 2.38-2.13 (m, 1H), 1.77-1.39 (m, 6H), 1.34-1.12 (m, 2H). ESI MS [M+H] for C17H25ClN5O7P, calcd. 478.1, found 478.2.

Example 42

Synthesis of ({[(2R,3S,4R,5R)-5-[6-(cyclopentylamino)-2-phenyl-9H-purin-9-yl]-3,4-dihydroxyoxolan-2-yl]methoxy}methyl)phosphonic acid

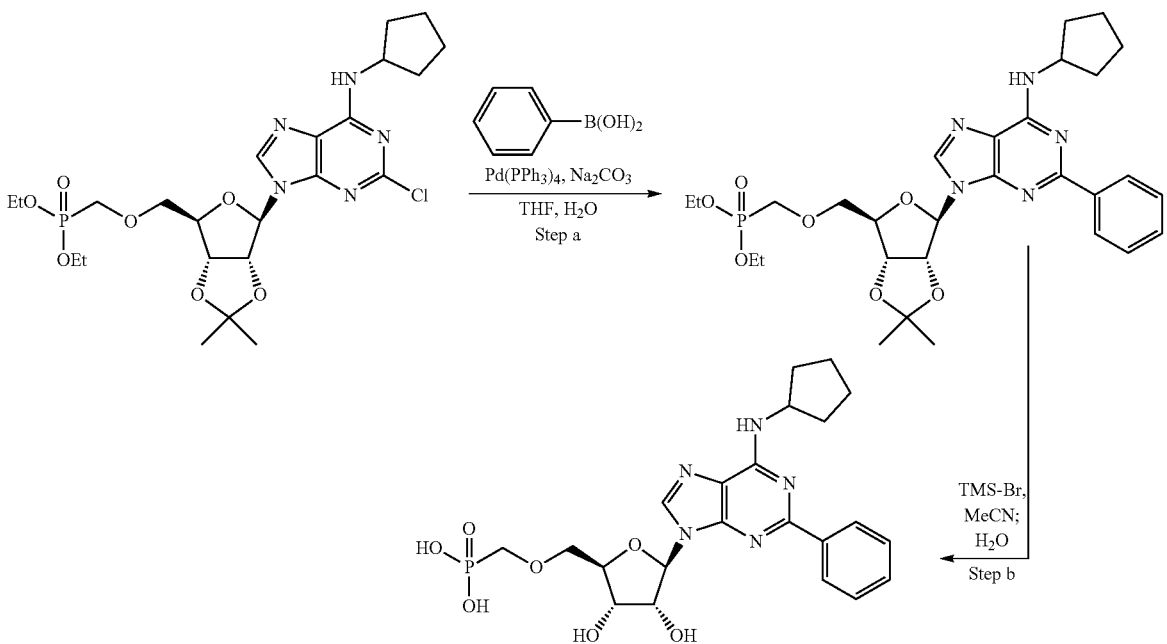

Step a: Product of Step c from example 1 (250 mg, 0.45 mmol), phenylboronic acid (82 mg, 0.67 mmol), and sodium carbonate (142 mg, 3.75 mmol) were suspended in 3:1 THF:H₂O (3 mL). This mixture was degassed by N₂ sparge for 10 minutes. Subsequently Pd(PPh₃)₄ (52 mg, 0.045 mmol) was added and the resulting mixture was degassed for an additional 5 minutes then sealed and heated to 80° C. overnight. After cooling to room temperature the reaction was diluted with EtOAc and washed with water and brine. The organics were dried over MgSO₄, filtered and concentrated under reduced pressure. The title compound (108 mg, 40%) was obtained following column chromatography (SiO₂, 0 to 10% gradient of MeOH and CH₂Cl₂). ESI MS [M+H]⁺ for $C_{29}H_{40}N_5O_7P$, calcd 602.3, found 602.4.

Step b: The title compound was obtained using identical procedure as for example 1 to give white solid: ¹H NMR (400 MHz, DMSO-d₆) δ 8.44-8.37 (m, 3H), 7.55-7.41 (m, 4H), 6.03 (d, J=6.0 Hz, 1H), 4.73 (t, J=5.6 Hz, 1H), 4.27-4.17 (m, 1H), 4.08 (app. q, J=4.0 Hz, 1H), 3.89-3.74 (m, 1H), 3.70 (dd, J=10.6, 4.8 Hz, 1H), 3.61 (d, J=8.8 Hz, 2H), 3.52 (dd, J=8.5, 3.6 Hz, 1H), 2.10-1.98 (m, 3H), 1.80-1.54 (m, 5H). ESI MS [M−H]⁻ for $C_{22}H_{28}N_5O_7P$, calcd 504.2, found 504.3.

Example 43

Synthesis of ({[(2R,3S,4R,5R)-5-[6-(cyclopentylamino)-2-(2-methylphenyl)-9H-purin-9-yl]-3,4-dihydroxyoxolan-2-yl]methoxy}methyl)phosphonic acid

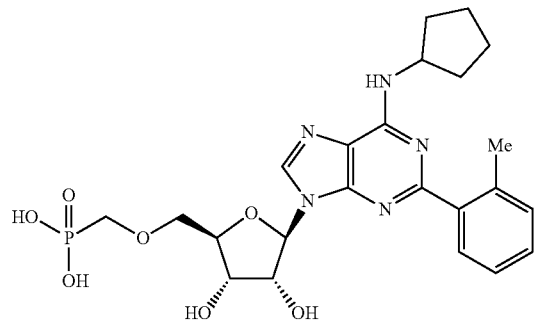 [SMILES: Cc1ccccc1-c1nc(NC2CCCC2)c2ncn([C@@H]3O[C@H](COCP(=O)(O)O)[C@@H](O)[C@H]3O)c2n1]

The title compound was obtained using identical procedure as for example 42 to give white solid: ¹H NMR (400 MHz, DMSO-d₆) δ 8.49 (s, 1H), 7.55-7.09 (m, 4H), 5.97 (d, J=5.8 Hz, 1H), 4.64 (t, J=5.4 Hz, 1H), 4.32-4.08 (m, 1H), 4.05 (app. q, J=3.9 Hz, 1H), 3.75 (dd, J=10.7, 3.6 Hz, 1H), 3.68 (dd, J=10.7, 4.6 Hz, 1H), 3.60 (dd, J=8.9, 1.9 Hz, 2H), 1.97 (br. s, 3H), 1.80-1.45 (m, 8H). ESI MS [M−H]⁻ for $C_{23}H_{30}N_5O_7P$, calcd 518.2, found 518.2.

Example 44

Synthesis of ({[(2R,3S,4R,5R)-5-[6-(cyclopentylamino)-2-(methoxymethyl)-9H-purin-9-yl]-3,4-dihydroxyoxolan-2-yl]methoxy}methyl)phosphonic acid

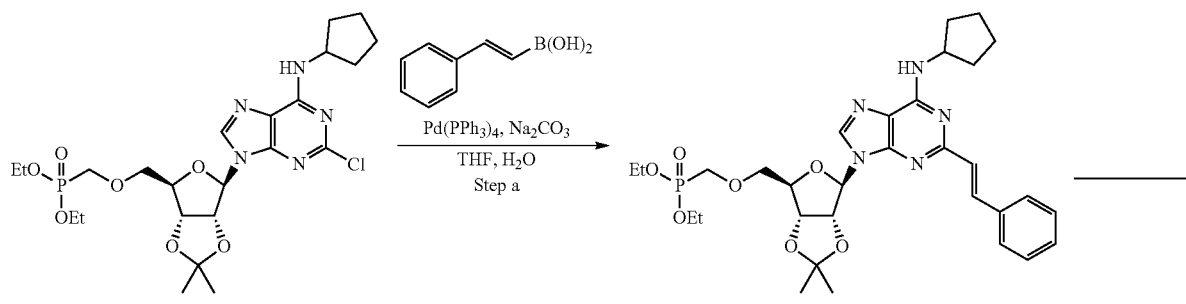

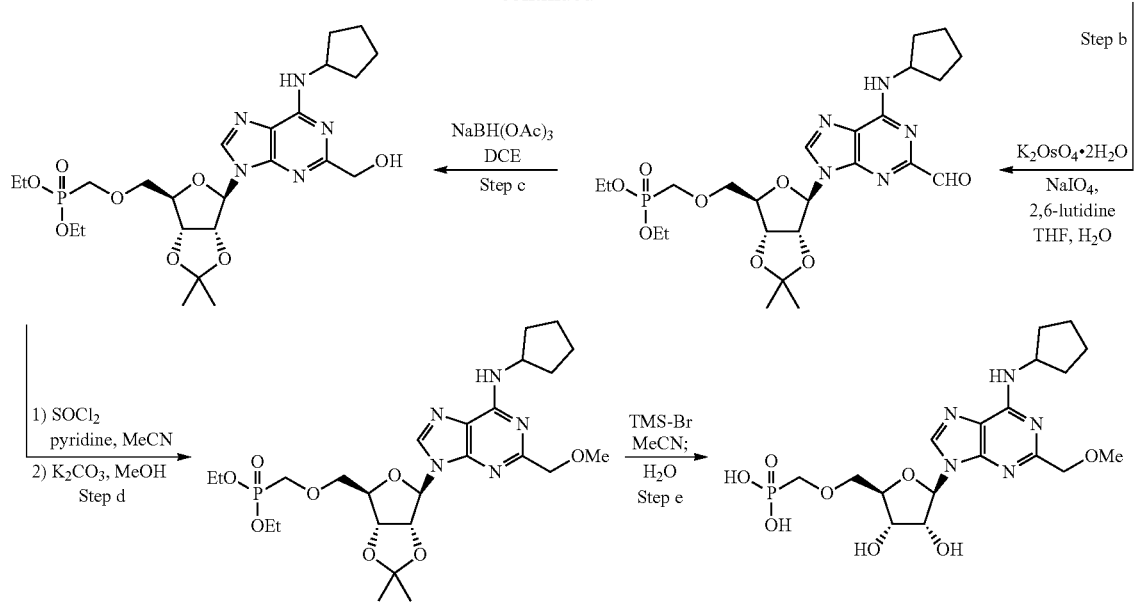

Step a: Product of Step c from example 1 (1.5 g, 2.68 mmol), phenylvinylboronic acid (595 mg, 4.02 mmol), and sodium carbonate (845 mg, 8.04 mmol) were suspended in 3:1 THF:H$_2$O (15 mL). This mixture was degassed by N$_2$ sparge for 10 minutes. Subsequently Pd(PPh$_3$)$_4$ (310 mg, 0.27 mmol) was added and the resulting mixture was degassed for an additional 5 minutes then heated to reflux overnight. After cooling to room temperature the reaction was diluted with EtOAc and washed with water and brine. The organics were dried over MgSO$_4$, filtered and concentrated under reduced pressure. The crude product obtained (1.89 g) was used directly in the following step without purification. ESI MS [M+H]$^+$ for C$_{31}$H$_{42}$N$_5$O$_7$P, calcd 628.3, found 628.4.

Step b: To a suspension of the product from Step a (1.62 g, 2.58 mmol), sodium periodate (3.31 g, 15.48 mmol), and 2,6-lutidine (601 μL, 5.16 mmol) in 2:1 THF:H$_2$O (28 mL) was added potassium osmate dihydrate (24 mg, 0.065 mmol). The resulting thick suspension was stirred overnight at room temperature then partitioned between EtOAc and water. The organics were washed sequentially with water and brine, dried over MgSO$_4$ and concentrated under reduced pressure. The crude product obtained was used directly in the following step without purification. ESI MS [M+H]$^+$ for C$_{24}$H$_{36}$N$_5$O$_8$P, calcd 554.2, found 554.3.

Step c: A solution of the product of Step b (471 g, 0.85 mmol) in dichloroethane (5.7 mL) was added sodium triacetoxyborohydride (216 mg, 1.02 mmol) in a single portion. The reaction was stirred at room temperature overnight then partitioned between EtOAc and water. The organics were washed with brine, dried over MgSO$_4$ and concentrated under reduced pressure to afford the title compound which was used without further purification. The title compound (285 mg, 60%) was obtained following column chromatography (SiO$_2$, 0 to 15% gradient of MeOH and CH$_2$Cl$_2$). ESI MS [M+H]$^+$ for C$_{24}$H$_{38}$N$_5$O$_8$P, calcd 556.3, found 556.3.

Step d: 1) To a solution of the product of Step c (285 mg, 0.51 mmol) in acetonitrile (5 mL) at 0° C. were added pyridine (125 μL, 1.54 mmol) followed by thionyl chloride (56 μL, 0.77 mmol). The reaction was kept at 0° C. for 1 hour. Subsequently saturated NaHCO$_3$ (aq) was added slowly until gas evolution ceased. The reaction was diluted with EtOAc and washed with sat. NaHCO$_3$, water and brine. The organics were dried over MgSO$_4$ and concentrated under reduced pressure. The title compound (115 mg, 40%) was obtained following column chromatography (SiO$_2$, 0 to 10% gradient of MeOH and CH$_2$C$_{12}$). ESI MS [M+H]$^+$ for C$_{24}$H$_{37}$ClN$_5$O$_7$P, calcd 574.2, found 574.3.

2) To a flask charged with the above product (115 mg, 0.20 mmol) in methanol (5 ml) was added potassium carbonate (138 mg, 1.0 mmol). The resulting suspension was stirred overnight at room temperature then diluted with EtOAc and washed with water and brine. The organics were dried over MgSO$_4$ and concentrated under reduced pressure. The crude mixture so obtained was comprised of the title compound as well as an inconsequential mixture of methylphosphonates resulting from transesterification. ESI MS [M+H]$^+$ for C$_{25}$H$_{40}$N$_5$O$_8$P, calcd 570.3, found 570.3.

Step e: The title compound was obtained using identical procedure as for example 1 to give white solid: $^1$H NMR (400 MHz, DMSO-d$_6$) δ 8.48 (br. s, 1H), 5.94 (d, J=6.2 Hz, 1H), 4.61 (t, J=5.6 Hz, 1H), 4.42 (s, 3H), 4.15 (dd, J=4.9, 3.1 Hz, 1H), 4.05 (t, J=3.8 Hz, 1H), 3.82-3.65 (m, 2H), 3.61 (d, J=8.9 Hz, 2H), 3.39 (d, J=1.3 Hz, 3H), 1.97 (br. s, 2H), 1.82-1.65 (m, 2H), 1.58 (br. s, 4H). ESI MS [M−H]$^-$ for C$_{18}$H$_{28}$N$_5$O$_8$P, calcd 472.2, found 472.3.

Example 45

Synthesis of ({[(2R,3S,4R,5R)-5-[6-(cyclopentylamino)-2-(phenoxymethyl)-9H-purin-9-yl]-3,4-dihydroxyoxolan-2-yl]methoxy}methyl)phosphonic acid

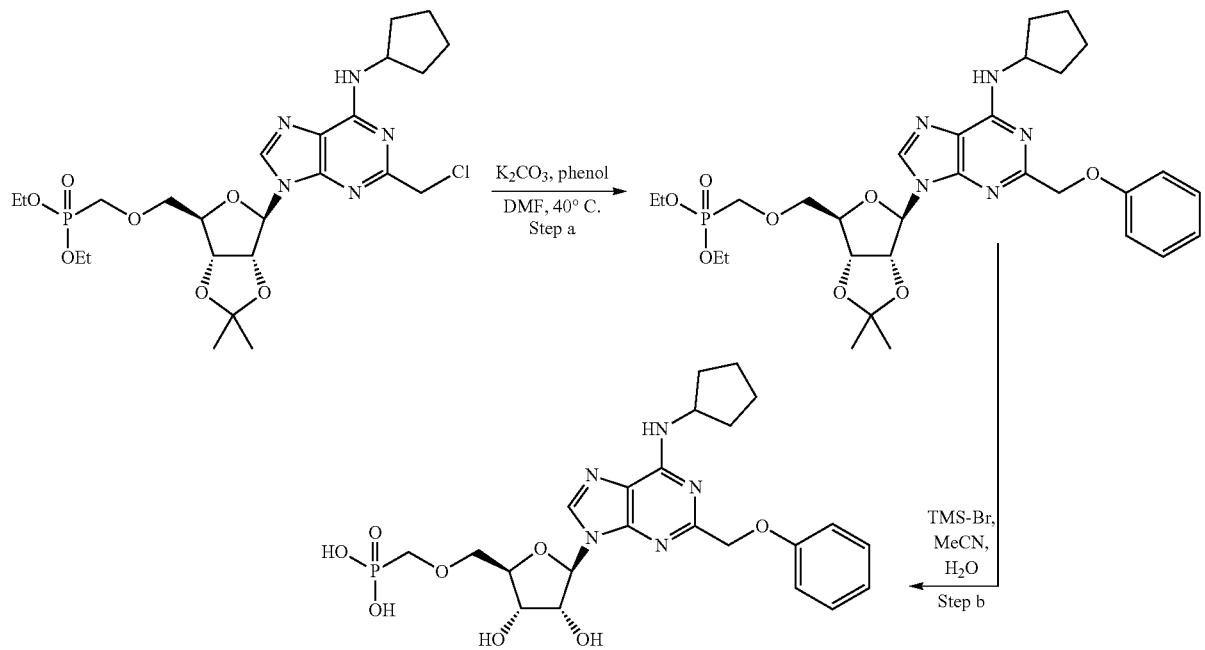 [SMILES: CCOP(=O)(COC[C@H]1O[C@@H](n2cnc3c(NC4CCCC4)nc(CCl)nc32)[C@@H]2OC(C)(C)O[C@@H]21)OCC ; CCOP(=O)(COC[C@H]1O[C@@H](n2cnc3c(NC4CCCC4)nc(COc4ccccc4)nc32)[C@@H]2OC(C)(C)O[C@@H]21)OCC ; O=P(O)(O)COC[C@H]1O[C@@H](n2cnc3c(NC4CCCC4)nc(COc4ccccc4)nc32)[C@H](O)[C@@H]1O]

Step a: To a flask charged with the product from step d of example 44 (50 mg, 0.09 mmol), potassium carbonate (26 mg, 0.44 mmol) and phenol (25 mg, 0.27 mmol) was added DMF (1 ml). The resulting suspension was heated to 40° C. overnight then diluted with EtOAc and washed with water and brine. The organics were dried over MgSO$_4$ and concentrated under reduced pressure. The crude mixture was used directly in the following step without further purification. ESI MS [M−H]$^-$ for C$_{30}$H$_{42}$N$_5$O$_8$P, calcd 632.3, found 632.4.

Step b: The title compound was obtained using identical procedure as for example 1 to give white solid: $^1$H NMR (400 MHz, DMSO-d$_6$) δ 8.33 (s, 1H), 7.30-7.12 (m, 3H), 6.93 (d, J=7.8 Hz, 2H), 6.84 (t, J=7.3 Hz, 1H), 5.84 (d, J=5.9 Hz, 1H), 4.99 (s, 3H), 4.53 (dd, J=6.1, 5.0 Hz, 1H), 4.07 (dd, J=5.0, 3.4 Hz, 1H), 3.95 (q, J=3.9 Hz, 1H), 3.65 (dd, J=10.7, 3.7 Hz, 1H), 3.59-3.49 (m, 3H), 1.81 (s, 3H), 1.63 (br. s, 3H), 1.46 (br. s, 5H). ESI MS [M+H]$^+$ for C$_{23}$H$_{30}$N$_5$O$_8$P, calcd 536.2, found 536.3.

Example 46

Synthesis of ({[(2R,3S,4R,5R)-5-[2-chloro-6-(cyclopentylamino)-9H-purin-9-yl]-3,4-dihydroxy-4-methyloxolan-2-yl]methoxy}methyl)phosphonic acid

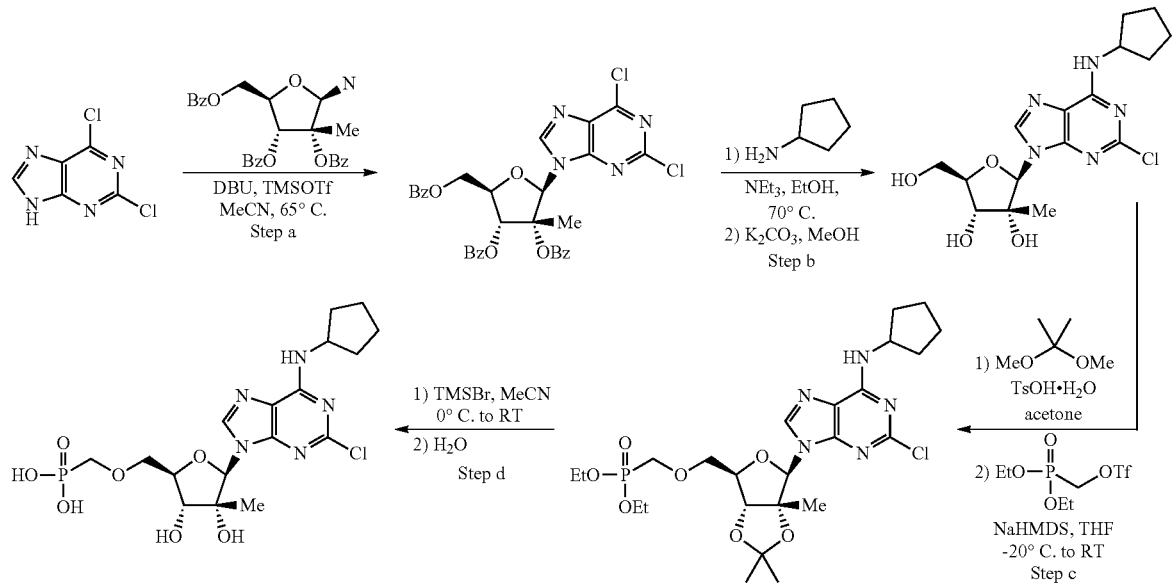

Step a: To β-D-ribofuranose, 2-C-methyl-, 1,2,3,5-tetrabenzoate (4.0 g, 6.89 mmol, 1 equiv.) and 2,6-dichloropurine (1.43 g, 7.58 mmol, 1.1 equiv.) in acetonitrile (23 mL) at 0° C. was added 1,8-Diazabicyclo[5.4.0]undec-7-ene (2.58 mL, 17.23 mmol, 2.5 equiv.) followed by trimethylsilyl trifluoromethanesulfonate (5.11 mL, 28.25 mmol, 4.1 equiv.) dropwise over 5 minutes. The reaction mixture was stirred at 0° C. for 15 minutes and heated at 65° C. for 5 hours. After cooling to room temperature the reaction was diluted with dichloromethane, washed with sat. aq. sodium bicarbonate (×2), and brine (×1). The organics were dried over MgSO$_4$, filtered and concentrated under reduced pressure. The desired product was obtained following column chromatography (SiO$_2$, 25% to 66% EtOAc/Hexane) as a white solid (1.30 g, 97%).

Step b: 1) A product from Step a (1.3 g, 2.01 mmol), cyclopentylamine (297 µL, 3.01 mmol, 1.5 equiv.), and triethylamine (560 µL, 4.02 mmol, 2.0 equiv.) were suspended in anhydrous EtOH (6.7 mL). The mixture was stirred at 70° C. for 4 hours. After cooling to room temperature the mixture was concentrated under reduced pressure and the material obtained used without further purification.

2) The above product was dissolved methanol (20 mL) and potassium carbonate (1.06 g, 7.63 mmol, 3.8 equiv.) was added. After stirring at ambient temperature for 2 hours the residue was adsorbed on celite and purified using column chromatography (SiO$_2$, 0% to 10% DCM/MeOH) as a colorless oil (612 mg, 79%, two steps).

Step c: 1) The product from Step c (290 mg, 0.755 mmol, 1.0 equiv.), 2,2-dimethoxypropane (1.8 mL, 15 mmol, 20 equiv.), and p-Toluenesulfonic acid monohydrate (179 mg, 0.944 mmol, 1.25 equiv.) were dissolved in acetone (10.8 mL). The reaction mixture was stirred at ambient temperature for 13 hours, adsorbed on silica, and purified using column chromatography (SiO$_2$, 0% to 5% DCM/MeOH) as a white foam (289 mg, 90%). ESI MS [M+H]$^+$ for $C_{19}H_{27}ClN_5O_4$, calcd 424.2, found 424.3.

2) To the above product (280 mg, 0.660 mmol) in 2.3 mL of anhydrous THF at −20° C. was added sodium bis(trimethylsilyl)amide (1.0 M in THF, 660 µL, 0.66 mmol, 1.0 equiv) dropwise over 2 minutes. After stirring at −20° C. for 25 min, a solution of (diethoxyphosphoryl)methyl trifluoromethanesulfonate (238 mg, 0.792 mmol, 1.2 equiv.) in 1.0 mL THF was added dropwise over 2 minutes. The reaction mixture was stirred at ambient temperature for 15 minutes, adsorbed on silica, and purified using column chromatography (SiO$_2$, 0% to 10% DCM/MeOH) as a white foam (189 mg, 50%).

Step d: 1) To the product from Step c (189 mg) in acetonitrile at 0° C. was added bromotrimethylsilane (217 µL, 1.65 mmol, 5.0 equiv.) dropwise. After stirring at 0° C. for 30 min, the reaction mixture was heated to 40° C. for 1 hour.

2) After cooling to 0° C., 1.0 mL water was added dropwise and the mixture was stirred at ambient temperature for 27 hours. The reaction mixture was purified by reverse phase HPLC (C18 column, 0 to 40% gradient of acetonitrile and water with 0.1% TFA) to give the product as a white solid (100 mg, 64%): $^1$H NMR (400 MHz, DMSO-d$_6$) δ 8.39 (d, J=7.7 Hz, 1H), 8.28 (s, 1H), 6.15 (s, 1H), 4.61 (d, J=2.3 Hz, 1H), 4.48-4.32 (m, 2H), 3.83 (td, J=10.8, 9.3, 4.1 Hz, 2H), 3.68 (d, J=8.5 Hz, 2H), 1.94-1.89 (m, 2H), 1.74-1.67 (m, 2H), 1.59-1.51 (m, 4H), 1.37 (s, 3H). ESI MS [M−H]$^-$ for $C_{17}H_{24}ClN_5O_7P$, calcd 476.1, found 476.2.

Example 47

Synthesis of ({[(2R,3S,4R,5R)-5-[5-chloro-7-(cyclopentylamino)-3H-imidazo[4,5-b]pyridin-3-yl]-3,4-dihydroxyoxolan-2-yl]methoxy}methyl)phosphonic acid

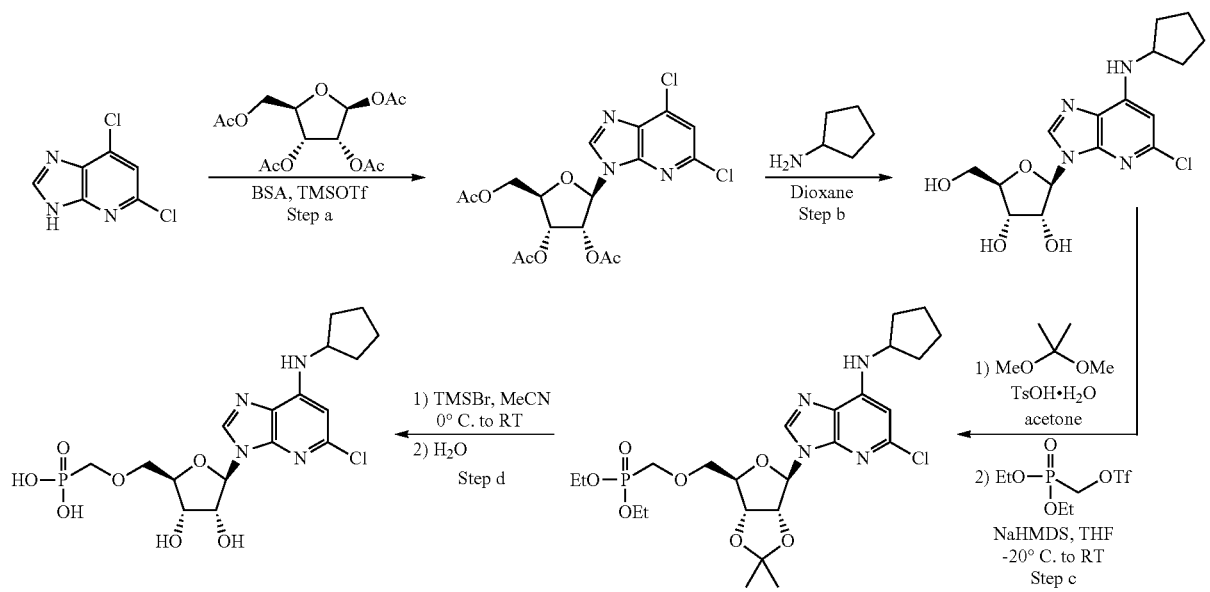

Step a: To a solution of 5,7-Dichloroimidazo[4,5-b]pyridine (376 mg, 2 mmol) in MeCN (14 mL) at r.t. was added N,O-Bis(trimethylsilyl)acetamide (0.523 mL, 2.14 mmol) dropwise and the reaction mixture heated to 85° C. for 1 hour. The mixture was cooled to r.t. and a solution of beta-D-Ribofuranose 1,2,3,5-tetraacetate (726 mg, 2.28 mmol) in MeCN (7 mL) and trimethylsilyl trifluoromethanesulfonate (0.471 mL, 2.60 mmol) were added sequentially dropwise. The reaction mixture was heated to 85° C. for 4 hours. The mixture was cooled and aqueous saturated sodium bicarbonate (50 mL) was added, subsequently extracted three times with EtOAc (100 mL), dried over sodium sulfate and concentrated.

Step b: To the residue was added dioxane (2 mL) and cyclopentylamine (0.987 mL, 10 mmol). The mixture was heated to 100° C. for 16 hours. The reaction mixture was loaded onto silica gel and purified by silica gel chromatography (0-10% MeOH in DCM) to afford the desired product as a brown solid (298 mg, 40%).

Step c: 1) A solution of the product from step a (298 mg; 0.808 mmol) and p-toluenesulfonic acid monohydrate (154 mg, 0.808 mmol) in 2,2-dimethoxypropane (1.6 mL) and acetone (1.6 mL) was stirred at r.t. for 20 hours. Triethylamine (0.5 mL) was added, the solvent removed, and the residue purified by silica gel chromatography (50 to 100% EtOAc in hexanes) to afford the desired product as a white solid (258 mg; 78%).

2) The title compound was synthesized as a white solid (107 mg; 62%) in similar fashion to example 46.

Step d: The title compound was synthesized as a white solid (14 mg; 15%) in similar fashion to example 1. $^1$H NMR (400 MHz, DMSO-$d_6$) δ 8.47 (s, 1H), 7.12 (d, J=7.4 Hz, 1H), 6.41 (s, 1H), 5.90 (d, J=5.8 Hz, 1H), 4.68-4.45 (m, 1H), 4.16-4.10 (m, 1H), 4.03 (q, J=3.9 Hz, 1H), 3.78-3.65 (m, 2H), 3.61 (d, J=8.9 Hz, 2H), 2.05-1.89 (m, 2H), 1.77-1.63 (m, 2H), 1.63-1.47 (m, 4H). ESI MS [M−H]$^−$ for $C_{17}H_{23}ClN_4O_7P$, calcd 461.8, found 461.2.

Example 48

Synthesis of ({[(2R,3S,4R,5R)-5-[6-chloro-4-(cyclopentylamino)-1H-pyrazolo[3,4-d]pyrimidin-1-yl]-3,4-dihydroxyoxolan-2-yl]methoxy}methyl)phosphonic acid

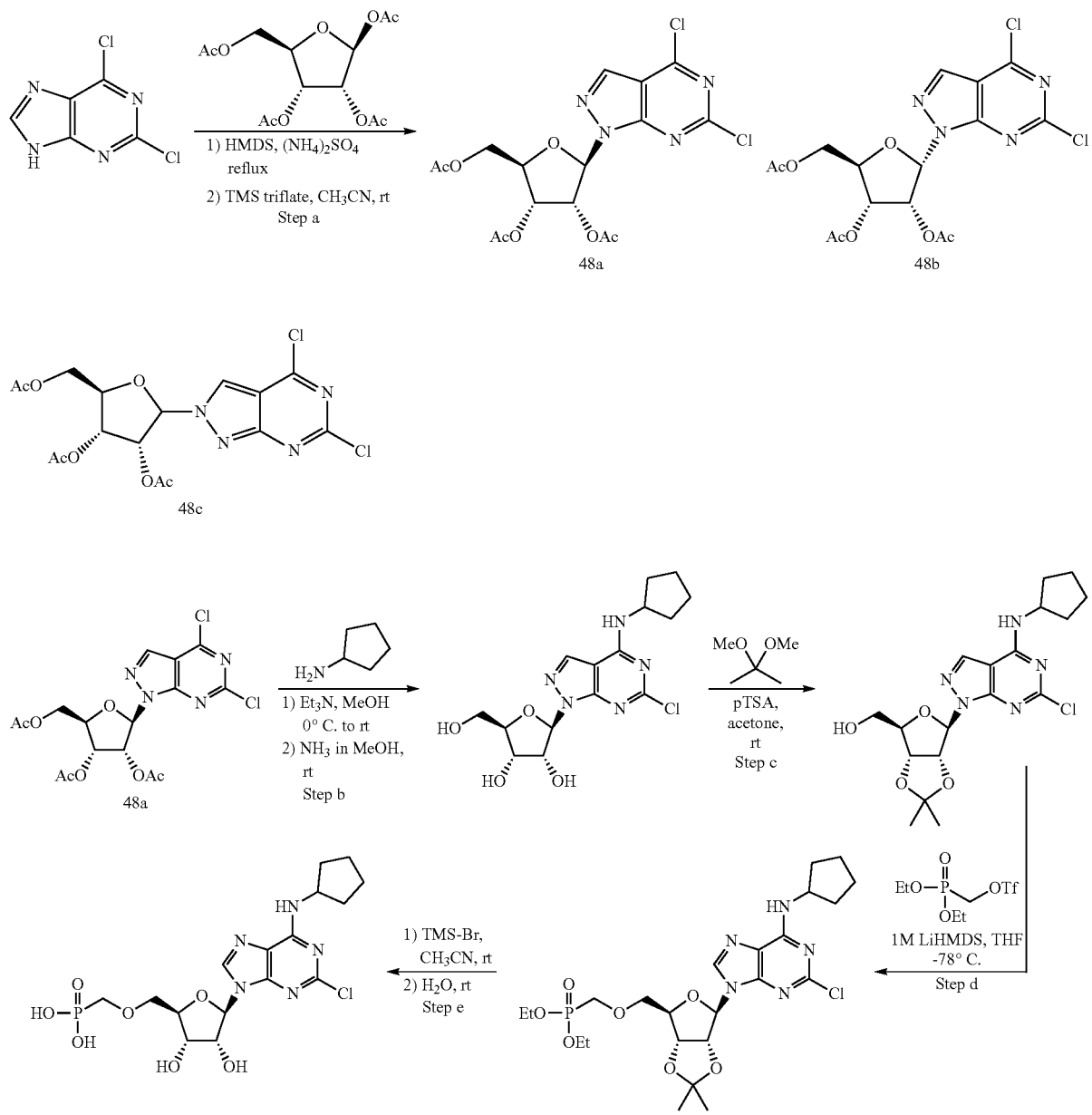

Step a: The mixture of 4,6-dichloro-1H-pyrazolo[3,4-d]pyrimidine (47.7 g, 252.4 mmol) and (NH$_4$)$_2$SO$_4$ (300 mg) in HMDS (200 mL) was stirred under reflux for 5 h, then concentrated under vacuum to give dark brown oil that was immediately used in the next step. Crude TMS protected heterocycle was dissolved in anhydrous CH$_3$CN (500 mL) and 1,2,3,5-tetraacetate-beta-D-ribofuranose (88.3 g, 277.6 mmol, 1.1 equiv.) was added. Reaction mixture was stirred at rt until all starting materials dissolved then TfO-TMS (68.3 mL, 378.6 mmol, 1.5 equiv.) was added dropwise. Stirred at rt for overnight and concentrated under vacuum to ~50% of the original volume then carefully quenched with saturated NaHCO$_3$ (1 L) and extracted with EtOAc (3×500 mL). Combined organics were dried over MgSO$_4$, filtered and evaporated to give dark brown oil that was purified by column chromatography (SiO$_2$, hexanes:EtOAc, 100 to 40%) to give three isomeric products: 48a (yellow oil, 28.5 g, 25%); 48b (yellow oil, 7 g, 6%); 48c (yellow solid, 25.8 g, 23%) and structures were tentatively assigned.

Product 48a: ¹H NMR (400 MHz, DMSO-d$_6$) δ 8.75 (s, 1H), 6.47 (d, J=3.2 Hz, 1H), 5.82 (dd, J=5.3, 3.2 Hz, 1H), 5.63 (t, J=5.8 Hz, 1H), 4.47-4.40 (m, 1H), 4.37-4.30 (m, 1H), 4.12-4.02 (m, 1H), 2.09 (s, 3H), 2.06 (s, 3H), 1.97 (s, 3H). ESI MS [M+Na]⁺ for C$_{16}$H$_{16}$Cl$_2$N$_4$NaO$_7$, calcd 469.0, found 469.0.

Product 48b: ¹H NMR (400 MHz, DMSO-d$_6$) δ 8.64 (s, 1H), 6.87 (d, J=5.7 Hz, 1H), 5.67 (dd, J=6.8, 5.7 Hz, 1H), 5.27 (t, J=6.7 Hz, 1H), 4.87-4.77 (m, 1H), 4.36 (dd, J=12.2, 3.0 Hz, 1H), 4.19 (dd, J=12.3, 5.7 Hz, 1H), 2.04 (s, 3H), 2.01 (s, 3H), 1.71 (s, 3H). ESI MS [M+Na]f for C$_{16}$H$_{16}$Cl$_2$N$_4$NaO$_7$, calcd 469.0, found 469.1.

Product 48c: ¹H NMR (400 MHz, DMSO-d$_6$) δ 9.22 (s, 1H), 6.49 (d, J=2.5 Hz, 1H), 5.74 (dd, J=5.1, 2.6 Hz, 1H), 5.67-5.60 (m, 1H), 4.54-4.47 (m, 1H), 4.42 (dd, J=12.3, 3.3 Hz, 1H), 4.16 (dd, J=12.2, 5.2 Hz, 1H), 2.10 (s, 3H), 2.07 (s, 3H), 1.98 (s, 3H). ESI MS [M+Na]⁺ for C$_{16}$H$_{16}$Cl$_2$N$_4$NaO$_7$, calcd 469.0, found 469.1.

Step b: Compound 48a from Step a (22 g, 49.3 mmol) was dissolved in MeOH (100 mL) and cooled to 0° C. Cyclopentylamine (5.1 g, 51.8 mmol, 1.05 equiv.), and triethylamine (7.2 mL, 51.8 mmol, 1.05 equiv.) were added and reaction mixture was stirred at 0° C. for 15 min then at rt for 4 h. 7M NH$_3$ in MeOH (60 mL) was added and reaction was stirred at rt for 1 day. Reaction mixture was evaporated and the crude product was used in the next step without purification. ESI MS [M+H]⁺ for C$_{15}$H$_{21}$ClN$_5$O$_4$, calcd 370.1, found 370.2.

Step c was similar to example 1: ¹H NMR (400 MHz, DMSO-d$_6$) δ 8.70 (d, J=7.2 Hz, 1H), 8.24 (s, 1H), 6.18 (s, 1H), 5.28 (dd, J=6.1, 1.8 Hz, 1H), 4.90 (dd, J=6.2, 2.1 Hz, 1H), 4.85 (t, J=5.8 Hz, 1H), 4.41 (q, J=6.9 Hz, 1H), 4.16-4.06 (m, 1H), 3.51-3.40 (m, 1H), 3.38-3.30 (m, 1H), 2.04-1.92 (m, 2H), 1.79-1.52 (m, 6H), 1.50 (s, 3H), 1.31 (s, 3H). ESI MS [M+H]⁺ for C$_{18}$H$_{25}$ClN$_5$O$_4$, calcd 410.2, found 410.2.

Step d: Product from Step c (3.2 g, 7.8 mmol) in anhydrous THF (50 mL) was cooled to 0° C. and 1M NaHMDS in THF (12.4 mL, 12.4 mmol, 1.6 equiv.) was added dropwise. Reaction mixture was stirred at 0° C. for 1 h then the (diethoxyphosphoryl)methyl trifluoromethanesulfonate (3.4 g, 12.4 mmol, 1.6 equiv.) was added. Cooling bath was removed and reaction was stirred at rt for overnight. Quenched with saturated solution of NH$_4$C$_1$ (50 mL), diluted with MTBE (100 mL). Organic layer was separated, dried over MgSO$_4$, filtered and evaporated. Crude product was purified by column chromatography (SiO$_2$, Hex→Hex: EtOAc, 2:8) to give white foamy solid (3.2 g, 73%). ¹H NMR (400 MHz, DMSO-d$_6$) δ 8.71 (d, J=7.1 Hz, 1H), 8.25 (s, 1H), 6.20 (s, 1H), 5.30 (d, J=6.1 Hz, 1H), 4.92-4.83 (m, 1H), 4.41 (q, J=6.8 Hz, 1H), 4.25 (t, J=6.6 Hz, 1H), 4.08-3.87 (m, 5H), 3.76-3.68 (m, 1H), 3.67-3.58 (m, 1H), 3.56-3.44 (m, 1H), 2.05-1.91 (m, 2H), 1.81-1.64 (m, 2H), 1.65-1.45 (m, 7H), 1.31 (s, 3H), 1.26-1.07 (m, 6H). ESI MS [M+H]⁺ for C$_{23}$H$_{36}$ClN$_5$O$_7$P, calcd 560.2, found 560.3.

Step e was similar to example 1: ¹H NMR (400 MHz, DMSO-d$_6$) 8.71 (d, J=7.2 Hz, 1H), 8.25 (s, 1H), 6.00 (d, J=3.9 Hz, 1H), 4.51-4.37 (m, 2H), 4.19 (t, J=5.2 Hz, 1H), 4.07-3.98 (m, 1H), 3.71 (dd, J=10.7, 4.0 Hz, 1H), 3.59-3.48 (m, 3H), 2.06-1.93 (m, 2H), 1.79-1.47 (m, 6H). ESI MS [M+H]⁺ for C$_{16}$H$_{24}$ClN$_5$O$_7$P, calcd 464.1, found 464.2.

Example 49

Synthesis of ({[(2R,3S,4R,5R)-5-[6-chloro-4-(cyclopentylamino)-2H-pyrazolo[3,4-d]pyrimidin-2-yl]-3,4-dihydroxyoxolan-2-yl]methoxy}methyl)phosphonic acid

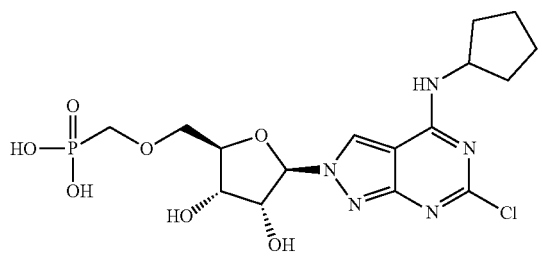 [SMILES: O=P(O)(O)COC[C@H]1O[C@@H](n2cc3c(NC4CCCC4)nc(Cl)nc3n2)[C@H](O)[C@@H]1O]

The title compound was synthesized in a similar fashion to example 48, starting from 48c: ¹H NMR (400 MHz, DMSO-d$_6$) δ 9.39 (d, J=7.1 Hz, 1H), 9.08 (s, 1H), 5.83 (d, J=1.8 Hz, 1H), 4.43 (p, J=6.7 Hz, 1H), 4.19 (dd, J=7.3, 4.5 Hz, 1H), 4.13-4.06 (m, 2H), 3.86 (dd, J=11.0, 2.3 Hz, 1H), 3.82-3.65 (m, 3H), 2.02-1.88 (m, 2H), 1.81-1.50 (m, 6H). ESI MS [M+H]⁺ for C$_{16}$H$_{24}$ClN$_5$O$_7$P, calcd 464.1, found 464.2.

Example 50

Synthesis of {[(2R,3S,4R,5R)-5-(6-chloro-4-{[(3S)-oxolan-3-yl]amino}-1H-pyrazolo[3,4-d]pyrimidin-1-yl)-3,4-dihydroxyoxolan-2-yl]methoxy}methyl)phosphonic acid

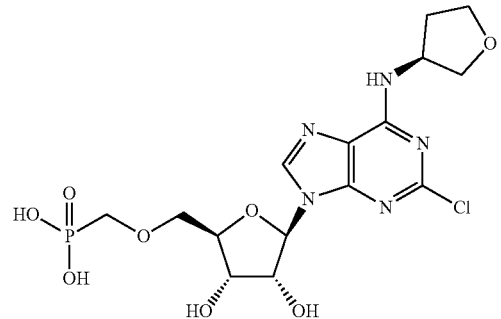 [SMILES: O=P(O)(O)COC[C@H]1O[C@@H](n2cnc3c(N[C@H]4CCOC4)nc(Cl)nc32)[C@H](O)[C@@H]1O]

The title compound was obtained using identical procedure as for example 48, starting from 48a to give white solid: ¹H NMR (400 MHz, DMSO-d$_6$) δ 8.94 (d, J=6.7 Hz, 1H), 8.26 (s, 1H), 5.99 (d, J=4.1 Hz, 1H), 4.66 (s, 1H), 4.46 (s, 1H), 4.18 (t, J=5.1 Hz, 1H), 3.99 (d, J=6.1 Hz, 1H), 3.98-3.79 (m, 3H), 3.80-3.58 (m, 4H), 3.48 (d, J=8.2 Hz, 2H), 2.39-2.16 (m, 1H), 1.91 (br. s, 1H). ESI MS [M−H]⁻ for C$_{15}$H$_{21}$ClN$_5$O$_8$P, calcd 464.1, found 464.1.

Example 51

Synthesis of ({[(2R,3R,4S,5R)-5-[2-chloro-6-(cyclopentylamino)-9H-purin-9-yl]-4-fluoro-3-hydroxyoxolan-2-yl]methoxy}methyl)phosphonic acid

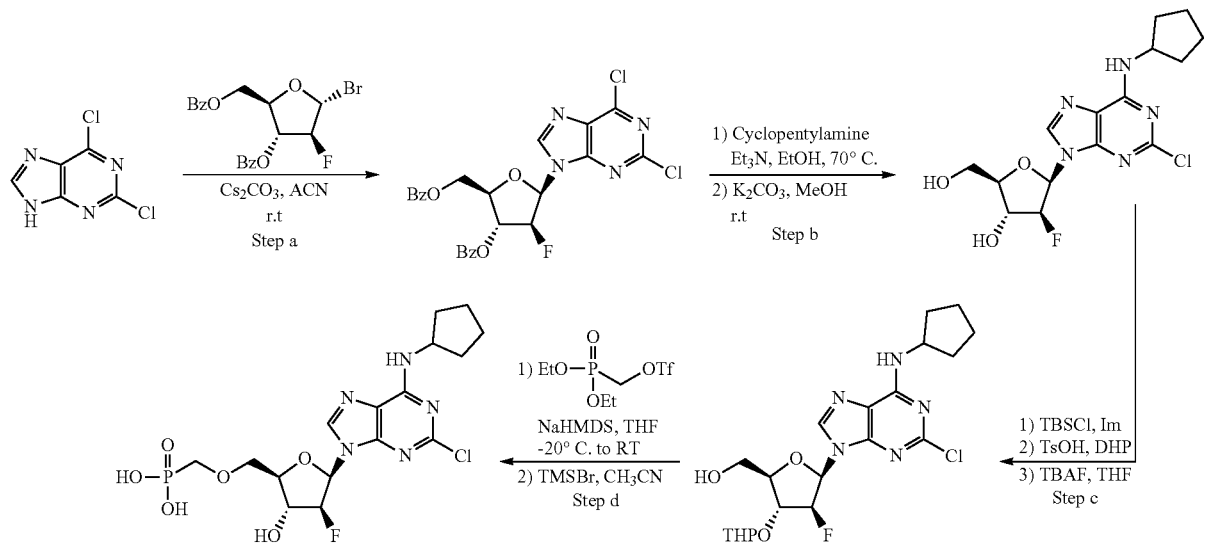

Step a: 2,6-dichloropurine (3.6 g, 18.8 mmol) was dissolved in 90 mL of acetonitrile and treated with $Cs_2CO_3$ (7.5 g, 23 mmol, 1.2 equiv.). The mixture was stirred at room temperature for 30 min. The known bromo derivative (8.75 g, 21 mmol, 1.1 equiv.) was dissolved in 100 mL of acetonitrile and added to the mixture dropwise via an addition funnel. The mixture was allowed to stir overnight at room temperature. The mixture was filtered on a pad of silica gel and concentrated. The residue was adsorbed on silica and purified using column chromatography (hexanes/ethyl acetate) to provide the product as a white solid in 77% yield (7.72 g). $^1$H NMR (400 MHz, Chloroform-d) δ 8.39 (d, J=3.0 Hz, 1H), 8.10 (ddt, J=8.5, 3.1, 0.9 Hz, 4H), 7.74-7.36 (m, 6H), 6.64 (dd, J=21.8, 2.8 Hz, 1H), 5.83-5.69 (m, 1H), 5.40 (ddd, J=49.9, 2.8, 0.8 Hz, 1H), 4.89-4.77 (m, 2H), 4.62 (q, J=4.0 Hz, 1H). ESI MS [M+H]$^+$ for $C_{24}H_{17}Cl_2FN_4O_5$, calcd 531.1, found 531.1.

Step b: 1) The dichloride (0.75 g, 1.4 mmol), cyclopentyl amine (0.2 mL, 2.1 mmol, 1.5 equiv.), and $Et_3N$ (0.4 mL, 2.8 mmol, 2.0 equiv.) in anhydrous EtOH (5 mL) was stirred at 70° C. for 4 hours. The reaction mixture was then cooled to room temperature and the product was collected by filtration and used without further purification (white solid, 0.69 g, 73%). ESI MS [M+H]$^+$ for $C_{29}H_{28}C_1FN_5O_5$, calcd 580.2, found 580.3.

2) The product from above (0.68 g, 1 mmol) and $K_2CO_3$ (0.4 g, 3 mmol, 3 equiv) were dissolved in 10 mL of methanol and stirred at room temperature for 4 hours. The reaction mixture was then filtered and concentrated on a pad of silica gel. The reaction mixture was purified using column chromatography (methylene chloride/methanol) to provide the product as a white solid. (88%, 0.33 g) ESI MS [M+H]$^+$ for $C_{15}H_{20}ClFN_5O_3$, calcd 372.1, found 372.3.

Step c: 1) A solution of the diol from the above step (875 mg; 2.35 mmol) and imidazole (456 mg, 6.70 mmol) in DCM (12 mL) was cooled to 0° C. and TBSCl (674 mg, 4.47 mmol) was added as a solid in one portion. The mixture was warmed to r.t. and stirred for 1 hour. The solvent was removed and the residue purified by silica gel chromatography (0 to 30% EtOAc in hexanes) to afford the desired product as a white solid (946 mg; 83%).

2) A solution of the product from the above step (987 mg, 2.03 mmol), p-toluenesulfonic acid monohydrate (34 mg; 0.203 mmol) in 3,4-dihydro-2H-pyran (4 mL) and THF (20 mL) was stirred at r.t. for 14 h. The reaction was quenched with triethylamine, the solvent was evaporated, and the residue was passed through a plug of silica gel (EtOAc).

3) The residue was redissolved in THF (17 mL), cooled to 0° C., and TBAF (2.05 mL, 1.0 M solution in THF) was added dropwise. The mixture was stirred at 0° C. for 30 minutes. The solvent was evaporated and the residue purified by silica gel chromatography (0-5% MeOH in DCM) to afford the desired product as a colorless oil (742 mg, 80%).

Step d: 1) A solution of the product from Step c (742 mg; 1.63 mmol) in THF (8.1 mL) was cooled to 0° C. and NaHMDS (2.4 mL, 1.0 M in THF) was added dropwise and the mixture was stirred at 0° C. for 15 minutes. A solution of diethylphosphonomethyl triflate (734 mg; 2.45 mmol) in THF (1.5 mL) was then added at 0° C., the mixture stirred at 0° C. for 15 minutes, and then warmed to r.t. and stirred for an additional 30 minutes. The solvent was removed and the residue purified by silica gel chromatography (0-5% MeOH in DCM) to afford the desired product as a colorless oil (424 mg, 43%).

2) A solution of the product from the above step (400 mg; 0.704 mmol) in MeCN (1.2 mL) was cooled to 0° C. and bromotrimethylsilane (0.464 mL; 3.52 mmol) was added dropwise. The reaction was warmed to r.t. over 45 minutes, cooled to 0° C. and water (0.607 mL) was added dropwise and stirred at r.t. for 15 min. The mixture was neutralized with 1 M sodium hydroxide and washed with MTBE (5 mL) three times. The aqueous layer was purified directly by reverse phase HPLC (C18 column, 0 to 50% gradient of acetonitrile and water with 0.1% TFA) to afford the desired product as a white solid (12 mg, 4%). $^1$H NMR (400 MHz, DMSO-d$_6$) δ 8.51-8.37 (m, 1H), 8.24 (d, J=2.1 Hz, 1H), 6.35 (dd, J=13.5, 4.8 Hz, 1H), 5.24 (dt, J=52.7, 4.4 Hz, 1H), 4.52-4.34 (m, 2H), 3.97 (q, J=5.6 Hz, 1H), 3.88-3.73 (m, 2H), 3.63 (d, J=8.6 Hz, 2H), 2.06-1.81 (m, 2H), 1.80-1.66 (m, 2H), 1.66-1.44 (m, 4H). ESI MS [M–H]$^-$ for C$_{16}$H$_{21}$ClFN$_5$O$_6$P, calcd 464.1, found 464.2.

Example 52

Synthesis of ({[(2R,3R,4S,5R)-5-{2-chloro-6-[cyclopentyl(methyl)amino]-9H-purin-9-yl}-4-fluoro-3-hydroxyoxolan-2-yl]methoxy}methyl)phosphonic acid

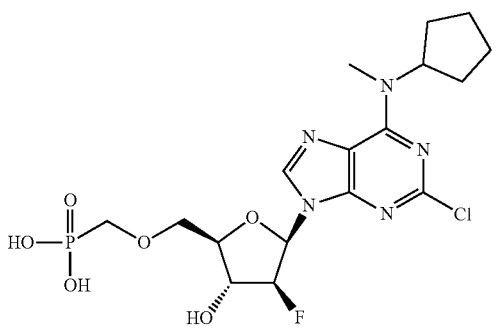 [SMILES: CN(c1nc(Cl)nc2c1ncn2[C@@H]1O[C@H](COCP(=O)(O)O)[C@@H](O)[C@@H]1F)C1CCCC1]

The title compound was synthesized in similar fashion to example 51 using N-methylcyclopentylamnine in place of cyclopentylamine: $^1$H NMR (400 MHz, DMSO-d$_6$) δ 8.25 (d, J=2.1 Hz, 1H), 6.37 (dd, J=13.9, 4.7 Hz, 1H), 6.00 (brs, 2H), 5.31 (t, J=4.4 Hz, 1H), 5.18 (t, J=4.4 Hz, 1H), 4.41 (ddd, J=19.1, 5.8, 4.1 Hz, 1H), 4.16-3.67 (m, 4H), 3.64 (d, J=8.6 Hz, 3H), 2.20-1.32 (m, 9H). ESI MS [M+H]$^+$ for C$_{17}$H$_{24}$ClN$_5$O$_6$P, calcd 480.8, found 480.2.

Example 53

Synthesis of ({[(2R,3R,4S,5R)-5-(2-chloro-6-{[(3R)-oxolan-3-yl]amino}-9H-purin-9-yl)-4-fluoro-3-hydroxyoxolan-2-yl]methoxy}methyl)phosphonic acid

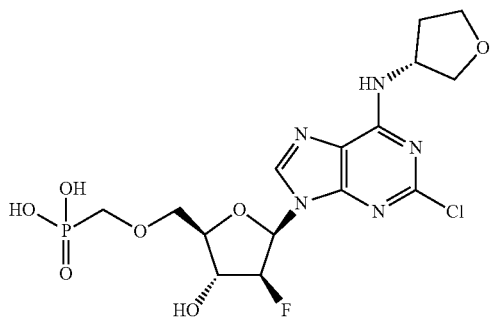 [SMILES: O=P(O)(O)COC[C@H]1O[C@@H](n2cnc3c(N[C@@H]4CCOC4)nc(Cl)nc32)[C@@H](F)[C@@H]1O]

The title compound was synthesized in similar fashion to example 51: $^1$H NMR (400 MHz, DMSO-d$_6$) δ 8.96 (s, 1H), 8.57 (d, J=2.2 Hz, 1H), 6.30 (s, 1H), 5.21-5.35 (m, 1H), 4.60 (t, J=5.6 Hz, 1H), 3.28-3.89 (m, 11H), 1.92-2.17 (m, 2H). ESI MS [M–H] for C$_{15}$H$_{20}$ClFN$_5$O$_7$P, calcd 466.1, found 466.2.

Example 54

Synthesis of ({[(2R,3R,4S,5R)-5-(2-chloro-6-{[(3S)-oxolan-3-yl]amino}-9H-purin-9-yl)-4-fluoro-3-hydroxyoxolan-2-yl]methoxy}methyl)phosphonic acid

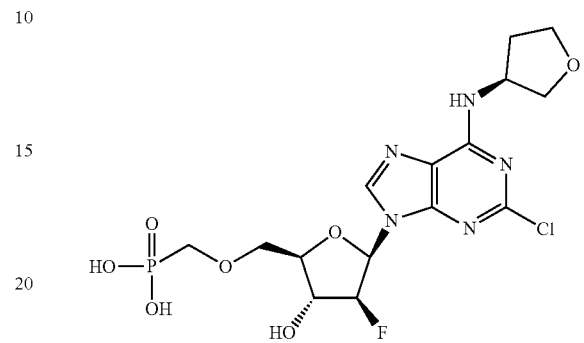

The title compound was synthesized as a white solid (42.1 mg; 18%) in similar fashion to example 51: $^1$H NMR (400 MHz, DMSO-d$_6$) δ 8.74-8.53 (m, 1H), 8.27 (d, J=2.1 Hz, 1H), 6.36 (dd, J=13.6, 4.8 Hz, 1H), 5.25 (dt, J=52.7, 4.4 Hz, 1H), 4.70-4.56 (m, 1H), 4.50-4.35 (m, 1H), 4.03-3.69 (m, 5H), 3.67-3.55 (m, 3H), 2.30-2.10 (m, 1H), 2.10-1.86 (m, 1H). ESI MS [M–H]$^-$ for C$_{15}$H$_{19}$ClFN$_5$O$_7$P, calcd 466.1, found 466.2.

Example 55

Synthesis of ({[(2R,3R,4S,5R)-5-[6-(benzylamino)-2-chloro-9H-purin-9-yl]-4-fluoro-3-hydroxyoxolan-2-yl]methoxy}methyl)phosphonic acid

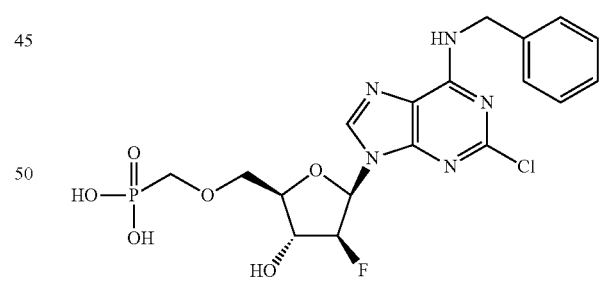

The title compound was synthesized in similar fashion to example 51 using benzylamine in place of cyclopentylamine: $^1$H NMR (400 MHz, DMSO-d$_6$) δ 9.02 (t, J=6.3 Hz, 1H), 8.30 (d, J=2.4 Hz, 1H), 7.42-7.17 (m, 4H), 7.26-7.17 (m, 1H), 6.30 (dd, J=17.1, 4.1 Hz, 1H), 5.54 (dd, J=4.1, 2.7 Hz, 1H), 5.41 (dd, J=4.1, 2.8 Hz, 1H), 5.15 (brs, 1H), 4.65 (m, 2H), 4.55-4.31 (m, 1H), 4.01 (d, m, 1H), 3.86-3.52 (m, 3H). ESI MS [M+H]$^+$ for C$_{17}$H$_{24}$ClN$_5$O$_6$P, calcd 488.8, found 488.1.

Example 56

Synthesis of ({[(2R,3R,4S,5R)-5-(2-chloro-6-{[(2-fluorophenyl)methyl]amino}-9H-purin-9-yl)-4-fluoro-3-hydroxyoxolan-2-yl]methoxy}methyl)phosphonic acid

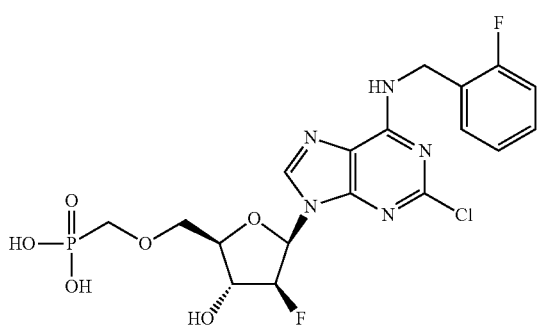 [SMILES: O=P(O)(O)COC[C@H]1O[C@@H](n2cnc3c(NCc4ccccc4F)nc(Cl)nc32)[C@@H](F)[C@@H]1O]

The title compound was synthesized as a white solid in similar fashion to example 51: $^1$H NMR (400 MHz, DMSO-$d_6$) δ 8.98 (t, J=6.0 Hz, 1H), 8.32-8.21 (m, 1H), 7.40-7.25 (m, 2H), 7.23-7.09 (m, 2H), 6.36 (dd, J=13.7, 4.8 Hz, 1H), 5.32 (t, J=4.5 Hz, 1H), 5.24-5.15 (m, 1H), 4.70 (s, 1H), 4.44 (dt, J=19.2, 5.0 Hz, 1H), 3.98 (q, J=5.6 Hz, 1H), 3.87-3.74 (m, 2H), 3.63 (d, J=8.6 Hz, 2H). ESI MS [M+H]$^+$ for $C_{18}H_{20}ClF_2N_5O_6P$, calcd 506.1, found 506.1.

Example 57

Synthesis of ({[(2R,3R,4S,5R)-5-(2-chloro-6-{[(2-chlorophenyl)methyl]amino}-9H-purin-9-yl)-4-fluoro-3-hydroxyoxolan-2-yl]methoxy}methyl)phosphonic acid

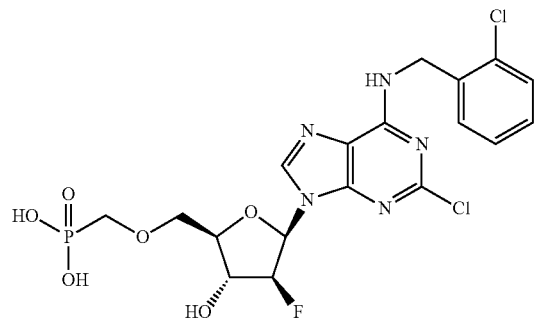 [SMILES: O=P(O)(O)COC[C@H]1O[C@@H](n2cnc3c(NCc4ccccc4Cl)nc(Cl)nc32)[C@@H](F)[C@@H]1O]

The title compound was obtained using identical procedure as for example 51 to give white solid: $^1$H NMR (400 MHz, DMSO-$d_6$) δ 9.00 (app. t, J=6.1 Hz, 1H), 8.32 (d, J=2.0 Hz, 1H), 7.51-7.43 (m, 1H), 7.42-7.18 (m, 4H), 6.37 (dd, J=13.5, 4.8 Hz, 1H), 5.40-5.06 (m, 1H), 4.83-4.60 (m, 2H), 4.45 (dt, J=19.2, 5.0 Hz, 1H), 3.99 (d, J=4.5 Hz, 1H), 3.93-3.71 (m, 2H), 3.64 (d, J=8.7 Hz, 2H). ESI MS [M+H]$^+$ for $C_{18}H_{19}Cl_2FN_5O_6P$, calcd 522.0, found 522.1.

Example 58

Synthesis of ({[(2R,3R,4S,5R)-5-(2-chloro-6-{[(2-chlorophenyl)methyl](methyl)amino}-9H-purin-9-yl)-4-fluoro-3-hydroxyoxolan-2-yl]methoxy}methyl)phosphonic acid

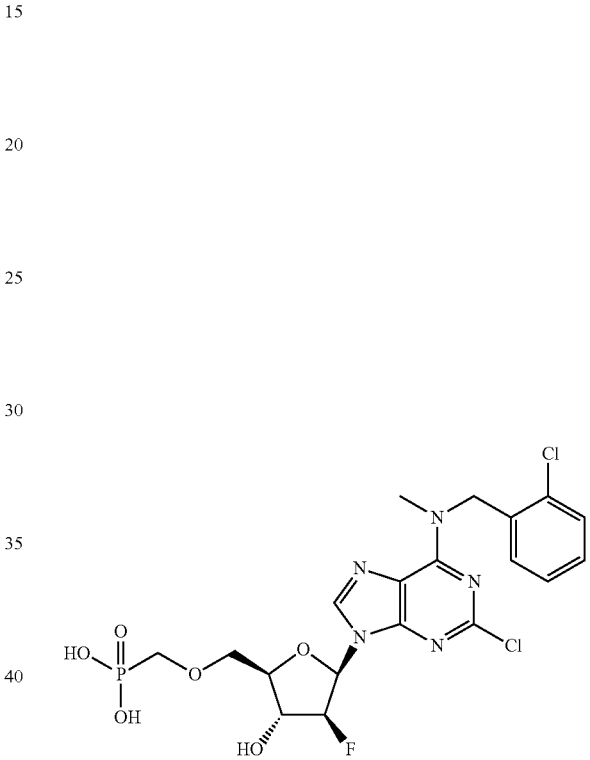

The title compound was obtained using identical procedure as for example 51 to give white solid: $^1$H NMR (400 MHz, DMSO-$d_6$) δ 8.27 (d, J=40.5 Hz, 1H), 7.51 (dd, J=7.3, 1.9 Hz, 1H), 7.31 (s, 2H), 7.15 (s, 1H), 6.67-6.20 (m, 1H), 5.62 (s, 1H), 5.26 (d, J=52.8 Hz, 1H), 5.00 (s, 1H), 4.56-4.29 (m, 1H), 3.98 (s, 1H), 3.89-3.54 (m, 5H), 3.18 (br. s, 1H). ESI MS [M+H]$^+$ for $C_{19}H_{21}Cl_2FN_5O_6P$, calcd 536.1, found 536.1.

Example 59

({[(2R,3R,4S,5R)-5-[5-chloro-7-(cyclopentylamino)-3H-imidazo[4,5-b]pyridin-3-yl]-4-fluoro-3-hydroxyoxolan-2-yl]methoxy}methyl)phosphonic acid

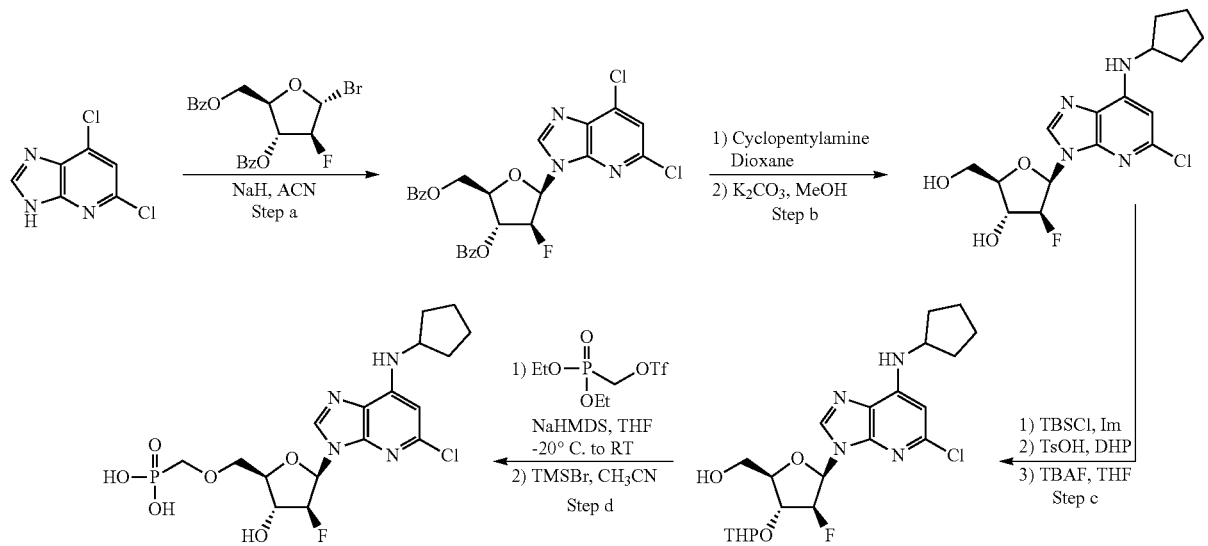

Step a: To a solution of 5,7-Dichloroimidazo[4,5-b]pyridine (564 mg, 3 mmol) in MeCN (18 mL) at r.t. was added sodium hydride (130 mg, 3.24 mmol, 60% suspension in oil). The reaction mixture was stirred at r.t. for 30 minutes. A solution of 2,3,5-Tri-O-benzoyl-D-ribofuranosyl bromide in MeCN (4 mL) was added at r.t. and the reaction mixture stirred at r.t. for 14 hours. The reaction mixture was quenched by addition of methanol (5 mL) and sodium bicarbonate (5 g), filtered through celite, and concentrated.

Step b: 1) To the residue was added dioxane (5 mL) and cyclopentylamine (1.48 mL, 15 mmol). The mixture was heated to 100° C. for 20 hours. The reaction mixture was cooled to r.t.

2) Potassium carbonate (4 g) and methanol (20 mL) were added at r.t. and the reaction mixture was stirred at r.t. for 1 hour. Excess solvent was removed in vacuo and the crude residue was purified by silica gel chromatography (0-15% MeOH in DCM) to afford the desired product as a brown solid (499 mg, 45%).

Step c and Step d were carried out in similar fashion to example 51. $^1$H NMR (400 MHz, DMSO-$d_6$) δ 8.23 (d, J=2.2 Hz, 1H), 7.18 (s, 1H), 6.42 (s, 1H), 6.39 (dd, J=15.0, 4.7 Hz, 1H), 5.22 (dt, J=52.6, 4.2 Hz, 1H), 4.47-4.36 (m, 1H), 4.01-3.93 (m, 1H), 3.86-3.74 (m, 2H), 3.64 (d, J=8.6 Hz, 2H), 2.05-1.90 (m, 2H), 1.77-1.63 (m, 2H), 1.63-1.48 (m, 4H). ESI MS [M−H]$^-$ for $C_{17}H_{22}ClFN_4O_6P$, calcd 463.1, found 463.2.

Example 60

Synthesis of ({[(2R,3R,4S,5R)-5-[2-chloro-4-(cyclopentylamino)-7H-pyrrolo[2,3-d]pyrimidin-7-yl]-4-fluoro-3-hydroxyoxolan-2-yl]methoxy}methyl)phosphonic acid

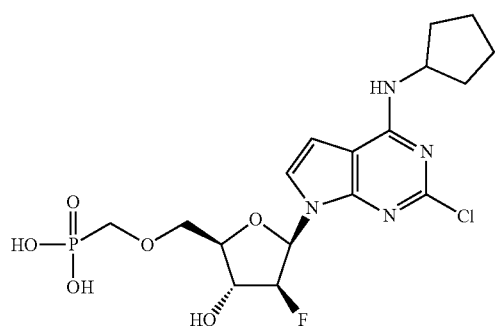 [SMILES: O=P(O)(O)COC[C@H]1O[C@@H](n2ccc3c(NC4CCCC4)nc(Cl)nc32)[C@@H](F)[C@@H]1O]

The title compound was obtained using identical procedure as for example 51 to give white solid: $^1$H NMR (400 MHz, DMSO-$d_6$) δ 7.91 (d, J=7.1 Hz, 1H), 7.24 (d, J=3.6 Hz, 1H), 6.72 (d, J=3.7 Hz, 1H), 6.43 (dd, J=15.2, 4.6 Hz, 1H), 5.14 (dt, J=52.8, 4.2 Hz, 1H), 4.44-4.27 (m, 2H), 3.96-3.87 (m, 1H), 3.82-3.68 (m, 2H), 2.10-1.87 (m, 2H), 1.79-1.64 (m, 2H), 1.64-1.41 (m, 4H). ESI MS [M+H]$^+$ for $C_{17}H_{24}ClFN_4O_6P$, calcd 465.1, found 465.2.

Example 61

Synthesis of ({[(2R,3R,4S,5R)-5-[4-(benzylamino)-2-chloro-7H-pyrrolo[2,3-d]pyrimidin-7-yl]-4-fluoro-3-hydroxyoxolan-2-yl]methoxy}methyl)phosphonic acid

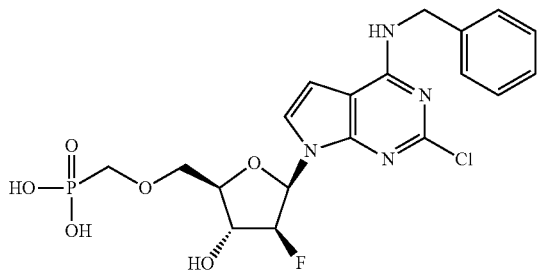 [SMILES: O=P(O)(O)COC[C@H]1O[C@@H](n2ccc3c(NCc4ccccc4)nc(Cl)nc32)[C@@H](F)[C@@H]1O]

The title compound was obtained using identical procedure as for example 51 to give white solid: $^1$H NMR (400 MHz, DMSO-d$_6$) δ 8.60 (t, J=6.0 Hz, 1H), 7.38-7.20 (m, 5H), 6.71 (d, J=3.7 Hz, 1H), 6.45 (dd, J=15.0, 4.7 Hz, 1H), 5.22 (t, J=4.2 Hz, 1H), 5.12-5.05 (m, 1H), 4.75-4.60 (m, 2H), 4.34 (ddd, J=19.2, 5.6, 3.9 Hz, 1H), 3.92 (td, J=5.6, 3.5 Hz, 1H), 3.83-3.69 (m, 2H), 3.63 (d, J=8.7 Hz, 2H). ESI MS [M−H]$^−$ for C$_{19}$H$_{20}$ClFN$_4$O$_6$P, calcd 485.1, found 485.2.

Example 62

Synthesis of diphenyl ({[(2R,3S,4R,5R)-5-[2-chloro-6-(cyclopentylamino)-9H-purin-9-yl]-3,4-dihydroxyoxolan-2-yl]methoxy}methyl)phosphonate Step a: To compound ({[(3aR,4R,6R,6aR)-6-[2-chloro-6-(cyclopentylamino)-9H-purin-9-yl]-2,2-dimethyl-tetrahydro-2H-furo[3,4-d][1,3]dioxol-4-yl]methoxy}methyl) phosphonic acid (from example 1, 2.34 g, 4.64 mmol) in dichloromethane (9.28 mL) at ambient temperature was added oxalyl chloride (902 µL, 10.67 mmol, 2.3 equiv.) followed by DMF (2 drops). The reaction mixture was stirred at ambient temperature for 30 min and the volatiles were then removed under reduced pressure. Anhydrous toluene was added and removed under reduced pressure; this procedure was completed twice. The crude material was used in the next step without further purification.

Step b: To a portion of the product of Step a (250 mg, 0.462 mmol) in dichloromethane (1.54 mL) at 0° C. was added phenol (109 mg, 1.16 mmol, 2.5 equiv) followed by triethylamine (345 µL, 2.54 mmol, 5.5 equiv). The reaction mixture was stirred at 0° C. for 20 min then ambient temperature for 15 minutes, adsorbed on silica, and purified using column chromatography (SiO$_2$, 33% to 100% Hexane/EtOAc, 3% MeOH) as a colorless oil (248 mg, 82%). ESI MS [M+H]$^+$ for C$_{31}$H$_{36}$ClN$_5$O$_7$P, calcd 656.2, found 656.1.

Step c: To a portion of the product of Step b (193 mg, 0.295 mmol) and 20 µL water at 0° C. was added 676 µL TFA. The mixture was sonicated to homogenize and stirred at ambient temperature for 1.5 hours. The volatiles were removed under reduced pressure and the resulting residue was purified using column chromatography (SiO$_2$, 0% to 10% DCM/MeOH) to give the product as a white solid: $^1$H NMR (400 MHz, DMSO-d$_6$) δ 8.38-8.31 (m, 2H), 7.41-7.31 (m, 4H), 7.27-7.15 (m, 6H), 5.87 (d, J=5.4 Hz, 1H), 4.56-4.49 (m, 1H), 4.45-4.38 (m, 1H), 4.27 (d, J=7.8 Hz, 2H), 4.16-4.13 (m, 1H), 4.10 (q, J=4.2, 3.7 Hz, 1H), 3.89 (dd, J=10.8, 3.3 Hz, 1H), 3.83 (dd, J=10.7, 5.1 Hz, 1H), 1.94-1.89 (m, 2H), 1.73-1.68 (m, 2H), 1.58-1.50 (m, 4H). ESI MS [M+H]$^+$ for C$_{28}$H$_{32}$ClN$_5$O$_7$P, calcd 616.2, found 616.3.

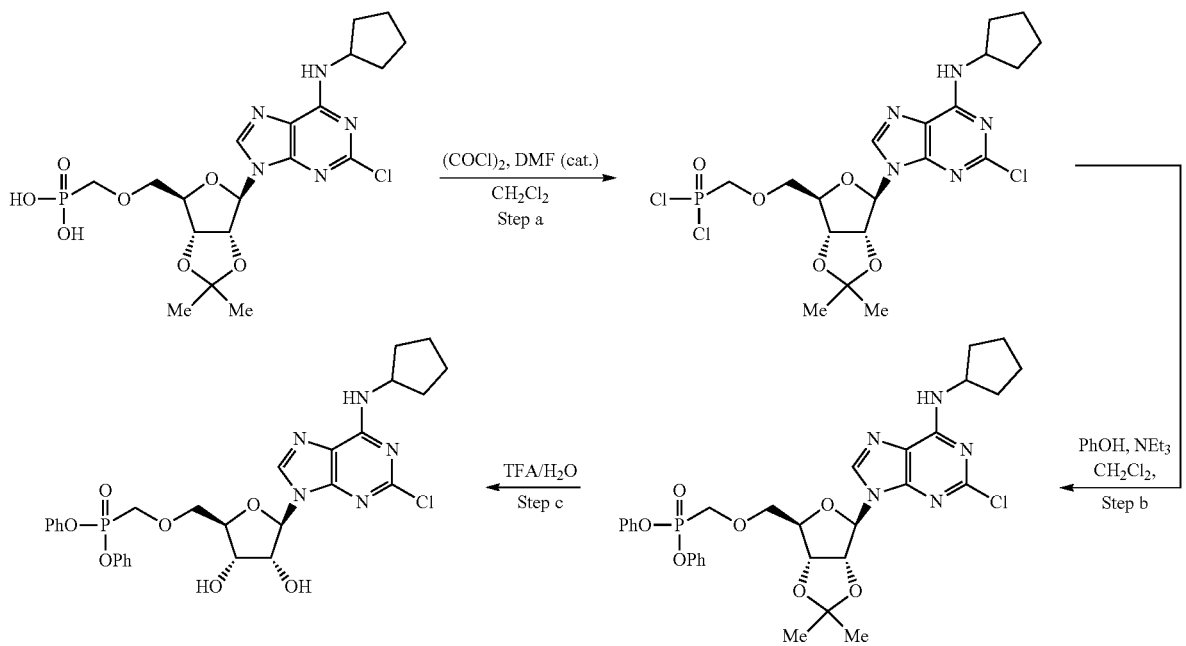 [SMILES: CC1(C)O[C@@H]2[C@H](O1)[C@@H](COCP(=O)(O)O)O[C@H]2n1cnc2c(NC3CCCC3)nc(Cl)nc21 ; CC1(C)O[C@@H]2[C@H](O1)[C@@H](COCP(=O)(Cl)Cl)O[C@H]2n1cnc2c(NC3CCCC3)nc(Cl)nc21 ; O=P(COC[C@H]1O[C@@H](n2cnc3c(NC4CCCC4)nc(Cl)nc32)[C@H](O)[C@@H]1O)(Oc1ccccc1)Oc1ccccc1 ; CC1(C)O[C@@H]2[C@H](O1)[C@@H](COCP(=O)(Oc1ccccc1)Oc1ccccc1)O[C@H]2n1cnc2c(NC3CCCC3)nc(Cl)nc21]

Example 63

Synthesis of ({[(2R,3S,4R,5R)-5-[2-chloro-6-(cyclopentylamino)-9H-purin-9-yl]-3,4-dihydroxyoxolan-2-yl]methoxy}methyl)(phenoxy)phosphinic acid

Example 64

Synthesis of ({[(2R,3S,4R,5R)-5-[2-chloro-6-(cyclopentylamino)-9H-purin-9-yl]-3,4-dihydroxyoxolan-2-yl]methoxy}methyl)(methoxy)phosphinic acid

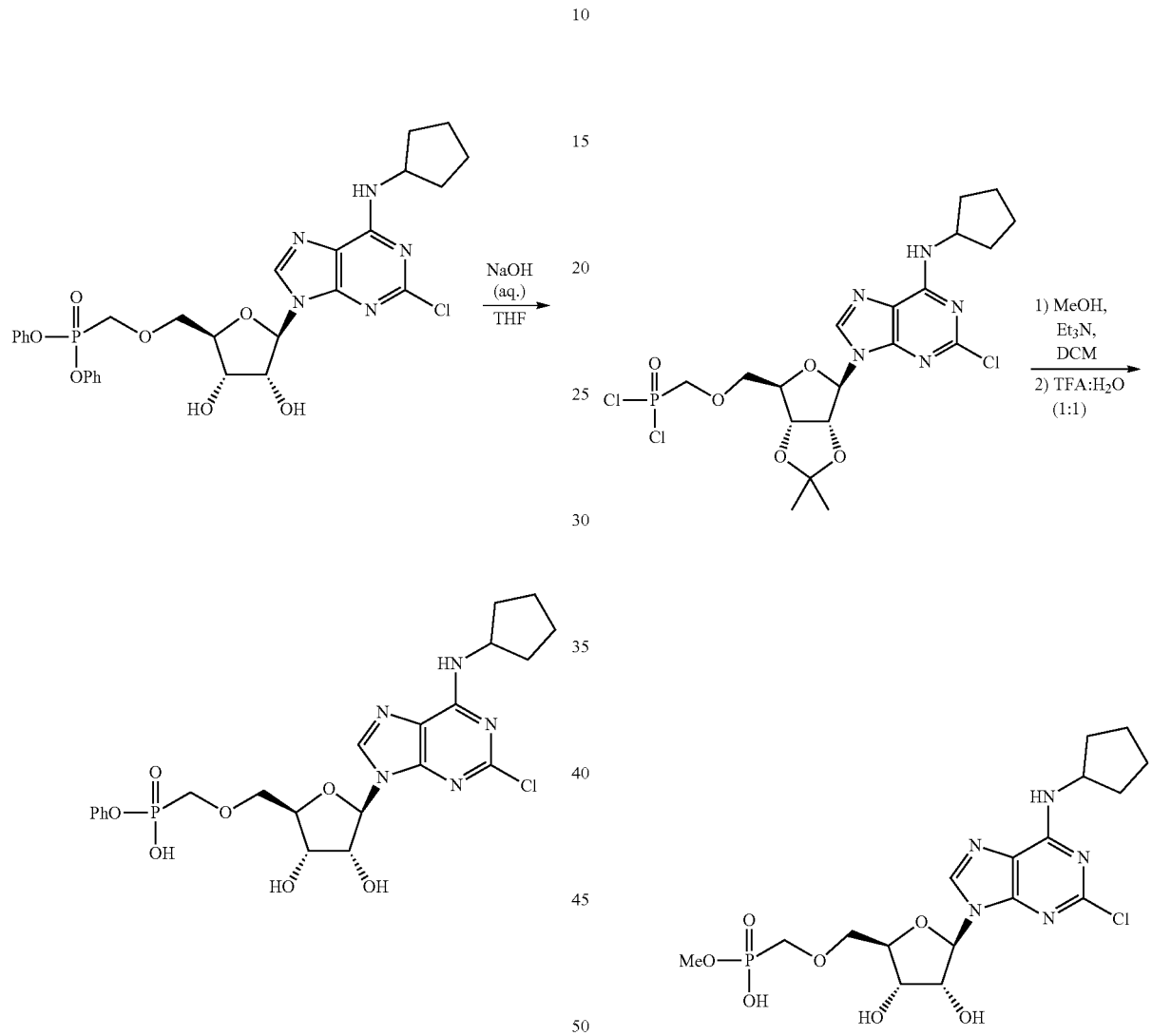

To the product from example 62 (26 mg, 42.2 µmol) was added 105 µL THF followed by 105 µL aq. NaOH (1N). The resulting mixture was stirred vigorously for 15 minutes, diluted with water and the THF was removed under reduced pressure. The reaction mixture was purified by reverse phase HPLC (C18 column, 0 to 40% gradient of acetonitrile and water with 0.1% TFA) to give the product as a white solid: $^1$H NMR (400 MHz, DMSO-$d_6$) δ 8.42-8.32 (m, 2H), 7.36-7.26 (m, 2H), 7.21-7.10 (m, 3H), 5.85 (d, J=5.8 Hz, 1H), 4.52 (t, J=5.4 Hz, 1H), 4.47-4.39 (m, 1H), 4.09 (ddd, J=17.3, 4.8, 3.4 Hz, 2H), 3.85 (d, J=8.3 Hz, 2H), 3.82-3.69 (m, 2H), 1.97-1.88 (m, 2H), 1.73-1.68 (m, 2H), 1.64-1.48 (m, 4H). ESI MS [M−H]$^-$ for $C_{22}H_{26}ClN_5O_7P$, calcd 538.1, found 538.2.

The title compound was synthesized as a white solid in similar fashion to example 63: $^1$H NMR (400 MHz, DMSO-$d_6$) δ 8.39 (s, 1H), 8.39-8.30 (m, 1H), 5.84 (d, J=5.8 Hz, 1H), 4.50 (t, J=5.4 Hz, 1H), 4.43 (q, J=7.1 Hz, 1H), 4.11 (dd, J=4.9, 3.5 Hz, 1H), 4.05 (q, J=3.7 Hz, 1H), 3.82-3.66 (m, 4H), 3.61 (d, J=10.7 Hz, 3H), 2.07-1.85 (m, 3H), 1.81-1.66 (m, 2H), 1.66-1.47 (m, 4H). ESI MS [M−H]$^-$ for $C_{17}H_{24}ClN_5O_7P$, calcd 476.1, found 476.2.

Example 65
Synthesis of bis({[(2,2-dimethylpropoxy)carbonyl]oxy}methyl) {[(2R,3S,4R,5R)-5-[2-chloro-6-(cyclopentylamino)-9H-purin-9-yl]-3,4-dihydroxyoxolan-2-yl]methoxy}methanephosphonate
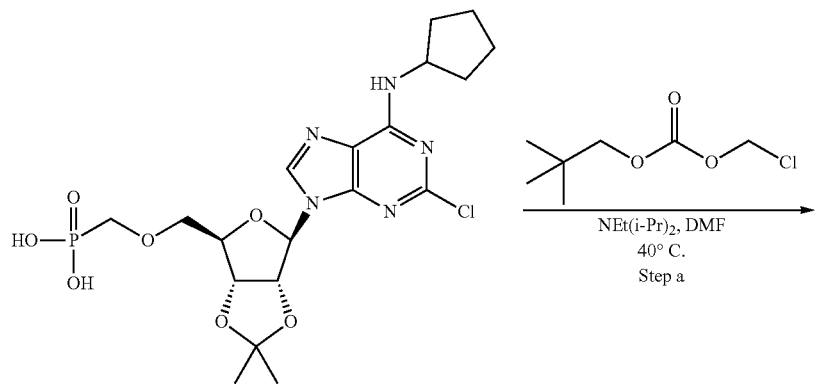
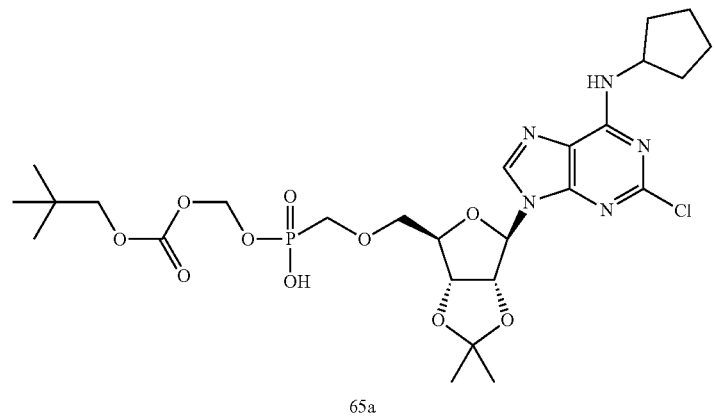
65a
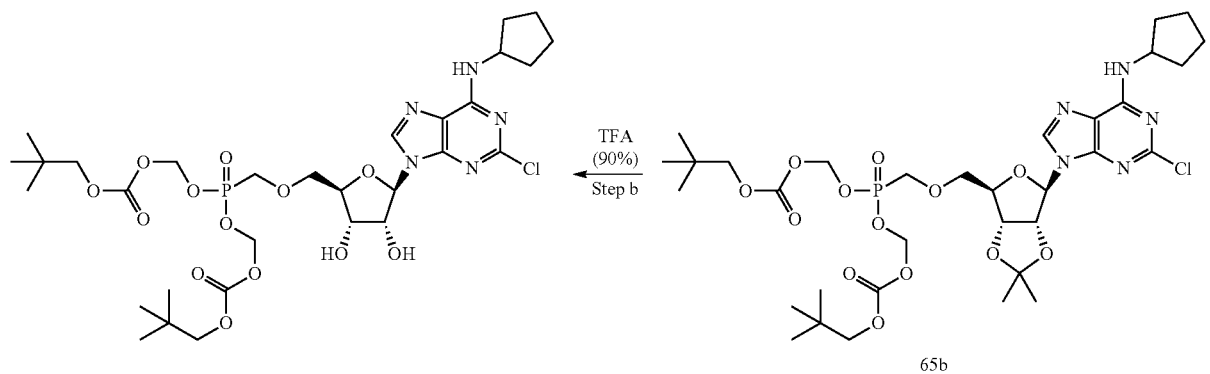
65b Step a: To compound ({[(3aR,4R,6R,6aR)-6-[2-chloro-6-(cyclopentylamino)-9H-purin-9-yl]-2,2-dimethyl-tetrahydro-2H-furo[3,4-d][1,3]dioxol-4-yl]methoxy}methyl)phosphonic acid (from example 1, 510 mg, 1.01 mmol) was placed under high vacuum at 45° C. for 1 hour. After cooling to ambient temperature, the material was placed under nitrogen and dissolved in 2.37 mL anhydrous DMF. To the resulting solution was added a solution of chloromethyl neopentyl carbonate (2.74 g, 15.2 mmol, 15 equiv.) in 1 mL DMF followed by N,N-diisopropylethylamine (2.64 mL, 15.2 mmol, 15 equiv.). The mixture was heated to 40° C. for 14 hours. After cooling to room temperature the mixture was concentrated under reduced pressure and the crude residue was purified by reverse phase flash chromatography (C18 column, 0 to 100% gradient of acetonitrile and water with 0.1% formic acid) to give the mono alkylated product as a white solid (65a, 110 mg, 17%) and the bis alkylated product as a white solid (65b, 370 mg, 46%).

Step b: 65b from step a (370 mg) was dissolved in 1.5 mL of 90% TFA/water at 0° C. After stirring at ambient temperature for 25 minutes, the mixture was concentrated under reduced pressure and the crude residue was purified by reverse phase flash chromatography (C18 column, 0 to 100% gradient of acetonitrile and water with 0.1% formic acid) to provide the product as a white solid: $^1$H NMR (400 MHz, DMSO-$d_6$) δ 8.34-8.29 (m, 2H), 5.83 (d, J=4.6 Hz, 1H), 5.64 (d, J=12.5 Hz, 4H), 5.54 (d, J=5.2 Hz, 1H), 5.30 (dd, J=5.3, 1.8 Hz, 1H), 4.48-4.43 (m, 2H), 4.10 (q, J=5.1, 4.6, 4.0 Hz, 1H), 4.05-3.98 (m, 4H), 3.86 (d, J=5.8 Hz, 1H), 3.82-3.76 (m, 1H), 3.72 (dd, J=11.1, 5.2 Hz, 1H), 1.96-1.91 (m, 2H), 1.73-1.68 (m, 2H), 1.64-1.48 (m, 4H), 0.91-0.80 (m, 18H). ESI MS [M+H]$^+$ for $C_{30}H_{48}ClN_5O_{13}P$, calcd 752.3, found 752.3.

Example 66

Synthesis of ({[(2R,3S,4R,5R)-5-[2-chloro-6-(cyclopentylamino)-9H-purin-9-yl]-3,4-dihydroxyoxolan-2-yl]methoxy}methyl)({[(2,2-dimethylpropoxy)carbonyl]oxy}-methoxy)phosphinic acid

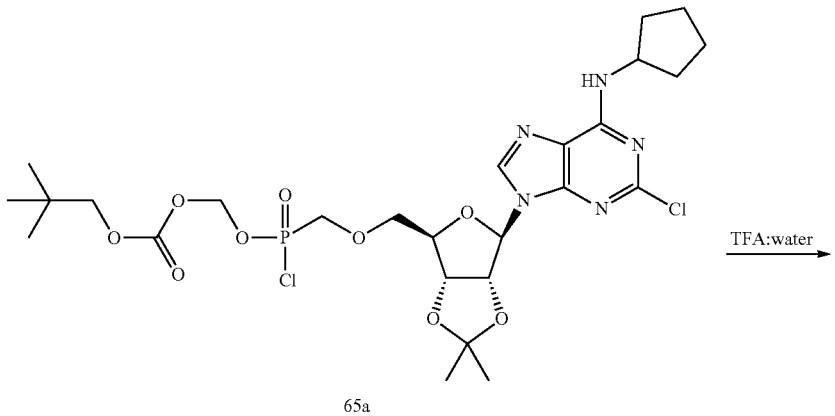

65a

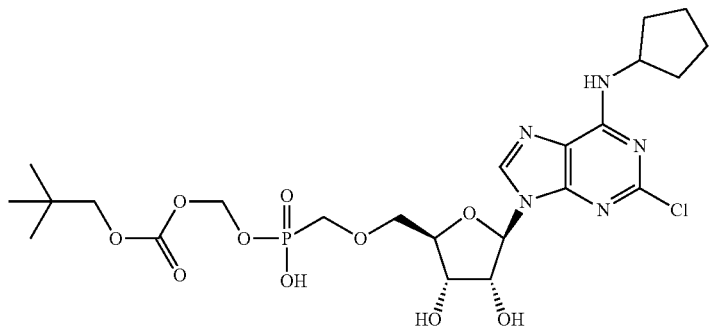

The title compound was obtained using identical procedure to example 65 from the compound 65a to give white solid: $^1$H NMR (400 MHz, DMSO-$d_6$) δ 8.46-8.39 (m, 1H), 8.34-8.29 (m, 1H), 5.89-5.80 (m, 1H), 5.59-5.48 (m, 2H), 4.57-4.48 (m, 1H), 4.43 (s, 1H), 4.17-4.08 (m, 1H), 4.08-4.00 (m, 1H), 3.87-3.79 (m, 2H), 3.75-3.62 (m, 4H), 1.97-1.92 (m, 2H), 1.74-1.69 (m, 2H), 1.59-1.54 (m, 4H), 0.95-0.81 (m, 9H). ESI MS [M+H]+ for $C_{23}H_{36}ClN_5O_{10}P$, calcd 608.2, found 608.3.

Example 67

Synthesis of bis({[(propan-2-yloxy)carbonyl]oxy}methyl) {[(2R,3S,4R,5R)-5-[2-chloro-6-(cyclopentylamino)-9H-purin-9-yl]-3,4-dihydroxyoxolan-2-yl]methoxy}methane-phosphonate

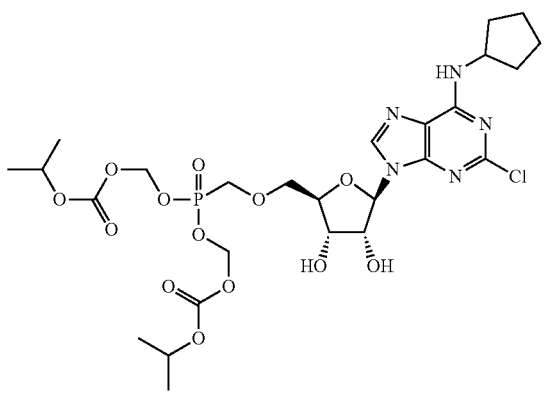 [SMILES: CC(C)OC(=O)OCOP(=O)(COC[C@H]1O[C@@H](n2cnc3c(NC4CCCC4)nc(Cl)nc32)[C@H](O)[C@@H]1O)OCOC(=O)OC(C)C]

The title compound was synthesized as a white solid in similar fashion to example 65: $^1$H NMR (400 MHz, DMSO) δ 8.38-8.28 (m, 2H), 5.83 (d, J=5.5 Hz, 1H), 5.60 (dd, J=12.8, 7.0 Hz, 4H), 4.88-4.75 (m, 1H), 4.50-4.35 (m, 2H), 4.10 (t, J=4.5 Hz, 1H), 4.05-3.96 (m, 3H), 3.82-3.70 (m, 1H), 3.67 (d, J=11.0 Hz, 1H), 1.99-1.89 (m, 2H), 1.74-1.67 (m, 2H), 1.61-1.50 (m, 4H), 1.23 (dd, J=6.2, 2.3 Hz, 12H). ESI MS [M+H]$^+$ for $C_{26}H_{39}ClN_5O_{13}P$, calcd 696.2, found 696.3.

Example 68

Synthesis of bis[(ethoxycarbonyl)oxy]methyl {[(2R,3S,4R,5R)-5-[2-chloro-6-(cyclopentylamino)-9H-purin-9-yl]-3,4-dihydroxyoxolan-2-yl]methoxy}methane-phosphonate

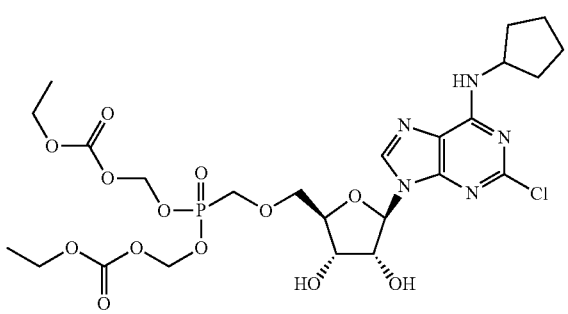 [SMILES: CCOC(=O)OCOP(=O)(COC[C@H]1O[C@@H](n2cnc3c(NC4CCCC4)nc(Cl)nc32)[C@H](O)[C@@H]1O)OCOC(=O)OCC]

The title compound was synthesized in similar fashion to example 65: $^1$H NMR (400 MHz, DMSO-d$_6$) δ 8.30 (s, 2H), 5.81 (d, J=5.4 Hz, 1H), 5.60 (d, J=12.7 Hz, 4H), 5.52 (d, J=5.9 Hz, 1H), 5.30 (dd, J=5.3, 0.9 Hz, 1H), 4.44 (t, J=5.5 Hz, 1H), 4.16 (qdd, J=7.1, 2.3, 0.9 Hz, 4H), 4.09 (q, J=4.8 Hz, 1H), 4.01 (dt, J=11.0, 5.7 Hz, 3H), 3.81-3.65 (m, 2H), 1.91 (s, 2H), 1.69 (s, 2H), 1.54 (d, J=9.1 Hz, 4H), 1.20 (tdd, J=7.1, 2.1, 0.9 Hz, 6H). ESI MS [M+H]+ $C_{24}H_{36}ClN_5O_{13}P$, calcd 668.2, found 668.3.

Example 69

Synthesis of ({[(2R,3S,4R,5R)-5-[2-chloro-6-(cyclopentylamino)-9H-purin-9-yl]-3,4-dihydroxyoxolan-2-yl]methoxy}methyl)({[(ethoxycarbonyl)oxy]methoxy})phosphinic acidoxy]methoxy})phosphinic acid

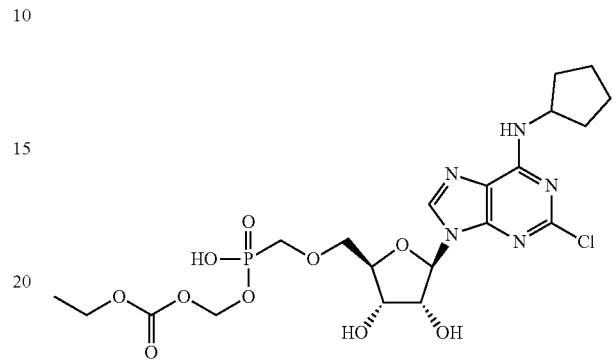

The title compound was synthesized in similar fashion to example 66: $^1$H NMR (400 MHz, DMSO-d$_6$) δ 8.45-8.40 (m, 1H), 8.39-8.28 (m, 1H), 5.84 (s, 1H), 5.51 (d, J=12.5 Hz, 3H), 4.51 (s, 1H), 4.45-4.40 (m, 1H), 4.19-4.08 (m, 3H), 4.03 (q, J=3.8 Hz, 1H), 3.71-3.57 (m, 3H), 1.96-1.91 (m, 2H), 1.74-1.68 (m, 2H), 1.58-1.53 (m, 4H), 1.21 (td, J=7.1, 3.5 Hz, 3H). ESI MS [M+H]$^+$ for $C_{20}H_{30}ClN_5O_{10}P$, calcd 566.1, found 566.3.

Example 70

Synthesis of bis[(methoxycarbonyl)oxy]methyl {[(2R,3S,4R,5R)-5-[2-chloro-6-(cyclopentylamino)-9H-purin-9-yl]-3,4-dihydroxyoxolan-2-yl]methoxy}methane-phosphonate

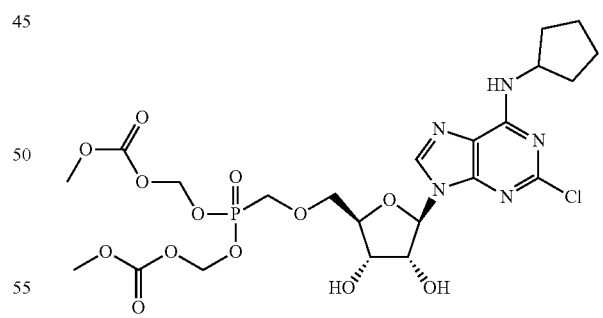

The title compound was synthesized in similar fashion to example 65: $^1$H NMR (400 MHz, DMSO-d$_6$) δ 8.32 (s, 2H), 5.83 (d, J=5.2 Hz, 1H), 5.63 (d, J=12.9 Hz, 4H), 5.55 (d, J=5.8 Hz, 1H), 5.32 (dd, J=5.3, 1.4 Hz, 1H), 4.50-4.39 (m, 2H), 4.10 (dd, J=7.4, 3.1 Hz, 1H), 4.02 (t, J=6.8 Hz, 3H), 3.83-3.68 (m, 6H), 1.96-1.91 (m, 2H), 1.74-1.69 (m, 2H), 1.59-1.52 (m, 4H). ESI MS [M+H]$^+$ for $C_{22}H_{32}ClN_5O_{13}P$, calcd 640.1, found 640.2.

Example 71

Synthesis of bis({[(2-methoxyethoxy)carbonyl]oxy}methyl) {[(2R,3S,4R,5R)-5-[2-chloro-6-(cyclopentylamino)-9H-purin-9-yl]-3,4-dihydroxyoxolan-2-yl]methoxy}methane-phosphonate

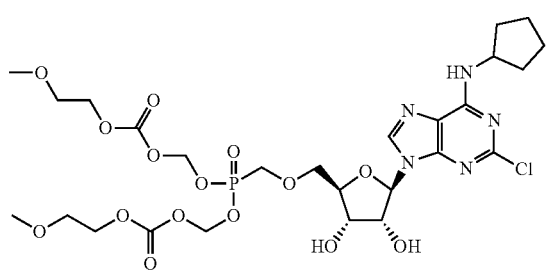 [SMILES: COCCOC(=O)OCOP(=O)(COC[C@H]1O[C@@H](n2cnc3c(NC4CCCC4)nc(Cl)nc32)[C@H](O)[C@@H]1O)OCOC(=O)OCCOC]

The title compound was synthesized in similar fashion to example 65: 1H NMR (400 MHz, DMSO-$d_6$) δ 8.34-8.19 (m, 2H), 5.83 (d, J=5.4 Hz, 1H), 5.63 (d, J=12.8 Hz, 4H), 5.54 (d, J=5.8 Hz, 1H), 5.31 (dd, J=5.4, 1.4 Hz, 1H), 4.51-4.34 (m, 2H), 4.30-4.22 (m, 4H), 4.15-4.06 (m, 1H), 4.07-3.98 (m, 3H), 3.79 (dd, J=11.1, 3.4 Hz, 1H), 3.72 (dd, J=11.3, 4.9 Hz, 1H), 3.57-3.49 (m, 4H), 3.31 (s, 1H), 3.24 (d, J=1.2 Hz, 4H), 1.95-1.90 (m, 2H), 1.73-1.68 (m, 2H), 1.58-1.53 (m, 4H). ESI MS [M+H]$^+$ for $C_{26}H_{40}ClN_5O_{15}P$, calcd 728.2, found 728.3.

Example 72

Synthesis of ({[(2R,3S,4R,5R)-5-[2-chloro-6-(cyclopentylamino)-9H-purin-9-yl]-3,4-dihydroxyoxolan-2-yl]methoxy}methyl)({[(2-methoxyethoxy)carbonyl]oxy}methoxy)-phosphinic acid

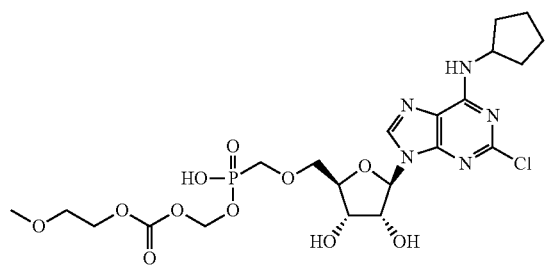 [SMILES: COCCOC(=O)OCOP(=O)(O)COC[C@H]1O[C@@H](n2cnc3c(NC4CCCC4)nc(Cl)nc32)[C@H](O)[C@@H]1O]

The title compound was synthesized in similar fashion to example 66: 1H NMR (400 MHz, DMSO-$d_6$) δ 8.35 (dd, J=18.5, 4.9 Hz, 2H), 5.87-5.80 (m, 1H), 5.55 (dd, J=12.7, 2.0 Hz, 2H), 4.49 (td, J=5.4, 2.0 Hz, 1H), 4.45-4.39 (m, 1H), 4.23 (dt, J=6.6, 2.4 Hz, 2H), 4.11 (dd, J=5.4, 2.8 Hz, 1H), 4.04 (s, 1H), 3.79-3.64 (m, 4H), 3.52 (dt, J=6.4, 2.4 Hz, 2H), 3.24 (d, J=2.2 Hz, 3H), 1.94 (s, 2H), 1.74-1.68 (m, 2H), 1.59-1.52 (m, 4H). ESI MS [M-H]$^-$ for $C_{21}H_{30}ClN_5O_{11}P$, calcd 594.1, found 594.1.

Example 73

Synthesis of {[({[(2R,3S,4R,5R)-5-[2-chloro-6-(cyclopentylamino)-9H-purin-9-yl]-3,4-dihydroxyoxolan-2-yl]methoxy}methyl)({[(2,2-dimethylpropanoyl)oxy]methoxy})phosphoryl]-oxy}methyl 2,2-dimethylpropanoate

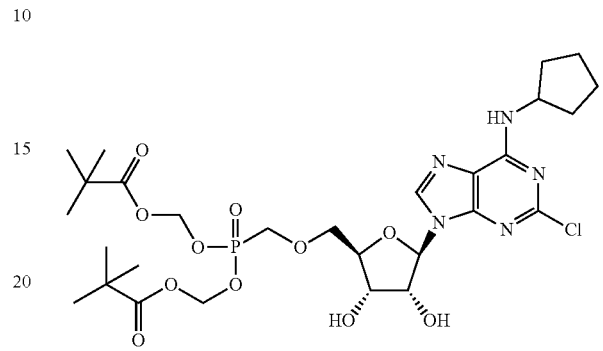

The title compound was synthesized in similar fashion to example 65: $^1$H NMR (400 MHz, DMSO-$d_6$) δ 8.29 (d, J=7.9 Hz, 2H), 5.81 (d, J=5.3 Hz, 1H), 5.60 (d, J=12.8 Hz, 4H), 5.53 (s, 1H), 5.29 (d, J=5.3 Hz, 1H), 4.46 (s, 1H), 4.09 (q, J=4.8 Hz, 1H), 4.01 (d, J=4.5 Hz, 1H), 3.95 (d, J=7.7 Hz, 2H), 3.82-3.67 (m, 2H), 1.91 (s, 2H), 1.69 (s, 2H), 1.54 (s, 3H), 1.15-1.07 (m, 18H). ESI MS [M+H]$^+$ $C_{28}H_{44}ClN_5O_{11}P$, calcd 692.2, found 692.3.

Example 74

Synthesis of bis({[(2,2-dimethylpropoxy)carbonyl]oxy}methyl) {[(2R,3S,4R,5R)-5-(2-chloro-6-{[(3S)-oxolan-3-yl]amino}-9H-purin-9-yl)-3,4-dihydroxyoxolan-2-yl]methoxy}methanephosphonate

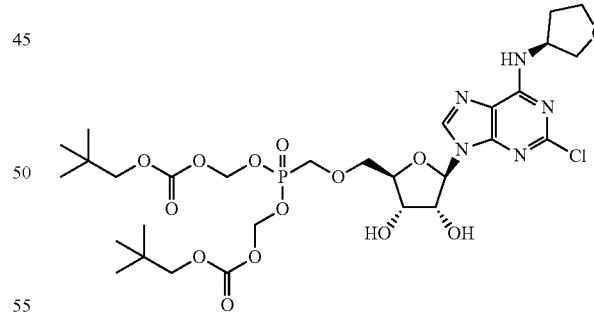

The title compound was obtained using identical procedure as for example 65 to give white solid: $^1$H NMR (400 MHz, DMSO-$d_6$) δ 8.53 (s, 1H), 8.34 (d, J=1.6 Hz, 1H), 5.88-5.78 (m, 1H), 5.68-5.48 (m, 5H), 5.30 (dd, J=5.4, 1.6 Hz, 1H), 4.45 (d, J=5.6 Hz, 1H), 4.09 (d, J=4.9 Hz, 1H), 4.05-3.93 (m, 3H), 3.93-3.81 (m, 6H), 3.81-3.68 (m, 3H), 3.63-3.55 (m, 1H), 3.35-3.24 (m, 5H), 2.17 (br. s, 1H), 2.08-1.83 (m, 1H), 1.00-0.73 (m, 18H).

ESI MS [M+H]$^+$ for $C_{29}H_{45}ClN_5O_{14}P$, calcd 754.2, found 754.3.

Example 75

Synthesis of ({[(2R,3S,4R,5R)-5-(2-chloro-6-{[(3S)-oxolan-3-yl]amino}-9H-purin-9-yl)-3,4-dihydroxyoxolan-2-yl]methoxy}methyl)({[(2,2-dimethylpropoxy)carbonyl]oxy}methoxy)phosphinic acid

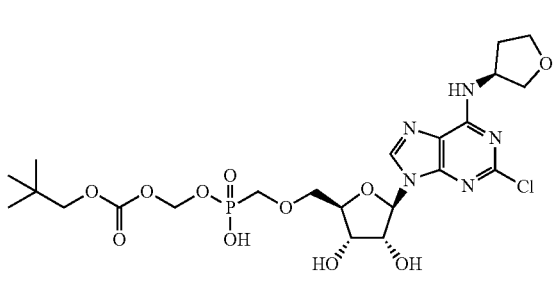 [SMILES: CC(C)(C)COC(=O)OCOP(=O)(O)COC[C@H]1O[C@@H](n2cnc3c(N[C@H]4CCOC4)nc(Cl)nc32)[C@H](O)[C@@H]1O]

The title compound was obtained using identical procedure as for example 66 to give white solid: $^1$H NMR (400 MHz, DMSO-$d_6$) δ 8.71-8.19 (m, 2H), 6.00-5.72 (m, 1H), 5.60-5.34 (m, 3H), 4.65-4.42 (m, 2H), 4.20-3.94 (m, 2H), 3.94-3.82 (m, 2H), 3.82-3.76 (m, 2H), 3.75-3.55 (m, 7H), 2.33-1.73 (m, 3H), 0.86 (s, 9H). ESI MS [M−H]$^−$ for $C_{22}H_{33}ClN_5O_{11}P$, calcd 608.2, found 608.2.

Example 76

Synthesis of bis({[(propan-2-yloxy)carbonyl]oxy}methyl){[(2R,3S,4R,5R)-5-(2-chloro-6-{[(3S)-oxolan-3-yl]amino}-9H-purin-9-yl)-3,4-dihydroxyoxolan-2-yl]methoxy}methanephosphonate

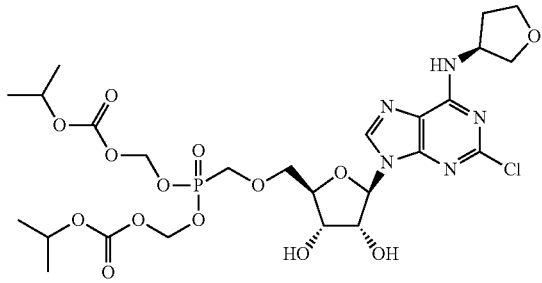 [SMILES: CC(C)OC(=O)OCOP(=O)(COC[C@H]1O[C@@H](n2cnc3c(N[C@H]4CCOC4)nc(Cl)nc32)[C@H](O)[C@@H]1O)OCOC(=O)OC(C)C]

The title compound was synthesized in similar fashion to example 65. $^1$H NMR (400 MHz, DMSO-$d_6$) δ 8.53 (s, 1H), 8.34 (s, 1H), 5.82 (d, J=5.4 Hz, 1H), 5.68-5.55 (m, 4H), 5.53 (d, J=5.9 Hz, 1H), 5.30 (d, J=5.3 Hz, 1H), 4.79 (pd, J=6.2, 1.7 Hz, 2H), 4.46 (q, J=5.5 Hz, 1H), 4.09 (q, J=4.8 Hz, 1H), 4.01 (dd, J=12.5, 6.1 Hz, 3H), 3.93-3.67 (m, 5H), 3.59 (dd, J=8.9, 4.5 Hz, 1H), 2.17 (s, 1H), 1.97 (d, J=38.8 Hz, 1H), 1.21 (dd, J=6.2, 2.0 Hz, 12H). ESI MS [M+H]$^+$ $C_{25}H_{38}ClN_5O_{14}P$, calcd 698.2, found 698.2.

Example 77

Synthesis of ({[(2R,3S,4R,5R)-5-(2-chloro-6-{[(3S)-oxolan-3-yl]amino}-9H-purin-9-yl)-3,4-dihydroxyoxolan-2-yl]methoxy}methyl)({[(propan-2-yloxy)carbonyl]oxy}methoxy)phosphinic acid

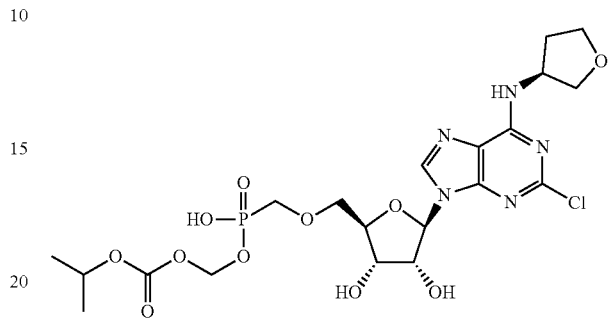

The title compound was synthesized in similar fashion to example 66. $^1$H NMR (400 MHz, DMSO-$d_6$) δ 8.50 (d, J=32.5 Hz, 2H), 5.88-5.75 (m, 1H), 5.47 (d, J=12.4 Hz, 2H), 4.84-4.68 (m, 1H), 4.49 (d, J=5.7 Hz, 1H), 4.10 (t, J=4.2 Hz, 1H), 4.01 (d, J=3.9 Hz, 1H), 3.87 (dt, J=15.4, 8.0 Hz, 2H), 3.76-3.54 (m, 5H), 2.17 (s, 1H), 2.01 (s, 1H), 1.23-1.16 (m, 6H). ESI MS [M+H]$^+$ $C_{20}H_{30}ClN_5O_{11}P$, calcd 582.1, found 582.2.

Example 78

Synthesis of bis[(ethoxycarbonyl)oxy]methyl {[(2R,3S,4R,5R)-5-(2-chloro-6-{[(3S)-oxolan-3-yl]amino}-9H-purin-9-yl)-3,4-dihydroxyoxolan-2-yl]methoxy}methanephosphonate

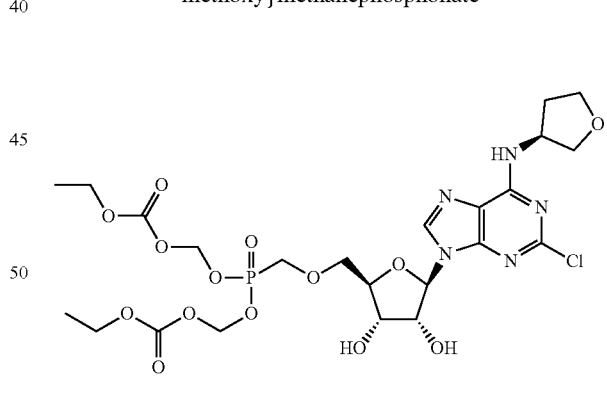

The title compound was synthesized in similar fashion to example 65. $^1$H NMR (400 MHz, DMSO-$d_6$) δ 8.54 (s, 1H), 8.34 (d, J=4.6 Hz, 1H), 5.82 (d, J=5.6 Hz, 1H), 5.60 (dd, J=12.6, 4.5 Hz, 4H), 5.53 (s, OH), 5.31 (t, J=5.1 Hz, 1H), 4.46 (t, J=5.4 Hz, 1H), 4.22-4.05 (m, 5H), 4.06-3.94 (m, 2H), 3.87 (d, J=16.2 Hz, 1H), 3.81-3.66 (m, 3H), 3.64-3.54 (m, 1H), 2.18 (s, 1H), 2.01 (s, 1H), 1.20 (dtd, J=9.1, 4.9, 2.6 Hz, 6H). ESI MS [M+H]$^+$ $C_{23}H_{34}ClN_5O_{14}P$, calcd 670.2, found 670.2.

Example 79

Synthesis of ({[(2R,3S,4R,5R)-5-(2-chloro-6-{[(3S)-oxolan-3-yl]amino}-9H-purin-9-yl)-3,4-dihydroxyoxolan-2-yl]methoxy}methyl)({[(ethoxycarbonyl)oxy]methoxy})phosphinic acid

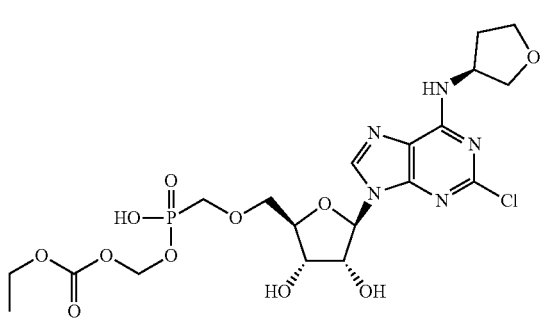 [SMILES: CCOC(=O)OCOP(=O)(O)COC[C@H]1O[C@@H](n2cnc3c(N[C@H]4CCOC4)nc(Cl)nc32)[C@H](O)[C@@H]1O]

The title compound was synthesized in similar fashion to example 66: $^1$H NMR (400 MHz, DMSO-d$_6$) δ 8.57 (s, 1H), 5.82 (d, J=5.9 Hz, 1H), 5.43 (d, J=12.1 Hz, 2H), 4.57 (d, J=34.1 Hz, 1H), 4.09 (q, J=7.0 Hz, 2H), 3.99 (d, J=3.4 Hz, 1H), 3.88 (dd, J=18.3, 8.0 Hz, 2H), 3.71 (q, J=7.7 Hz, 1H), 3.66-3.53 (m, 2H), 2.17 (s, 1H), 2.01 (s, 1H), 1.25-1.19 (m, 3H). ESI MS [M+H]$^+$ C$_{19}$H$_{28}$ClN$_5$O$_{11}$P, calcd 568.1, found 568.3.

Example 80

Synthesis of bis({[(propan-2-yloxy)carbonyl]oxy}methyl) {[(2R,3S,4R,5R)-5-[6-chloro-4-(cyclopentylamino)-1H-pyrazolo[3,4-d]pyrimidin-1-yl]-3,4-dihydroxyoxolan-2-yl]methoxy}methanephosphonate

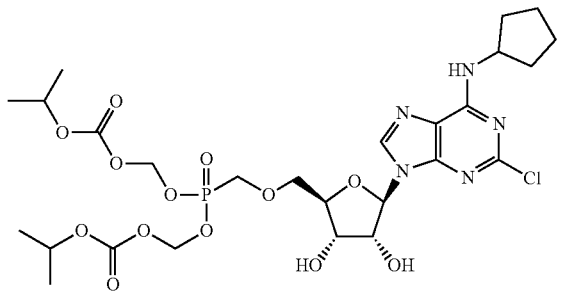 [SMILES: CC(C)OC(=O)OCOP(=O)(COC[C@H]1O[C@@H](n2cnc3c(NC4CCCC4)nc(Cl)nc32)[C@H](O)[C@@H]1O)OCOC(=O)OC(C)C]

The title compound was synthesized in similar fashion to example 65: $^1$H NMR (400 MHz, DMSO-d$_6$) δ 8.70-8.62 (m, 1H), 8.30-8.18 (m, 1H), 6.07-5.95 (m, 1H), 5.61-5.49 (m, 4H), 4.86-4.73 (m, 2H), 4.50-4.35 (m, 2H), 4.23-4.16 (m, 1H), 4.04-3.95 (m, 1H), 3.94-3.86 (m, 2H), 3.75-3.66 (m, 1H), 3.61-3.51 (m, 1H), 2.04-1.91 (m, 2H), 1.78-1.45 (m, 6H), 1.28-1.15 (m, 12H). ESI MS [M+H]$^+$ for C$_{26}$H$_{40}$ClN$_5$O$_{13}$P, calcd 696.2, found 696.3.

Example 81

Synthesis of ({[(2R,3S,4R,5R)-5-[6-chloro-4-(cyclopentylamino)-1H-pyrazolo[3,4-d]pyrimidin-1-yl]-3,4-dihydroxyoxolan-2-yl]methoxy}methyl)({[(propan-2-yloxy)carbonyl]oxy}methoxy)phosphinic acid

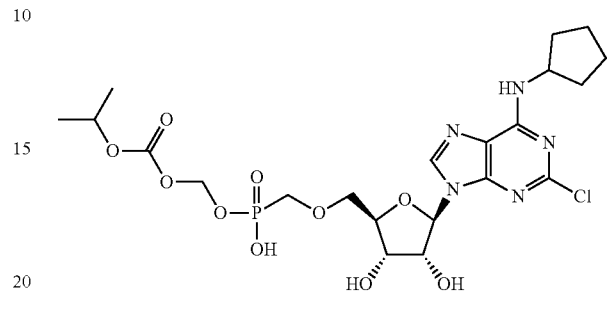

The title compound was synthesized in similar fashion to Example 66: $^1$H NMR (400 MHz, DMSO-d$_6$) δ 8.70-8.62 (m, 1H), 8.34-8.15 (m, 1H), 6.04-5.95 (m, 1H), 5.51-5.41 (m, 2H), 4.77 (h, J=5.9 Hz, 1H), 4.51-4.35 (m, 2H), 4.18 (q, J=5.0 Hz, 1H), 4.05-3.94 (m, 1H), 3.75-3.59 (m, 3H), 3.59-3.47 (m, 1H), 2.05-1.89 (m, 2H), 1.83-1.41 (m, 6H), 1.30-1.11 (m, 6H). ESI MS ESI MS [M+H]$^+$ for C$_{21}$H$_{32}$ClN$_5$O$_{10}$P, calcd 580.2, found 580.3.

Example 82

Synthesis of bis[(ethoxycarbonyl)oxy]methyl {[(2R,3S,4R,5R)-5-[6-chloro-4-(cyclopentylamino)-1H-pyrazolo[3,4-d]pyrimidin-1-yl]-3,4-dihydroxyoxolan-2-yl]methoxy}methanephosphonate

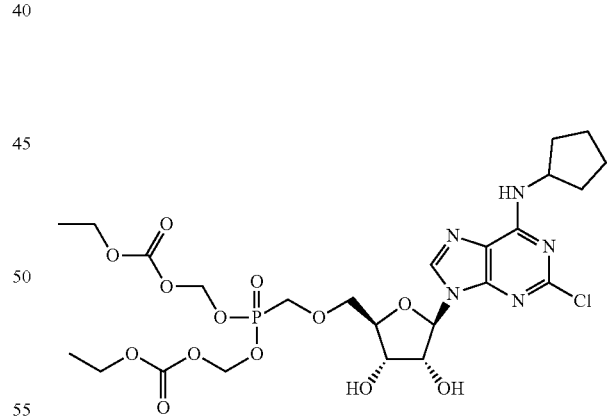

The title compound was synthesized in similar fashion to example 65: $^1$H NMR (400 MHz, DMSO-d$_6$) δ 8.66 (d, J=7.3 Hz, 1H), 8.33-8.15 (m, 1H), 5.99 (d, J=3.9 Hz, 1H), 5.61-5.48 (m, 4H), 4.51-4.35 (m, 2H), 4.23-4.09 (m, 5H), 4.03-3.95 (m, 1H), 3.94-3.87 (m, 2H), 3.77-3.65 (m, 1H), 3.61-3.51 (m, 1H), 2.03-1.91 (m, 2H), 1.76-1.42 (m, 6H), 1.27-1.13 (m, 6H). ESI MS [M+H]$^+$ for C$_{24}$H$_{36}$ClN$_5$O$_{13}$P, calcd 668.2, found 668.3.

Example 83

Synthesis of ({[(2R,3S,4R,5R)-5-[6-chloro-4-(cyclopentylamino)-1H-pyrazolo[3,4-d]pyrimidin-1-yl]-3,4-dihydroxyoxolan-2-yl]methoxy}methyl)({[(ethoxycarbonyl)-oxy]methoxy})phosphinic acid

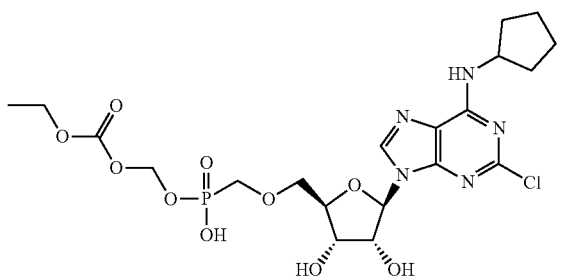 [SMILES: CC(C)OC(=O)OCOP(=O)(O)COC[C@H]1O[C@@H](n2cnc3c(NC4CCCC4)nc(Cl)nc32)[C@H](O)[C@@H]1O]

The title compound was synthesized in similar fashion to example 66: $^1$H NMR (400 MHz, DMSO-$d_6$) δ 8.66 (d, J=7.2 Hz, 1H), 8.29-8.17 (m, 1H), 5.98 (d, J=3.9 Hz, 1H), 5.53-5.40 (m, 2H), 4.49-4.34 (m, 2H), 4.22-4.07 (m, 3H), 3.98 (q, J=5.4 Hz, 1H), 3.66 (d, J=7.8 Hz, 3H), 3.53 (dd, J=10.9, 6.6 Hz, 1H), 2.03-1.92 (m, 2H), 1.78-1.43 (m, 6H), 1.24-1.14 (m, 3H). ESI MS [M+H]$^+$ for $C_{20}H_{30}ClN_5O_{10}P$, calcd 566.1, found 566.3.

Example 84

Synthesis of bis({[(2-methoxyethoxy)carbonyl]oxy}methyl) {[(2R,3S,4R,5R)-5-[6-chloro-4-(cyclopentylamino)-1H-pyrazolo[3,4-d]pyrimidin-1-yl]-3,4-dihydroxyoxolan-2-yl]methoxy}methanephosphonate

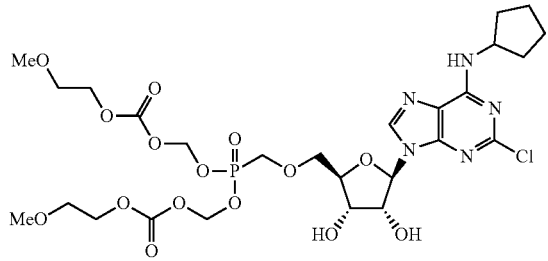 [SMILES: COCCOC(=O)OCOP(=O)(COC[C@H]1O[C@@H](n2cnc3c(NC4CCCC4)nc(Cl)nc32)[C@H](O)[C@@H]1O)OCOC(=O)OCCOC]

The title compound was synthesized in similar fashion to example 65: $^1$H NMR (400 MHz, Methanol-$d_4$) δ 8.11 (s, 1H), 6.17 (d, J=3.4 Hz, 1H), 5.71-5.60 (m, 4H), 4.65 (dd, J=5.0, 3.4 Hz, 1H), 4.59-4.44 (m, 2H), 4.33-4.28 (m, 4H), 4.18-4.10 (m, 1H), 4.06-3.91 (m, 2H), 3.87-3.72 (m, 2H), 3.65-3.57 (m, 4H), 3.37-3.32 (m, 6H), 2.17-2.03 (m, 2H), 1.87-1.50 (m, 6H). ESI MS [M+H]$^+$ for $C_{26}H_{40}ClN_5O_{15}P$, calcd 728.2, found 728.3.

Example 85

Synthesis of ({[(2R,3S,4R,5R)-5-[6-chloro-4-(cyclopentylamino)-1H-pyrazolo[3,4-d]pyrimidin-1-yl]-3,4-dihydroxyoxolan-2-yl]methoxy}methyl)({[(2-methoxyethoxy)carbonyl]oxy}methoxy)phosphinic acid

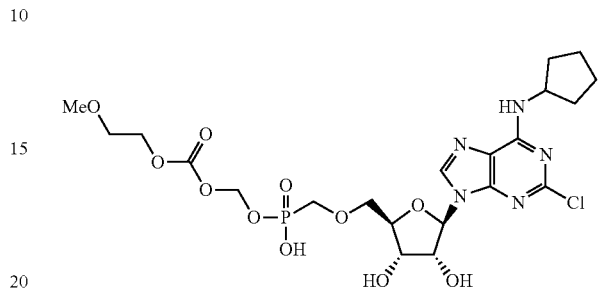

The title compound was synthesized in similar fashion to example 66: $^1$H NMR (400 MHz, DMSO-$d_6$) δ 8.67 (d, J=7.0 Hz, 1H), 8.22 (s, 1H), 5.98 (d, J=3.8 Hz, 1H), 5.52-5.43 (m, 2H), 4.48-4.36 (m, 2H), 4.26-4.14 (m, 3H), 3.98 (q, J=5.4 Hz, 1H), 3.72-3.63 (m, 3H), 3.56-3.47 (m, 3H), 3.27-3.18 (m, 3H), 2.04-1.92 (m, 2H), 1.77-1.47 (m, 6H). ESI MS [M+H]$^+$ for $C_{21}H_{32}ClN_5O_{11}P$, calcd 596.1, found 596.2.

Example 86

Synthesis of bis({[(propan-2-yloxy)carbonyl]oxy}methyl) {[(2R,3S,4R,5R)-5-(6-chloro-4-{[(3S)-oxolan-3-yl]amino}-1H-pyrazolo[3,4-d]pyrimidin-1-yl)-3,4-dihydroxyoxolan-2-yl]methoxy}methanephosphonate

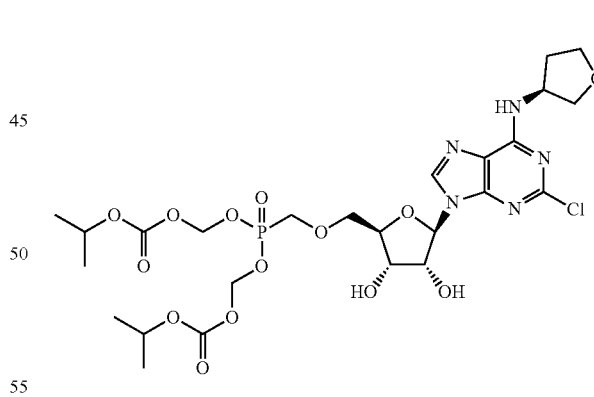

The title compound was obtained using identical procedure as for example 65 to give white solid: $^1$H NMR (400 MHz, DMSO-$d_6$) δ 8.93 (d, J=6.6 Hz, 1H), 8.30-8.20 (m, 1H), 6.00 (d, J=3.8 Hz, 1H), 5.60-5.49 (m, 4H), 5.46 (dd, J=5.5, 1.4 Hz, 1H), 5.22 (dd, J=6.1, 1.3 Hz, 1H), 4.86-4.73 (m, 2H), 4.71-4.55 (m, 1H), 4.42 (q, J=4.3 Hz, 1H), 4.19 (q, J=5.2 Hz, 1H), 4.01-3.96 (m, 1H), 3.94-3.82 (m, 4H), 3.77-3.61 (m, 3H), 3.56 (dd, J=10.9, 6.5 Hz, 1H), 2.36-2.15 (m, 1H), 1.91 (d, J=12.4 Hz, 1H), 1.28-1.16 (m, 12H). ESI MS [M+H]+ for $C_{25}H_{37}ClN_5O_{14}P$, calcd 698.2, found 698.3.

Example 87

Synthesis of (2R,3S,4R,5R)-2-({[bis({[(propan-2-yloxy)carbonyl]oxy}methoxy)phosphoryl]-methoxy}methyl)-5-[2-chloro-6-(cyclopentylamino)-9H-purin-9-yl]-4-hydroxyoxolan-3-yl 2-methylpropanoate

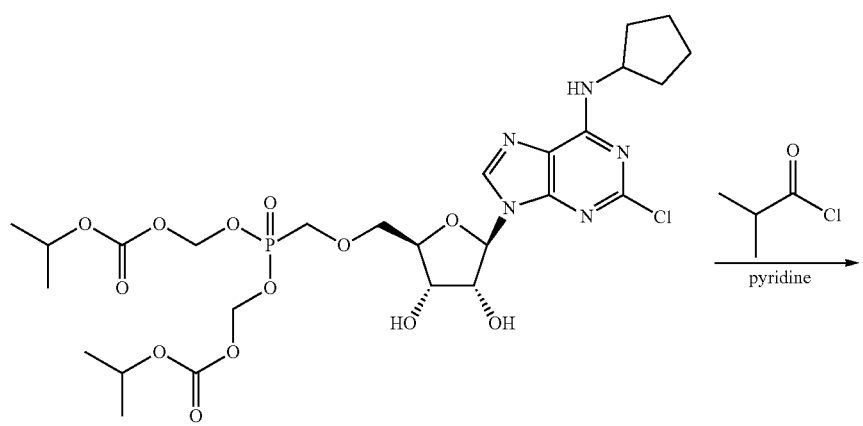

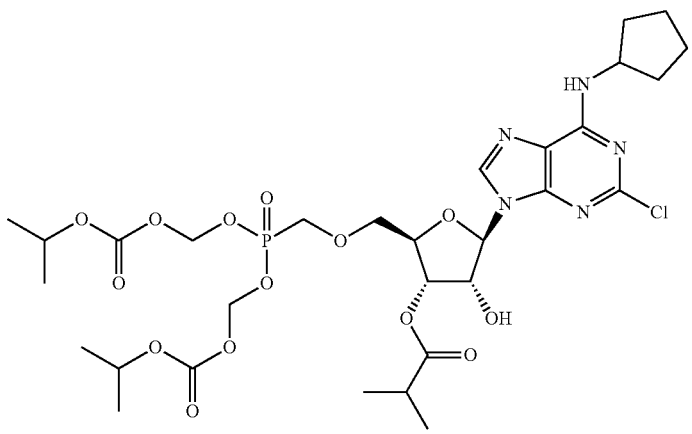

To a solution of example 67 (1.07 g, 1.54 mmol) in pyridine at 0° C. was added isobutyryl chloride (182 μL, 1.84 mmol) dropwise via syringe. The reaction was allowed to warm to room temperature and stir for two hours. The reaction was concentrated under reduced pressure and resulting residue was reconstituted in ethyl acetate and washed sequentially with saturated sodium bicarbonate, water and brine. The organics were dried over magnesium sulfate and concentrated to dryness. The crude produce was purified by column chromatography (C18, gradient of MeCN and $H_2O$ containing 0.1% formic acid) to provide the title compound (372 mg, 32%) as a white powder following lyophilization. $^1$H NMR (400 MHz, DMSO-$d_6$) δ 8.61-8.05 (m, 2H), 6.06 (d, J=4.8 Hz, 1H), 5.69 (d, J=5.9 Hz, 1H), 5.64-5.54 (m, 3H), 4.78 (dtq, J=9.3, 6.2, 3.1 Hz, 2H), 4.42 (q, J=5.4 Hz, 1H), 4.06 (td, J=5.2, 3.0 Hz, 1H), 4.00 (d, J=7.7 Hz, 2H), 3.82 (dd, J=10.9, 3.1 Hz, 1H), 3.78-3.68 (m, 1H), 2.67-2.52 (m, 1H), 2.00-1.84 (m, 2H), 1.76-1.63 (m, 2H), 1.63-1.42 (m, 4H), 1.25-1.17 (m, 10H), 1.07 (dd, J=7.0, 1.8 Hz, 3H), 1.03 (dd, J=7.0, 1.8 Hz, 3H). ESI MS [M+H]$^+$ for $C_{30}H_{45}ClN_5O_{14}P$, calcd 766.2, found 766.3.

Example 88

Synthesis of propan-2-yl (2R)-2-{[({[(2R,3S,4R,5R)-5-[2-chloro-6-(cyclopentylamino)-9H-purin-9-yl]-3,4-dihydroxyoxolan-2-yl]methoxy}methyl)(phenoxy)phosphoryl]-amino}propanoate

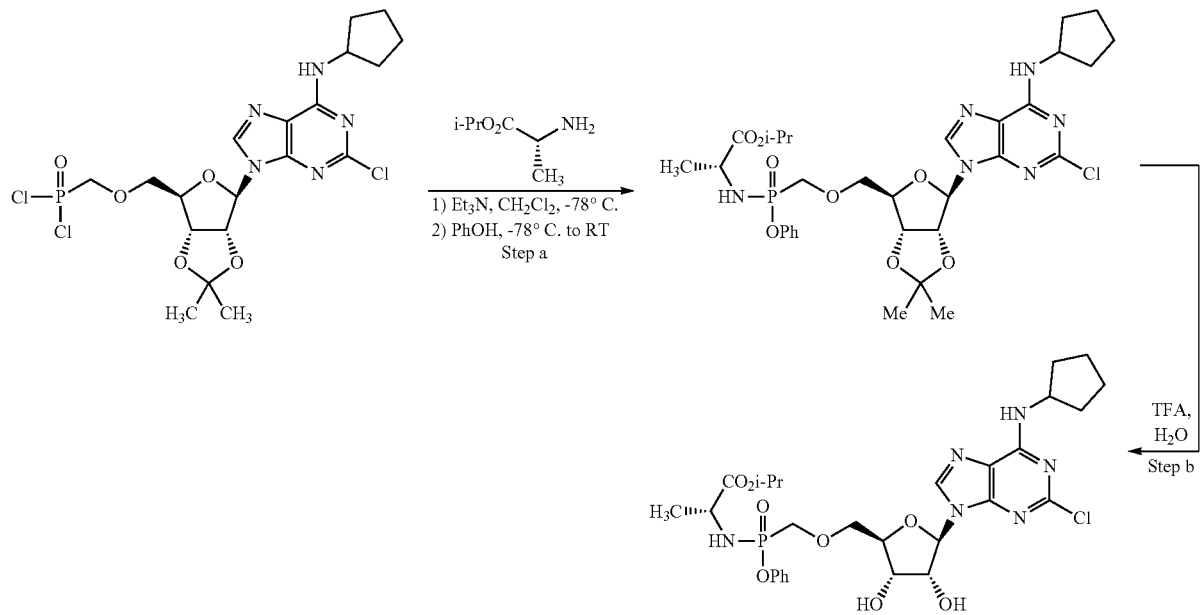

Step a: The product from Step a of example 62 (ca. 0.5 mmol) and L-alanine isopropyl ester HCl (84 mg, 0.5 mmol) were dissolved in $CH_2Cl_2$ (2.5 mL) under an atmosphere of $N_2$. The reaction mixture was cooled in a dry/ice acetone bath, and $Et_3N$ (0.28 mL, 2 mmol) was added. After one hour at this temperature, phenol (47 mg, 0.5 mmol) was added in one portion. The reaction mixture was allowed to warm to room temperature overnight, at which point the reaction mixture was concentrated. The crude residue was purified by flash chromatography on $SiO_2$ (0 to 10% MeOH/$CH_2Cl_2$ to give the product as a pale yellow oil in 34% yield (117 mg).

Step b: The product from Step a (97 mg, 0.14 mmol) was dissolved in 1.2 mL TFA and 0.2 mL $H_2O$. The reaction mixture stirred for 80 minutes and was concentrated. The crude residue was purified by reverse phase HPLC (C18 column, 0 to 50% gradient of acetonitrile and water with 0.1% TFA) to give the product as a white solid in 7% yield (6.7 mg): $^1$H NMR (400 MHz, DMSO) δ 8.46-8.29 (m, 2H), 7.31 (dt, J=8.3, 7.0 Hz, 2H), 7.24-7.10 (m, 3H), 5.89-5.81 (m, 1H), 5.78-5.59 (m, 1H), 4.90-4.77 (m, 1), 4.59-4.48 (m, 1H), 4.45-4.37 (m, 1H), 4.15-4.10 (m, 1H), 4.08-4.04 (m, 1H), 3.92-3.87 (m, 3H), 3.82-3.70 (m, 1H), 2.04-1.86 (m, 2H), 1.79-1.65 (m, 2H), 1.65-1.47 (m, 4H), 1.21-1.05 (m, 9H). ESI MS [M+H]+ for $C_{28}H_{38}ClN_6O_8P$, calcd 653.2, found 653.3.

Example 89

Synthesis of ({[(2R,3S,4R,5R)-5-(6-chloro-4-{[(1S)-1-phenylethyl]amino}-1H-pyrazolo[3,4-d]pyrimidin-1-yl)-3,4-dihydroxyoxolan-2-yl]methoxy}methyl)phosphonic acid

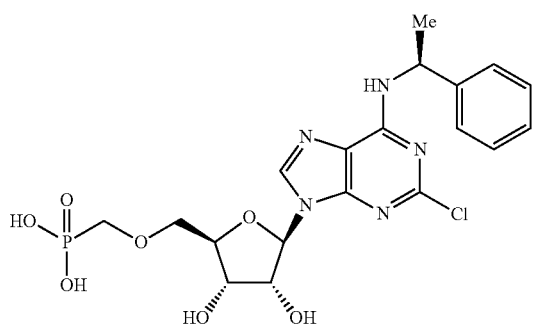 [SMILES: C[C@H](Nc1nc(Cl)nc2c1ncn2[C@@H]1O[C@H](COCP(=O)(O)O)[C@@H](O)[C@H]1O)c1ccccc1]

The title compound was obtained using identical procedure as for example 48, starting from 48a to give white solid. $^1$H NMR (400 MHz, DMSO-$d_6$) δ 9.16 (d, J=8.1 Hz, 1H), 8.30 (d, J=0.7 Hz, 1H), 7.42-7.36 (m, 2H), 7.36-7.29 (m, 2H), 7.26-7.20 (m, 1H), 5.98 (d, J=4.0 Hz, 1H), 5.46-5.37 (m, 1H), 4.53-4.36 (m, 1H), 4.17 (t, J=5.1 Hz, 1H), 4.08-3.91 (m, 1H), 3.69 (dd, J=10.7, 4.1 Hz, 1H), 3.57-3.46 (m, 3H), 1.64-1.41 (m, 3H). ESI MS [M–H]− for $C_{19}H_{23}ClN_5O_7P$, calcd 498.1, found 498.1.

Example 90

Synthesis of ({[(2R,3S,4R,5R)-5-(6-chloro-4-{[(1S)-1-(4-fluorophenyl)ethyl]amino}-1H-pyrazolo[3,4-d]pyrimidin-1-yl)-3,4-dihydroxyoxolan-2-yl]methoxy}methyl)phosphonic acid

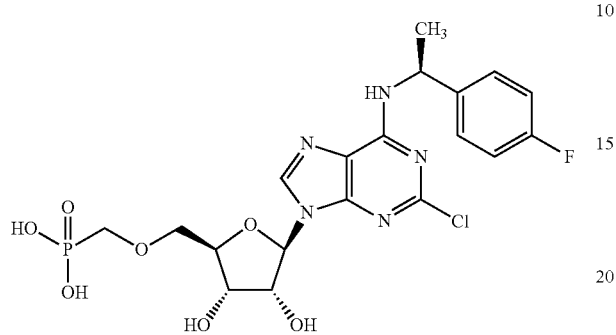

The title compound was obtained using identical procedure as for example 48, starting from 48a to give white solid. $^1$H NMR (400 MHz, DMSO-d$_6$) δ 9.14 (d, J=7.8 Hz, 1H), 8.29 (d, J=1.2 Hz, 1H), 7.42 (dd, J=8.0, 5.4 Hz, 2H), 7.15 (td, J=8.9, 1.3 Hz, 2H), 5.98 (d, J=4.1 Hz, 1H), 5.45-5.29 (m, 1H), 4.44 (t, J=4.6 Hz, 1H), 4.17 (t, J=5.1 Hz, 1H), 3.99 (d, J=5.9 Hz, 1H), 3.69 (dd, J=10.8, 4.0 Hz, 1H), 3.51 (d, J=8.6 Hz, 3H), 1.55-1.46 (m, 3H). ESI MS [M+H]$^+$ C$_{19}$H$_{22}$ClFN$_5$O$_7$P, calcd 518.1, found 518.2.

Example 91

Synthesis of ({[(2R,3S,4R,5R)-5-(6-chloro-4-{[(1S)-1-(3-fluorophenyl)ethyl]amino}-1H-pyrazolo[3,4-d]pyrimidin-1-yl)-3,4-dihydroxyoxolan-2-yl]methoxy}methyl)phosphonic acid

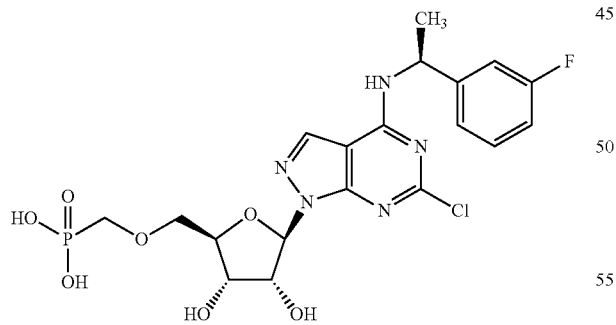

The title compound was obtained using identical procedure as for example 48, starting from 48a to give white solid. $^1$H NMR (400 MHz, DMSO-d$_6$) δ 9.16 (d, J=7.8 Hz, 1H), 8.35-8.22 (m, 1H), 7.44-7.31 (m, 1H), 7.22 (d, J=8.6 Hz, 2H), 7.07 (t, J=8.7 Hz, 1H), 5.99 (d, J=4.1 Hz, 1H), 5.41 (t, J=7.2 Hz, 1H), 4.44 (t, J=4.5 Hz, 1H), 4.17 (t, J=5.1 Hz, 1H), 3.99 (s, 1H), 3.69 (dd, J=10.6, 3.9 Hz, 1H), 3.51 (d, J=8.7 Hz, 3H), 1.53 (d, J=7.0 Hz, 3H). ESI MS [M+H]$^+$ C$_{19}$H$_{22}$ClFN$_5$O$_7$P, calcd 518.1, found 518.2.

Example 92

Synthesis of ({[(2R,3S,4R,5R)-5-(6-chloro-4-{[(1S)-1-(2-fluorophenyl)ethyl]amino}-1H-pyrazolo[3,4-d]pyrimidin-1-yl)-3,4-dihydroxyoxolan-2-yl]methoxy}methyl)phosphonic acid

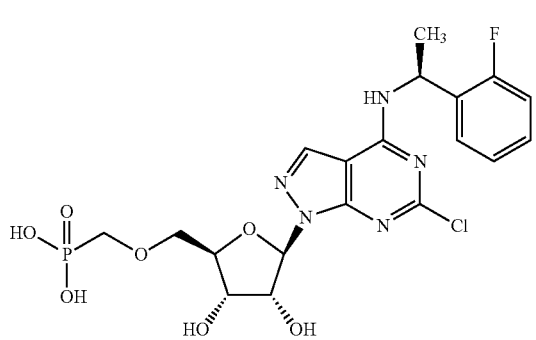 [SMILES: C[C@H](Nc1nc(Cl)nc2c1cnn2[C@@H]1O[C@H](COCP(=O)(O)O)[C@@H](O)[C@H]1O)c1ccccc1F]

The title compound was obtained using identical procedure as for example 48, starting from 48a to give white solid. $^1$H NMR (400 MHz, DMSO-d$_6$) δ 9.21 (t, J=6.5 Hz, 1H), 8.32 (dt, J=4.7, 1.0 Hz, 1H), 7.43 (t, J=7.8 Hz, 1H), 7.29 (t, J=6.9 Hz, 1H), 7.24-7.11 (m, 2H), 6.01-5.91 (m, 1H), 5.58 (q, J=6.9 Hz, 1H), 4.44 (t, J=4.4 Hz, 1H), 4.16 (d, J=5.6 Hz, 1H), 3.99 (d, J=5.8 Hz, 1H), 3.69 (dd, J=10.8, 4.0 Hz, 1H), 3.52 (t, J=8.1 Hz, 3H), 1.53 (d, J=6.9 Hz, 3H). ESI MS [M+H]$^+$ C$_{19}$H$_{22}$ClFN$_5$O$_7$P, calcd 518.1, found 518.2.

Example 93

Synthesis of ({[(2R,3S,4R,5R)-5-(6-chloro-4-{[(1S)-1-phenylethyl]amino}-1H-pyrazolo[3,4-b]pyridin-1-yl)-3,4-dihydroxyoxolan-2-yl]methoxy}methyl)phosphonic acid

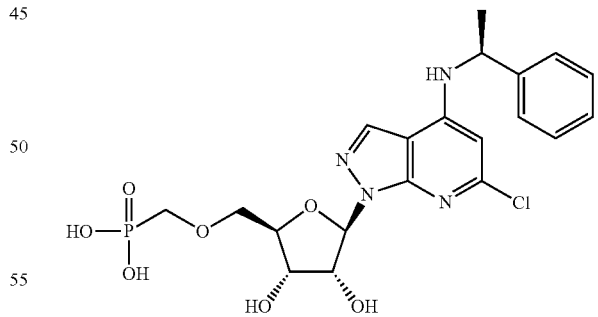

The title compound was obtained from the intermediate nucleoside using identical procedures as for example 1 to get a white solid. $^1$H NMR (400 MHz, DMSO-d$_6$) δ 8.37 (s, 1H), 8.19 (d, J=7.2 Hz, 1H), 7.42-7.35 (m, 2H), 7.35-7.27 (m, 2H), 7.25-7.18 (m, 1H), 6.04 (d, J=4.1 Hz, 2H), 4.85 (s, 1H), 4.46 (t, J=4.6 Hz, 1H), 4.17 (t, J=5.4 Hz, 1H), 4.02-3.91 (m, 1H), 3.68 (dd, J=10.7, 4.1 Hz, 1H), 3.55-3.48 (m, 3H), 1.52 (d, J=6.7 Hz, 3H). ESI MS [M+H]$^+$ for C$_{20}$H$_{25}$ClN$_4$O$_7$P, calcd 499.1, found 499.2.

Example 94

Synthesis of ({[(2R,3S,4R,5R)-5-(6-chloro-4-{[(1R)-1-phenylethyl]amino}-1H-pyrazolo[3,4-b]pyridin-1-yl)-3,4-dihydroxyoxolan-2-yl]methoxy}methyl)phosphonic acid

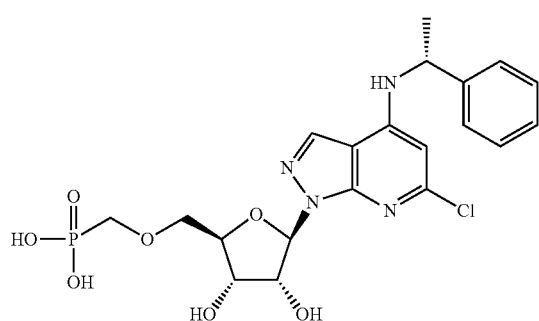 [SMILES: C[C@@H](Nc1cc(Cl)nc2c1cnn2[C@@H]1O[C@H](COCP(=O)(O)O)[C@@H](O)[C@H]1O)c1ccccc1]

The title compound was obtained from the intermediate nucleoside using identical procedures as for example 1 to get a white solid. $^1$H NMR (400 MHz, DMSO-d$_6$) δ 8.37 (s, 1H), 8.19 (d, J=7.2 Hz, 1H), 7.42-7.36 (m, 2H), 7.36-7.28 (m, 2H), 7.25-7.18 (m, 1H), 6.04 (d, J=4.1 Hz, 2H), 4.85 (s, 1H), 4.51-4.45 (m, 1H), 4.16 (t, J=5.2 Hz, 1H), 4.00-3.92 (m, 1H), 3.68 (dd, J=11.0, 3.9 Hz, 1H), 3.54-3.46 (m, 3H), 1.52 (d, J=6.7 Hz, 3H). ESI MS [M+H]+ for C$_{20}$H$_{25}$ClN$_4$O$_7$P, calcd 499.1, found 499.2.

Example 95

Synthesis of ({[(2R,3S,4R,5R)-5-(6-chloro-4-{[(1S)--(4-fluorophenyl)ethyl]amino}-1H-pyrazolo[3,4-b]pyridin-1-yl)-3,4-dihydroxyoxolan-2-yl]methoxy}methyl)phosphonic acid

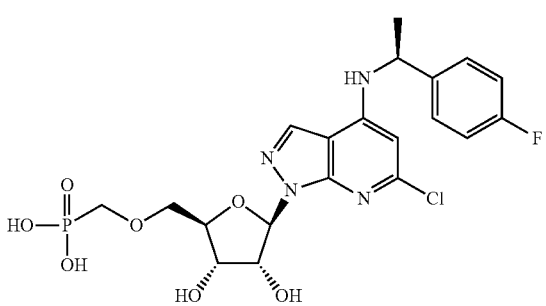 [SMILES: C[C@H](Nc1cc(Cl)nc2c1cnn2[C@@H]1O[C@H](COCP(=O)(O)O)[C@@H](O)[C@H]1O)c1ccc(F)cc1]

The title compound was obtained from the intermediate nucleoside using identical procedures as for example 1 to get a white solid. $^1$H NMR (400 MHz, DMSO-d$_6$) δ 8.35 (s, 1H), 8.17 (d, J=7.2 Hz, 1H), 7.47-7.39 (m, 2H), 7.19-7.10 (m, 2H), 6.04 (d, J=4.1 Hz, 2H), 4.89 (s, 1H), 4.49-4.43 (m, 1H), 4.17 (t, J=5.1 Hz, 1H), 4.01-3.92 (m, 1H), 3.68 (dd, J=10.9, 4.0 Hz, 1H), 3.51 (d, J=8.1 Hz, 3H), 1.50 (d, J=6.6 Hz, 3H). ESI MS [M+H]+ for C$_{20}$H$_{24}$ClFN$_4$O$_7$P, calcd 517.1, found 517.2.

Example 96

Synthesis of ({[(2R,3S,4R,5R)-5-(6-chloro-4-{[(1S)-1-(3-fluorophenyl)ethyl]amino}-1H-pyrazolo[3,4-b]pyridin-1-yl)-3,4-dihydroxyoxolan-2-yl]methoxy}methyl)phosphonic acid

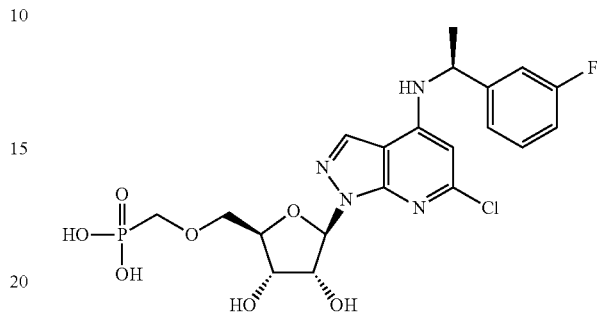

The title compound was obtained in a similar fashion to example 95 get a white solid. $^1$H NMR (400 MHz, DMSO-d$_6$) δ 8.35 (s, 1H), 8.18 (d, J=7.3 Hz, 1H), 7.41-7.32 (m, 1H), 7.27-7.19 (m, 2H), 7.09-7.00 (m, 1H), 6.04 (d, J=4.1 Hz, 2H), 4.91 (s, 1H), 4.46 (t, J=4.6 Hz, 1H), 4.17 (t, J=5.3 Hz, 1H), 4.01-3.93 (m, 1H), 3.69 (dd, J=10.8, 4.0 Hz, 1H), 3.57-3.43 (m, 3H), 1.51 (d, J=7.4 Hz, 3H). ESI MS [M+H]+ for C$_{20}$H$_{24}$ClFN$_4$O$_7$P, calcd 517.1, found 517.2.

Example 97

Synthesis of ({[(2R,3S,4R,5R)-5-[6-chloro-4-(cyclopentylamino)-1H-pyrazolo[3,4-b]pyridin-1-yl]-3,4-dihydroxyoxolan-2-yl]methoxy}methyl)phosphonic acid

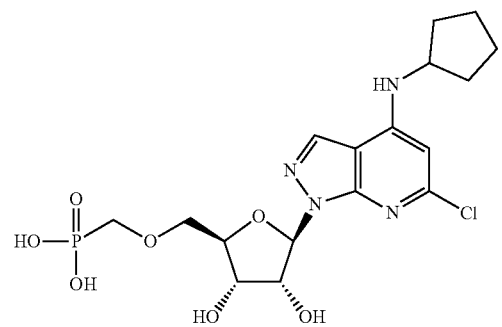 [SMILES: O=P(O)(O)COC[C@H]1O[C@@H](n2ncc3c(NC4CCCC4)cc(Cl)nc32)[C@H](O)[C@@H]1O]

The title compound was obtained from the intermediate nucleoside using identical procedures as for example 1 to get a white solid. $^1$H NMR (400 MHz, DMSO-d$_6$) δ 8.26 (s, 1H), 7.65 (d, J=6.7 Hz, 1H), 6.22 (s, 1H), 6.06 (d, J=3.9 Hz, 1H), 4.47 (t, J=4.5 Hz, 1H), 4.17 (t, J=5.2 Hz, 1H), 4.02-3.92 (m, 2H), 3.69 (dd, J=10.9, 3.9 Hz, 1H), 3.50 (d, J=8.6 Hz, 3H), 2.06-1.88 (m, 2H), 1.75-1.47 (m, 6H). ESI MS [M+H]+ for C$_{17}$H$_{25}$ClN$_4$O$_7$P, calcd 463.1, found 463.2.

Example 98

Synthesis of ({[(2R,3S,4R,5R)-5-(6-chloro-4-{[(1S)-1-(2-fluorophenyl)ethyl]amino}-1H-pyrazolo[3,4-b]pyridin-yl)-3,4-dihydroxyoxolan-2-yl]methoxy}methyl)phosphonic acid

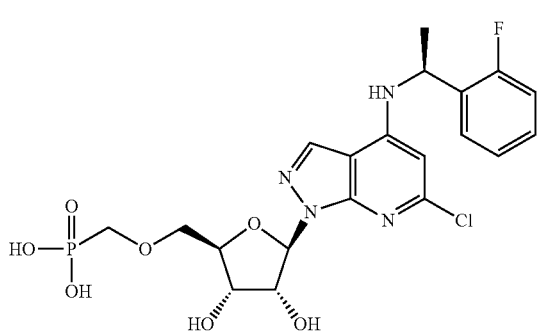 [SMILES: C[C@H](Nc1cc(Cl)nc2c1cnn2[C@@H]1O[C@H](COCP(=O)(O)O)[C@@H](O)[C@H]1O)c1ccccc1F]

The title compound was obtained from the intermediate nucleoside using identical procedures as for example 1 to get a white solid. $^1$H NMR (400 MHz, DMSO-$d_6$) δ 8.37 (s, 1H), 8.23 (d, J=7.0 Hz, 1H), 7.42-7.34 (m, 1H), 7.33-7.25 (m, 1H), 7.24-7.10 (m, 2H), 6.05 (d, J=4.0 Hz, 1H), 6.01-5.90 (m, 1H), 5.04 (s, 1H), 4.51-4.42 (m, 1H), 4.17 (t, J=5.2 Hz, 1H), 4.03-3.92 (m, 1H), 3.69 (dd, J=10.8, 4.0 Hz, 1H), 3.51 (d, J=8.2 Hz, 3H), 1.56 (d, J=6.6 Hz, 3H). ESI MS [M+H]$^+$ for $C_{20}H_{24}ClFN_4O_7P$, calcd 517.1, found 517.2.

Example 99

Synthesis of ({[(2R,3S,4R,5R)-5-(2-chloro-4-{[(1S)-1-(2-fluorophenyl)ethyl]amino}-7H-pyrrolo[2,3-d]pyrimidin-7-yl)-3,4-dihydroxyoxolan-2-yl]methoxy}methyl)phosphonic acid

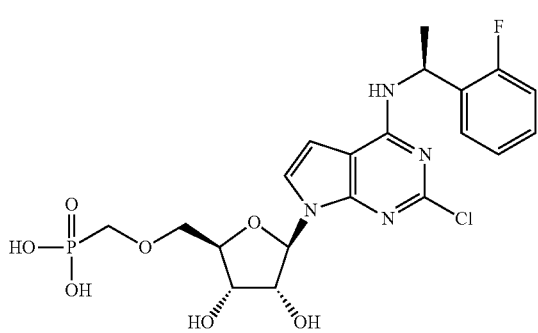 [SMILES: C[C@H](Nc1nc(Cl)nc2c1ccn2[C@@H]1O[C@H](COCP(=O)(O)O)[C@@H](O)[C@H]1O)c1ccccc1F]

The title compound was obtained from the intermediate nucleoside using identical procedures as for example 1 to get a white solid. $^1$H NMR (400 MHz, DMSO-$d_6$) δ 8.36 (d, J=7.8 Hz, 1H), 7.48-7.37 (m, 2H), 7.32-7.21 (m, 1H), 7.20-7.11 (m, 2H), 6.79 (s, 1H), 5.95 (d, J=6.9 Hz, 1H), 5.63-5.51 (m, 1H), 4.35-4.28 (m, 1H), 4.07-4.00 (m, 1H), 3.99-3.93 (m, 1H), 3.71-3.55 (m, 4H), 1.51 (d, J=6.9 Hz, 3H). ESI MS [M+H]$^+$ for $C_{20}H_{24}ClFN_4O_7P$, calcd 517.1, found 517.2.

Example 100

Synthesis of ({[(2R,3S,4R,5R)-5-(2-chloro-4-{[(1S)-1-(3-fluorophenyl)ethyl]amino}-7H-pyrrolo[2,3-d]pyrimidin-7-yl)-3,4-dihydroxyoxolan-2-yl]methoxy}methyl)phosphonic acid

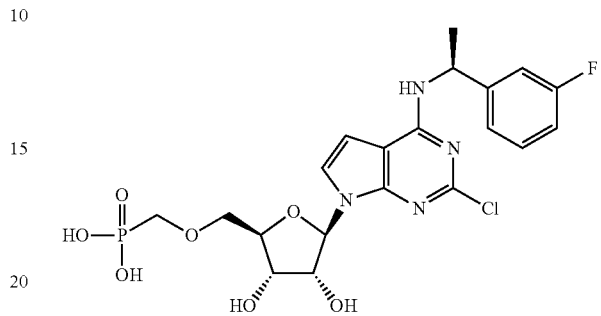

The title compound was obtained from the intermediate nucleoside using identical procedures as for example 1 to get a white solid. $^1$H NMR (400 MHz, DMSO-$d_6$) δ 8.32 (d, J=8.1 Hz, 1H), 7.44 (d, J=3.6 Hz, 1H), 7.39-7.30 (m, 1H), 7.25-7.16 (m, 2H), 7.09-6.98 (m, 1H), 6.75 (s, 1H), 5.96 (d, J=6.3 Hz, 1H), 5.45-5.33 (m, 1H), 4.36-4.26 (m, 1H), 4.07-4.00 (m, 1H), 3.99-3.92 (m, 1H), 3.71-3.53 (m, 4H), 1.50 (d, J=6.8 Hz, 3H). ESI MS [M+H]$^+$ for $C_{20}H_{24}ClFN_4O_7P$, calcd 517.1, found 517.2.

Example 101

Synthesis of ({[(2R,3S,4R,5R)-5-(2-chloro-4-{[(1S)-1-(4-fluorophenyl)ethyl]amino}-7H-pyrrolo[2,3-d]pyrimidin-7-yl)-3,4-dihydroxyoxolan-2-yl]methoxy}methyl)phosphonic acid

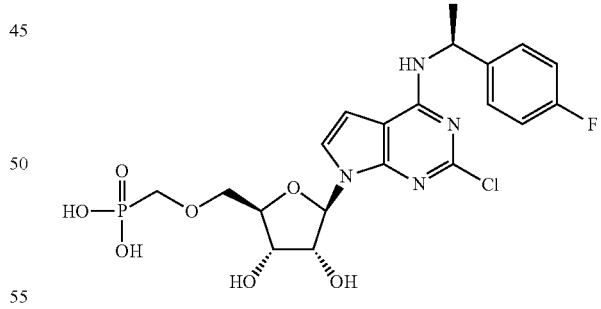

The title compound was obtained from the intermediate nucleoside using identical procedures as for example 1 to get a white solid. $^1$H NMR (400 MHz, DMSO-$d_6$) δ 8.30 (d, J=8.1 Hz, 1H), 7.46-7.37 (m, 3H), 7.17-7.08 (m, 2H), 6.74 (s, 1H), 5.95 (d, J=6.4 Hz, 1H), 5.44-5.32 (m, 1H), 4.34-4.28 (m, 1H), 4.06-4.01 (m, 1H), 3.99-3.93 (m, 1H), 3.69-3.53 (m, 4H), 1.50 (t, J=6.8 Hz, 3H). ESI MS [M+H]$^+$ for $C_{20}H_{24}ClFN_4O_7P$, calcd 517.1, found 517.2.

Example 102

Synthesis of ({[(2R,3S,4R,5R)-5-[2-chloro-4-(pyrrolidin-1-yl)-7H-pyrrolo[2,3-d]pyrimidin-7-yl]-3,4-dihydroxyoxolan-2-yl]methoxy}methyl)phosphonic acid

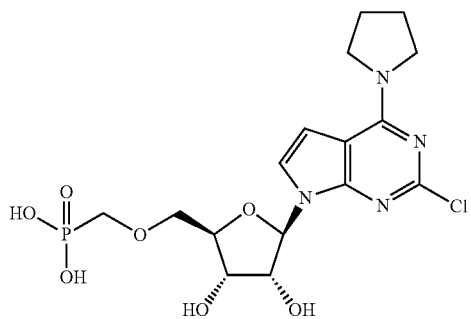 [SMILES: O=P(O)(O)COC[C@H]1O[C@@H](n2ccc3c(N4CCCC4)nc(Cl)nc32)[C@H](O)[C@@H]1O]

The title compound was obtained from the intermediate nucleoside using identical procedures as for example 1 to get a white solid. $^1$H NMR (400 MHz, DMSO-$d_6$) δ 7.45 (d, J=3.8 Hz, 1H), 6.64 (d, J=3.8 Hz, 1H), 6.01 (d, J=6.3 Hz, 1H), 4.33 (dd, J=6.3, 5.1 Hz, 1H), 4.05 (dd, J=5.2, 3.2 Hz, 1H), 4.00-3.91 (m, 1H), 3.73-3.47 (m, 6H), 2.15-1.78 (m, 5H). ESI MS [M–H]$^-$ for $C_{15}H_{21}ClN_5O_7P$, calcd 447.1, found 447.2.

Example 103

Synthesis of ({[(2R,3S,4R,5R)-5-[2-chloro-6-(cyclopentylamino)-9H-purin-9-yl]-3,4-dihydroxyoxolan-2-yl]methoxy}methyl)({[(propan-2-yloxy)carbonyl]oxy}methoxy)phosphinic acid

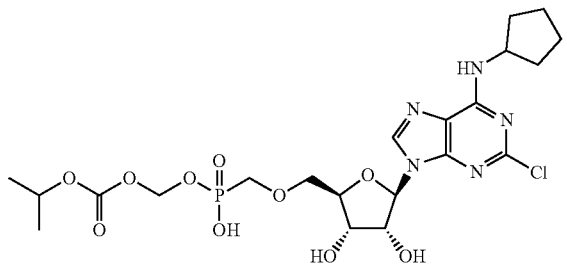 [SMILES: CC(C)OC(=O)OCOP(=O)(O)COC[C@H]1O[C@@H](n2cnc3c(NC4CCCC4)nc(Cl)nc32)[C@H](O)[C@@H]1O]

The title compound was synthesized in similar fashion to Example 66: $^1$H NMR (400 MHz, DMSO-$d_6$) δ 8.50-8.13 (m, 2H), 5.92-5.70 (m, 1H), 5.51 (dt, J=12.8, 4.2 Hz, 1H), 4.88-4.64 (m, 1H), 4.55-4.30 (m, 2H), 4.10 (q, J=4.3 Hz, 1H), 4.02 (p, J=4.1 Hz, 1H), 3.83-3.60 (m, 4H), 1.92 (s, 2H), 1.69 (s, 2H), 1.54 (s, 4H), 1.32-1.10 (m, 6H). ESI MS [M–H]$^-$ for $C_{21}H_{31}ClN_5O_{10}P$, calcd 578.2, found 578.4.

Example 104

Synthesis of bis({[(propan-2-yloxy)carbonyl]oxy}methyl) {[(2R,3S,4R,5R)-5-(2-chloro-6-{[(1S)-1-(4-fluorophenyl)ethyl]amino}-9H-purin-9-yl)-3,4-dihydroxyoxolan-2-yl]methoxy}methanephosphonate

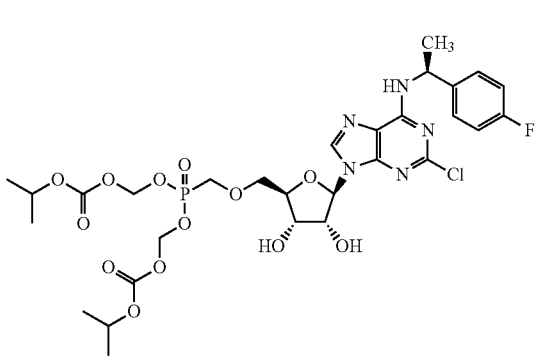 [SMILES: CC(C)OC(=O)OCOP(=O)(COC[C@H]1O[C@@H](n2cnc3c(N[C@@H](C)c4ccc(F)cc4)nc(Cl)nc32)[C@H](O)[C@@H]1O)OCOC(=O)OC(C)C]

The title compound was synthesized in similar fashion to Example 65: $^1$H NMR (400 MHz, DMSO-$d_6$) δ 8.83 (dd, J=23.3, 9.2 Hz, 1H), 8.34 (s, 1H), 7.45 (t, J=6.5 Hz, 2H), 7.11 (t, J=8.6 Hz, 2H), 5.80 (dd, J=5.5, 1.4 Hz, 1H), 5.64-5.48 (m, 5H), 5.38 (t, J=7.5 Hz, 1H), 5.35-5.25 (m, 1H), 4.78 (dtt, J=12.5, 6.2, 1.9 Hz, 2H), 4.43 (d, J=5.5 Hz, 1H), 4.08 (s, 1H), 3.99 (t, J=8.3 Hz, 3H), 3.83-3.73 (m, 1H), 3.69 (dd, J=10.9, 5.1 Hz, 1H), 1.51 (d, J=7.2 Hz, 3H), 1.20 (ddd, J=6.2, 2.8, 1.3 Hz, 12H). ESI MS [M+H]$^+$ $C_{29}H_{38}ClFN_5O_{13}P$, calcd 750.2, found 750.3.

Example 105

Synthesis of bis({[(propan-2-yloxy)carbonyl]oxy}methyl) {[(2R,3S,4R,5R)-5-(2-chloro-6-{[(1R)-1-(4-fluorophenyl)ethyl]amino}-9H-purin-9-yl)-3,4-dihydroxyoxolan-2-yl]methoxy}methanephosphonate

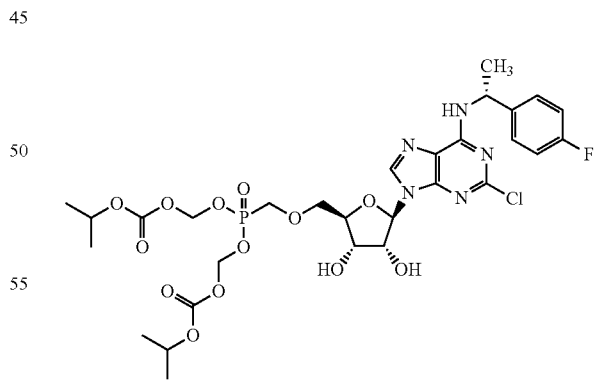

The title compound was synthesized in similar fashion to Example 65: H NMR (400 MHz, DMSO-$d_6$) δ 8.85 (d, J=8.4 Hz, 1H), 8.33 (d, J=10.0 Hz, 1H), 7.45 (dd, J=8.4, 5.4 Hz, 2H), 7.11 (t, J=8.7 Hz, 2H), 5.80 (dd, J=5.5, 1.4 Hz, 1H), 5.59 (d, J=12.7 Hz, 5H), 5.45-5.18 (m, 2H), 4.78 (p, J=6.4 Hz, 2H), 4.44 (d, J=19.9 Hz, 1H), 4.08 (s, 1H), 3.99 (dd, J=10.3, 6.0 Hz, 3H), 3.82-3.62 (m, 2H), 1.51 (d, J=7.2 Hz, 3H), 1.20 (dt, J=6.4, 2.1 Hz, 12H). ESI MS [M+H]+ C29H38ClFN5O13P, calcd 750.2, found 750.3.

Example 106

Synthesis of bis({[(2-methoxyethoxy)carbonyl]oxy}methyl) {[(2R,3S,4R,5R)-5-(2-chloro-6-{[(3S)-oxolan-3-yl]amino}-9H-purin-9-yl)-3,4-dihydroxyoxolan-2-yl]methoxy}methanephosphonate

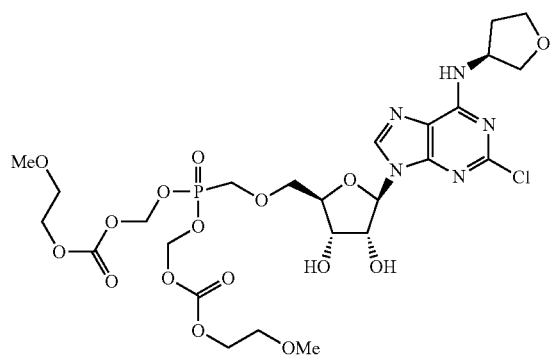 [SMILES: COCCOC(=O)OCOP(=O)(COC[C@H]1O[C@@H](n2cnc3c(N[C@H]4CCOC4)nc(Cl)nc32)[C@H](O)[C@@H]1O)OCOC(=O)OCCOC]

The title compound was synthesized in similar fashion to Example 65: 1H NMR (400 MHz, DMSO-$d_6$) δ 8.63-8.49 (m, 1H), 8.40-8.32 (m, 1H), 5.85 (t, J=4.2 Hz, 1H), 5.64 (d, J=13.4 Hz, 4H), 5.59-5.51 (m, 1H), 5.35-5.26 (m, 1H), 4.63 (s, 1H), 4.54-4.41 (m, 1H), 4.33-4.21 (m, 3H), 4.14-4.07 (m, 1H), 4.07-3.98 (m, 2H), 3.95-3.83 (m, 2H), 3.83-3.69 (m, 2H), 3.65-3.57 (m, 1H), 3.57-3.49 (m, 3H), 3.32 (s, 8H), 2.27-2.11 (m, 1H), 2.09-1.87 (m, 1H). ESI MS [M+H]+ for C25H38ClN5O16P, calcd 730.2, found 730.3.

Example 107

Synthesis of bis[(methoxycarbonyl)oxy]methyl {[(2R,3S,4R,5R)-5-(2-chloro-6-{[(3S)-oxolan-3-yl]amino}-9H-purin-9-yl)-3,4-dihydroxyoxolan-2-yl]methoxy}methanephosphonate

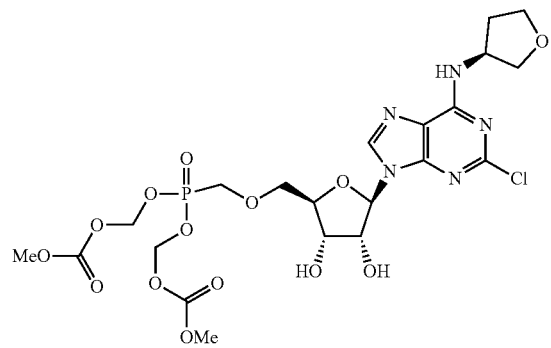 [SMILES: COC(=O)OCOP(=O)(COC[C@H]1O[C@@H](n2cnc3c(N[C@H]4CCOC4)nc(Cl)nc32)[C@H](O)[C@@H]1O)OCOC(=O)OC]

The title compound was synthesized in similar fashion to Example 65: $^1$H NMR (400 MHz, DMSO-$d_6$) δ 8.56 (d, J=6.9 Hz, 1H), 8.35 (d, J=1.2 Hz, 1H), 5.85 (d, J=5.4 Hz, 1H), 5.68-5.59 (m, 4H), 5.55 (d, J=5.9 Hz, 1H), 5.38-5.27 (m, 1H), 4.63 (s, 1H), 4.47 (q, J=5.2 Hz, 1H), 4.15-4.08 (m, 1H), 4.08-3.96 (m, 3H), 3.96-3.84 (m, 2H), 3.83-3.66 (m, 8H), 3.61 (dd, J=9.0, 4.5 Hz, 1H), 2.26-2.12 (m, 1H), 2.09-1.87 (m, 1H). ESI MS [M+H]+ for C21H30ClN5O14P, calcd 642.1, found 642.3.

Example 108

Synthesis of ({[(2R,3S,4R,5R)-5-(2-chloro-6-{[(3S)-oxolan-3-yl]amino}-9H-purin-9-yl)-3,4-dihydroxyoxolan-2-yl]methoxy}methyl)({[(methoxycarbonyl)oxy]methoxy})phosphinic acid

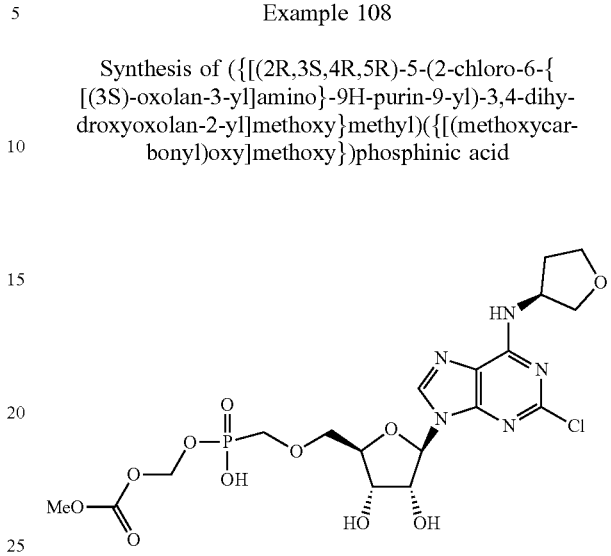

The title compound was synthesized in similar fashion to Example 66: $^1$H NMR (400 MHz, DMSO-$d_6$) δ 8.54 (s, 1H), 8.41 (d, J=7.9 Hz, 1H), 5.83 (d, J=5.8 Hz, 1H), 5.52 (d, J=12.8 Hz, 3H), 4.61 (s, 1H), 4.48 (t, J=5.5 Hz, 1H), 4.10 (t, J=4.2 Hz, 1H), 4.02 (q, J=3.9 Hz, 1H), 3.95-3.80 (m, 3H), 3.75-3.63 (m, 9H), 3.59 (dd, J=8.9, 4.4 Hz, 1H), 2.27-2.09 (m, 1H), 2.05-1.83 (m, 1H). ESI MS [M−H]− for C18H24ClN5O11P, calcd 552.1, found 552.2.

Example 109

Synthesis of ({[(2R,3S,4R,5R)-5-(2-chloro-6-{[(3S)-oxolan-3-yl]amino}-9H-purin-9-yl)-3,4-dihydroxyoxolan-2-yl]methoxy}methyl)({[(2-methoxyethoxy)carbonyl]oxy}methoxy)phosphinic acid

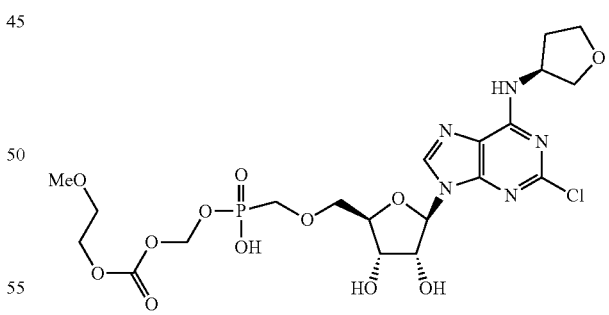

The title compound was synthesized in similar fashion to Example 66: $^1$H NMR (400 MHz, DMSO-$d_6$) δ 8.61-8.47 (m, 1H), 8.47-8.34 (m, 1H), 5.83 (d, J=5.6 Hz, 1H), 5.52 (d, J=12.7 Hz, 3H), 5.29-5.15 (m, 1H), 4.66-4.54 (m, 1H), 4.54-4.44 (m, 1H), 4.21 (dq, J=4.4, 2.1 Hz, 2H), 4.09 (d, J=4.7 Hz, 1H), 4.02 (d, J=4.1 Hz, 1H), 3.87 (dt, J=15.5, 8.4 Hz, 2H), 3.77-3.64 (m, 4H), 3.59 (dd, J=8.8, 4.5 Hz, 1H), 3.54-3.48 (m, 2H), 3.40-3.34 (m, 4H), 2.31-2.11 (m, 1H), 2.11-1.82 (m, 1H). ESI MS [M−H]− for C20H28ClN5O12P, calcd 596.1, found 596.1.

Example 110

Synthesis of bis({[(propan-2-yloxy)carbonyl]oxy}methyl) {[(2R,3S,4R,5R)-5-(6-chloro-4-{[(3S)-oxolan-3-yl]amino}-1H-pyrazolo[3,4-d]pyrimidin-1-yl)-3,4-dihydroxyoxolan-2-yl]methoxy}methanephosphonate

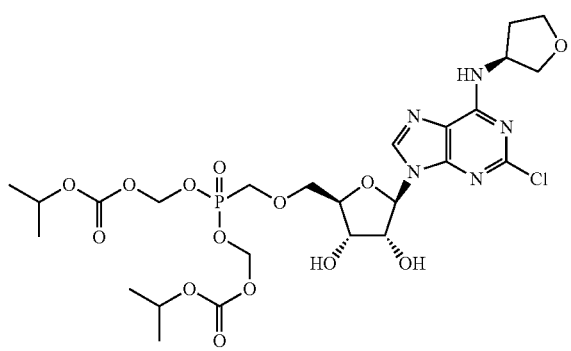 [SMILES: CC(C)OC(=O)OCOP(=O)(COC[C@H]1O[C@@H](n2cnc3c(N[C@H]4CCOC4)nc(Cl)nc32)[C@H](O)[C@@H]1O)OCOC(=O)OC(C)C]

The title compound was synthesized in similar fashion to Example 65: $^1$H NMR (400 MHz, DMSO-$d_6$) δ 8.93 (d, J=6.6 Hz, 1H), 8.30-8.20 (m, 1H), 6.00 (d, J=3.8 Hz, 1H), 5.60-5.49 (m, 4H), 5.46 (dd, J=5.5, 1.4 Hz, 1H), 5.22 (dd, J=6.1, 1.3 Hz, 1H), 4.86-4.73 (m, 2H), 4.71-4.55 (m, 1H), 4.42 (td, J=5.5, 2.7 Hz, 1H), 4.19 (q, J=5.2 Hz, 1H), 4.01-3.96 (m, 1H), 3.94-3.82 (m, 4H), 3.77-3.61 (m, 3H), 3.56 (dd, J=10.9, 6.5 Hz, 1H), 2.36-2.15 (m, 1H), 1.91 (d, J=12.4 Hz, 1H), 1.28-1.16 (m, 13H). ESI MS [M+H]$^+$ for $C_{25}H_{37}ClN_5O_{14}P$, calcd 698.2, found 698.3.

Example 111

Synthesis of bis({[(propan-2-yloxy)carbonyl]oxy}methyl) {[(2R,3S,4R,5R)-5-(6-chloro-4-{[(1S)-1-phenylethyl]amino}-1H-pyrazolo[3,4-d]pyrimidin-1-yl)-3,4-dihydroxyoxolan-2-yl]methoxy}methanephosphonate

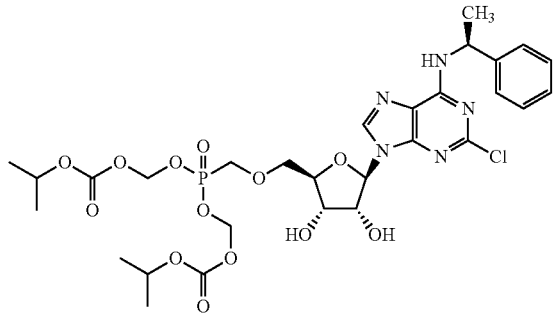 [SMILES: CC(C)OC(=O)OCOP(=O)(COC[C@H]1O[C@@H](n2cnc3c(N[C@@H](C)c4ccccc4)nc(Cl)nc32)[C@H](O)[C@@H]1O)OCOC(=O)OC(C)C]

The title compound was synthesized in similar fashion to Example 65: $^1$H NMR (400 MHz, DMSO-$d_6$) δ 9.15 (d, J=7.9 Hz, 1H), 8.29 (s, 1H), 7.39 (d, J=8.2 Hz, 2H), 7.36-7.30 (m, 2H), 7.27-7.19 (m, 1H), 5.98 (d, J=3.8 Hz, 1H), 5.63-5.49 (m, 5H), 5.41 (p, J=7.4 Hz, 1H), 4.85-4.70 (m, 2H), 4.41 (t, J=4.4 Hz, 1H), 4.19 (t, J=5.2 Hz, 1H), 3.98 (q, J=2.5 Hz, 1H), 3.91 (d, J=7.5 Hz, 2H), 3.71 (dd, J=10.9, 3.6 Hz, 1H), 3.56 (dd, J=11.0, 6.6 Hz, 1H), 1.53 (d, J=6.9 Hz, 3H), 1.30-1.12 (m, 12H). ESI MS [M+H]$^+$ for $C_{29}H_{39}ClN_5O_{13}P$, calcd 732.2, found 732.3.

Example 112

Synthesis of bis({[(propan-2-yloxy)carbonyl]oxy}methyl) {[(2R,3S,4R,5R)-5-(6-chloro-4-{[(1S)-1-(4-fluorophenyl)ethyl]amino}-1H-pyrazolo[3,4-d]pyrimidin-1-yl)-3,4-dihydroxyoxolan-2-yl]methoxy}methanephosphonate

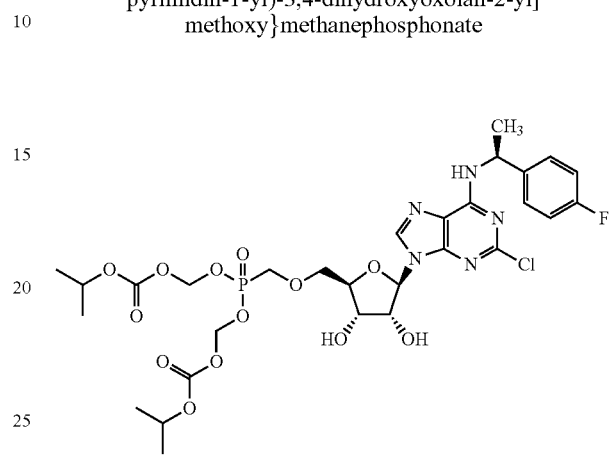

The title compound was synthesized in similar fashion to Example 65: $^1$H NMR (400 MHz, DMSO-$d_6$) δ 9.13 (d, J=7.9 Hz, 1H), 8.32-8.20 (m, 1H), 7.48-7.36 (m, 2H), 7.15 (td, J=8.3, 7.7, 3.4 Hz, 2H), 5.99 (d, J=3.8 Hz, 1H), 5.63-5.48 (m, 5H), 5.46-5.35 (m, 2H), 5.22 (d, J=6.1 Hz, 1H), 4.86-4.72 (m, 2H), 4.41 (d, J=4.9 Hz, 1H), 4.19 (d, J=5.7 Hz, 1H), 4.09-3.82 (m, 3H), 3.71 (dd, J=10.9, 3.5 Hz, 1H), 3.62-3.53 (m, 1H), 1.55-1.48 (m, 3H), 1.23 (ddd, J=8.8, 5.0, 1.9 Hz, 12H). ESI MS [M+H]$^+$ $C_{29}H_{38}ClFN_5O_{13}P$, calcd 750.2, found 750.3.

Example 113

Synthesis of bis({[(propan-2-yloxy)carbonyl]oxy}methyl) {[(2R,3S,4R,5R)-5-(6-chloro-4-{[(1R)-1-(4-fluorophenyl)ethyl]amino}-1H-pyrazolo[3,4-d]pyrimidin-1-yl)-3,4-dihydroxyoxolan-2-yl]methoxy}methanephosphonate

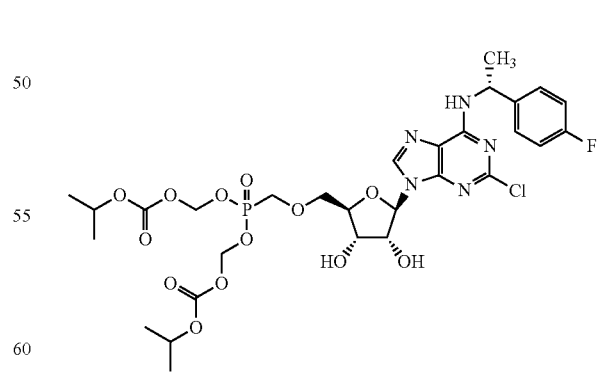

The title compound was synthesized in similar fashion to Example 65: $^1$H NMR (400 MHz, DMSO-$d_6$) δ 9.14 (d, J=7.9 Hz, 1H), 8.28 (s, 1H), 7.43 (dd, J=8.4, 5.4 Hz, 2H), 7.15 (t, J=8.8 Hz, 2H), 5.99 (d, J=3.9 Hz, 1H), 5.62-5.46 (m, 5H), 5.41 (q, J=7.5 Hz, 1H), 5.24 (t, J=6.2 Hz, 1H), 4.83-4.70 (m, 2H), 4.43 (q, J=4.9 Hz, 1H), 4.19 (q, J=5.6 Hz, 1H), 3.98 (q, J=5.4 Hz, 1H), 3.90 (d, J=7.7 Hz, 2H), 3.70 (dd, J=11.0, 3.7 Hz, 1H), 3.55 (dd, J=11.0, 6.5 Hz, 1H), 1.52 (d, J=7.0 Hz, 3H), 1.19 (t, J=6.0 Hz, 12H). ESI MS [M+H]$^+$ $C_{29}H_{38}ClFN_5O_{13}P$, calcd 750.2, found 750.3.

Example 114

Synthesis of bis({[(propan-2-yloxy)carbonyl]oxy}methyl) {[(2R,3S,4R,5R)-5-(6-chloro-4-{[(1S)-1-(4-fluorophenyl)ethyl]amino}-1H-pyrazolo[3,4-b]pyridin-1-yl)-3,4-dihydroxyoxolan-2-yl]methoxy}methanephosphonate

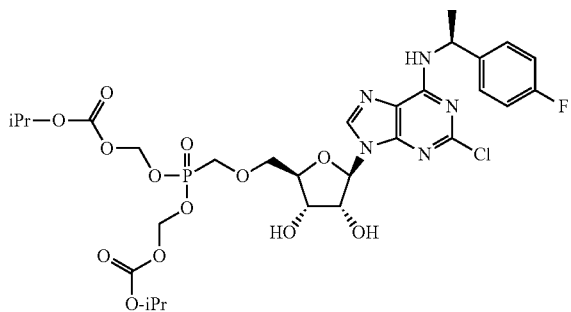

The title compound was synthesized in similar fashion to Example 65: $^1$H NMR (400 MHz, DMSO-d$_6$) δ 8.35 (s, 1H), 8.17 (d, J=7.2 Hz, 1H), 7.47-7.38 (m, 2H), 7.19-7.09 (m, 2H), 6.05 (d, J=4.0 Hz, 2H), 5.61-5.15 (m, 5H), 4.88 (s, 1H), 4.84-4.73 (m, 2H), 4.47-4.40 (m, 1H), 4.19 (t, J=5.3 Hz, 1H), 4.00-3.94 (m, 1H), 3.90 (d, J=7.5 Hz, 2H), 3.70 (dd, J=11.0, 3.6 Hz, 1H), 3.55 (dd, J=10.9, 6.6 Hz, 1H), 1.54-1.46 (m, 3H), 1.26-1.18 (m, 12H). ESI MS [M+H]$^+$ for $C_{30}H_{40}ClFN_4O_{13}P$, calcd 749.2, found 749.3.

Example 115

Synthesis of bis({[(propan-2-yloxy)carbonyl]oxy}methyl) {[(2R,3S,4R,5R)-5-[2-chloro-4-(pyrrolidin-1-yl)-7H-pyrrolo[2,3-d]pyrimidin-7-yl]-3,4-dihydroxyoxolan-2-yl]methoxy}methanephosphonate

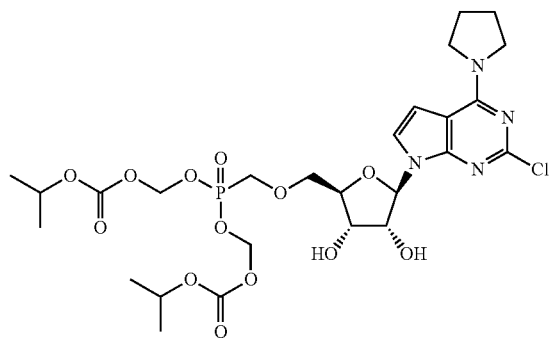 [SMILES: CC(C)OC(=O)OCOP(=O)(COC[C@H]1O[C@@H](n2ccc3c(N4CCCC4)nc(Cl)nc32)[C@H](O)[C@@H]1O)OCOC(=O)OC(C)C]

The title compound was synthesized in similar fashion to Example 65: $^1$H NMR (400 MHz, DMSO-d$_6$) δ 7.35 (d, J=3.7 Hz, 1H), 6.69 (d, J=3.7 Hz, 1H), 6.00 (d, J=5.8 Hz, 1H), 5.66-5.53 (m, 4H), 5.42-5.33 (m, 1H), 5.25 (d, J=5.3 Hz, 1H), 4.80 (p, J=6.2 Hz, 2H), 4.26 (q, J=5.8 Hz, 1H), 4.10-3.91 (m, 4H), 3.86-3.52 (m, 7H), 1.95 (d, J=41.4 Hz, 5H), 1.22 (dt, J=6.3, 1.0 Hz, 12H). ESI MS [M+H]$^+$ for $C_{26}H_{38}ClN_4O_{13}P$, calcd 681.2, found 681.4.

Example 116

Synthesis of bis({[(propan-2-yloxy)carbonyl]oxy}methyl) {[(2R,3S,4R,5R)-5-(2-chloro-4-{[(1S)-1-(4-fluorophenyl)ethyl]amino}-7H-pyrrolo[2,3-d]pyrimidin-7-yl)-3,4-dihydroxyoxolan-2-yl]methoxy}methanephosphonate

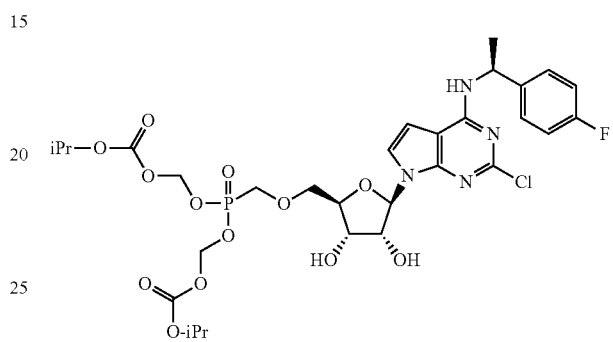

The title compound was synthesized in similar fashion to Example 65: $^1$H NMR (400 MHz, DMSO-d$_6$) δ 8.32 (d, J=8.1 Hz, 1H), 7.41 (dd, J=8.4, 5.5 Hz, 2H), 7.31 (d, J=3.7 Hz, 1H), 7.16-7.08 (m, 2H), 6.76 (s, 1H), 5.94 (d, J=5.8 Hz, 1H), 5.64-5.54 (m, 4H), 5.43-5.33 (m, 1H), 4.85-4.74 (m, 2H), 4.24 (t, J=5.6 Hz, 1H), 4.04-3.91 (m, 4H), 3.76-3.61 (m, 2H), 1.50 (d, J=6.9 Hz, 3H), 1.21 (d, J=6.5 Hz, 12H). ESI MS [M+H]$^+$ for $C_{30}H_{40}ClFN_4O_{13}P$, calcd 749.2, found 749.3.

Biological Examples

Materials and Methods

The following general materials and methods were used, where indicated, or may be used in the Examples below:

Standard methods in molecular biology are described in the scientific literature (see, e.g., Sambrook and Russell (2001) Molecular Cloning, 3$^{rd}$ ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, CA); and DeCypher™ (TimeLogic Corp., Crystal Bay, NV).

The literature is replete with assays and other experimental techniques that can serve as a basis for evaluation of the compounds described herein.

Inhibition of Ecto-5′-nucleotidase Activity. Compounds were evaluated to determine their ecto-5′-nucleotidase (CD73) inhibitory activity. Briefly, CHO-K1 cells stably transfected with human CD73 were generated by LakePharma (Belmont, CA) using molecular cloning of human CD73 (http://www.uniprot.org/uniprot/P21589) and mammalian transient expression vector (P21589.1). After antibiotic selection in CD OptiCHO cell media (Invitrogen, Catalog #12681-011) containing 5 μg/mL Puromycin and 200 μg/mL Hygromycin B, a suspension pool of CHO-CD73 cells was collected and frozen in 7.5% DMSO in cell media without antibiotics.

On the day of the experiment, one vial of CHO-CD73 cells was thawed and suspended in assay media which consisted of 20 mM HEPES, pH 7.4, 137 mM NaCl, 5.4 mM KCl, 1.3 mM CaCl$_2$), 4.2 mM NaHCO$_3$ and 0.1% glucose. To test the ability of compounds to inhibit CD73 enzymatic activity, 2 μL of 500 μM of compounds dissolved in DMSO (50×) were added to a 96-well polystyrene plate containing 58 μL of assay buffer. Next, 20 μL of CHO-CD73 cells in assay buffer were added to assay plate followed by 20 μL of 125 μM AMP (Adenosine 5′-monophosphate monohydrate) in assay buffer. Final assay conditions consisted of 2500 cells per well in 2% DMSO and 25 μM of AMP substrate. After 50 minutes of incubation (37° C. and 5% CO$_2$) and centrifugation at 225×g for 5 mins, 80 μL of supernatant were transferred to a 96-well Spectra Plate (PerkinElmer, cat #6005640) which was pre-dispensed with 20 μL of PiColorLock Gold colorimetric assay reagents (Thermo, cat #30 300 30). The amount of inorganic phosphate was determined by reading the absorbance at 620 nm on an EnVision Multilabel Plate Reader (PerkinElmer). Enzymatic activity of CD73 was based on the amount of phosphate generated. Percentage of activity was calculated based on DMSO and no cells control wells. IC$_{50}$ values of compounds were determined by four parameter non-linear regression fitting of percentage of activity in GraphPad Prism software.

Pharmacodynamic and Pharmacokinetic Evaluation. A pharmacodynamic assay can be based on measuring CD73 mediated serum levels of adenosine. Adenosine levels can be determined by HPLC analysis, and serum compound levels can optionally also be determined in the same HPLC run.

Particular embodiments of this invention are described herein, including the best mode known to the inventors for carrying out the invention. Upon reading the foregoing description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A process for preparing a CD73 inhibitor, said process comprising:

a) contacting a compound of formula (i):

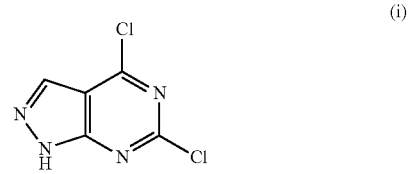 [SMILES: Clc1nc(Cl)c2cn[nH]c2n1]

with a protected analog of ribofuranose to form a protected analog of compound of formula (iii):

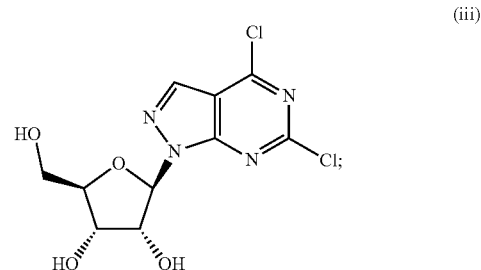 [SMILES: OC[C@H]1O[C@@H](n2ncc3c(Cl)nc(Cl)nc32)[C@H](O)[C@@H]1O]

and b) contacting the protected analog of compound of formula (iii) with cyclopentyl amine to form a protected analog of compound of formula (iv):

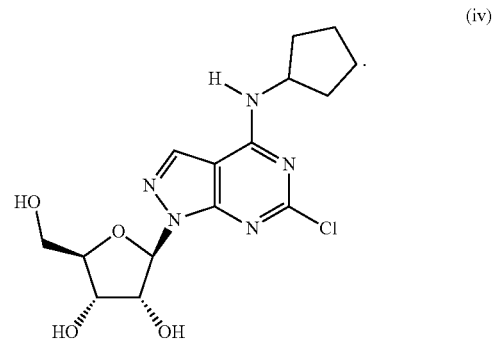 [SMILES: OC[C@H]1O[C@@H](n2ncc3c(NC4CCCC4)nc(Cl)nc32)[C@H](O)[C@@H]1O]

2. The process of claim 1, wherein each of the protected analog of ribofuranose, the protected analog of compound of formula (iii), and the protected analog of compound of formula (iv) are protected with one or more protecting groups.

3. The process of claim 2, wherein the one or more protecting groups are independently selected from acyl and acetonide.

4. The process of claim 3, wherein the acyl is an acetate.

5. The process of claim 1, wherein the protected analog of ribofuranose is a compound of formula (ii):

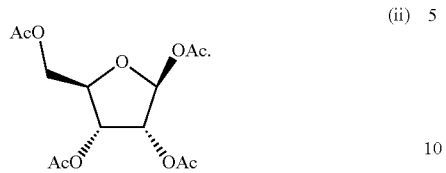
(ii)

6. The process of claim 1, wherein the protected analog of compound of formula (iii) is a compound of formula (iii-a):

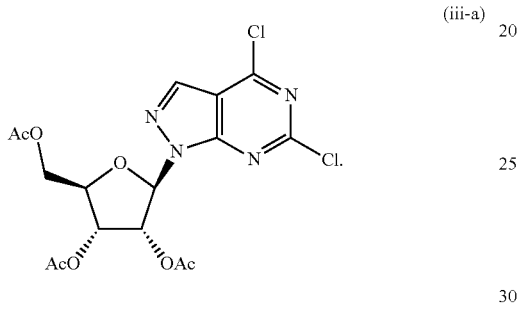
(iii-a)

7. The process of claim 1, wherein the protected analog of compound of formula (iv) is a compound of formula (iv-a):

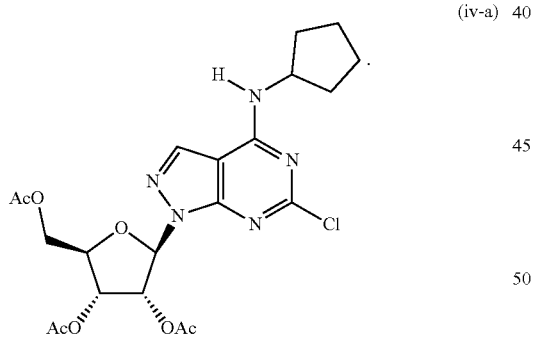
(iv-a)

8. The process of claim 1, wherein step b) further comprises a base.

9. The process of claim 8, wherein the base is an amine.

10. The process of claim 9, wherein the amine is triethylamine.

11. The process of claim 1, wherein step b) is conducted in a solvent.

12. The process of claim 11, wherein the solvent is an alcohol.

13. The process of claim 12, wherein the alcohol is methanol.

14. A process for preparing a CD73 inhibitor, said process comprising converting a compound of formula (i):

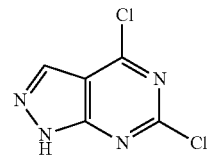
(i)

to a compound of formula (iv):

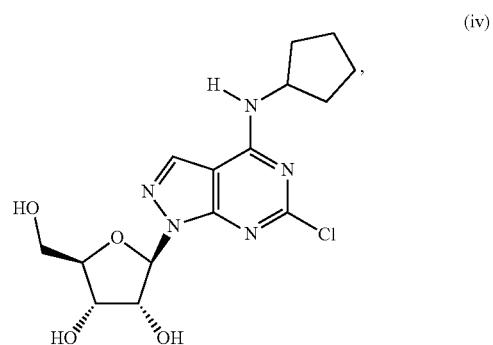 [SMILES: OC[C@H]1O[C@@H](n2ncc3c(NC4CCCC4)nc(Cl)nc32)[C@H](O)[C@@H]1O]
(iv)

or a protected analog thereof.

15. The process of claim 14, wherein converting the compound of formula (i) comprises contacting the compound of formula (i) with a protected analog of ribofuranose to form a protected analog of compound of formula (iii):

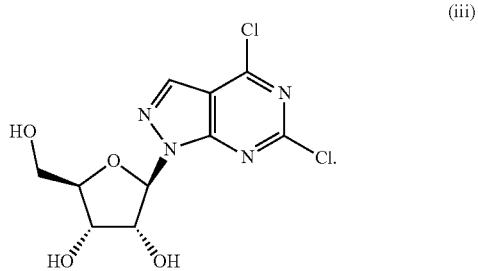 [SMILES: OC[C@H]1O[C@@H](n2ncc3c(Cl)nc(Cl)nc32)[C@H](O)[C@@H]1O]
(iii)

16. The process of claim 15, wherein the protected analog of ribofuranose is a compound of formula (ii):

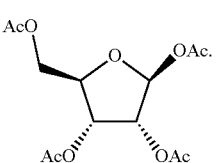
(ii)

17. The process of claim 15, wherein the protected analog of compound of formula (iii) has a structure of formula (iii-a):

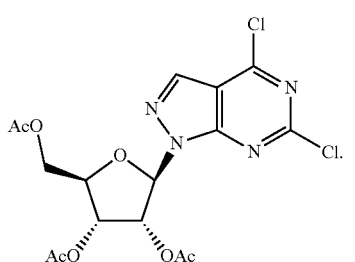

(iii-a)

18. The process of claim 15, further comprising contacting the protected analog of compound of formula (iii) with cyclopentyl amine to form a protected analog of a compound of formula (iv):

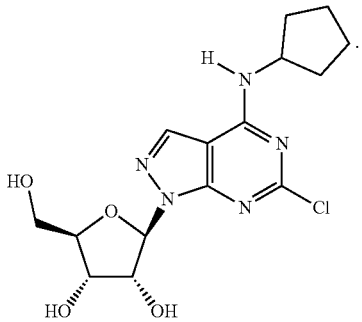 [SMILES: OC[C@H]1O[C@@H](n2ncc3c(NC4CCCC4)nc(Cl)nc32)[C@H](O)[C@@H]1O]

(iv)

19. The process of claim 18, wherein the protected analog of a compound of formula (iv) is a compound of formula (iv-a):

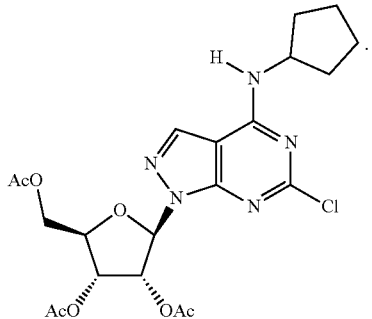

(iv-a)

20. A process for preparing a CD73 inhibitor, said process comprising: starting with a compound of formula (i):

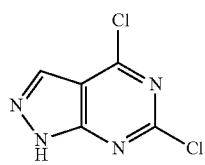

(i)

and using a means for converting said compound of formula (i) to a compound of formula (iv):

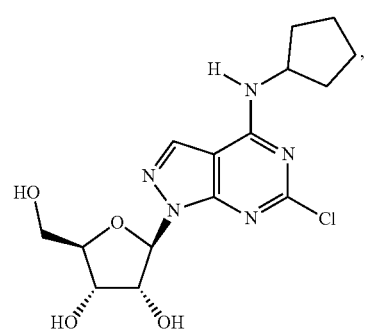

(iv)

or a protected form thereof.

21. The process of claim 20, wherein the protected form of the compound of formula (iv) is a compound of formula (iv-a) or a compound of formula (iv-b):

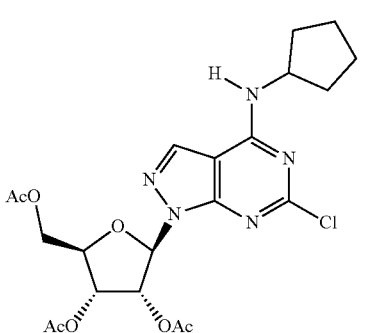

(iv-a)

-continued
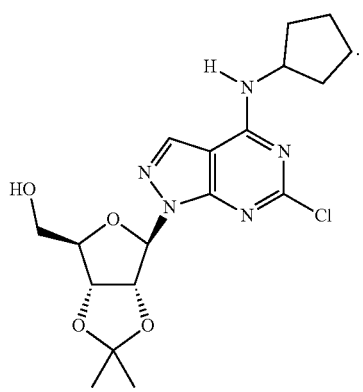
(iv-b)
22. A compound having the structure
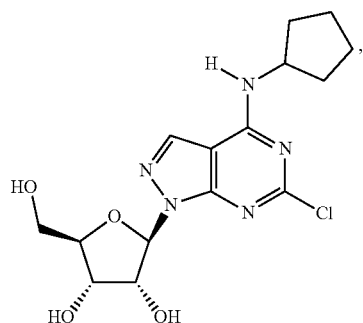
or a protected form thereof.
23. The compound of claim 22, having the structure
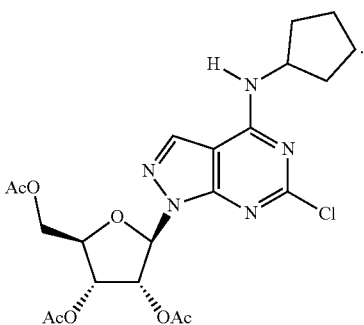 [SMILES: CC(=O)OC[C@H]1O[C@@H](n2ncc3c(NC4CCCC4)nc(Cl)nc32)[C@H](OC(C)=O)[C@@H]1OC(C)=O]
24. The compound of claim 22, having the structure
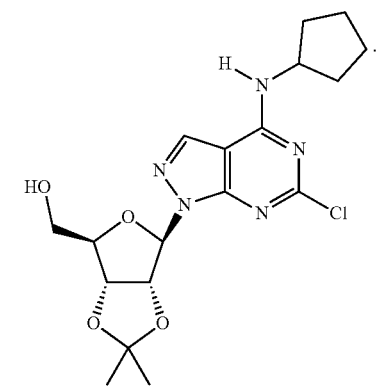
* * * * *

UNITED STATES PATENT AND TRADEMARK OFFICE
CERTIFICATE OF CORRECTION

| | |
|---|---|
| PATENT NO. | : 12,168,023 B2 |
| APPLICATION NO. | : 18/629820 |
| DATED | : December 17, 2024 |
| INVENTOR(S) | : Debien et al. |

Page 1 of 6

It is certified that error appears in the above-identified patent and that said Letters Patent is hereby corrected as shown below:

In the Claims

In Claim 1, Column 134, Lines 42 to 57, please replace:

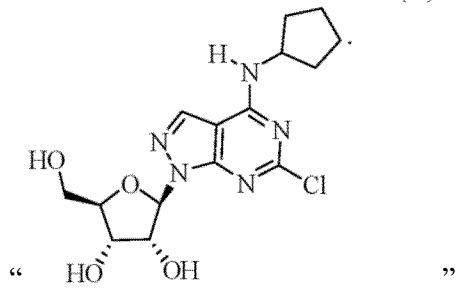

With:

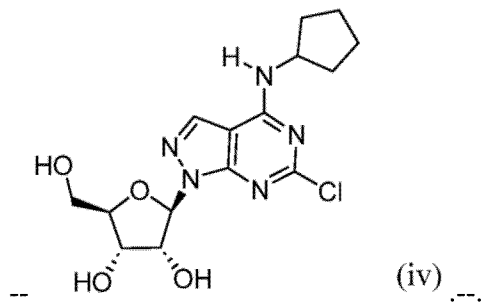

In Claim 5, Column 135, Lines 3 to 12, please replace:

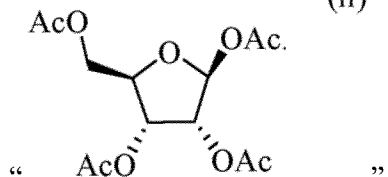

Signed and Sealed this
Thirteenth Day of May, 2025

Coke Morgan Stewart
*Acting Director of the United States Patent and Trademark Office*

With:
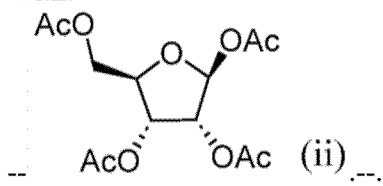
-- (ii) --.
In Claim 6, Column 135, Lines 15 to 30, please replace:
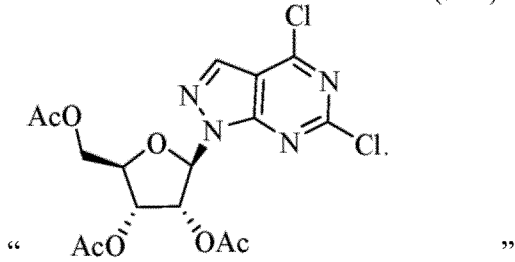
" (iii-a) "
With:
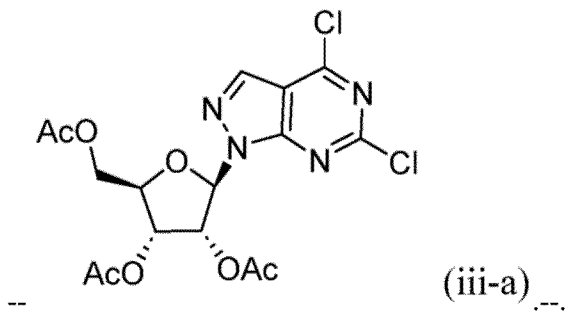
-- (iii-a) --.
In Claim 7, Column 135, Lines 36 to 55, please replace:
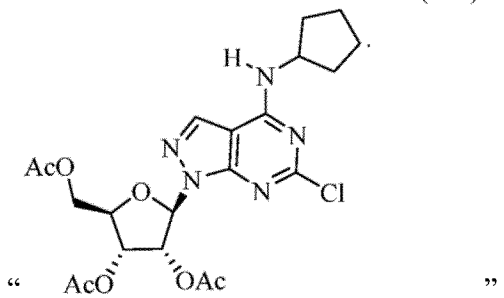
" (iv-a) "

With:
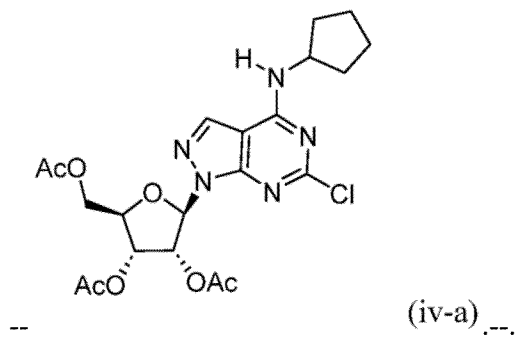
(iv-a) --.
In Claim 15, Column 136, Lines 42 to 55, please replace:
" 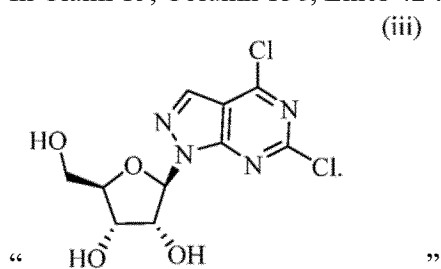 (iii) "
With:
-- 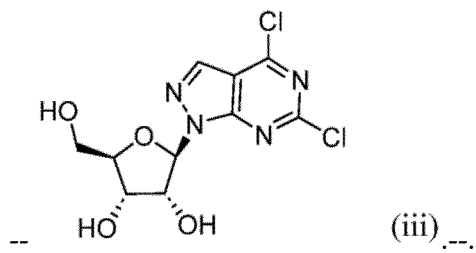 (iii) --.
In Claim 16, Column 136, Lines 59 to 66, please replace:
" 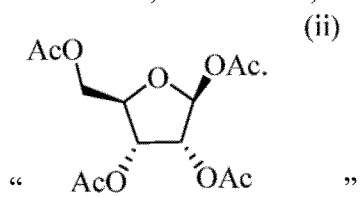 (ii) "
With:
-- 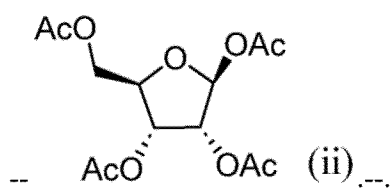 (ii) --.

In Claim 17, Column 137, Lines 6 to 20, please replace:
" 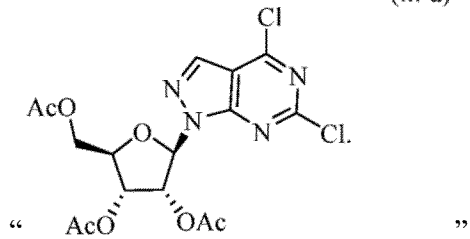 (iii-a) "
With:
-- 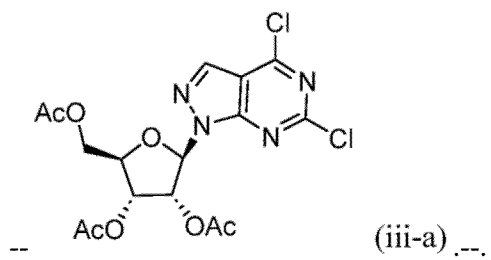 (iii-a) --.
In Claim 18, Column 137, Lines 30 to 45, please replace:
" 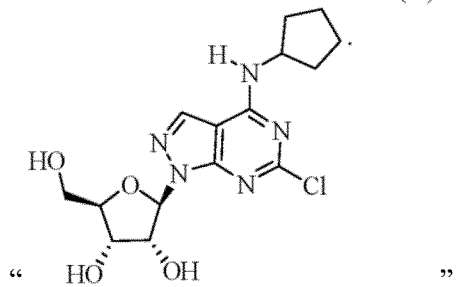 (iv) "
With:
-- 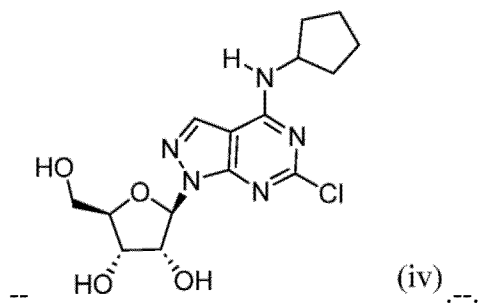 (iv) --.

In Claim 19, Column 137, Lines 52 to 66, please replace:
" 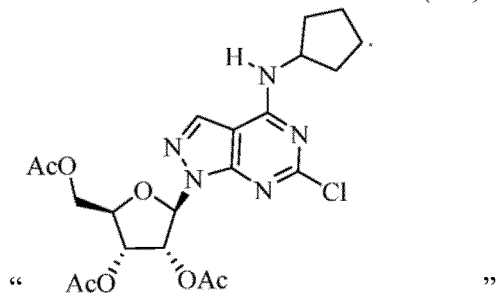 (iv-a) "
With:
-- 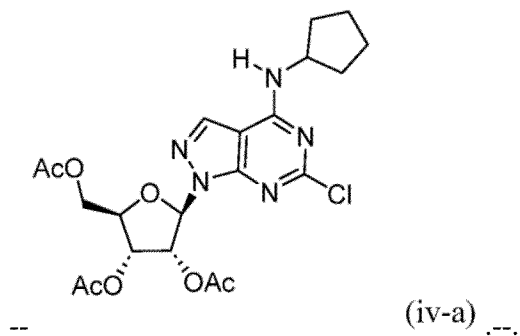 (iv-a) --.
In Claim 21, Column 139, Lines 2 to 18, please replace:
" 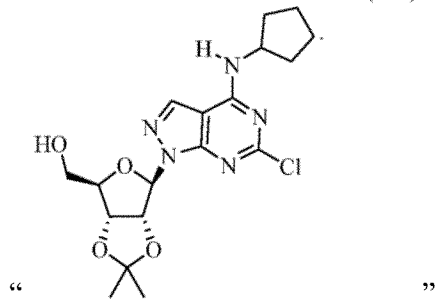 (iv-b) "
With:
-- 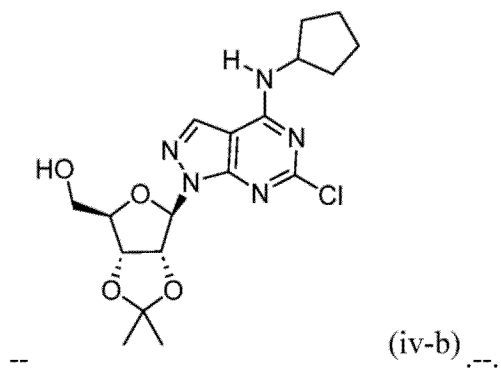 (iv-b) --.

In Claim 23, Column 140, Lines 2 to 16, please replace:
" 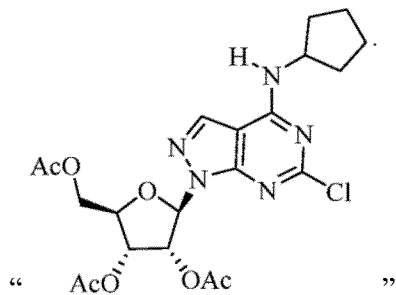 "
With:
-- 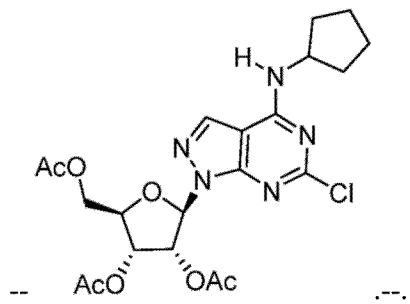 --.
In Claim 24, Column 140, Lines 19 to 35, please replace:
" 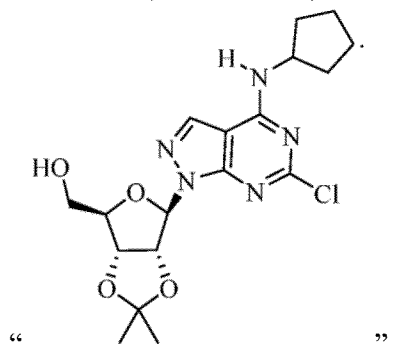 "
With:
-- 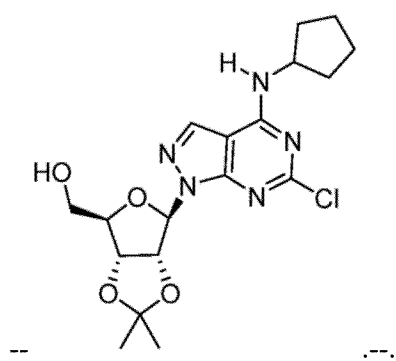 --.